US010563126B2

(12) United States Patent
Yano

(10) Patent No.: US 10,563,126 B2
(45) Date of Patent: *Feb. 18, 2020

(54) LIQUID CRYSTAL COMPOUND HAVING BENZOTHIOPHENE, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventor: Tomohiro Yano, Chiba (JP)

(73) Assignees: JNC CORPORATION, Tokyo (JP); JNC PETROCHEMICAL CORPORATION, Tokyo (JP)

(*) Notice: Subject to any disclaimer, the term of this patent is extended or adjusted under 35 U.S.C. 154(b) by 63 days.

This patent is subject to a terminal disclaimer.

(21) Appl. No.: 15/579,193

(22) PCT Filed: May 10, 2016

(86) PCT No.: PCT/JP2016/063815
§ 371 (c)(1),
(2) Date: Dec. 1, 2017

(87) PCT Pub. No.: WO2016/199528
PCT Pub. Date: Dec. 15, 2016

(65) Prior Publication Data
US 2018/0127652 A1 May 10, 2018

(30) Foreign Application Priority Data
Jun. 8, 2015 (JP) ................. 2015-115768

(51) Int. Cl.
G02F 1/1334 (2006.01)
C09K 19/34 (2006.01)
(Continued)

(52) U.S. Cl.
CPC .......... C09K 19/3491 (2013.01); C09K 19/12 (2013.01); C09K 19/32 (2013.01);
(Continued)

(58) Field of Classification Search
CPC ...... C09K 2019/0466; C09K 2019/122; C09K 2019/123; C09K 2019/181;
(Continued)

(56) References Cited
U.S. PATENT DOCUMENTS
3,697,513 A 10/1972 Siegrist
5,073,564 A 12/1991 Roush et al.
(Continued)

FOREIGN PATENT DOCUMENTS
CN 103102887 A 5/2013
CN 103724319 A 4/2014
(Continued)

OTHER PUBLICATIONS

Kurfuerst, M. et al., "Liquid crystalline benzothiophene derivatives", Liquid Crystals, 2008, pp. 21-31, vol. 35, No. 1, 11pp.
Ekisho Binran Henshuu Iinkai, "Ekisho Binran", Oct. 30, 2000, pp. 267, 269, 272, 277-278, 312, 317-321, Maruzen Co., Ltd., Japan, 55pp.
Lamanna, G. et al., "2,3-Disubstituted benzo[b]thiophenes from diarylalkynes via electrophilic addition-cyclization and palladium-catalyzed cross-coupling", Advanced Synthesis & Catalysis, Sep. 11, 2007, pp. 2188-2194, vol. 349, No. 13, 7pp.
Sun, L. et al., "CuI/TMEDA-Catalyzed Annulation of 2-Bromo Alkynylbenzenes with Na2S: Synthesis of Benzo[b] thiophenes", Journal of Organic Chemistry, 2011, pp. 7546-7550, vol. 76, No. 18, 5pp.
(Continued)

Primary Examiner — Geraldina Visconti
(74) Attorney, Agent, or Firm — Hauptman Ham, LLP

(57) ABSTRACT

A liquid crystal compound is represented by formula (1):

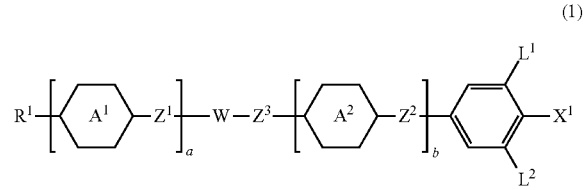

In formula (1), $R^1$ is alkyl or the like; ring $A^1$ and ring $A^2$ are independently 1,4-cyclohexylene, 1,4-phenylene or the like; $Z^1$, $Z^2$ and $Z^3$ are independently a single bond, —$CF_2O$— or the like; $X^1$ is fluorine, chlorine, —$CF_3$ or the like; $L^1$ and $L^2$ are independently hydrogen, fluorine or the like; a and b are independently 0, 1, 2 or 3; and W is a group represented by formula (1a) or formula (1b);

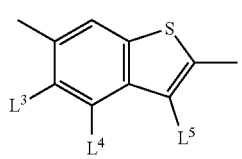

(1a)

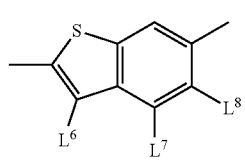

(1b)

In formula (1a) and formula (1b), $L^3$ to $L^8$ are independently hydrogen, fluorine or the like.

14 Claims, No Drawings

(51) Int. Cl.
   *C09K 19/32* (2006.01)
   *C09K 19/42* (2006.01)
   *C09K 19/54* (2006.01)
   *C09K 19/12* (2006.01)
   *G02F 1/1333* (2006.01)

(52) U.S. Cl.
   CPC .............. *C09K 19/42* (2013.01); *C09K 19/54* (2013.01); *G02F 1/1333* (2013.01); *C09K 2019/122* (2013.01)

(58) Field of Classification Search
   CPC .... C09K 2019/3004; C09K 2019/3009; C09K 2019/301; C09K 2019/3016; C09K 2019/3021; C09K 2019/3025; C09K 2019/3027; C09K 2019/304; C09K 2019/3042; C09K 2019/3077; C09K 2019/3422; C09K 2019/3425; C09K 19/3491; C09K 19/12; C09K 19/3028; C09K 19/32; C09K 19/34; C09K 19/42; C09K 19/52; C09K 19/54; G02F 1/1333; G02F 1/1334; G02F 1/13; C07D 333/54; C07D 333/56; C07D 333/62
   USPC .................................................... 252/299.63
   See application file for complete search history.

(56) References Cited

U.S. PATENT DOCUMENTS

| 6,403,172 B1 | 6/2002 | Wingen et al. |
| 10,100,252 B2* | 10/2018 | Okabe ................ C09K 19/3491 |
| 2014/0138582 A1 | 5/2014 | Gotoh et al. |
| 2014/0235660 A1 | 8/2014 | Burks et al. |

FOREIGN PATENT DOCUMENTS

| DE | 102004053279 A1 | 6/2005 |
| JP | 6-234973 A | 8/1994 |
| JP | 2000-328062 A | 11/2000 |
| JP | 2003-509507 A | 3/2003 |
| JP | 2014-114276 A | 6/2014 |
| WO | 98/04544 A1 | 2/1998 |
| WO | 2012/126570 A1 | 9/2012 |
| WO | 2014/130310 A1 | 8/2014 |

OTHER PUBLICATIONS

Grese, T.A. et al., "Structure-Activity Relationships of Selective Estrogen Receptor Modulators: Modifications to the 2-Arylbenzothiophene Core of Raloxifene", Journal of Medicinal Chemistry, 1997, pp. 146-167, vol. 40, No. 2, 22pp.
Patel, M. V. et al., "An efficient one-pot synthesis of substituted 2-arylbenzo[b]thiophene derivatives", Tetrahedron Letters, 2003, pp. 6665-6667, vol. 44, No. 35, 3pp.
Lu, W. et al., "Halocyclization of 2-alkynylthioanisoles by cupric halides: synthesis of 2-substituted 3-halobenzo[b] thiophenes", Tetrahedron, 2007, pp. 356-362, vol. 63, No. 2, 7pp.
Duez, S. et al., "Benzylic Arylation of 2-Methyl-5-membered Heterocycles Using TMP-Bases", Organic Letters, 2012, pp. 1951-1953, vol. 14, No. 8, 3pp.
Moreno-Manas, M. et al., "New imidazole anti-fungal agents derived from benzo[b]thiophene. Part II", European Journal of Medicinal Chemistry, 1988, pp. 477-482, vol. 23, No. 5, 6pp.
Kucharczyk, N. et al., "Sodium borohydride reduction of 2,3-dihydrothianaphthen-3-ones", Collection of Czechoslovak Chemical Communications, 1968, pp. 92-99, vol. 33, No. 1, 8pp.
RN: 930734-85-3, Apr. 18, 2007, Database Registry [online], Retrieved from: STN.
RN: 339350-59-3, Jun. 5, 2001, Database Registry [online], Retrieved from: STN.
RN: 797020-80-5, Dec. 14, 2004, Database Registry [online], Retrieved from: STN.
RN: 565223-80-5, Aug. 12, 2003, Database Registry [online], Retrieved from: STN.
RN: 511250-36-5, May 6, 2003, Database Registry [online], Retrieved from: STN.
RN: 511241-79-5, May 6, 2003, Database Registry [online], Retrieved from: STN.
RN: 502910-87-4, Apr. 14, 2003, Database Registry [online], Retrieved from: STN.
RN: 454683-62-6, Sep. 25, 2002, Database Registry [online], Retrieved from: STN.
RN: 454452-82-5, Sep. 24, 2002, Database Registry [online], Retrieved from: STN.
RN: 879738-45-1, Apr. 9, 2006, Database Registry [online], Retrieved from: STN.
RN: 1003482-14-1, Feb. 14, 2008, Database Registry [online], Retrieved from: STN.
RN: 561017-24-1, Aug. 5, 2003, Database Registry [online], Retrieved from: STN.
RN: 1539184-00-3, Feb. 7, 2014, Database Registry [online], Retrieved from: STN.
RN:1408597-78-3, Nov. 30, 2012, Database Registry [online], Retrieved from: STN.
Han, J. et al, "Insights into the reaction of trans-diarylethenes with thionyl chloride: a practical synthesis of chlorobenzo[b] thiophenes", Tetrahedron, 2011, pp. 8865-8872, vol. 67, No. 46, 8pp.
Kozmik, V. et al., "Liquid crystalline benzothiophene derivatives. Part 2: 2, 5-disubstituted benzothiophenes", Liquid Crystals, Oct. 2011, pp. 1245-1261, vol. 38, No. 10, 19pp.
International Search Report in PCT/JP2016/063815, dated Aug. 2, 2016, 10pp.
Written Opinion of the ISA in PCT/JP2016/063815, dated Aug. 2, 2016, 23pp.

* cited by examiner

LIQUID CRYSTAL COMPOUND HAVING BENZOTHIOPHENE, LIQUID CRYSTAL COMPOSITION AND LIQUID CRYSTAL DISPLAY DEVICE

RELATED APPLICATIONS

The present application is a National Phase of International Application Number PCT/JP2016/063815, filed May 10, 2016, which claims priority to JP 2015-115768 filed Jun. 8, 2015.

TECHNICAL FIELD

The invention relates to a liquid crystal compound and a liquid crystal composition. More specifically, the invention relates to a liquid crystal compound having benzothiophene, a liquid crystal composition containing the compound and having a nematic phase, and a liquid crystal display device including the composition.

A liquid crystal display device has been widely utilized for a display of a personal computer, a television or the like. The device utilizes optical anisotropy, dielectric anisotropy and so forth of a liquid crystal compound. An operating mode of the liquid crystal display device includes a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode and a polymer sustained alignment (PSA) mode.

In such a liquid crystal display device, a liquid crystal composition having suitable physical properties is used. In order to further improve characteristics of the liquid crystal display device, the liquid crystal compound contained in the composition preferably has physical properties described in (1) to (8) as described below. (1) High stability to heat, light and so forth, (2) a high clearing point, (3) a low minimum temperature of a liquid crystal phase, (4) small viscosity (η), (5) suitable optical anisotropy (Δn), (6) large dielectric anisotropy (Δε), (7) a suitable elastic constant (K) and (8) excellent compatibility with other liquid crystal compounds.

An effect of the physical properties of the liquid crystal compound on the characteristics of the device is as described below. A compound having the high stability to heat, light and so forth as described in (1) increases a voltage holding ratio of the device. Therefore, a service life of the device becomes long. A compound having the high clearing point as described in (2) extends a temperature range in which the device can be used. A compound having the low minimum temperature of the liquid crystal phase such as the nematic phase and a smectic phase as described in (3), in particular, a compound having the low minimum temperature of the nematic phase also extends the temperature range in which the device can be used. A compound having the small viscosity as described in (4) shortens a response time of the device.

A compound having the large optical anisotropy as described in (5) improves contrast of the device. According to a design of the device, a compound having the large optical anisotropy or small optical anisotropy, more specifically, a compound having the suitable optical anisotropy is required. When the response time is shortened by decreasing a cell gap of the device, a compound having the large optical anisotropy is suitable. A compound having the large dielectric anisotropy as described in (6) decreases a threshold voltage of the device. Thus, electric power consumption of the device is decreased. On the other hand, a compound having small dielectric anisotropy shortens the response time of the device by decreasing viscosity of the composition.

With regard to (7), a compound having the large elastic constant decreases the response time of the device. A compound having the small elastic constant decreases the threshold voltage of the device. Therefore, the suitable elastic constant is required according to characteristics to be desirably improved. A compound having the excellent compatibility with other liquid crystal compounds as described in (8) is preferred. The reason is that the physical properties of the composition are adjusted by mixing liquid crystal compounds having different physical properties.

Various liquid crystal compounds having the large dielectric anisotropy have been prepared so far. Various liquid crystal compounds having the large optical anisotropy have been also prepared. The reason is that good physical properties that have not existed in a conventional compound are expected in a new compound. The reason is that a suitable balance between at least two physical properties is expected to be obtained in the liquid crystal composition by adding the new compound to the composition. From such a situation, a compound having the good physical properties and the suitable balance regarding the physical properties (1) to (8) is desired.

Several liquid crystal compounds having a benzothiophene skeleton have been prepared so far. Patent literature Nos. 1 and 2 describe compounds (A) to (D) and so forth. However, the above compounds have the dielectric anisotropy being not sufficiently large, and so forth, and therefore have been far from sufficiently suitable as the liquid crystal compound to be used in the liquid crystal device.

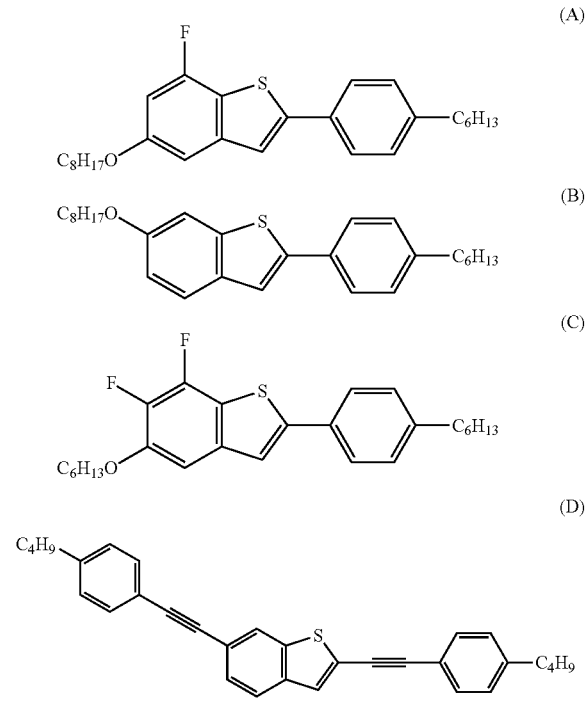

CITATION LIST

Patent Literature

Patent literature No. 1: JP 2000-328062 A.
Patent literature No. 2: WO 2012/126570 A.

SUMMARY OF INVENTION

Technical Problem

A first objective of the invention is to provide a liquid crystal compound satisfying at least one of physical properties such as high stability to heat and light, a high clearing point (or a high maximum temperature of a nematic phase), a low minimum temperature of a liquid crystal phase, small viscosity, suitable optical anisotropy, large positive dielectric anisotropy, a suitable elastic constant and excellent compatibility with other liquid crystal compounds. A second objective of the invention is to provide a liquid crystal composition containing the compound, and satisfying at least one of physical properties such as high stability to heat and light, a high maximum temperature of a nematic phase, a low minimum temperature of the nematic phase, small viscosity, suitable optical anisotropy, large dielectric anisotropy, large specific resistance and a suitable elastic constant. The objective is to provide a liquid crystal composition having a suitable balance regarding at least two of the physical properties. A third objective is to provide a liquid crystal display device including the composition and having a wide temperature range in which the device can be used, a short response time, a large voltage holding ratio, a low threshold voltage, a large contrast ratio and a long service life.

Solution to Problem

The invention concerns a liquid crystal compound represented by formula (1), a liquid crystal composition containing the compound and a liquid crystal display device including the composition:

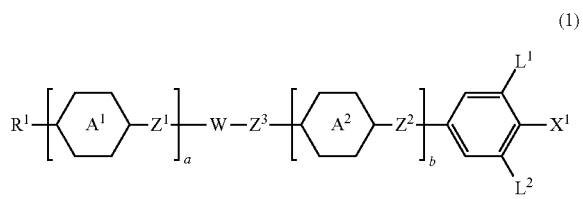

(1)

wherein, in formula (1), $R^1$ is hydrogen, fluorine or alkyl having 1 to 20 carbons, and in the alkyl, at least one piece of —$CH_2$— may be replaced by —O— or —S—, and at least one piece of —$CH_2CH_2$— may be replaced by —CH=CH—, and in the groups, at least one hydrogen may be replaced by fluorine;

ring $A^1$ and ring $A^2$ are independently 1,4-cyclohexylene, 1,4-cyclohexenylene, 1,4-phenylene, tetrahydropyran-2,5-diyl, 1,3-dioxane-2,5-diyl, pyrimidine-2,5-diyl, 2,6,7-trioxabicyclo[2.2.2]octane-1,4-diyl, naphthalene-2,6-diyl or pyridine-2,5-diyl, and at least one hydrogen on the rings may be replaced by halogen;

$Z^1$ and $Z^2$ are independently a single bond or alkylene having 1 to 4 carbons, and in the alkylene, at least one piece of —$CH_2$— may be replaced by —O— or —COO—, and at least one piece of —$(CH_2)_2$— may be replaced by —CH=CH— or —C≡C—, and in the groups, at least one hydrogen may be replaced by halogen;

$X^1$ is fluorine, chlorine, —$SF_5$, —C≡N, —N=C=S, —C≡C—$CF_3$, —C≡C—CN, polyfluoroalkyl having 1 to 7 carbons, perfluoroalkyl having 1 to 7 carbons, polyfluoroalkenyl having 1 to 7 carbons, perfluoroalkoxy having 1 to 7 carbons, polyfluoroalkoxy having 1 to 7 carbons or perfluoroalkoxy having 1 to 7 carbons;

$L^1$ and $L^2$ are independently hydrogen, fluorine or chlorine;

a and b are independently 0, 1, 2 or 3, and a sum of a and b is 3 or less, and when a or b is 2 or more, two rings $A^1$ and $A^2$ and two of $Z^1$ or $Z^2$ may be identical or different; and W is a group represented by formula (1a) or formula (1b);

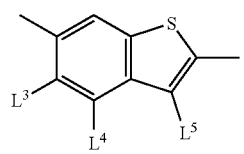

(1a)

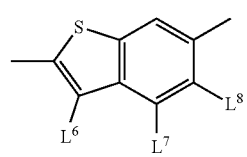

(1b)

wherein, in formula (1a) and formula (1b),
$L^3$, $L^4$, $L^5$, $L^6$, $L^7$ and $L^8$ are independently hydrogen, fluorine or chlorine.

Advantageous Effects of Invention

A first advantage is to provide a liquid crystal compound satisfying at least one of physical properties such as high stability to heat and light, a high clearing point (or a high maximum temperature of a nematic phase), a low minimum temperature of a liquid crystal phase, small viscosity, suitable optical anisotropy, large positive dielectric anisotropy, a suitable elastic constant and excellent compatibility with other liquid crystal compounds. A second advantage of the invention is to provide a liquid crystal composition containing the compound, and satisfying at least one of physical properties such as high stability to heat and light, a high maximum temperature of a nematic phase, a low minimum temperature of a nematic phase, small viscosity, suitable optical anisotropy, large dielectric anisotropy, large specific resistance and a suitable elastic constant. The advantage is to provide a liquid crystal composition having a suitable balance regarding at least two of the physical properties. A third advantage is to provide a liquid crystal display device including the composition and having a wide temperature range in which the device can be used, a short response time, a large voltage holding ratio, a low threshold voltage, a large contrast ratio and a long service life.

DESCRIPTION OF EMBODIMENTS

Usage of terms herein is as described below. Terms "liquid crystal compound," "liquid crystal composition" and "liquid crystal display device" may be occasionally abbreviated as "compound," "composition" and "device," respectively. "Liquid crystal compound" is a generic term for a compound having a liquid crystal phase such as a nematic phase and a smectic phase, and a compound having no liquid crystal phase but to be added for the purpose of adjusting physical properties of a composition, such as a maximum temperature, a minimum temperature, viscosity and dielectric anisotropy. The compound has a six-membered ring such as 1,4-cyclohexylene and 1,4-phenylene, and has rodlike molecular structure. "Liquid crystal display device" is a generic term for a liquid crystal display panel and a liquid crystal display module. "Polymerizable compound" includes a compound to be added to the composition for the purpose of forming a polymer in the composition.

The liquid crystal composition is prepared by mixing a plurality of liquid crystal compounds. A proportion (content) of the liquid crystal compound is expressed in terms of weight percent (% by weight) based on the weight of the liquid crystal composition. An additive such as a polymerizable compound, a polymerization initiator, a polymerization inhibitor, an optically active compound, an antioxidant, an ultraviolet light absorber, a light stabilizer, a heat stabilizer, a dye and an antifoaming agent is added when necessary. A proportion (amount of addition) of the additive is expressed in terms of weight percent (% by weight) based on the weight of the liquid crystal composition in a manner similar to the proportion of the liquid crystal compounds. Weight parts per million (ppm) may be occasionally used. A proportion of the polymerization initiator and the polymerization inhibitor is exceptionally expressed based on the weight of the polymerizable compound.

"Clearing point" is a transition temperature between a liquid crystal phase and an isotropic phase in the liquid crystal compound. "Minimum temperature of the liquid crystal phase" is a transition temperature between a solid and the liquid crystal phase (the smectic phase, the nematic phase or the like) in the liquid crystal compound. "Maximum temperature of the nematic phase" is a transition temperature between the nematic phase and the isotropic phase in a mixture of the liquid crystal compound and a base liquid crystal or in the liquid crystal composition, and may be occasionally abbreviated as "maximum temperature." "Minimum temperature of the nematic phase" may be occasionally abbreviated as "minimum temperature." An expression "increase the dielectric anisotropy" means that a value of dielectric anisotropy positively increases in a liquid crystal composition having positive dielectric anisotropy, and the value of dielectric anisotropy negatively increases in a liquid crystal composition having negative dielectric anisotropy.

A compound represented by formula (1) may be occasionally abbreviated as compound (1). At least one compound selected from the group of compounds represented by formula (1) may be occasionally abbreviated as "compound (1)." "Compound (1)" means one compound, a mixture of two compounds or a mixture of three or more compounds represented by formula (1). A same rule applies also to any other compound represented by any other formula. In formula (1) to formula (15), a symbol $A^1$ and so forth surrounded by a hexagonal shape correspond to ring $A^1$ and so forth, respectively. The hexagonal shape represents a six-membered ring such as cyclohexane and benzene. The hexagonal shape may occasionally represents a condensed ring such as naphthalene or a bridged ring such as adamantane.

A symbol of terminal group $R^1$ is used in a plurality of compounds in chemical formulas of component compounds. In the compounds, two groups represented by two pieces of arbitrary $R^1$ may be identical or different. In one case, for example, $R^1$ of compound (1-1) is ethyl and $R^1$ of compound (1-2) is ethyl. In another case, $R^1$ of compound (1-1) is ethyl and $R^1$ of compound (1-2) is propyl. A same rule applies also to symbols such as $R^{11}$ and $Z^{11}$. In compound (8), when i is 2, two of rings $D^1$ exist. In the compound, two groups represented by two of rings $D^1$ may be identical or different. A same rule applies also to two of arbitrary rings $D^1$ when i is larger than 2. A same rule applies also to other symbols.

An expression "at least one piece of 'A'" means that the number of 'A' is arbitrary. An expression "at least one piece of 'A' may be replaced by 'B'" means that, when the number of 'A' is 1, a position of 'A' is arbitrary, and also when the number of 'A' is 2 or more, positions thereof can be selected without limitation. A same rule applies also to an expression "at least one piece of 'A' is replaced by 'B'." An expression "at least one of A may be replaced by B, C or D" means inclusion of a case where arbitrary A is replaced by B, a case where arbitrary A is replaced by C, and a case where arbitrary A is replaced by D, and also a case where a plurality of A are replaced by at least two of B, C or D. For example, alkyl in which at least one of —$CH_2$— may be replaced by —O— or —CH=CH— includes alkyl, alkenyl, alkoxy, alkoxyalkyl, alkoxyalkenyl and alkenyloxyalkyl. In addition, a case where replacement of two successive —$CH_2$— by —O— results in forming —O—O— is not preferred. In the alkyl or the like, a case where replacement of —$CH_2$— of a methyl part (—$CH_2$—H) by —O— results in forming —O—H is not preferred, either.

Halogen means fluorine, chlorine, bromine and iodine. Preferred halogen is fluorine and chlorine. Further preferred halogen is fluorine. Alkyl is straight-chain alkyl or branched-chain alkyl, but includes no cyclic alkyl. In general, straight-chain alkyl is preferred to branched-chain alkyl. A same rule applies also to a terminal group such as alkoxy and alkenyl. With regard to a configuration of 1,4-cyclohexylene, trans is preferred to cis for increasing the maximum temperature. Then, 2-fluoro-1,4-phenylene means two divalent groups described below. In a chemical formula, fluorine may be leftward (L) or rightward (R). A same rule also applies to an asymmetrical divalent group formed by removing two pieces of hydrogen from a ring, such as tetrahydropyran-2,5-diyl.

The invention includes items described below.

Item 1. A liquid crystal compound, represented by formula (1):

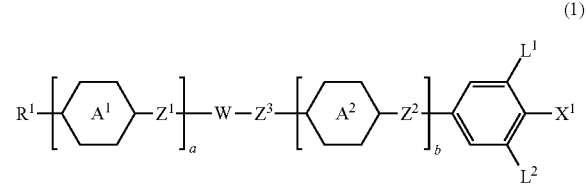

(1)

wherein, in formula (1), $R^1$ is hydrogen, fluorine or alkyl having 1 to 20 carbons, and in the alkyl, at least one piece of —$CH_2$— may be replaced by —O— or —S—, and at least one piece of —$CH_2CH_2$— may be replaced by —CH=CH—, and in the groups, at least one hydrogen may be replaced by fluorine;

ring $A^1$ and ring $A^2$ are independently 1,4-cyclohexylene, 1,4-cyclohexenylene, 1,4-phenylene, tetrahydropyran-2,5-diyl, 1,3-dioxane-2,5-diyl, pyrimidine-2,5-diyl, 2,6,7-trioxabicyclo[2.2.2]octane-1,4-diyl, naphthalene-2,6-diyl or pyridine-2,5-diyl, and at least one hydrogen on the rings may be replaced by halogen;

$Z^1$, $Z^2$ and $Z^3$ are independently a single bond or alkylene having 1 to 4 carbons, and in the alkylene, at least one piece of —CH$_2$— may be replaced by —O— or —COO—, and at least one piece of —(CH$_2$)$_2$— may be replaced by —CH=CH— or —C≡C—, and in the groups, at least one hydrogen may be replaced by halogen;

$X^1$ is fluorine, chlorine, —SF$_5$, —C≡N, —N=C=S, —C≡C—CF$_3$, —C≡C—CN, polyfluoroalkyl having 1 to 7 carbons, perfluoroalkyl having 1 to 7 carbons, polyfluoroalkenyl having 1 to 7 carbons, perfluoroalkoxy having 1 to 7 carbons, polyfluoroalkoxy having 1 to 7 carbons or perfluoroalkoxy having 1 to 7 carbons;

$L^1$ and $L^2$ are independently hydrogen, fluorine or chlorine;

a and b are independently 0, 1, 2 or 3, and a sum of a and b is 3 or less, and when a or b is two or more, two of rings $A^1$ and $A^2$ and two of $Z^1$ and $Z^2$ may be identical or different; and W is a group represented by formula (1a) or formula (1b);

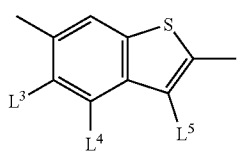

(1a)

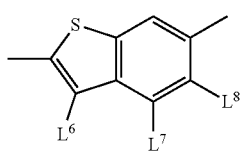

(1b)

wherein, in formula (1a) and formula (1b), $L^3$, $L^4$, $L^5$, $L^6$, $L^7$ and $L^8$ are independently hydrogen, fluorine or chlorine.

Item 2. The compound according to item 1, wherein, in formula (1), $R^1$ is hydrogen, fluorine or alkyl having 1 to 20 carbons, and in the alkyl, at least one piece of —CH$_2$— may be replaced by —O—, and at least one piece of —CH$_2$CH$_2$— may be replaced by —CH=CH—, and in the groups, at least one hydrogen may be replaced by fluorine;

ring $A^1$ and ring $A^2$ are independently 1,4-cyclohexylene, 1,4-cyclohexenylene, 1,4-phenylene in which one at least hydrogen may be replaced by halogen, 1,3-dioxane-2,5-diyl or tetrahydropyran-2,5-diyl;

$Z^1$, $Z^2$ and $Z^3$ are independently a single bond, —(CH$_2$)$_2$—, —CH=CH—, —CF=CF—, —C≡C—, —COO—, —OCO—, —CF$_2$O—, —OCF$_2$—, —CH$_2$O—, —OCH$_2$—, —(CH$_2$)$_4$—, (CH$_2$)$_2$CF$_2$O—, —(CH$_2$)$_2$OCF$_2$—, —CF$_2$O(CH$_2$)$_2$—, —OCF$_2$(CH$_2$)$_2$—, —CH=CH—(CH$_2$)$_2$— or —(CH$_2$)$_2$—CH=CH—;

$X^1$ is fluorine, chlorine, —SF$_5$, —C≡N, —N=C=S, —C≡C—CF$_3$, —C≡C—C≡N, polyfluoroalkyl having 1 to 3 carbons, perfluoroalkyl having 1 to 3 carbons, polyfluoroalkenyl having 1 to 3 carbons, perfluoroalkenyl having 1 to 3 carbons, polyfluoroalkoxy having 1 to 3 carbons or perfluoroalkoxy having 1 to 3 carbons; and $L^1$ and $L^2$ are independently hydrogen or fluorine.

Item 3. The compound according to item 1 or 2, wherein, in formula (1), a sum of a and b is 0, 1 or 2.

Item 4. The compound according to any one of items 1 to 3, represented by any one of formulas (1-1) to (1-12):

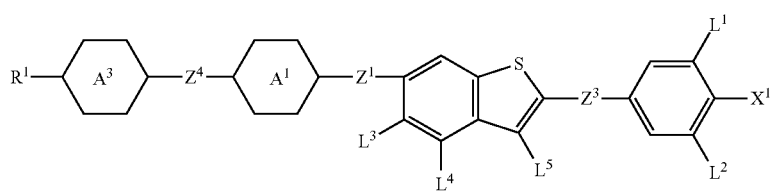

(1-1)

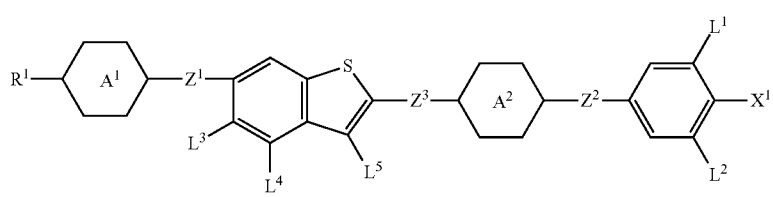

(1-2)

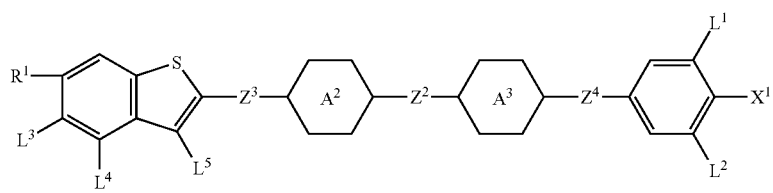

(1-3)

-continued
(1-4)
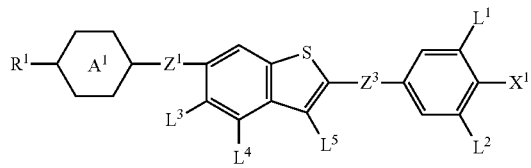
(1-5)
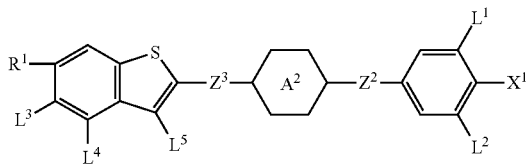
(1-6)
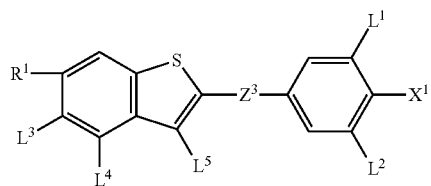
(1-7)
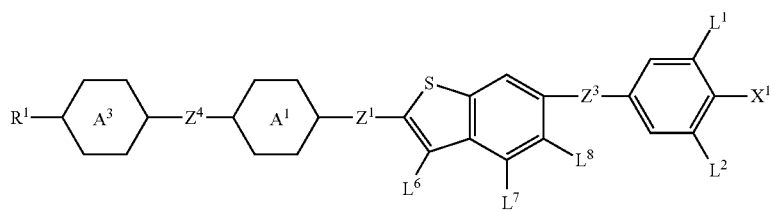
(1-8)
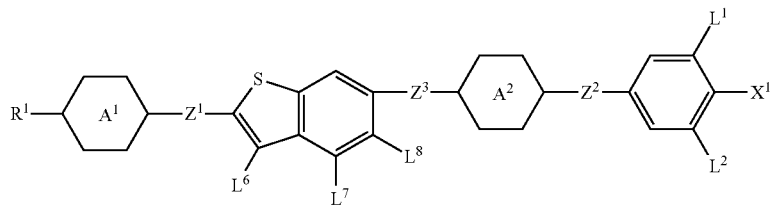
(1-9)
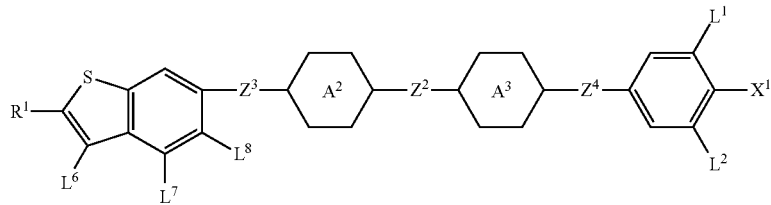
(1-10)
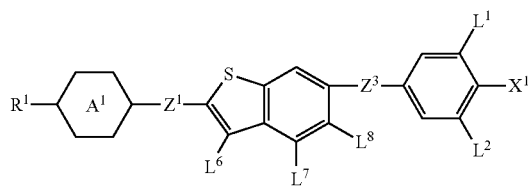
(1-11)
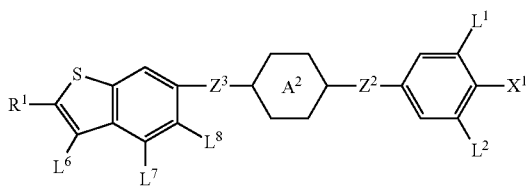
(1-12)
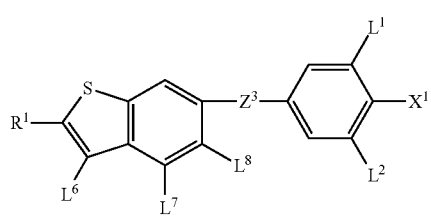

wherein, in formulas (1-1) to (1-12), $R^1$ is hydrogen, fluorine or alkyl having 1 to 10 carbons, and in the alkyl, at least one piece of —$CH_2$— may be replaced by —O—, and at least one piece of —$CH_2CH_2$— may be replaced by —CH=CH—, and in the groups, at least one hydrogen may be replaced by fluorine;

$Z^1$, $Z^2$, $Z^3$ and $Z^4$ are independently a single bond, —$(CH_2)_2$—, —CH=CH—, —$CF_2O$—, —$OCF_2$—, —$CH_2O$—, —C≡C—, —$(CH_2)_2OCF_2$— or —$OCH_2$—.

Item 6. The compound according to item 5, represented by any one of formulas (1-3), (1-5), (1-6), (1-9), (1-11) and (1-12):

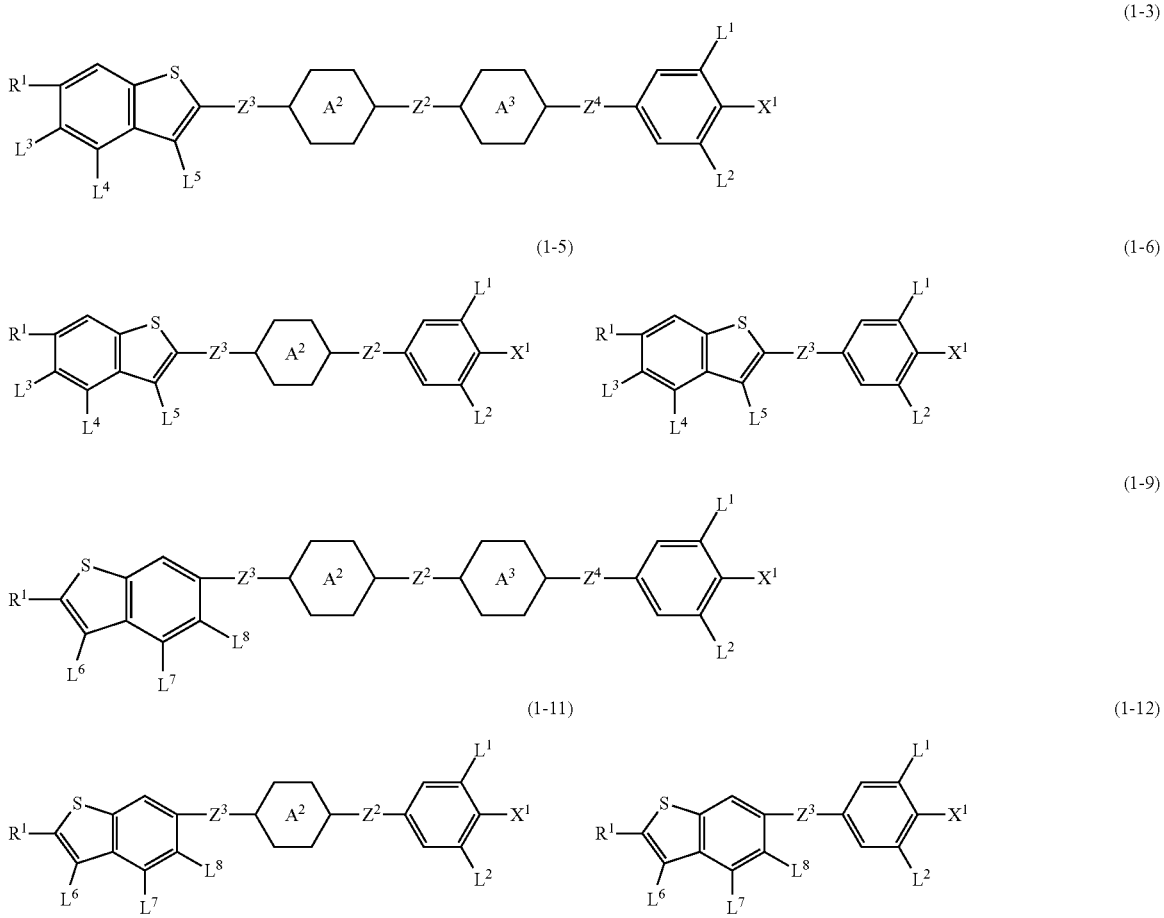

(1-3)

(1-5)

(1-6)

(1-9)

(1-11)

(1-12)

ring $A^1$, ring $A^2$ and ring $A^3$ are independently 1,4-cyclohexylene, 1,4-cyclohexenylene, 1,4-phenylene in which at least one hydrogen may be replaced by halogen, 1,3-dioxane-2,5-diyl or tetrahydropyran-2,5-diyl;

$Z^1$, $Z^2$, $Z^3$ and $Z^4$ are independently a single bond, —$(CH_2)_2$—, —CH=CH—, —CF=CF—, —C≡C—, —COO—, —OCO—, —$CF_2O$—, —$OCF_2$—, —$CH_2O$—, —$OCH_2$—, —$(CH_2)_4$—, —$(CH_2)_2CF_2O$—, —$(CH_2)_2OCF_2$—, —$CF_2O(CH_2)_2$—, —$OCF_2(CH_2)_2$—, —CH=CH—$(CH_2)_2$— or —$(CH_2)_2$—CH=CH—;

$X^1$ is fluorine, —$CF_3$ or —$OCF_3$;

$L^1$ and $L^2$ are independently hydrogen or fluorine; and $L^3$, $L^4$, $L^5$, $L^6$, $L^7$ and $L^8$ are independently hydrogen or fluorine.

Item 5. The compound according to item 4, wherein, in formulas (1-1) to (1-12), $R^1$ is alkyl having 1 to 10 carbons, and in the alkyl, at least one piece of —$CH_2$— may be replaced by —O—, and at least one piece of —$CH_2CH_2$— may be replaced by —CH=CH—, and in the groups, at least one hydrogen may be replaced by fluorine; and wherein $R^1$ is alkyl having 1 to 10 carbons, and in the alkyl, at least one piece of —$CH_2$— may be replaced by —O—, and at least one piece of —$CH_2CH_2$— may be replaced by —CH=CH—, and in the groups, at least one hydrogen may be replaced by fluorine;

ring $A^2$ and ring $A^3$ are independently 1,4-cyclohexylene, 1,4-cyclohexenylene, 1,4-phenylene in which at least one hydrogen may be replaced by halogen, 1,3-dioxane-2,5-diyl or tetrahydropyran-2,5-diyl;

$Z^2$, $Z^3$ and $Z^4$ are independently a single bond, —$(CH_2)_2$—, —CH=CH—, —$CF_2O$—, —$OCF_2$—, —$CH_2O$—, —C≡C—, —$(CH_2)_2OCF_2$— or —$OCH_2$—;

$X^1$ is fluorine, —$CF_3$ or —$OCF_3$;

$L^1$ and $L^2$ are independently hydrogen or fluorine; and $L^3$, $L^4$, $L^5$, $L^6$, $L^7$ and $L^8$ are independently hydrogen or fluorine.

Item 7. The compound according to item 5, represented by any one of formulas (1-3), (1-5) and (1-6), and $R^1$ being alkoxy having 1 to 6 carbons:

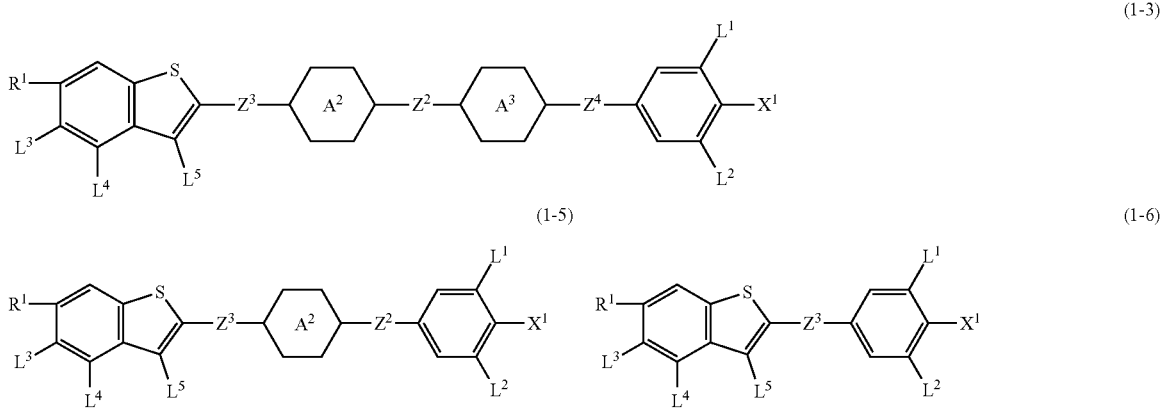

(1-3)

(1-5)

(1-6)

wherein $R^1$ is alkyl having 1 to 10 carbons, and in the alkyl, at least one piece of —$CH_2$— may be replaced by —O—, and at least one piece of —$CH_2CH_2$— may be replaced by —CH=CH—, and in the groups, at least one hydrogen may be replaced by fluorine;

ring $A^2$ and ring $A^3$ are independently 1,4-cyclohexylene, 1,4-cyclohexenylene, 1,4-phenylene in which at least one hydrogen may be replaced by halogen, 1,3-dioxane-2,5-diyl or tetrahydropyran-2,5-diyl;

$Z^2$, $Z^3$ and $Z^4$ are independently a single bond, —$(CH_2)_2$—, —CH=CH—, —$CF_2O$—, —$OCF_2$—, —$CH_2O$—, —C≡C—, —$(CH_2)_2OCF_2$— or —$OCH_2$;

$X^1$ is fluorine, —$CF_3$ or —$OCF_3$;

$L^1$ and $L^2$ are independently hydrogen, fluorine or chlorine; and $L^3$, $L^4$ and $L^5$ are independently hydrogen or fluorine.

Item 8. A liquid crystal composition, containing the compound according to any one of items 1 to 7.

Item 9. The liquid crystal composition according to item 8, further containing at least one compound selected from the group of compounds represented by formulas (2) to (4):

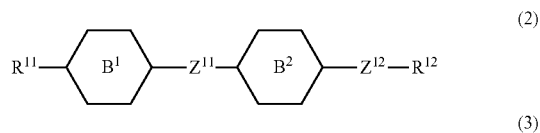

(2)

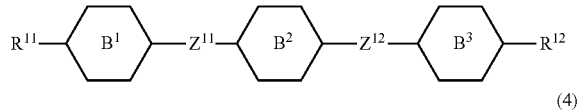

(3)

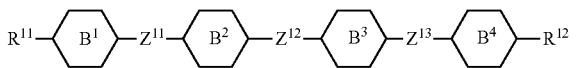

(4)

wherein, in formulas (2) to (4), $R^{11}$ and $R^{12}$ are independently alkyl having 1 to 10 carbons or alkenyl having 2 to 10 carbons, and in the alkyl or the alkenyl, at least one piece of —$CH_2$— may be replaced by —O—, and at least one hydrogen may be replaced by fluorine;

ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and $Z^{11}$, $Z^{12}$, and $Z^{13}$ are independently a single bond, —$CH_2CH_2$—, —CH=CH—, —C≡C— or —COO—.

Item 10. The liquid crystal composition according to item 8 or 9, further containing at least one compound selected from the group of compounds represented by formulas (5) to (7):

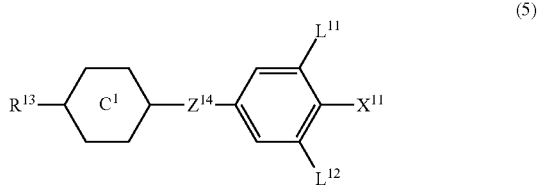

(5)

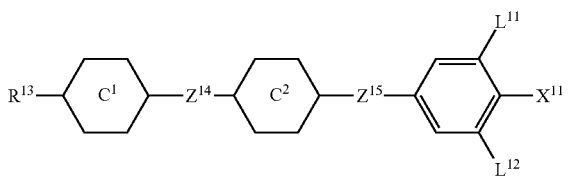

(6)

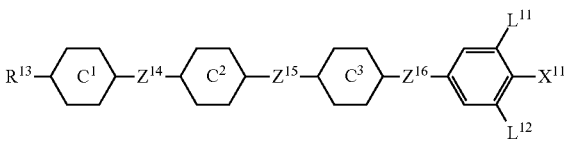

(7)

wherein, in formulas (5) to (7), $R^{13}$ is alkyl having 1 to 10 carbons or alkenyl having 2 to 10 carbons, and in the alkyl and the alkenyl, at least one piece of —$CH_2$— may be replaced by —O—, and at least one hydrogen may be replaced by fluorine;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $C^1$, ring $C^2$ and ring $C^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

$Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

Item 11. The liquid crystal composition according to any one of items 8 to 10, further containing at least one compound selected from the group of compounds represented by formula (8):

(8)

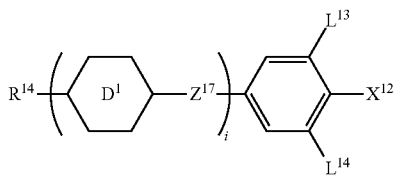

wherein, in formula (8),

R$^{14}$ is alkyl having 1 to 10 carbons or alkenyl having 2 to 10 carbons, and in the alkyl and the alkenyl, at least one piece of —CH$_2$— may be replaced by —O—, and at least one hydrogen may be replaced by fluorine;

X$^{12}$ is —C≡N or —C≡C—C≡N;

ring D$^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;

Z$^{17}$ is a single bond, —CH$_2$CH$_2$—, —C≡C—, —COO—, —CF$_2$O—, —OCF$_2$— or —CH$_2$O—;

L$^{13}$ and L$^{14}$ are independently hydrogen or fluorine; and i is 1, 2, 3 or 4.

Item 12. The liquid crystal composition according to any one of items 8 to 11, further containing at least one compound selected from the group of compounds represented by formulas (9) to (15):

(9)

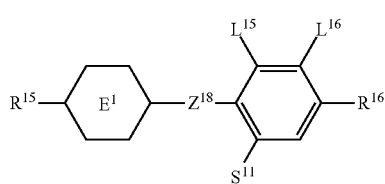

(10)

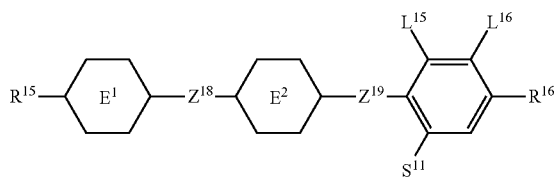

(11)

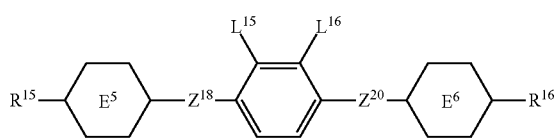

(12)

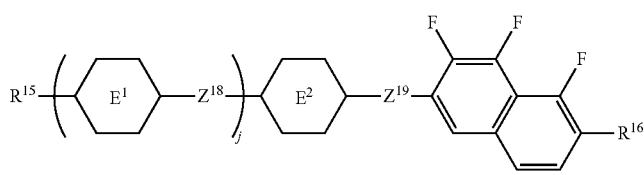

(13)

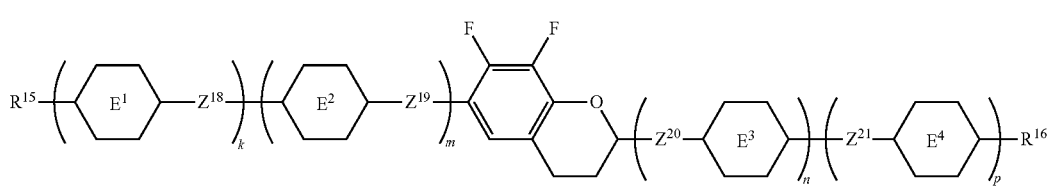

(14)

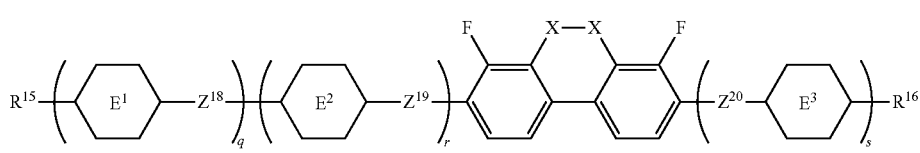

(15)

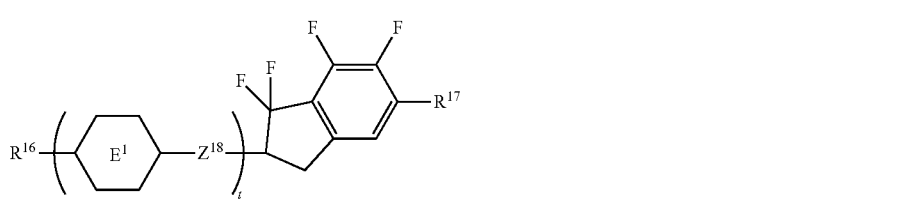

wherein, in formulas (9) to (15), $R^{15}$ and $R^{16}$ are independently alkyl having 1 to 10 carbons or alkenyl having 2 to 10 carbons, and in the alkyl and the alkenyl, at least one piece of —$CH_2$— may be replaced by —O—, and at least one hydrogen may be replaced by fluorine;

$R^{12}$ is hydrogen, fluorine, alkyl having 1 to 10 carbons or alkenyl having 2 to 10 carbons, and in the alkyl and the alkenyl, at least one piece of —$CH_2$— may be replaced by —O—, and at least one hydrogen may be replaced by fluorine;

ring $E^1$, ring $E^2$, ring $E^3$ and ring $E^4$ are independently 1,4-cyclohexylene, 1,4-cyclohexenylene, 1,4-phenylene in which at least one hydrogen may be replaced by fluorine, tetrahydropyran-2,5-diyl or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —$CH_2CH_2$—, —COO—, —$CH_2O$—, —$OCF_2$— or —$OCF_2CH_2CH_2$—;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, a sum of k, m, n and p is 1 or 2, a sum of q, r and s is 0, 1, 2 or 3, and t is 1, 2 or 3.

Item 13. The liquid crystal composition according to any one of items 8 to 12, further containing at least one of a polymerizable compound, a polymerization initiator, a polymerization inhibitor, an optically active compound, an antioxidant, an ultraviolet light absorber, a light stabilizer, a heat stabilizer, a dye and an antifoaming agent.

Item 14. A liquid crystal device, including the liquid crystal composition according to any one of items 8 to 13.

1. Aspect of Compound (1)

Compound (1) of the invention has a 1-benzothiophene ring structure. Preferred examples of compound (1) will be described. Preferred examples of a terminal group, a ring structure, a bonding group and a substituent in compound (1) are also applied to a subordinate formula of compound (1), such as compound (1-1) and compound (1-2). In compound (1), physical properties can be arbitrarily adjusted by appropriately combining kinds of the above groups. Compound (1) may contain an isotope such as $^2H$ (deuterium) and $^{13}C$ in an amount larger than an amount of natural abundance because no significant difference is found in the physical properties of the compound. Moreover, definitions of the symbols of compound (1) are as described in item 1.

(1)

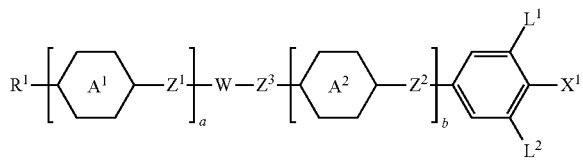

$R^1$ is hydrogen, fluorine or alkyl having 1 to 20 carbons, and in the alkyl, at least one piece of —$CH_2$— may be replaced by —O— or —S—, and at least one piece of —$CH_2CH_2$— may be replaced by —CH=CH—, and in the groups, at least one hydrogen may be replaced by fluorine.

Specific examples of $R^1$ include hydrogen, alkyl, alkoxy, alkoxyalkyl, alkoxyalkoxy, alkenyl, alkenyloxy, alkenyloxyalkyl, alkoxyalkenyl, alkylthio, alkylthio alkyl, alkenylthio, alkenylthioalkyl and alkylthioalkenyl. Preferred $R^1$ is alkyl, alkoxy, alkoxyalkyl, alkoxyalkoxy, alkenyl, alkenyloxy, alkenyloxyalkyl or alkoxyalkenyl. Further preferred $R^1$ is alkyl, alkoxy, alkoxyalkyl, alkenyl or alkenyloxy. Particularly preferred $R^1$ is alkyl or alkenyl. Most preferred $R^1$ is alkyl.

Preferred alkyl is —$CH_3$, —$C_2H_5$, —$C_3H_7$, —$C_4H_9$, —$C_5H_{11}$, —$C_6H_{13}$, or —$C_7H_{15}$.

Preferred alkoxyalkyl is —$CH_2OCH_3$, —$CH_2OC_2H_5$, —$CH_2OC_3H_7$, —$(CH_2)_2$—$OCH_3$, —$(CH_2)_2$—$OC_2H_5$, —$(CH_2)_2$—$OC_3H_7$, —$(CH_2)_3$—$OCH_3$, —$(CH_2)_4$—$OCH_3$ or —$(CH_2)_5$—$OCH_3$.

Preferred alkenyl is —CH=$CH_2$, —CH=$CHCH_3$, —$CH_2CH$=$CH_2$, —CH=$CHC_2H_5$, —$CH_2CH$=$CHCH_3$, —$(CH_2)_2$—CH=$CH_2$, —CH=$CHC_3H_7$, —$CH_2CH$=$CHC_2H_5$, —$(CH_2)_2$—CH=$CHCH_3$ or —$(CH_2)_3$—CH=$CH_2$.

Preferred alkenyloxy is —$OCH_2CH$=$CH_2$, —$OCH_2CH$=$CHCH_3$ or —$OCH_2CH$=$CHC_2H_5$.

Preferred $R^1$ is hydrogen, —$CH_3$, —$C_2H_5$, —$C_3H_7$, —$C_4H_9$, —$C_5H_{11}$, —$C_6H_{13}$, —$OCH_3$, —$OC_2H_5$, —$OC_3H_7$, —$OC_4H_9$, —$OC_5H_{11}$, —$CH_2OCH_3$, —CH=$CH_2$, —CH=$CHCH_3$, —$(CH_2)_2$—CH=$CH_2$, $CH_2CH$=$CHC_2H_5$, —$(CH_2)_2$—CH=$CHCH_3$, —$OCH_2CH$=$CH_2$, —$OCH_2CH$=$CHCH_3$ or —$OCH_2CH$=$CHC_2H_5$. Further preferred $R^1$ is —$C_3H_7$, —$C_4H_9$, —$C_5H_{11}$, —$C_6H_{13}$, —$(CH_2)_2$—CH=$CH_2$ or —$(CH_2)_2$—CH=$CHCH_3$.

When $R^1$ has a straight chain, the temperature range of the liquid crystal phase is wide and the viscosity is small. When $R^1$ has a branched chain, the compatibility with other liquid crystal compounds is good. A compound in which $R^1$ is optically active is useful as a chiral dopant. A reverse twisted domain to be generated in the liquid crystal display device can be prevented by adding the compound to the composition. A compound in which $R^1$ is not an optically active is useful as a component of the composition. When $R^1$ is alkenyl, a preferred configuration depends on a position of a double bond. An alkenyl compound having the preferred configuration has the small viscosity, the high maximum temperature or the wide temperature range of the liquid crystal phase.

A preferred configuration of —CH=CH— in the alkenyl depends on a position of the double bond. In alkenyl having a double bond in an odd-numbered position, such as —CH=$CHCH_3$, —CH=$CHC_2H_5$, —CH=$CHC_3H_7$, —CH=$CHC_4H_9$, —$C_2H_4CH$=$CHCH_3$ and —$C_2H_4CH$=$CHC_2H_5$, a trans configuration is preferred. In alkenyl having the double bond in an even-numbered position, such as —$CH_2CH$=$CHCH_3$, —$CH_2CH$=$CHC_2H_5$ and —$CH_2CH$=$CHC_3H_7$, a cis configuration is preferred. An alkenyl compound having the preferred configuration has a high clearing point or a wide temperature range of the liquid crystal phase. A detailed description is found in Mol. Cryst. Liq. Cryst., 1985, 131, 109 and Mol. Cryst. Liq. Cryst., 1985, 131 and 327.

In formula (1), ring $A^1$ and ring $A^2$ are independently 1,4-cyclohexylene, 1,4-cyclohexenylene, 1,4-phenylene, tetrahydropyran-2,5-diyl, 1,3-dioxane-2,5-diyl, pyrimidine-2,5-diyl, 2,6,7-trioxabicyclo[2.2.2]octane-1,4-diyl, naphthalene-2,6-diyl and pyridine-2,5-diyl, and at least one hydrogen on the rings may be replaced by halogen.

Preferred ring $A^1$ or ring $A^2$ is 1,4-cyclohexylene, 1,4-phenylene, 2-fluoro-1,4-phenylene, 2,3-difluoro-1,4-phenylene, 2,6-difluoro-1,4-phenylene, 2,3,5-trifluoro-1,4-phenylene, tetrahydropyran-2,5-diyl, 1,3-dioxane-2,5-diyl or pyrimidine-2,5-diyl. Further preferred ring $A^1$ or ring $A^2$ is 1,4-cyclohexylene, 1,4-phenylene, 2-fluoro-1,4-phenylene, 2,6-difluoro-1,4-phenylene or tetrahydropyran-2,5-diyl. Particularly preferred ring $A^1$ or ring $A^2$ is 1,4-cyclohexylene, 1,4-phenylene, 2-fluoro-1,4-phenylene or 2,6-difluoro-1,4-phenylene.

When ring $A^1$ or ring $A^2$ is 1,4-cyclohexylene, the clearing point is high and the viscosity is small. When ring $A^1$ or ring $A^2$ is 1,4-phenylene or 1,4-phenylene in which at least one hydrogen is replaced by fluorine, the optical anisotropy is large, and an orientational order parameter is comparatively large. When ring $A^1$ or ring $A^2$ is 1,4-phenylene in which at least one hydrogen is replaced by fluorine, the dielectric anisotropy is large.

$Z^2$, $Z^2$ and $Z^3$ are independently a single bond or alkylene having 1 to 4 carbons, and in the alkylene, at least one piece of —$CH_2$— may be replaced by —O— or —COO—, and at least one piece of —$(CH_2)_2$— may replace by —CH=CH— or —C≡C—, and in the groups, at least one hydrogen may be replaced by halogen.

Preferred $Z^1$, $Z^2$ and $Z^3$ are a single bond, —$(CH_2)_2$—, —CH=CH—, —CF=CF—, —C≡C—, —COO—, —OCO—, —$CF_2O$—, —$OCF_2$—, —$CH_2O$—, —$OCH_2$—, —$(CH_2)_4$—, —$(CH_2)_2CF_2O$—, —$(CH_2)_2OCF_2$—, —$CF_2O(CH_2)_2$—, —$OCF_2(CH_2)_2$—, —CH=CH—$(CH_2)_2$— or —$(CH_2)_2$—CH=CH—. Further preferred $Z^2$ and $Z^2$ are a single bond, —$(CH_2)_2$—, —CH=CH—, —$CF_2O$—, —$OCF_2$—, —$CH_2O$—, —C≡C—, —$(CH_2)_2OCF_2$— or —$OCH_2$—.

When $Z^1$, $Z^2$ or $Z^3$ is a single bond, chemical stability is high and the viscosity is small. When $Z^1$, $Z^2$ or $Z^3$ is —$CF_2O$—, the viscosity is small, and the dielectric anisotropy is large, and the maximum temperature is high.

In formula (1), $X^1$ is hydrogen, fluorine, chlorine, —$SF_5$, —C≡N, —N=C=S, —C≡C—$CF_3$, —C≡C—CN, polyfluoroalkyl having 1 to 7 carbons, perfluoroalkyl having 1 to 7 carbons, alkyl having 1 to 7 carbons or alkenyl having 2 to 7 carbons, and in the alkyl and the alkenyl, at least one piece of —$CH_2$— may be replaced by —O—, and at least one hydrogen may be replaced by fluorine. Preferred $X^1$ is hydrogen, fluorine, —$CF_3$, —C≡C—$CF_3$ or —$OCF_3$.

When $X^1$ is fluorine, the viscosity is small. When $X^1$ is —$CF_3$, the dielectric anisotropy is large. When $X^1$ is —$OCF_3$, the compatibility with other liquid crystal compounds is excellent.

In formula (1), $L^1$ and $L^2$ are independently hydrogen or fluorine. Preferred $L^1$ and $L^2$ are a combination of hydrogen and fluorine. Preferred $L^1$ and $L^2$ are a combination of fluorine and fluorine.

When $L^1$ and $L^2$ are a combination of hydrogen and fluorine, the dielectric anisotropy is large. When $L^1$ and $L^2$ are a combination of fluorine and fluorine, the dielectric anisotropy is particularly large.

In formula (1), a and b are independently 0, 1, 2 or 3, a sum of a and b is 3 or less. Preferred b is 0. A preferred sum of a and b is 0, 1 or 2.

When a sum of a and b is 0, the viscosity is small. When a sum of a and b is 1 or 2, the clearing point is high.

In formula (1), W is a group represented by formula (1a) or formula (1b).

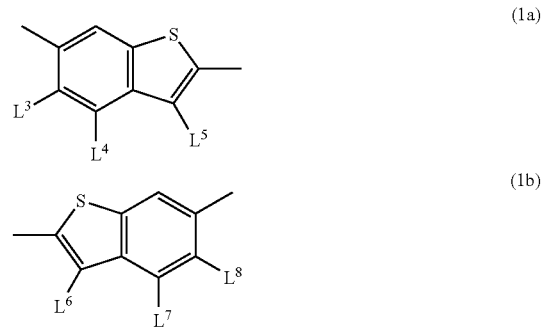

In formula (1a) and formula (1b), $L^3$, $L^4$, $L^5$, $L^6$, $L^7$ and $L^8$ are independently hydrogen, fluorine or chlorine. Preferred $L^3$, $L^4$, $L^5$, $L^6$, $L^7$ and $L^8$ are a combination of fluorine and hydrogen.

When $L^5$ and $L^8$ are fluorine, the dielectric anisotropy is large.

Specific examples of preferred compound (1) include compounds (1-1) to (1-12) described in item 4. Specific examples of further preferred compound (1) include compounds (1-3) to (1-12) described in item 5.

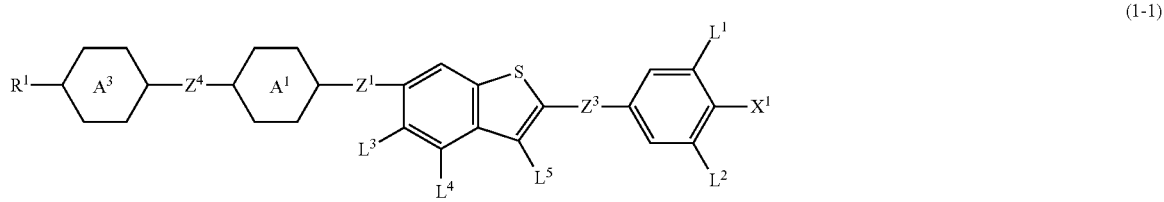

(1-1)

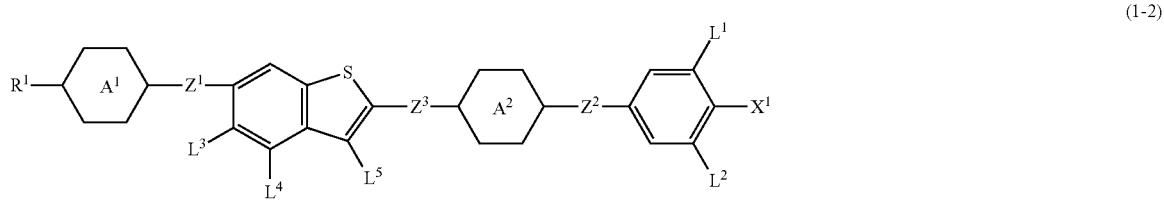

(1-2)

(1-3)
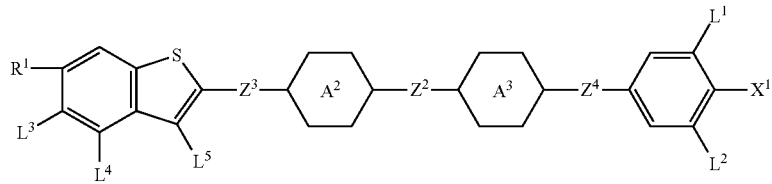
(1-4)
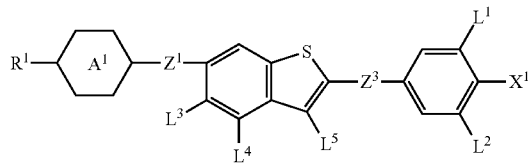
(1-5)
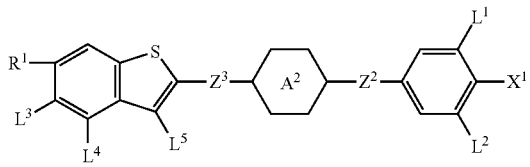
(1-6)
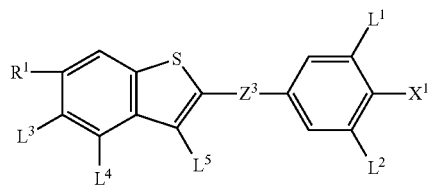
(1-7)
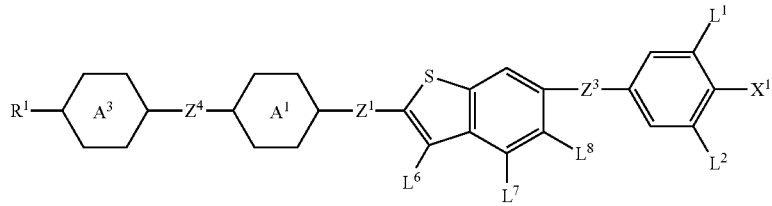
(1-8)
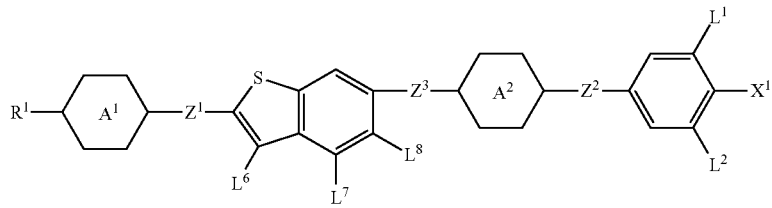
(1-9)
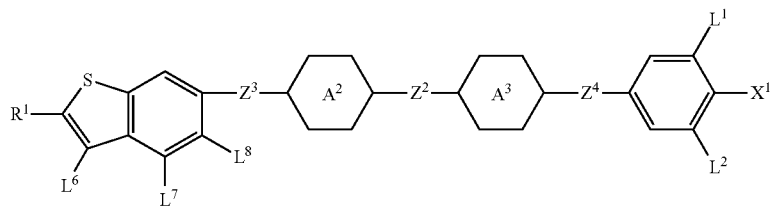
(1-10)
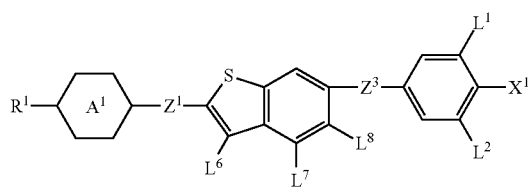
(1-11)
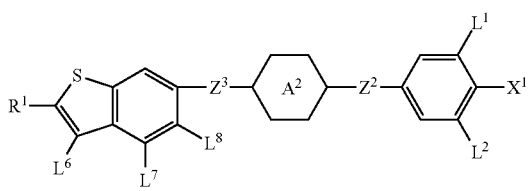

-continued (1-12)

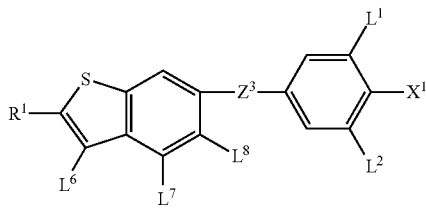

In compounds (1-1) to (1-12), preferred examples of ring $A^3$, and an effect of the groups on the physical properties are similar thereto in ring $A^1$ and ring $A^2$ in formula (1), and preferred examples of $Z^4$, and an effect of the groups on the physical properties are similar thereto in $Z^1$, $Z^2$ and $Z^3$ in formula (1).

2. Synthesis of Compound (1)

A synthetic method of compound (1) will be described. Compound (1) can be prepared by appropriately combining methods of synthetic organic chemistry. Methods for introducing an objective terminal group, ring and bonding group into a starting material are described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course (Shin Jikken Kagaku Koza in Japanese)" (Maruzen Co., Ltd.).

2-1. Formation of Bonding Group Z

A scheme is first shown regarding a method of forming bonding groups $Z^1$ to $Z^3$. Next, reactions described in the scheme will be described in sections (1) to (11). In the scheme, $MSG^1$ (or $MSG^2$) is a monovalent organic group having at least one ring. The monovalent organic groups represented by a plurality of $MSG^1$ (or $MSG^2$) used in the scheme may be identical or different. Compounds (1A) to (1J) correspond to compound (1).

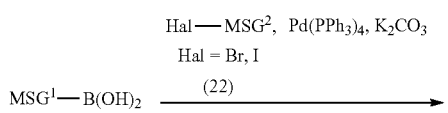

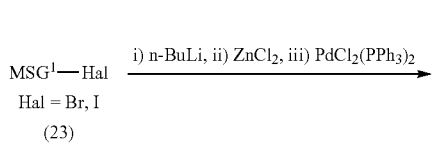

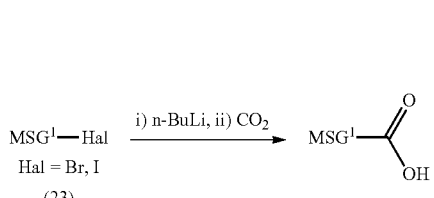

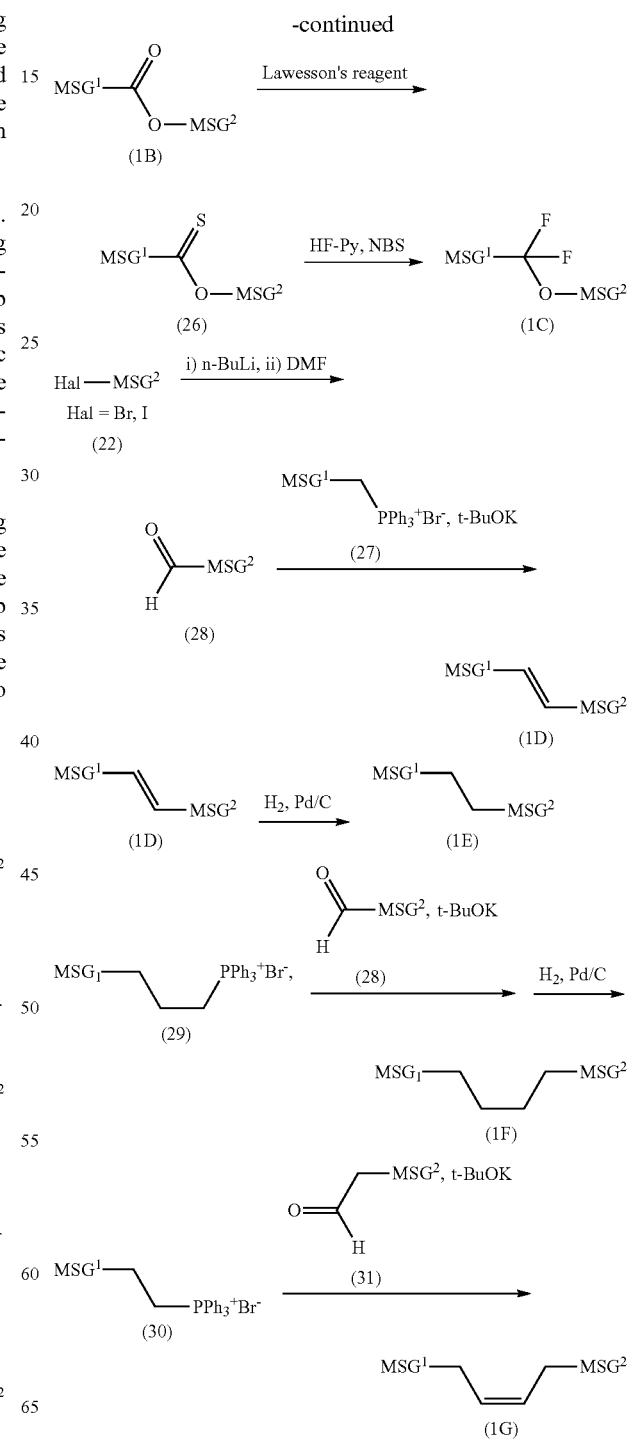

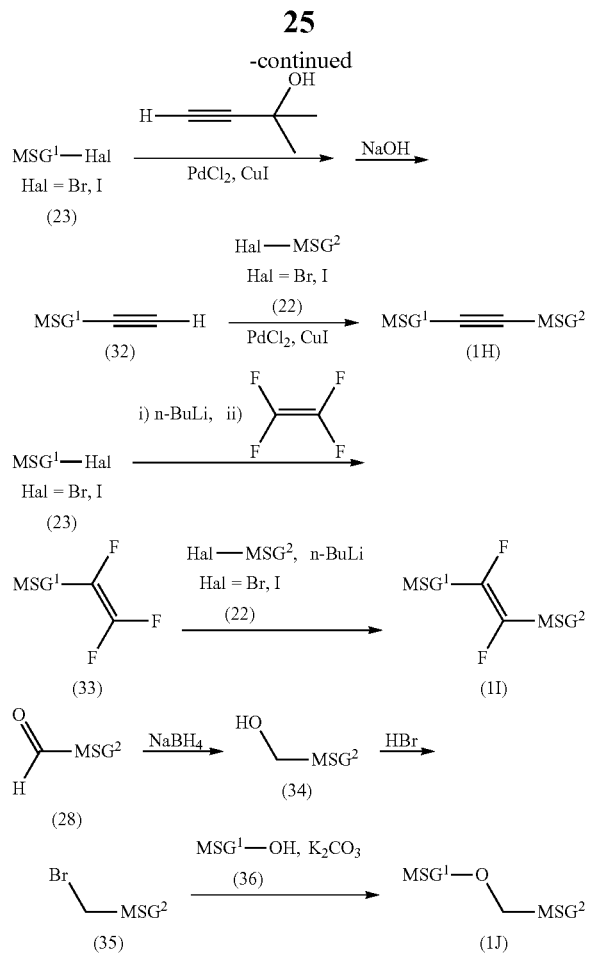

(1) Formation of a Single Bond

Compound (1A) is prepared by allowing aryl boronic acid (21) prepared according to a known method to react with halide (22), in the presence of carbonate and a catalyst such as tetrakis(triphenylphosphine)palladium. Compound (1A) is also prepared by allowing halide (23) prepared according to a known method to react with n-butyllithium and subsequently with zinc chloride, and further with halide (22) in the presence of a catalyst such as dichlorobis(triphenylphosphine)palladium.

(2) Formation of —COO—

Carboxylic acid (24) is obtained by allowing halide (23) to react with n-butyllithium and subsequently with carbon dioxide. Compound (1B) is prepared by dehydration of compound (25) prepared according to a known method and carboxylic acid (24) in the presence of 1,3-dicyclohexylcarbodiimide (DCC) and 4-dimethylaminopyridine (DMAP).

(3) Formation of —CF$_2$O—

Thionoester (26) is obtained by treating compound (1B) with a thiation reagent such as Lawesson's reagent. Compound (1C) is prepared by fluorinating thionoester (26) with a hydrogen fluoride-pyridine complex and N-bromosuccinimide (NBS). Refer to M. Kuroboshi et al., Chem. Lett., 1992, 827. Compound (1C) is also prepared by fluorinating thionoester (26) with (diethylamino)sulfur trifluoride (DAST). Refer to W. H. Bunnelle et al., J. Org. Chem. 1990, 55, 768. The above bonding groups can be also formed by the method described in Peer. Kirsch et al., Angew. Chem. Int. Ed. 2001, 40, and 1480.

(4) Formation of —CH=CH—

Aldehyde (28) is obtained by treating halide (22) with n-butyllithium and then allowing the treated halide to react with formamide such as N,N-dimethylformamide (DMF). Compound (1D) is prepared by allowing phosphorus ylide generated by treating phosphonium salt (27) prepared by a known method with a base such as potassium t-butoxide to react with aldehyde (28). A cis isomer may be generated depending on reaction conditions, and the cis isomer is isomerized into a trans isomer according to a known method when necessary.

(5) Formation of —(CH$_2$)$_2$—

Compound (1E) is prepared by hydrogenating compound (1D) in the presence of a catalyst such as palladium on carbon.

(6) Formation of —(CH$_2$)$_4$—

A compound having —(CH$_2$)$_2$—CH=CH— is obtained according to the method in section (4) by using phosphonium salt (29) in place of phosphonium salt (27). Compound (1F) is prepared by performing catalytic hydrogenation of the compound obtained.

(7) Formation of —CH$_2$CH=CHCH$_2$—

Compound (1G) is prepared according to the method in section (4) by using phosphonium salt (30) in place of phosphonium salt (27), and aldehyde (31) in place of aldehyde (28). A trans isomer may be generated depending on reaction conditions, and the trans isomer is isomerized to a cis isomer according to a known method when necessary.

(8) Formation of —C≡C—

Compound (32) is obtained by allowing halide (23) to react with 2-methyl-3-butyn-2-ol in the presence of a catalyst including dichloropalladium and copper halide, and then performing deprotection under basic conditions. Compound (1H) is prepared by allowing compound (32) to react with halide (22) in the presence of the catalyst including dichloropalladium and copper halide.

(9) Formation of —CF=CF—

Compound (33) is obtained by treating halide (23) with n-butyllithium, and then allowing the treated halide to react with tetrafluoroethylene. Compound (1I) is prepared by treating halide (22) with n-butyllithium, and then allowing the treated halide to react with compound (33).

(10) Formation of —OCH$_2$—

Compound (34) is obtained by reducing aldehyde (28) with a reducing agent such as sodium borohydride. Bromide (35) is obtained by brominating compound (34) with hydrobromic acid or the like. Compound (1J) is prepared by allowing bromide (35) to react with compound (36) in the presence of a base such as potassium carbonate.

(11) Formation of —(CF$_2$)$_2$—

A compound having —(CF$_2$)$_2$— is obtained by fluorinating diketone (—COCO—) with sulfur tetrafluoride, in the presence of a hydrogen fluoride catalyst, according to the method described in J. Am. Chem. Soc., 2001, 123, 5414.

2-2. Formation of Ring A$^1$ and Ring A$^2$

With regard to a ring such as 1,4-cyclohexylene, 1,4-Phenylene, 2-fluoro-1,4-phenylene, 2,6-difluoro-1,4-phenylene, tetrahydropyran-2,5-diyl, 1,3-dioxane-2,5-diyl, pyrimidine-2,5-diyl or pyridine-2,5-diyl, a starting material is commercially available or a synthetic method is known well.

2-3. Method of Preparing Compound (1)

A specific example of a method of preparing compound (1) is as described below. Compound (51) is obtained by using Mg from compound (50) prepared by a known method to prepare a Grignard reagent, and then allowing the Grignard reagent to react with S and bromoacetaldehyde diethyl acetal. Compound (52) is obtained by allowing compound (51) to react with polyphosphoric acid in toluene or chlorobenzene. Various intermediates are obtained by subjecting compound (52) to lithiation with LDA, and then allowing the lithiated product to react with various reagents. The intermediates are used and derived to compound (1) by a known method. In the compounds, definitions of the symbols such as $R^1$, ring $A^1$ are identical to the definitions of the symbols described in item 1.

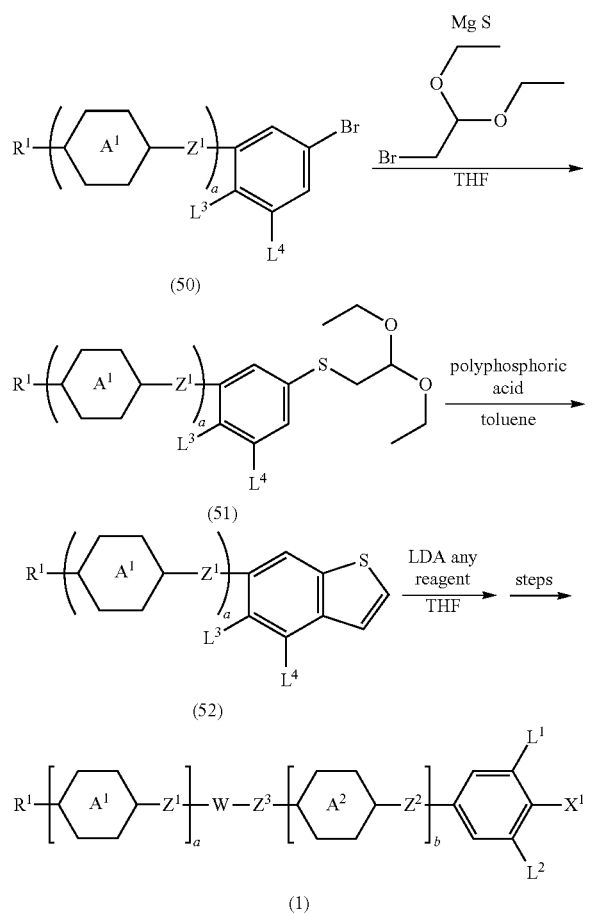

3. Liquid Crystal Composition
3-1. Component Compound

A liquid crystal composition according to the invention will be described. The composition contains at least one compound (1) as component A. Compound (1) is useful for increasing the maximum temperature of the composition. The composition may contain two or three or more compounds (1). A component in the compound may be compound (1) only. In order to develop excellent physical properties, the composition preferably contains at least one of compounds (1) in the range of 1 to 99% by weight. In the composition having the positive dielectric anisotropy, a preferred content of compound (1) is in the range of 5 to 60% by weight. In the composition having the negative dielectric anisotropy, a preferred content of compound (1) is 30% by weight or less. The composition may contain compound (1) and liquid crystal compounds that are not described herein.

The composition contains compound (1) as component A, and preferably further contains a liquid crystal compound selected from component B, C, D and E described below. Component B includes compounds (2) to (4). Component C includes compounds (5) to (7). Component D includes compound (8). Component E includes compounds (9) to (15). The composition may contain other liquid crystal compounds different from compounds (2) to (15). When the composition is prepared, components B, C, D and E are preferably selected by taking the positive or negative dielectric anisotropy, magnitude of the dielectric anisotropy, and so forth into account. The composition in which the components are appropriately selected has high stability to heat and light, a high maximum temperature, a low minimum temperature, small viscosity, suitable optical anisotropy (more specifically, large optical anisotropy or small optical anisotropy), large dielectric anisotropy, large specific resistance and a suitable elastic constant (more specifically, a large elastic constant or a small elastic constant.

Component B includes a compound in which two terminal groups are alkyl or the like. Preferred examples of component B include compounds (2-1) to (2-11), compounds (3-1) to (3-19) and compounds (4-1) to (4-7). In the compound of component B, $R^{11}$ and $R^{12}$ are independently alkyl having 1 to 10 carbons or alkenyl having 2 to 10 carbons, and in the alkyl or the alkenyl, at least one piece of —$CH_2$— may be replaced by —O—, and at least one hydrogen may be replaced by fluorine.

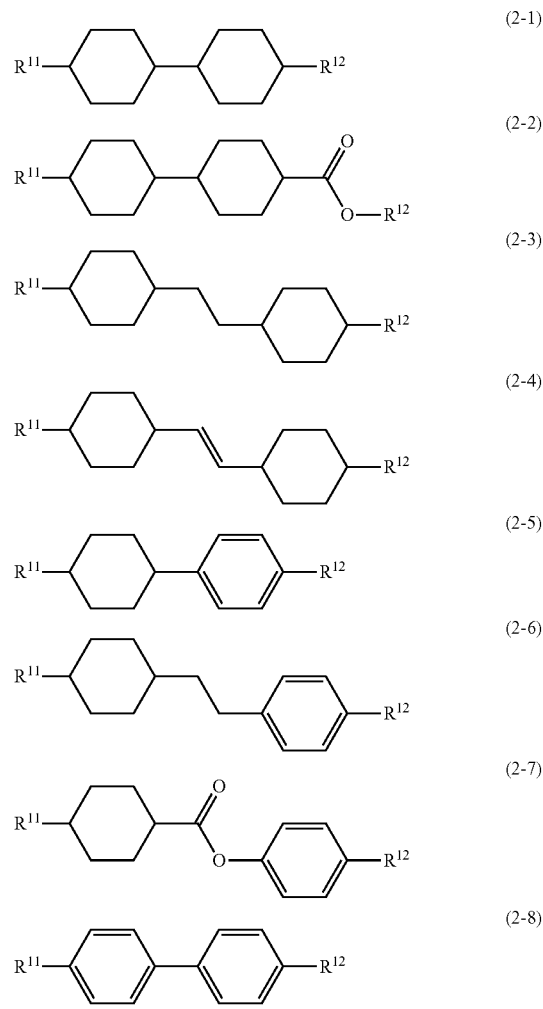

-continued
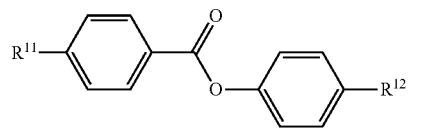 (2-9)
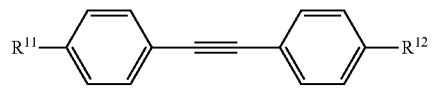 (2-10)
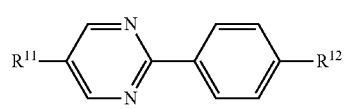 (2-11)
 (3-1)
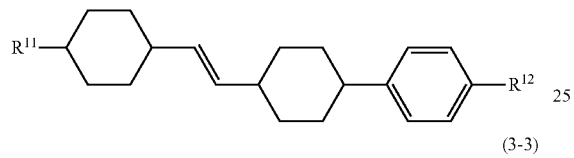 (3-2)
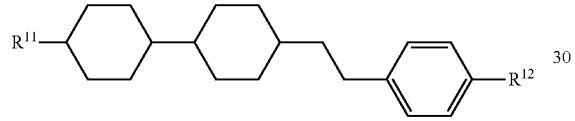 (3-3)
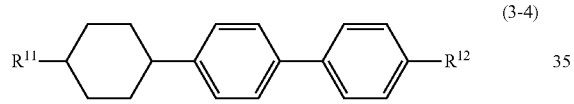 (3-4)
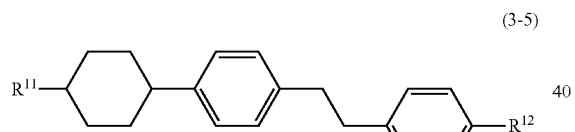 (3-5)
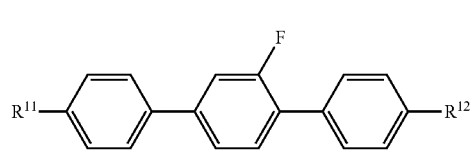 (3-6)
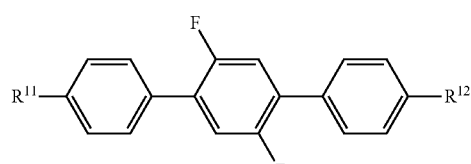 (3-7)
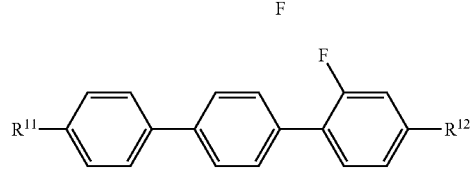 (3-8)
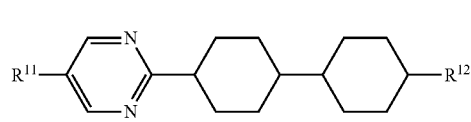 (3-9)
-continued
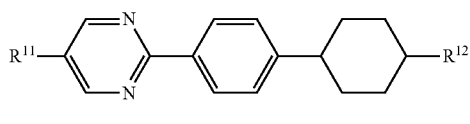 (3-10)
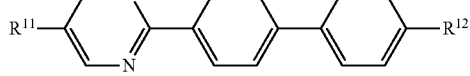 (3-11)
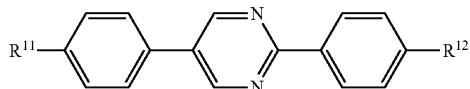 (3-12)
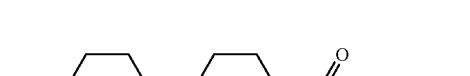 (3-13)
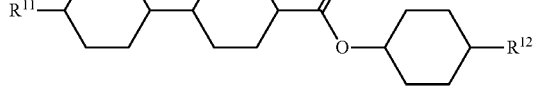 (3-14)
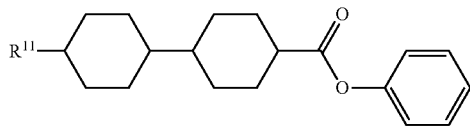 (3-15)
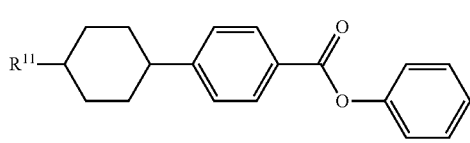 (3-16)
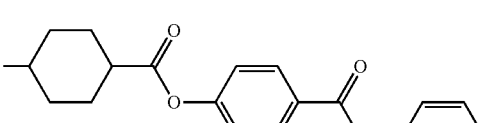 (3-17)
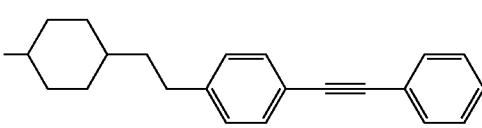 (3-18)
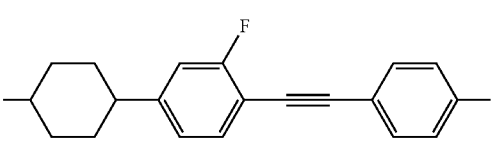 (3-19)
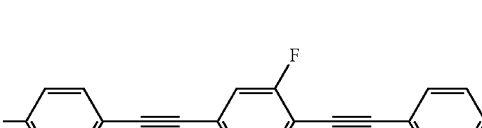 
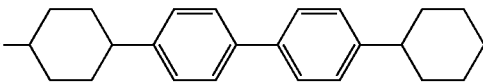 (4-1)

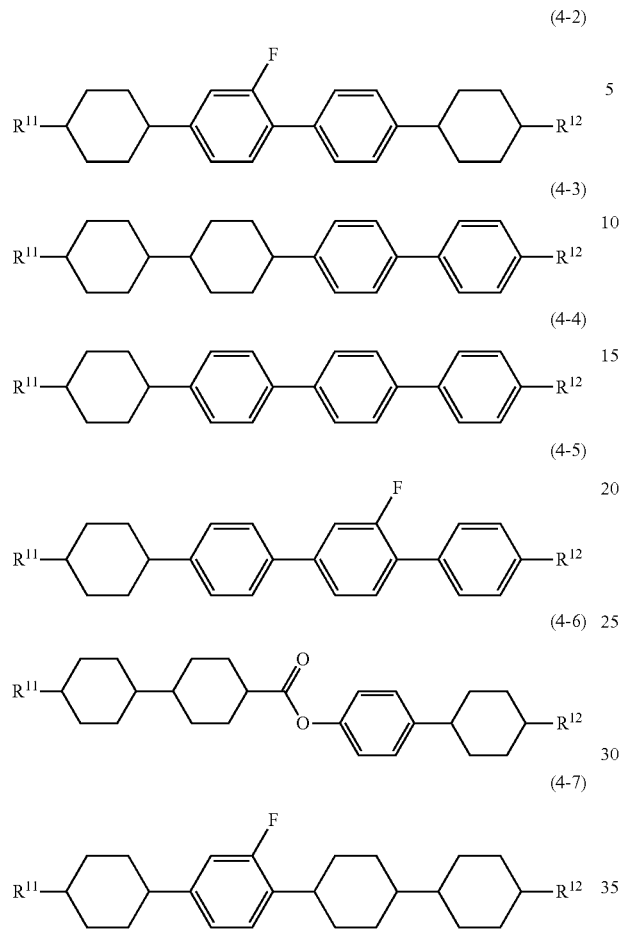

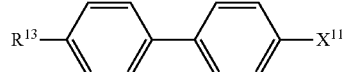
(5-1)

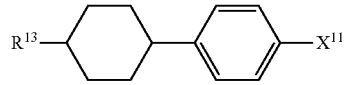
(5-2)

(5-3)

(5-4)

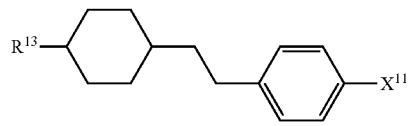
(5-5)

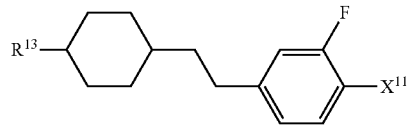
(5-6)

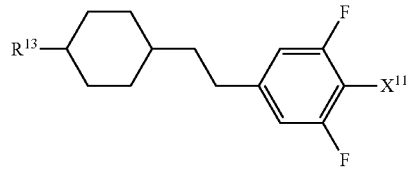
(5-7)

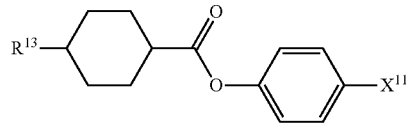
(5-8)

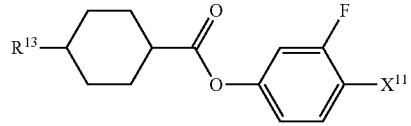
(5-9)

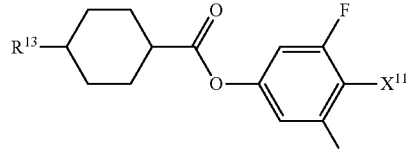
(5-10)

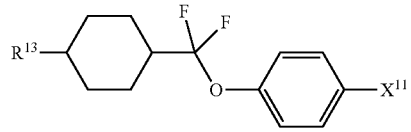
(5-11)

Component B has a small absolute value of the dielectric anisotropy, and therefore is a compound close to neutrality. Compound (2) is effective mainly in decreasing the viscosity or effective in adjusting the optical anisotropy. Compounds (3) and (4) are effective in extending the temperature range of the nematic phase by increasing the maximum temperature, or effective in adjusting the optical anisotropy.

As a content of component B is increased, the viscosity of the composition is decreased, and the dielectric anisotropy is decreased. Thus, as long as a desired value of threshold voltage of the device is met, the content is preferably as large as possible. When a composition for the IPS mode, the VA mode or the like is prepared, the content of component B is preferably 30% by weight or more, and further preferably 40% by weight or more, based on the weight of the liquid crystal composition.

Component C is a compound having a halogen-containing group or a fluorine-containing group at a right terminal. Specific examples of preferred component C include compounds (5-1) to (5-16), compounds (6-1) to (6-113) and compounds (7-1) to (7-57). In the compound of component C, $R^{13}$ is alkyl having 1 to 10 carbons or alkenyl having 2 to 10 carbons, and in the alkyl and the alkenyl, at least one piece of —CH$_2$— may be replaced by —O—, and at least one hydrogen may be replaced by fluorine; and $X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$.

-continued
(5-12)
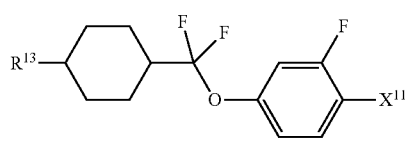
(5-13)
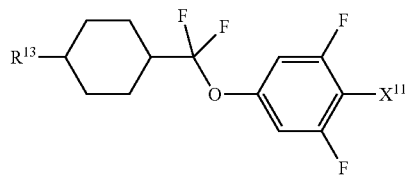
(5-14)
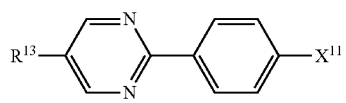
(5-15)
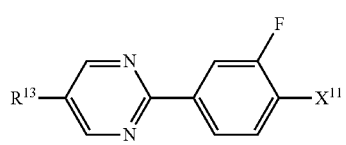
(5-16)
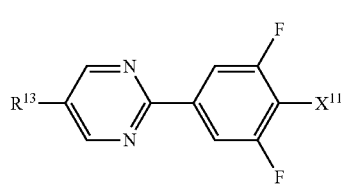
(6-1)
(6-2)
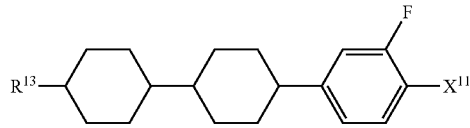
(6-3)
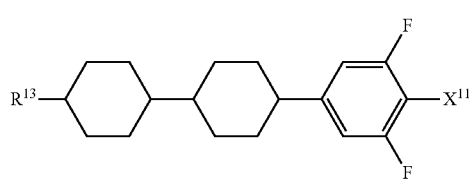
(6-4)
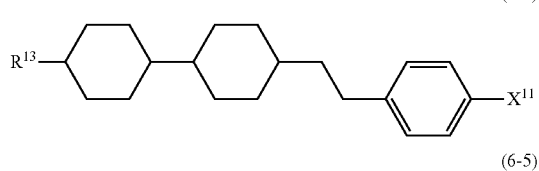
(6-5)
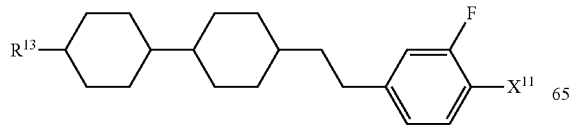
-continued
(6-6)
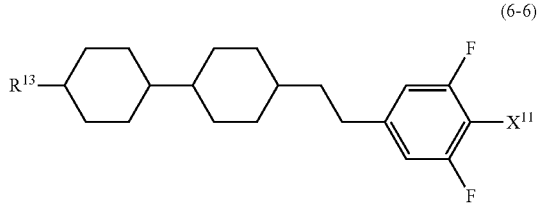
(6-7)
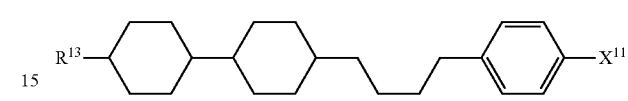
(6-8)
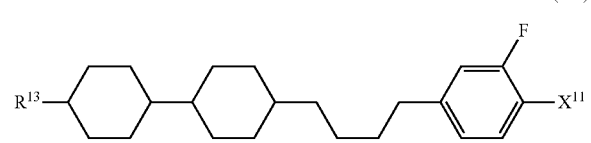
(6-9)
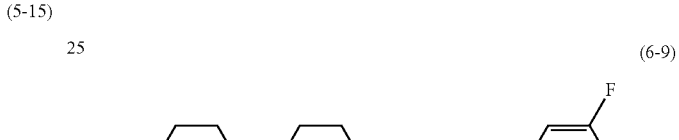
(6-10)
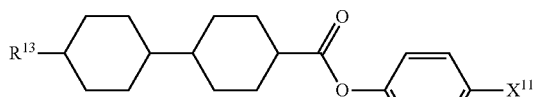
(6-11)
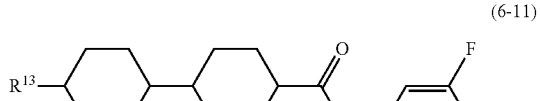
(6-12)
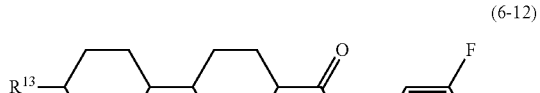
(6-13)
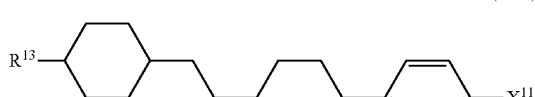
(6-14)
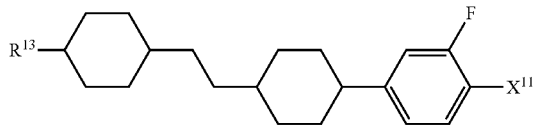

(6-15) 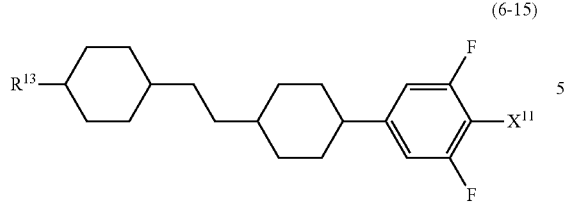
(6-16) 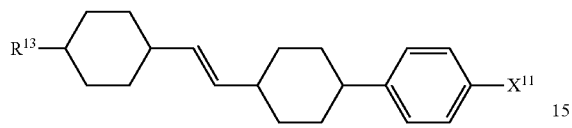
(6-17) 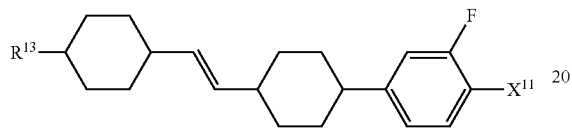
(6-18) 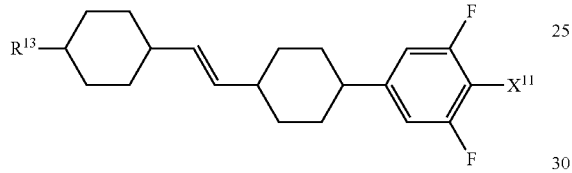
(6-19) 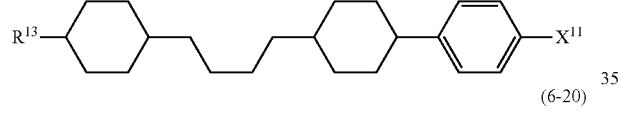
(6-20) 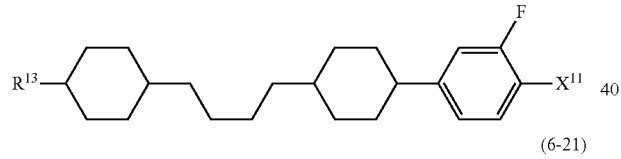
(6-21) 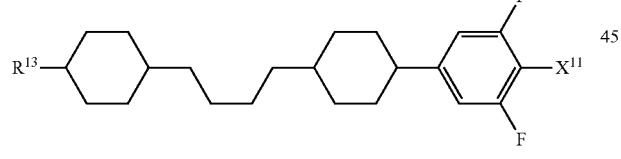
(6-22) 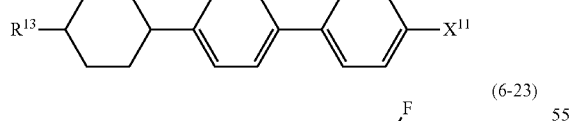
(6-23) 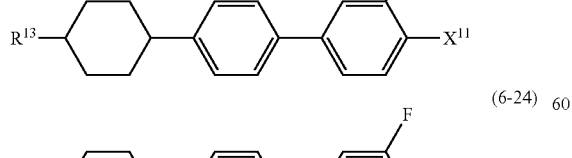
(6-24) 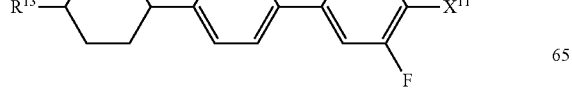
(6-25) 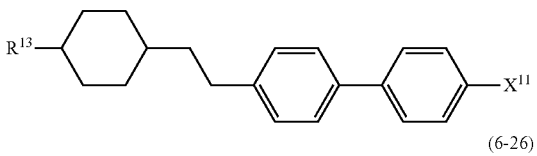
(6-26) 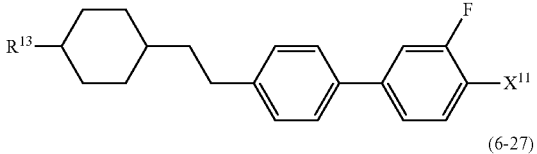
(6-27) 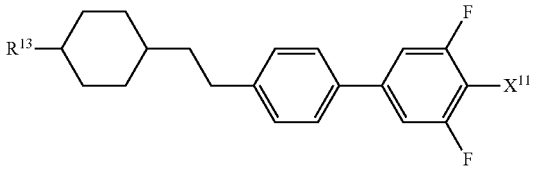
(6-28) 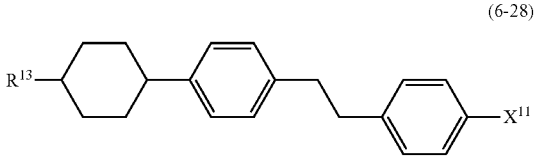
(6-29) 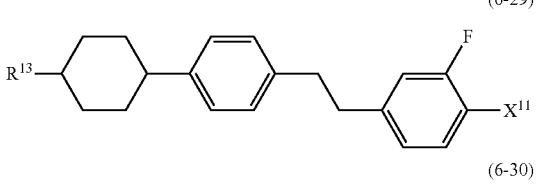
(6-30) 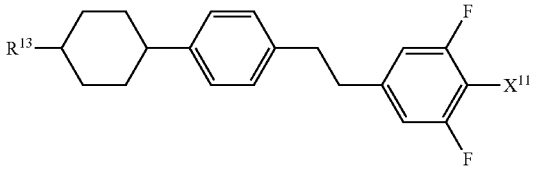
(6-31) 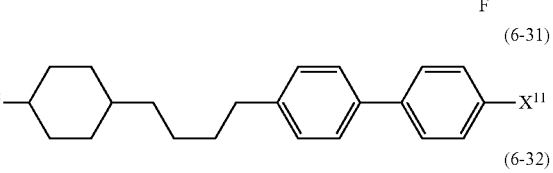
(6-32) 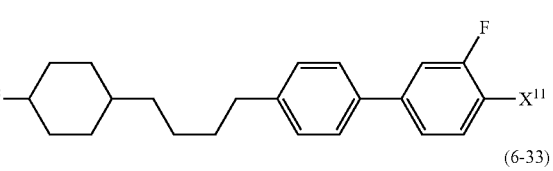
(6-33) 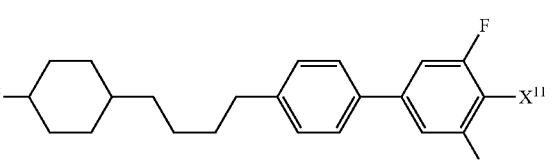
(6-34) 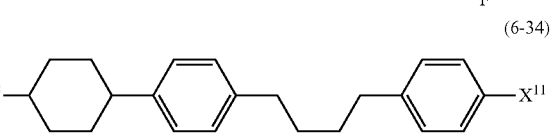

(6-35) 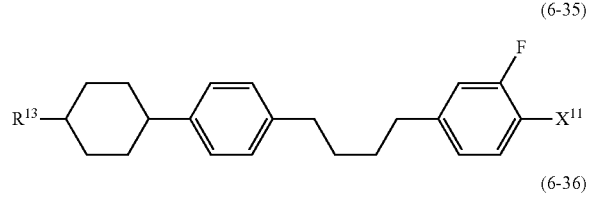
(6-36) 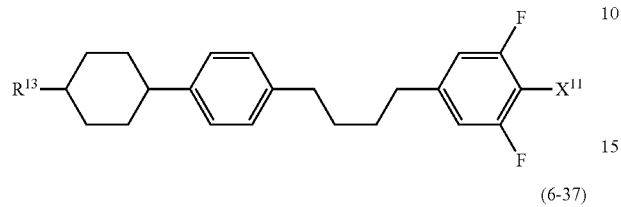
(6-37) 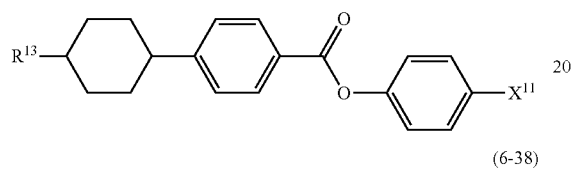
(6-38) 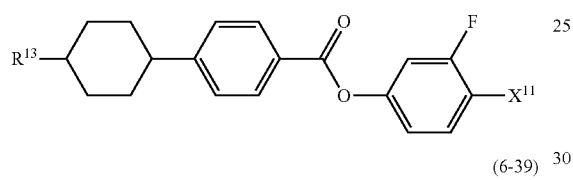
(6-39) 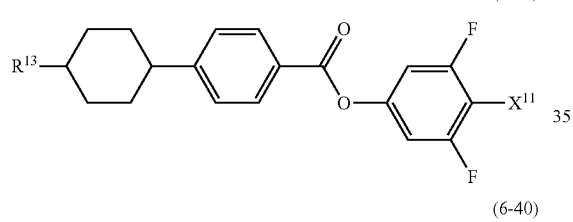
(6-40) 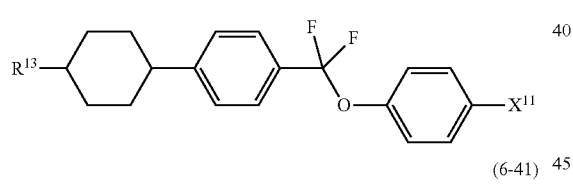
(6-41) 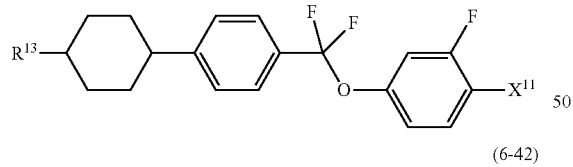
(6-42) 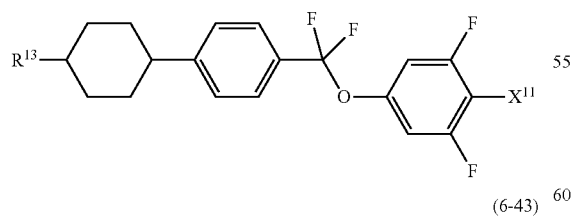
(6-43) 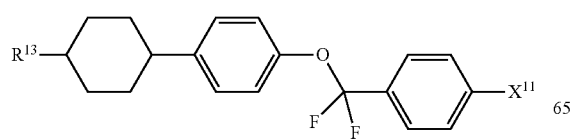
(6-44) (6-45) 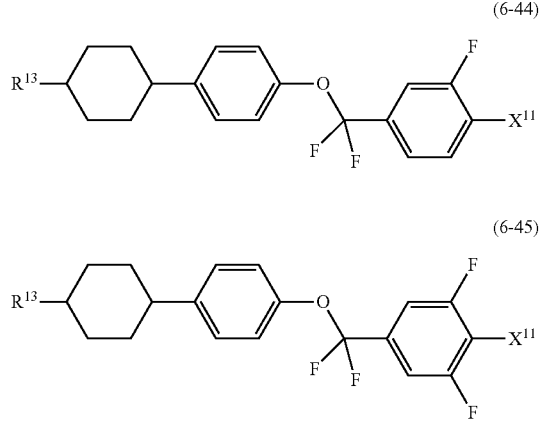
(6-46) (6-47) 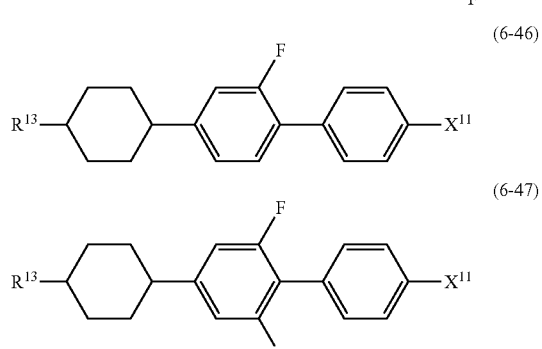
(6-48) 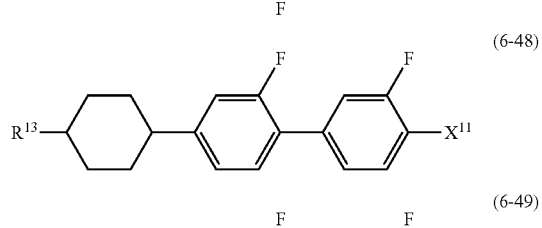
(6-49) 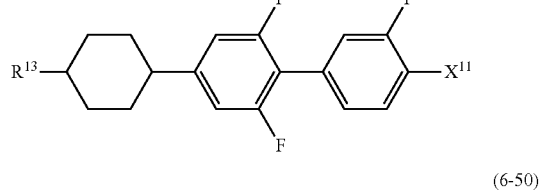
(6-50) 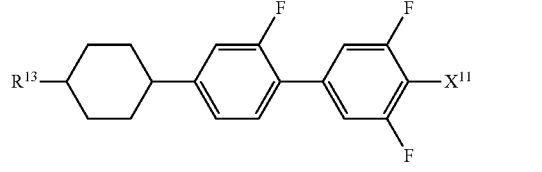
(6-51) 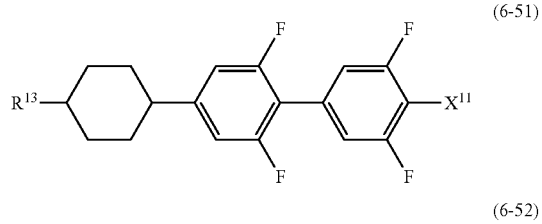
(6-52) 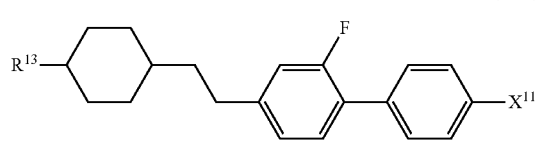

-continued
(6-53)
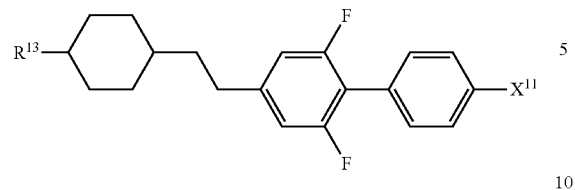
(6-54)
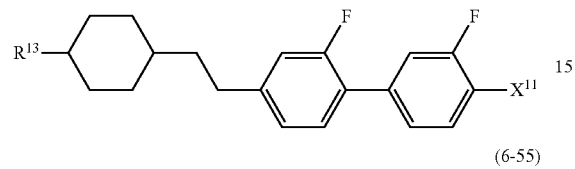
(6-55)
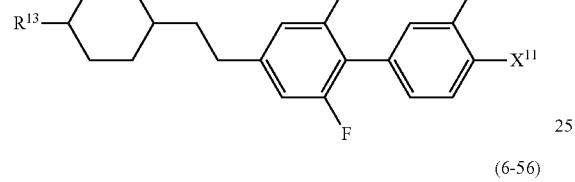
(6-56)
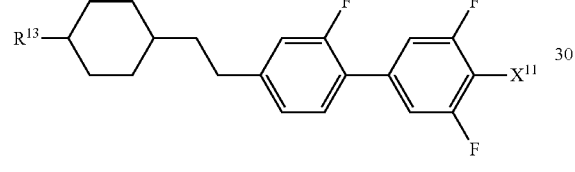
(6-57)
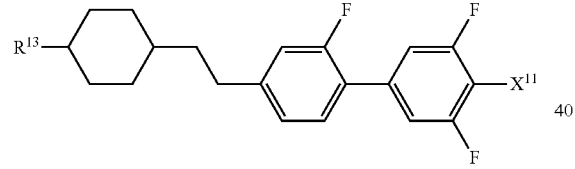
(6-58)
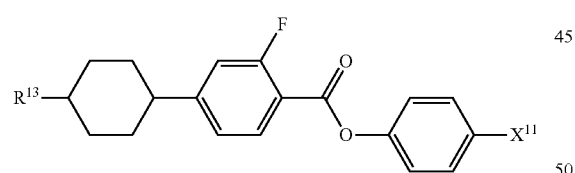
(6-59)
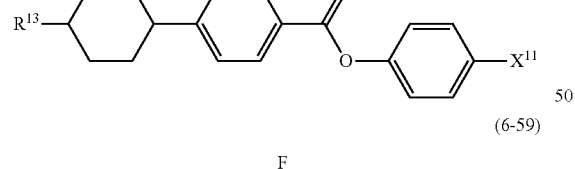
(6-60)
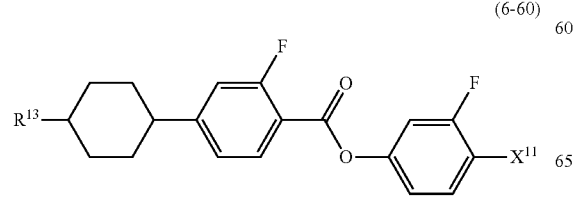
-continued
(6-61)
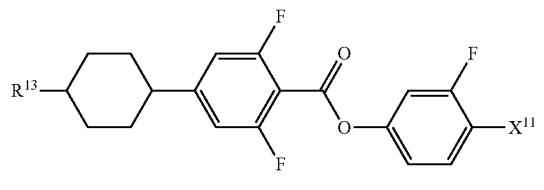
(6-62)
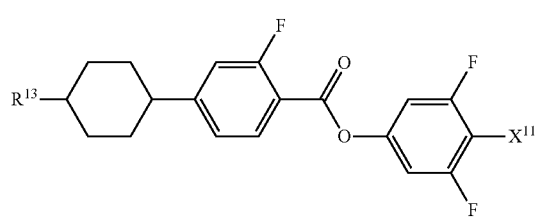
(6-63)
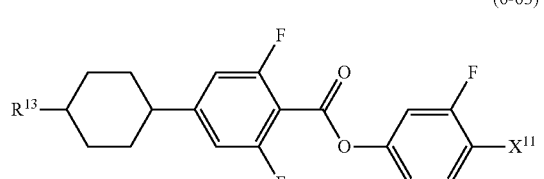
(6-64)
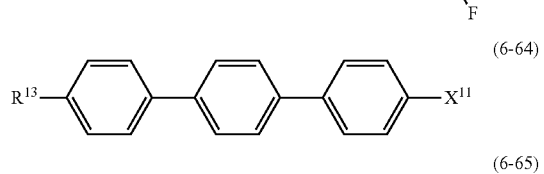
(6-65)
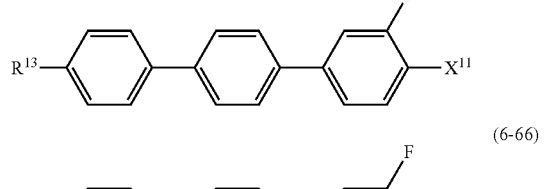
(6-66)
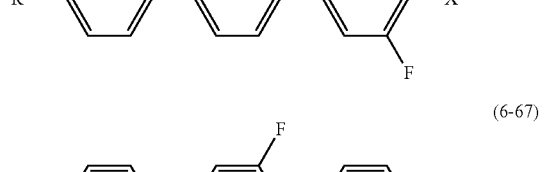
(6-67)
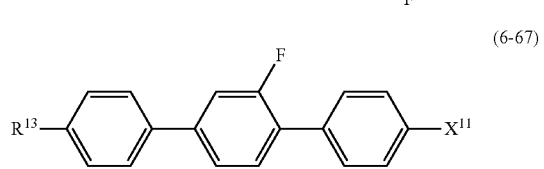
(6-68)
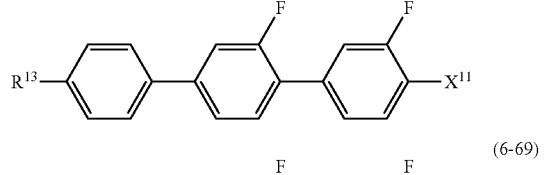
(6-69)

(6-70) 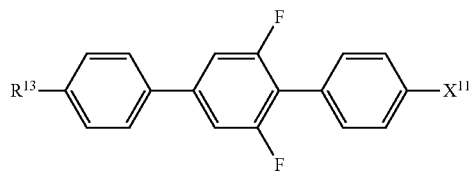
(6-71) 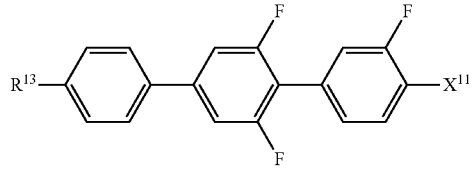
(6-72) 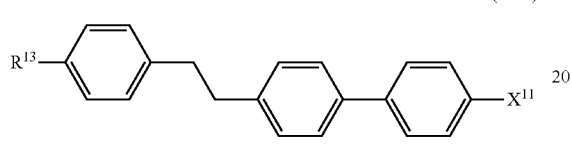
(6-73) 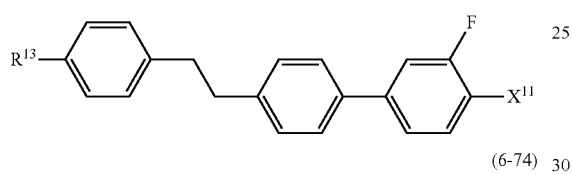
(6-74) 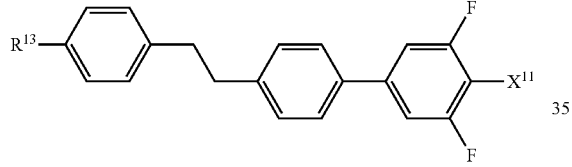
(6-75) 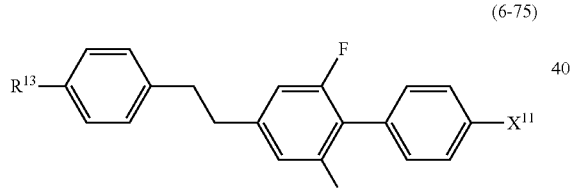
(6-76) 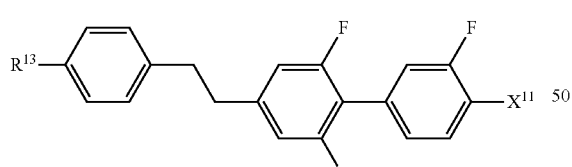
(6-77) 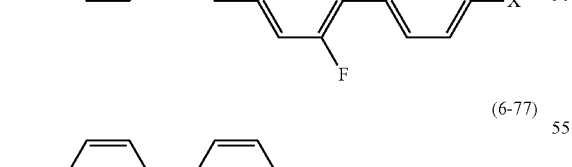
(6-78) 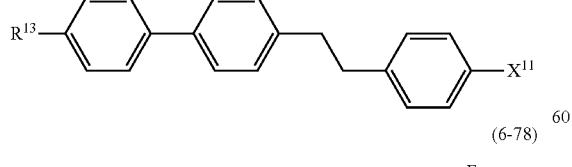
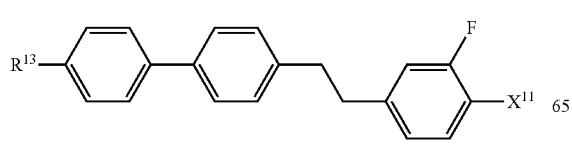
(6-79) 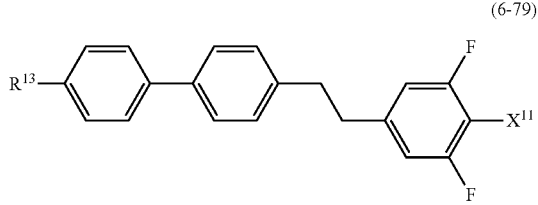
(6-80) 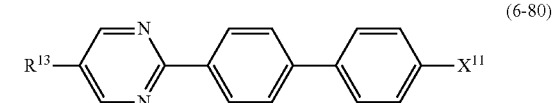
(6-81) 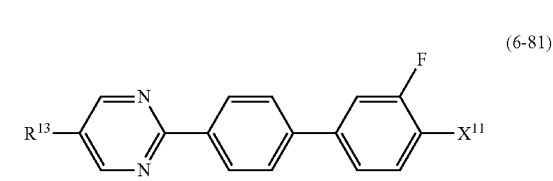
(6-82) 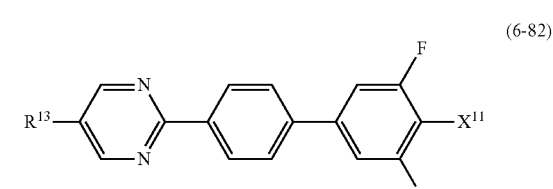
(6-83) 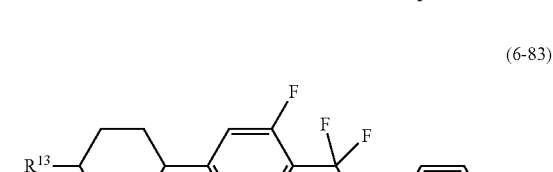
(6-84) 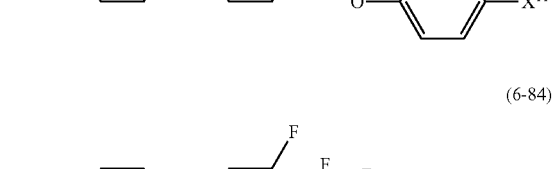
(6-85) 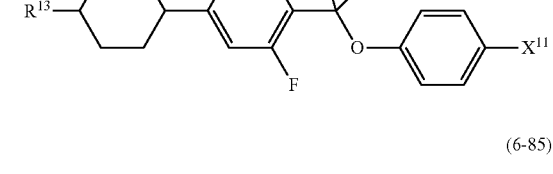
(6-86) 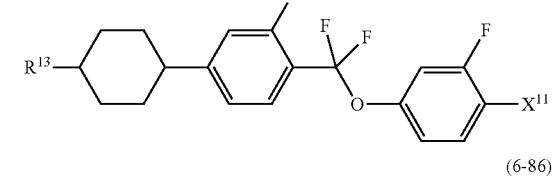
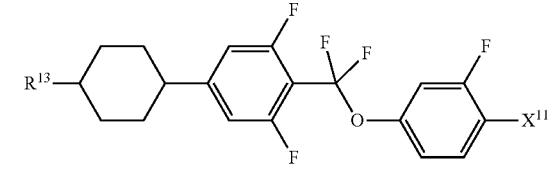

(6-87)
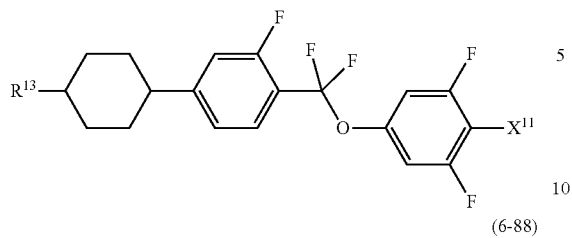
(6-88)
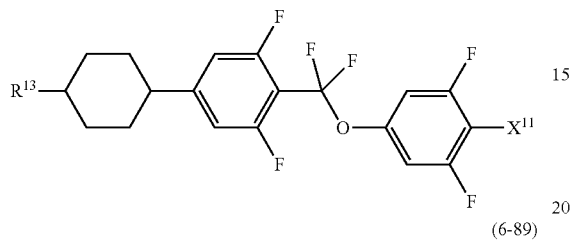
(6-89)
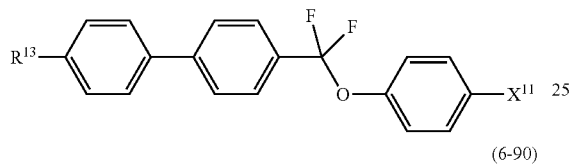
(6-90)
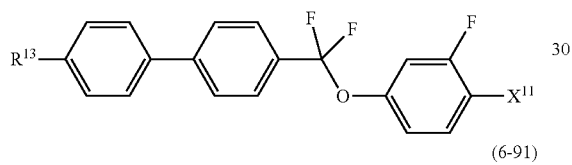
(6-91)
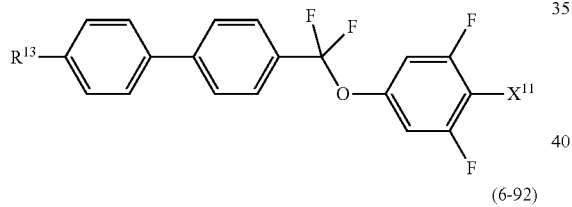
(6-92)
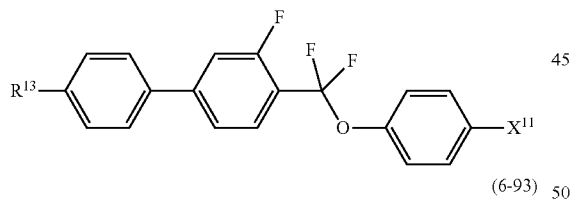
(6-93)
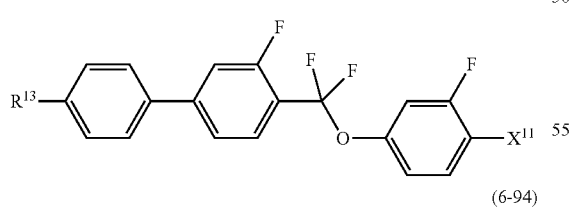
(6-94)
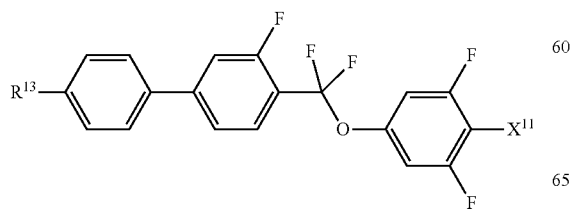
(6-95)
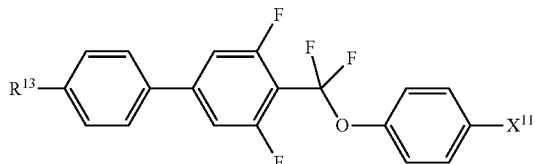
(6-96)
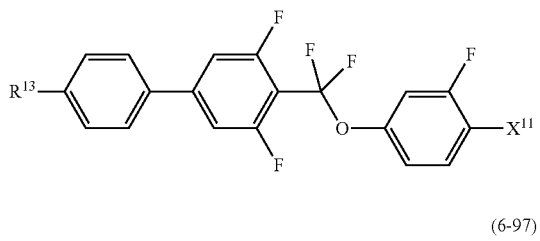
(6-97)
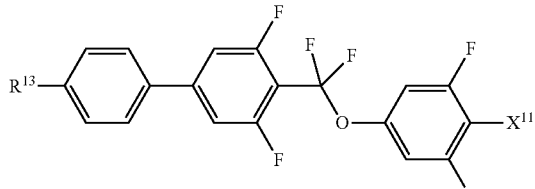
(6-98)
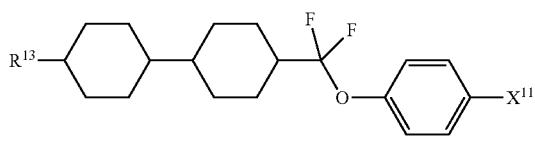
(6-99)
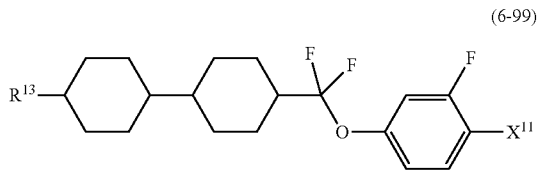
(6-100)
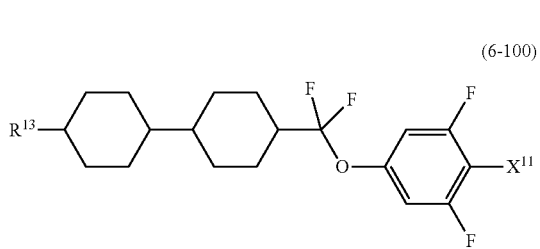
(6-101)
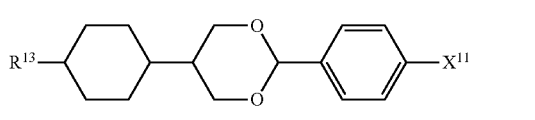
(6-102)
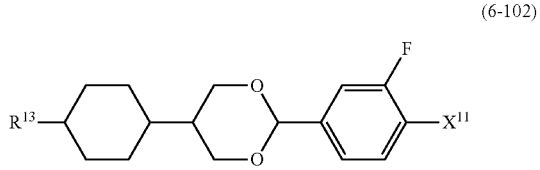

(6-103) 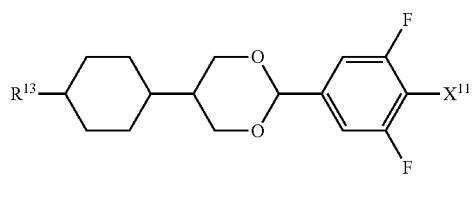
(6-104) 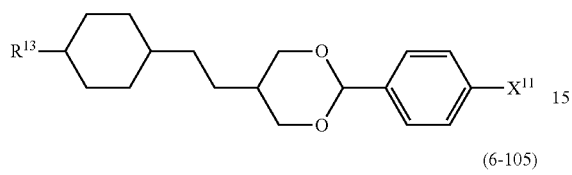
(6-105) 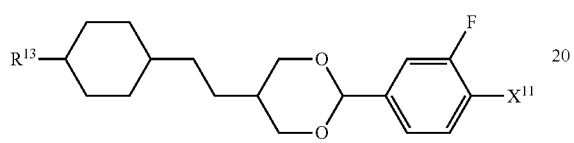
(6-106) 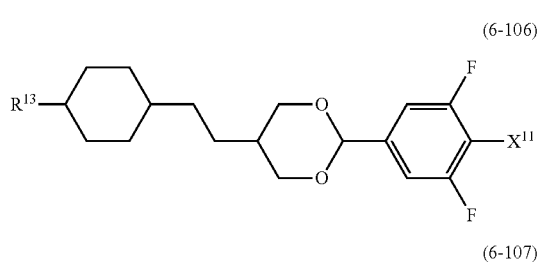
(6-107) 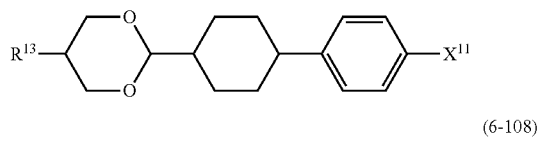
(6-108) 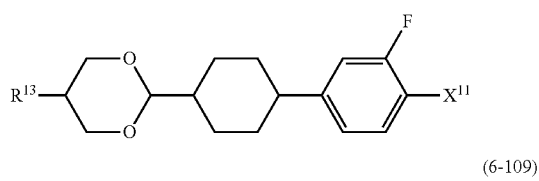
(6-109) 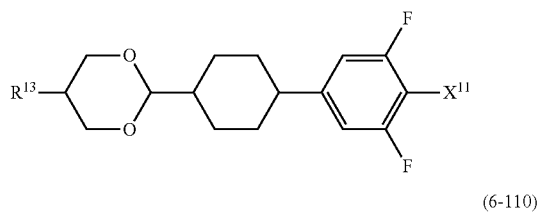
(6-110) 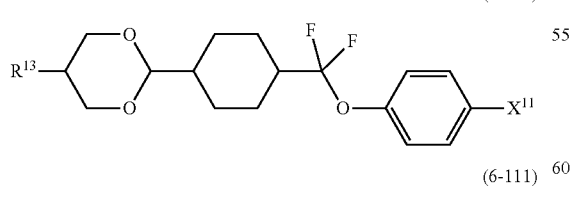
(6-111) 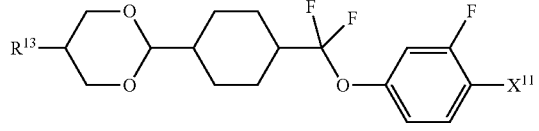
(6-112) 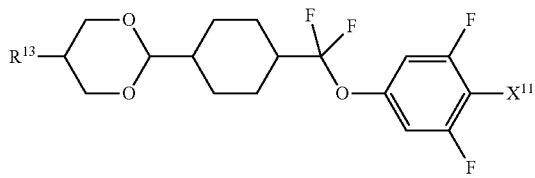
(6-113) 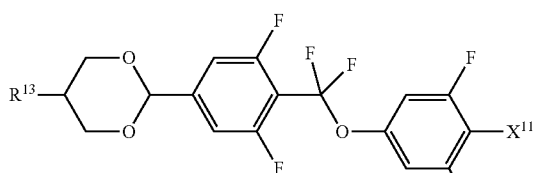
(7-1) 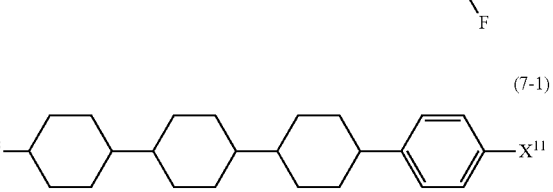
(7-2) 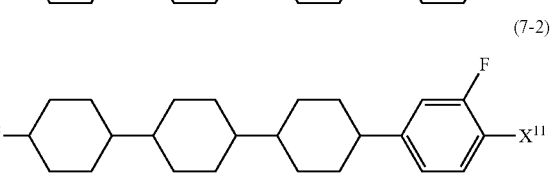
(7-3) 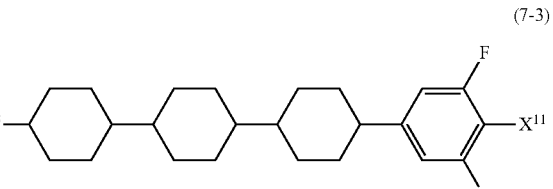
(7-4) 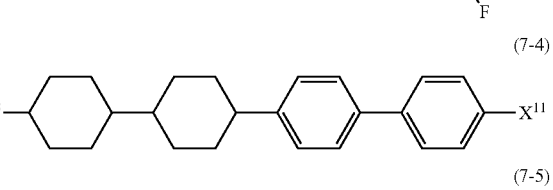
(7-5) 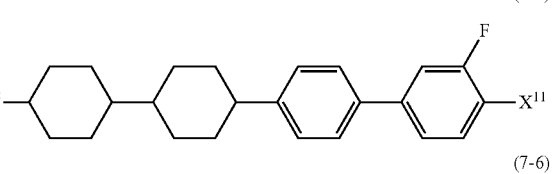
(7-6) 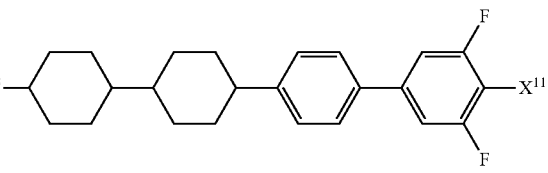
(7-7) 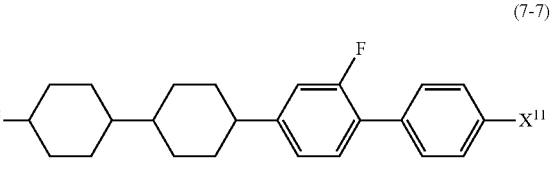

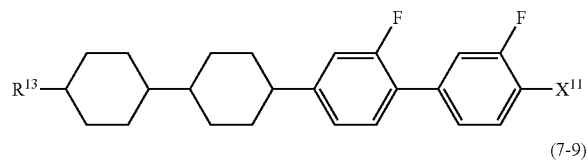
(7-8)
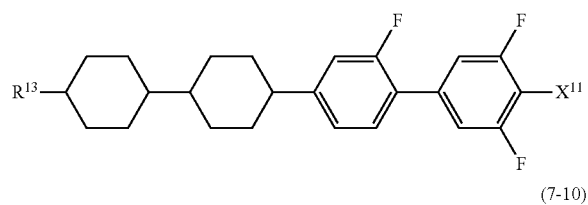
(7-9)
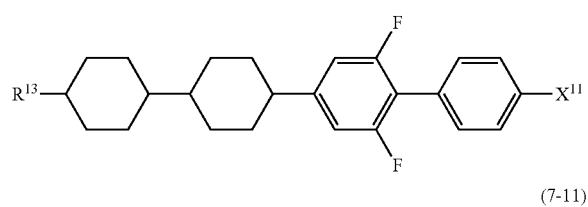
(7-10)
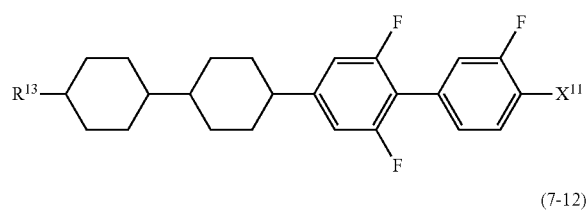
(7-11)
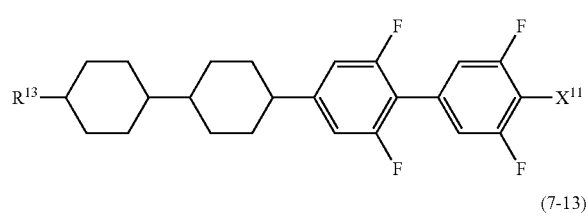
(7-12)
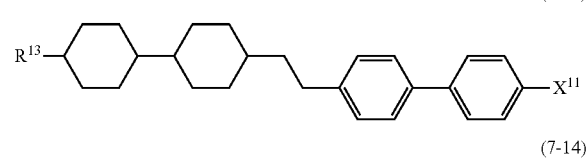
(7-13)
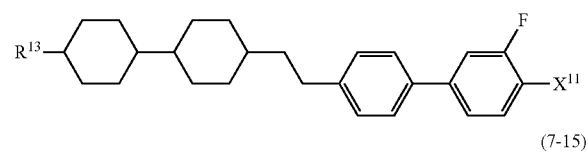
(7-14)
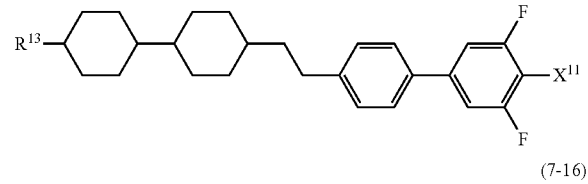
(7-15)
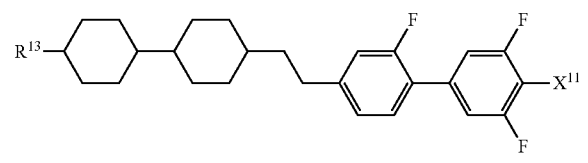
(7-16)
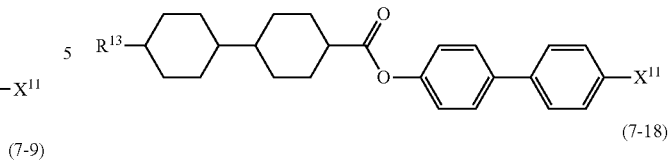
(7-17)
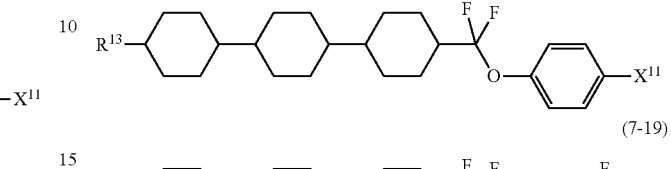
(7-18)
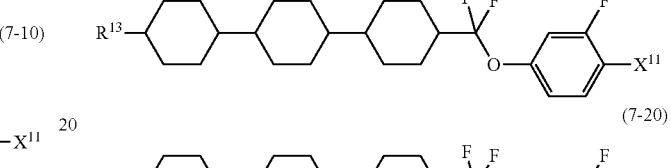
(7-19)
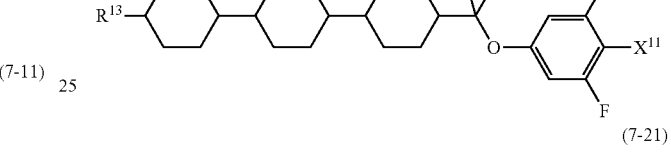
(7-20)
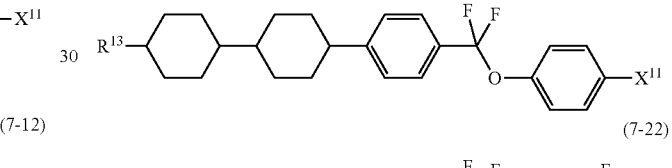
(7-21)
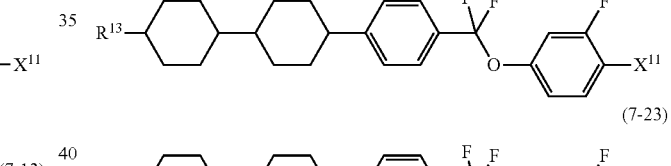
(7-22)
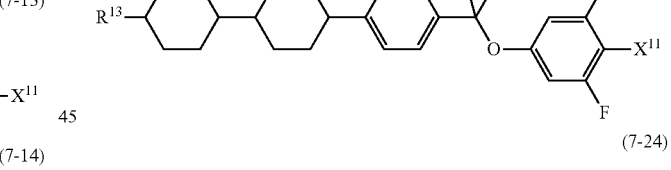
(7-23)
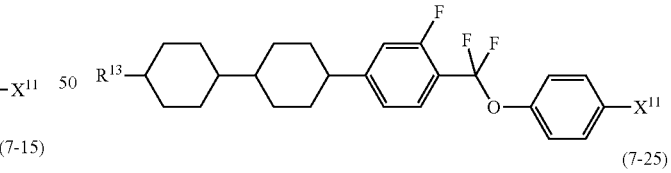
(7-24)
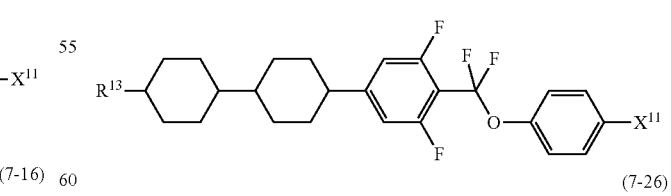
(7-25)
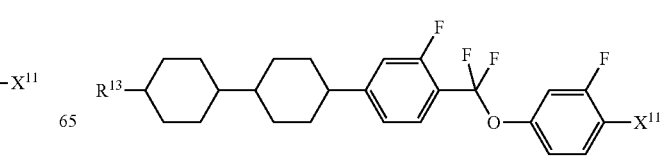
(7-26)

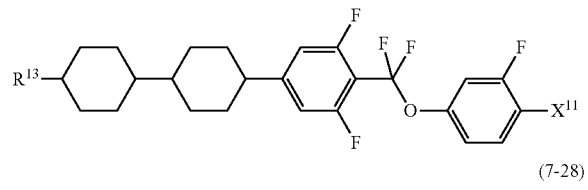
(7-27)
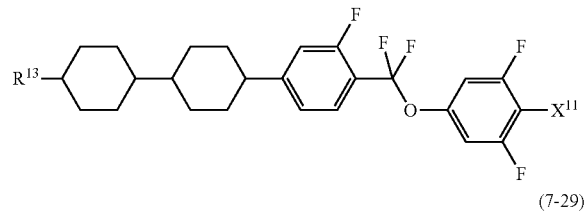
(7-28)
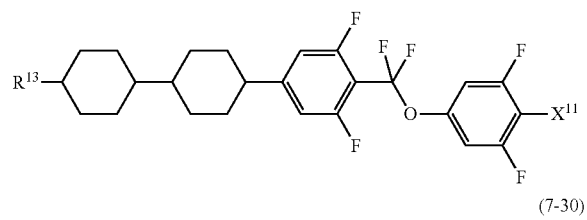
(7-29)
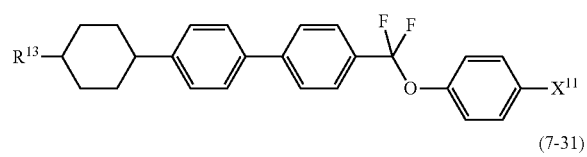
(7-30)
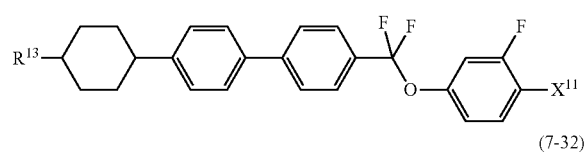
(7-31)
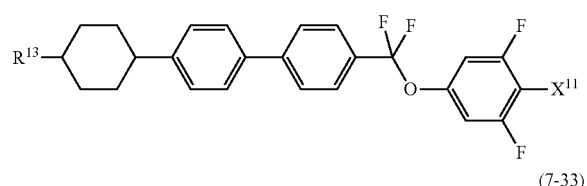
(7-32)
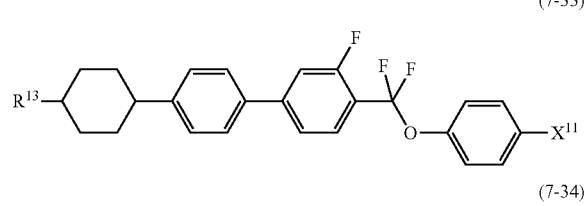
(7-33)
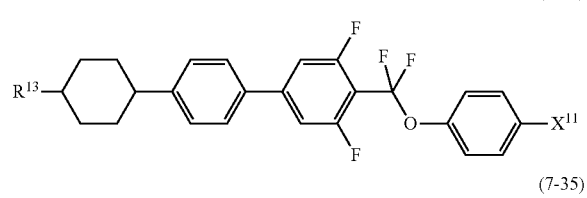
(7-34)
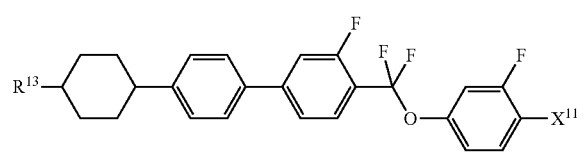
(7-35)
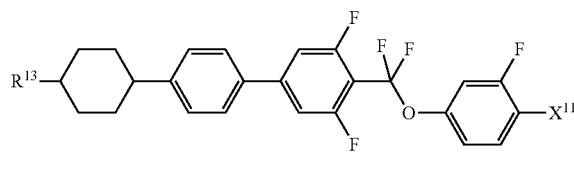
(7-36)
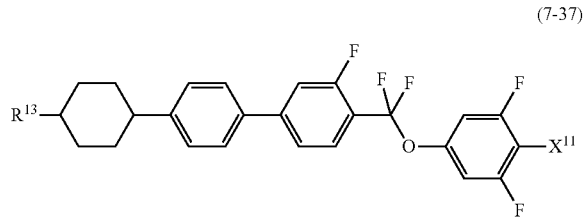
(7-37)
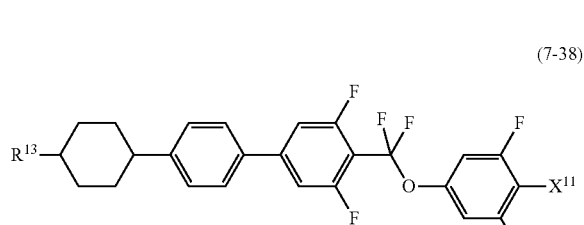
(7-38)
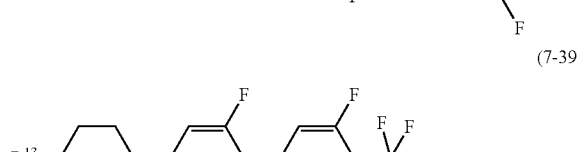
(7-39)
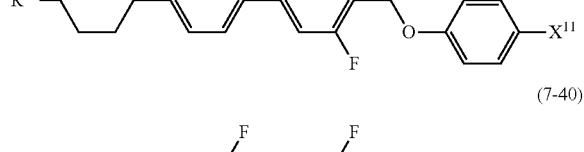
(7-40)
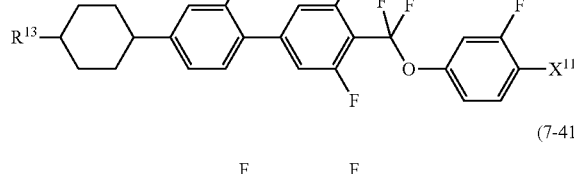
(7-41)
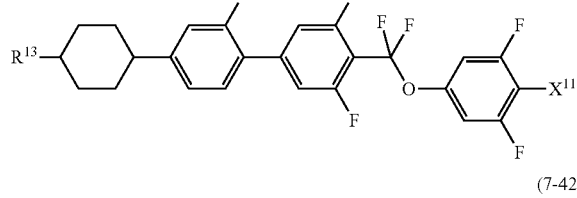
(7-42)
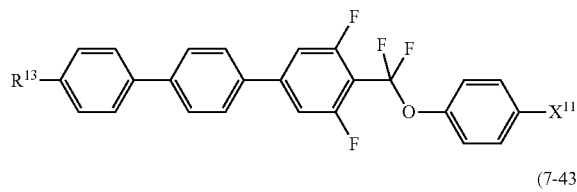
(7-43)
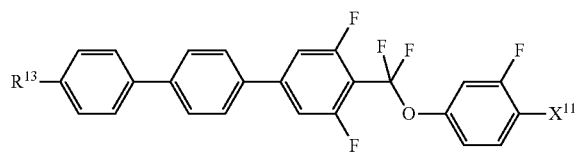

(7-44) 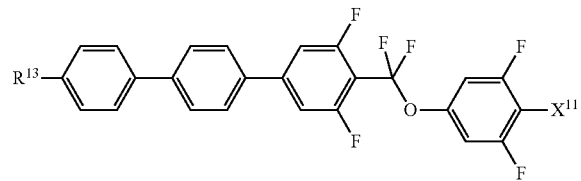

(7-45) 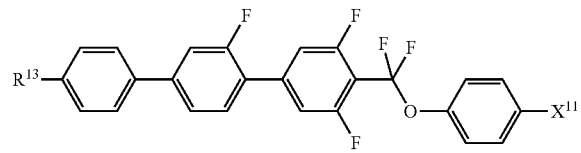

(7-46) 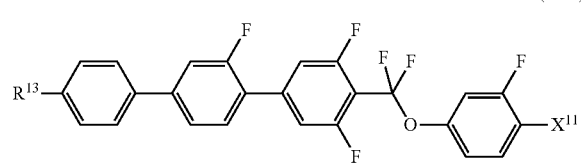

(7-47) 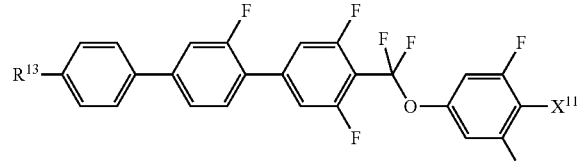

(7-48) 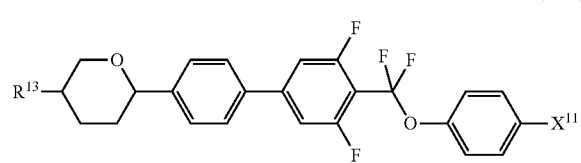

(7-49) 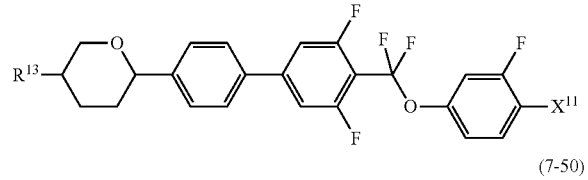

(7-50) 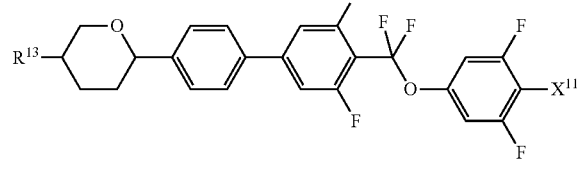

(7-51) 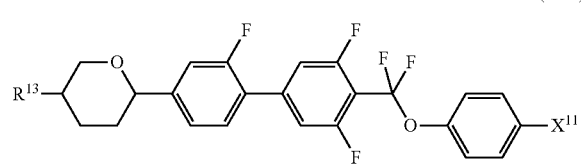

(7-52) 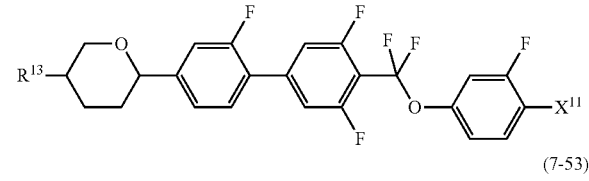

(7-53) 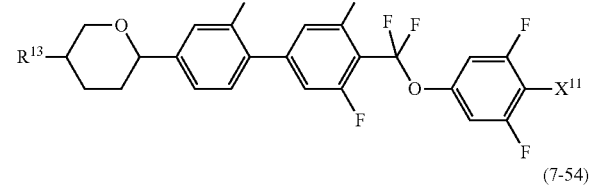

(7-54) 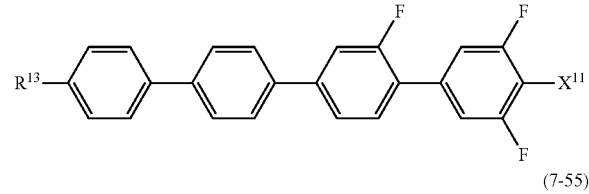

(7-55) 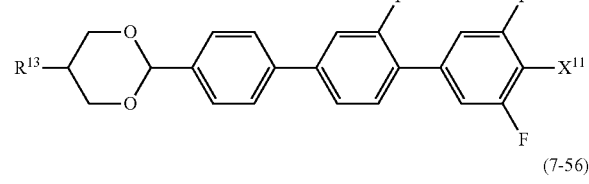

(7-56) 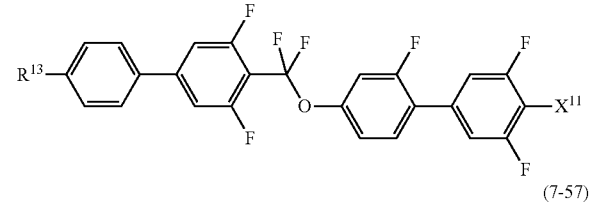

(7-56) 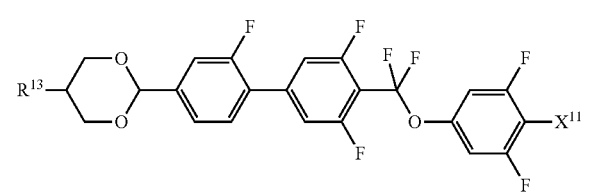

(7-57) 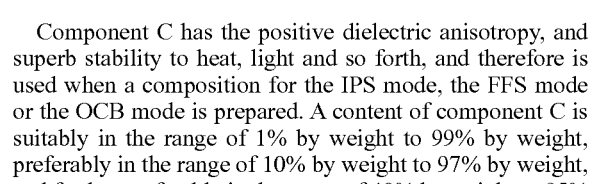

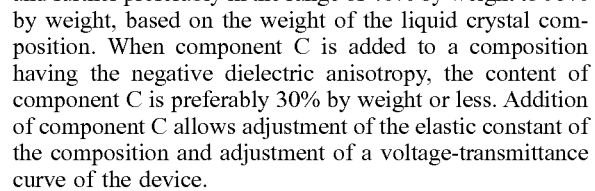

Component C has the positive dielectric anisotropy, and superb stability to heat, light and so forth, and therefore is used when a composition for the IPS mode, the FFS mode or the OCB mode is prepared. A content of component C is suitably in the range of 1% by weight to 99% by weight, preferably in the range of 10% by weight to 97% by weight, and further preferably in the range of 40% by weight to 95% by weight, based on the weight of the liquid crystal composition. When component C is added to a composition having the negative dielectric anisotropy, the content of component C is preferably 30% by weight or less. Addition of component C allows adjustment of the elastic constant of the composition and adjustment of a voltage-transmittance curve of the device.

Component D is compound (8) in which a right-terminal group is —C≡N or —C≡C—C≡N. Preferred examples of component D include compounds (8-1) to (8-64). In the compound of component D, $R^{14}$ is alkyl having 1 to 10 carbons or alkenyl having 2 to 10 carbons, and in the alkyl and the alkenyl, at least one piece of —$CH_2$— may be replaced by —O—, and at least one hydrogen may be replaced by fluorine; and $X^{12}$ is —C≡N or —C≡C—C≡N.
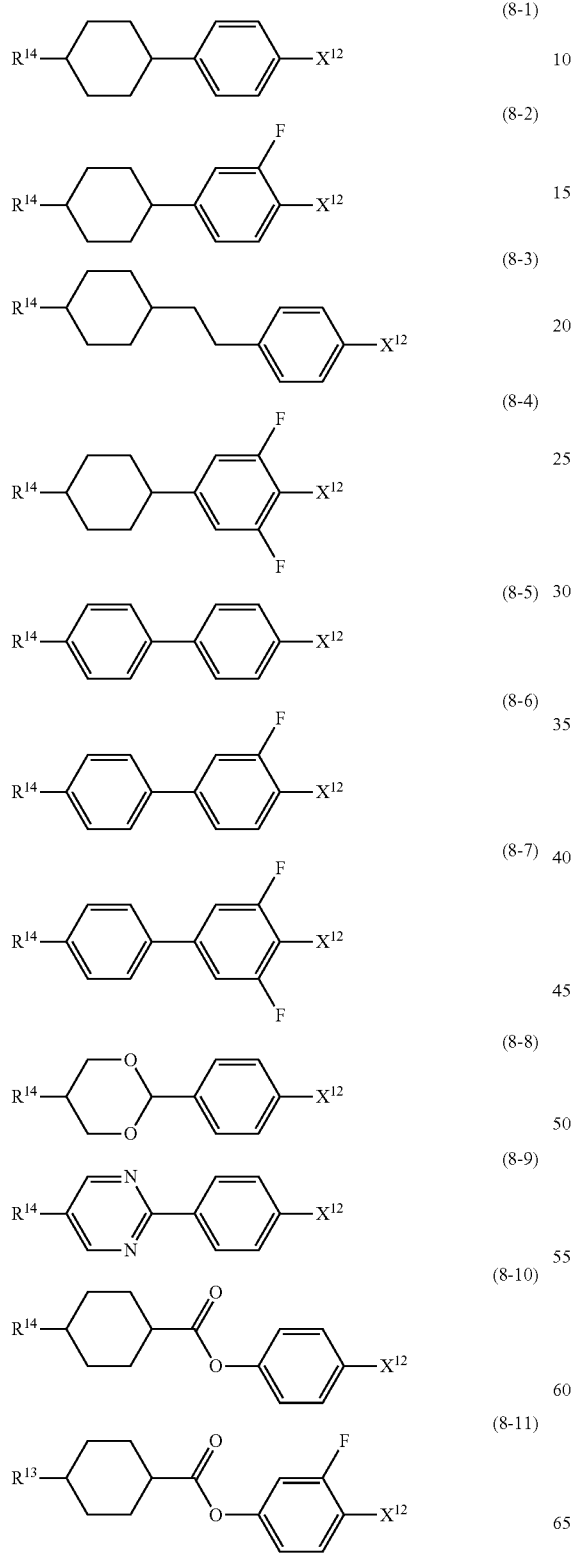
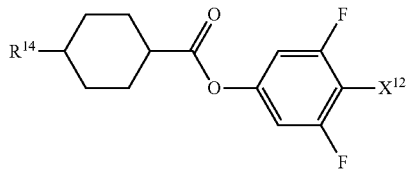
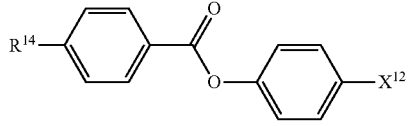
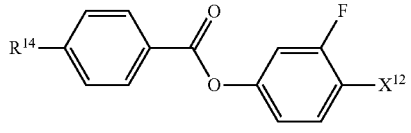
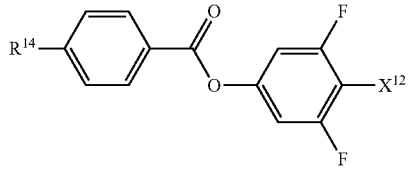
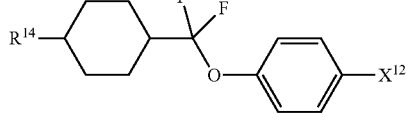
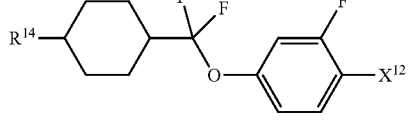
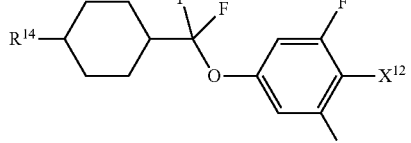
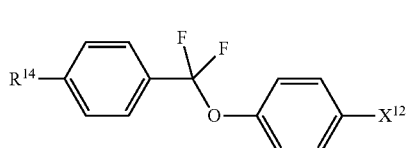
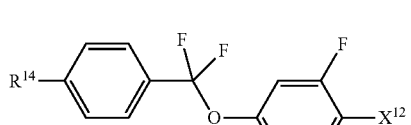
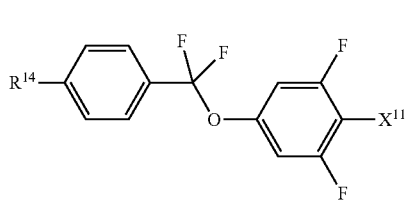

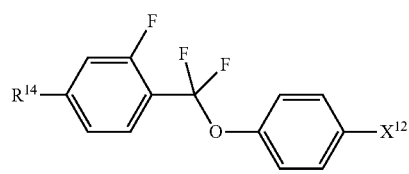 (8-22)
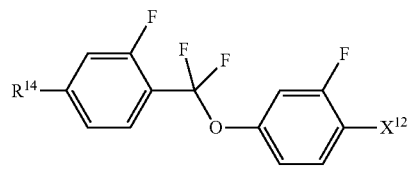 (8-23)
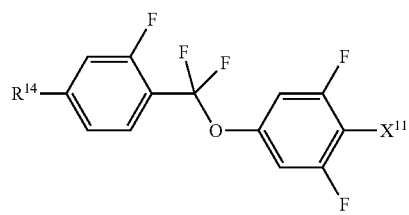 (8-24)
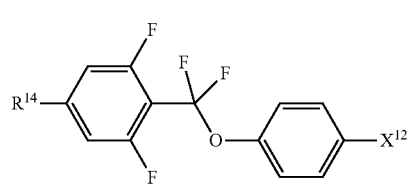 (8-25)
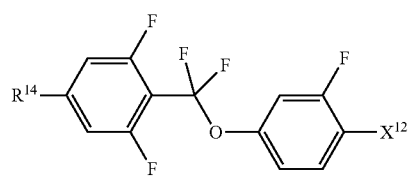 (8-26)
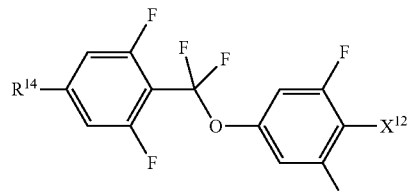 (8-27)
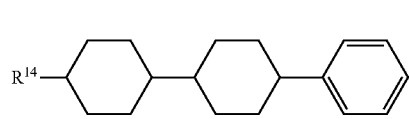 (8-28)
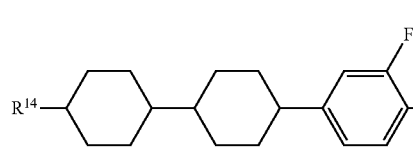 (8-29)
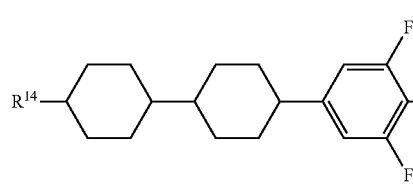 (8-30)
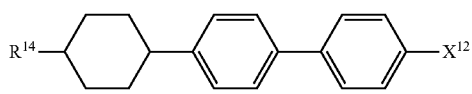 (8-31)
 (8-32)
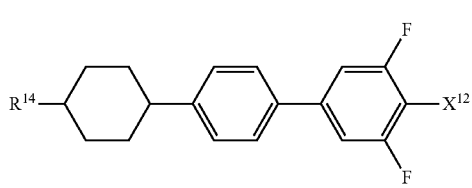 (8-33)
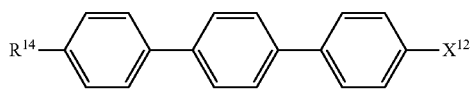 (8-34)
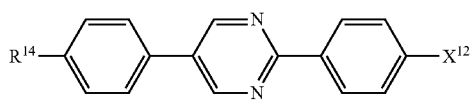 (8-35)
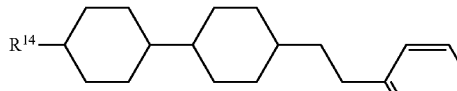 (8-36)
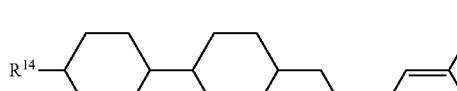 (8-37)
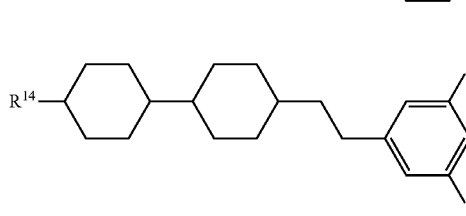 (8-38)
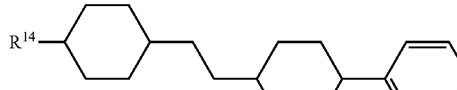 (8-39)
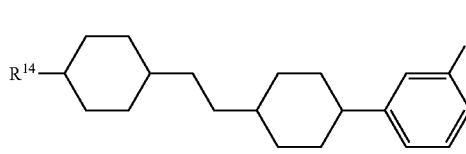 (8-40)

(8-41) 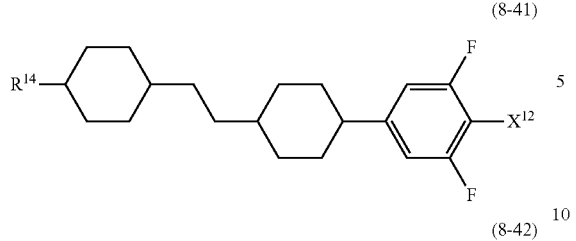
(8-42) 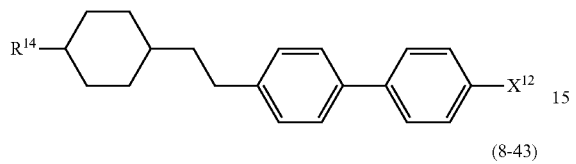
(8-43) 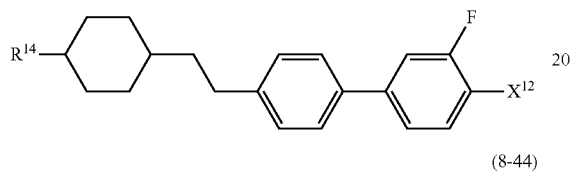
(8-44) 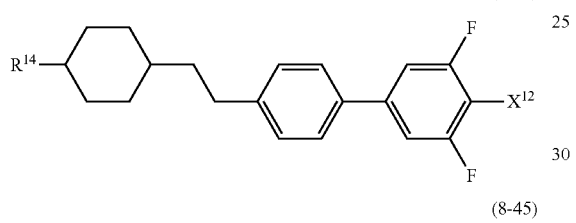
(8-45) 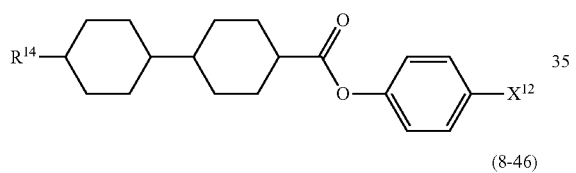
(8-46) 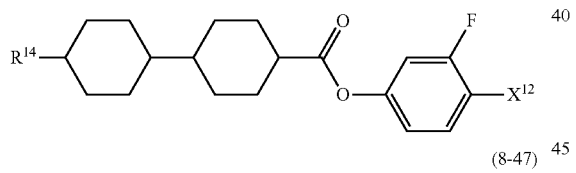
(8-47) 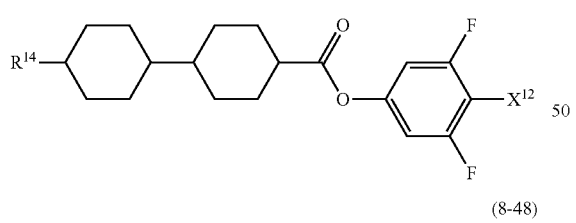
(8-48) 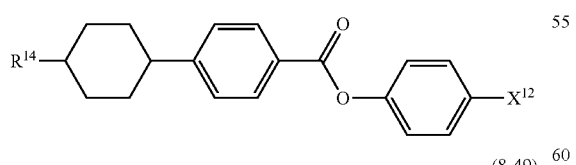
(8-49) 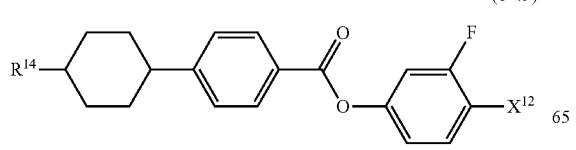
(8-50) 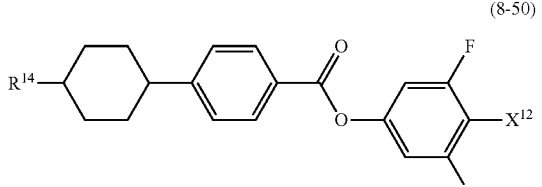
(8-51) 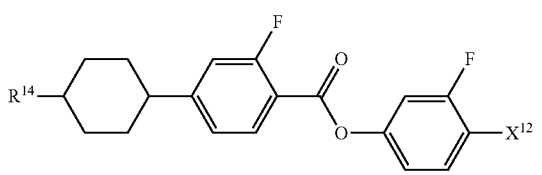
(8-52) 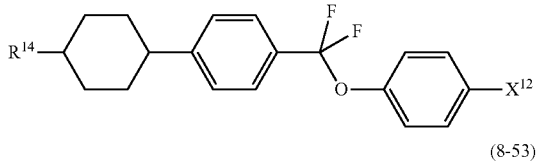
(8-53) 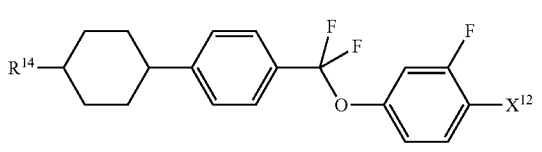
(8-54) 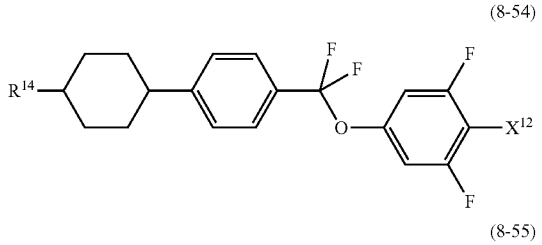
(8-55) 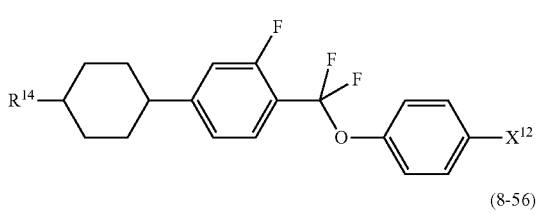
(8-56) 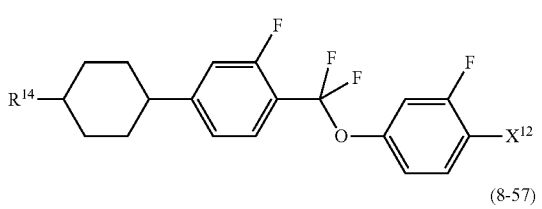
(8-57) 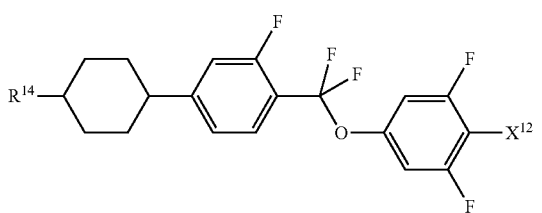

-continued

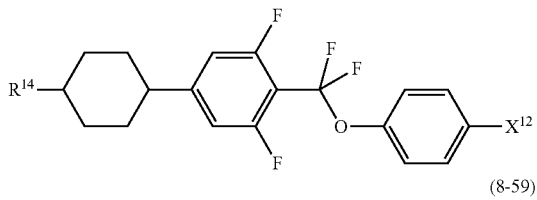
(8-58)

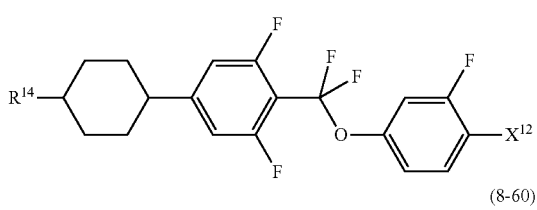
(8-59)

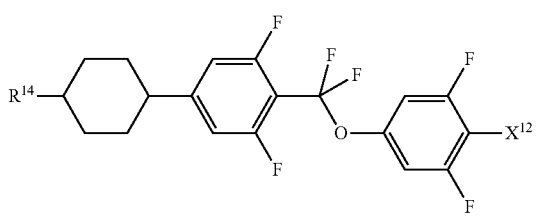
(8-60)

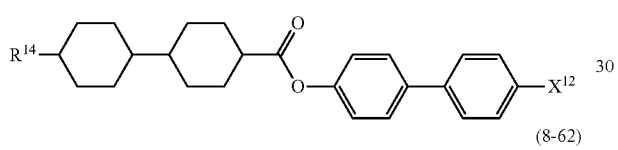
(8-61)

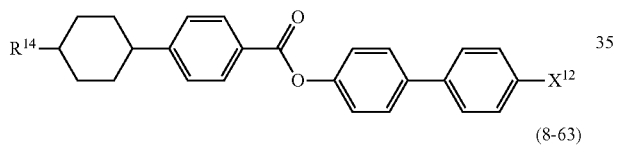
(8-62)

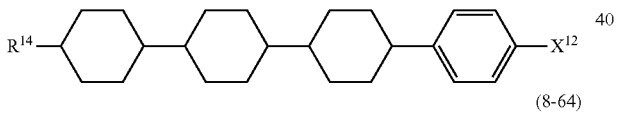
(8-63)

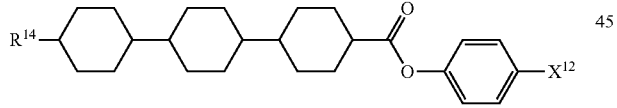
(8-64)

Component D has the positive dielectric anisotropy and a value thereof is large, and therefore is mainly used when the composition for the TN mode or the like is prepared. The dielectric anisotropy of the composition can be increased by adding component D. Component D is effective in extending the temperature range of the liquid crystal phase, adjusting the viscosity or adjusting the optical anisotropy. Component D is also useful for adjustment of the voltage-transmittance curve of the device.

When the composition for the TN mode or the like is prepared, a content of component D is suitably in the range of 1% by weight to 99% by weight, preferably in the range of 10% by weight to 97% by weight, and further preferably in the range of 40% by weight to 95% by weight, based on the weight of the liquid crystal composition. When component D is added to the composition having the negative dielectric anisotropy, the content of component D is preferably 30% by weight or less. Addition of component D allows adjustment of the elastic constant of the composition and adjustment of the voltage-transmittance curve of the device.

Component E includes compounds (9) to (15). The compounds have phenylene in which hydrogen in lateral positions are replaced by two halogen, such as 2,3-difluoro-1,4-phenylene. Specific examples of preferred component E include compounds (9-1) to (9-8), compounds (10-1) to (10-17), compound (11-1), compounds (12-1) to (12-3), compounds (13-1) to (13-11), compounds (14-1) to (14-3) and compounds (15-1) to (15-3). In the above compounds, $R^{15}$ and $R^{16}$ are independently alkyl having 1 to 10 carbons or alkenyl having 2 to 10 carbons, and in the alkyl and the alkenyl, at least one piece of —CH$_2$— may be replaced by —O—, and at least one hydrogen may be replaced by fluorine; and $R^{17}$ is hydrogen, fluorine, alkyl having 1 to 10 carbons or alkenyl having 2 to 10 carbons, and in the alkyl and the alkenyl, at least one piece of —CH$_2$— may be replaced by —O—, and at least one hydrogen may be replaced by fluorine.

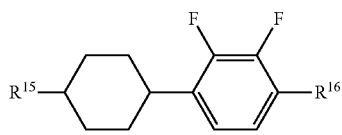
(9-1)

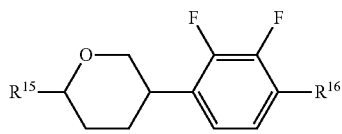
(9-2)

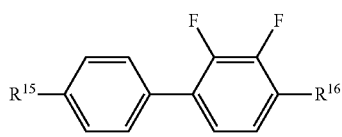
(9-3)

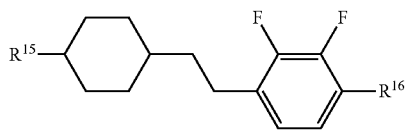
(9-4)

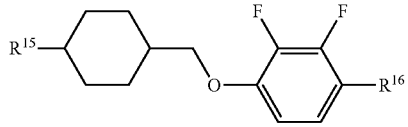
(9-5)

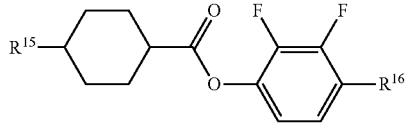
(9-6)

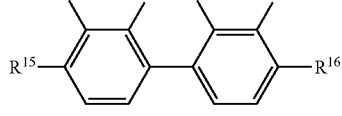
(9-7)

(9-8) 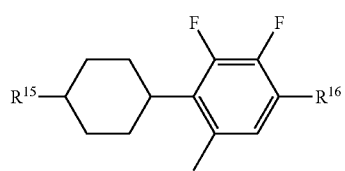
(10-1) 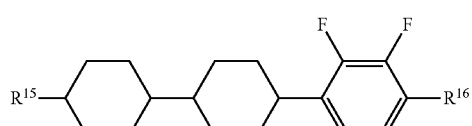
(10-2) 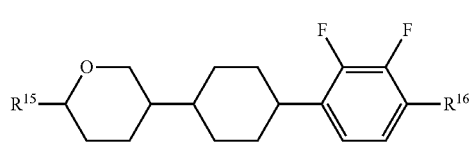
(10-3) 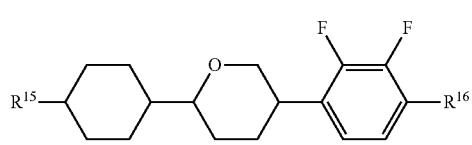
(10-4) 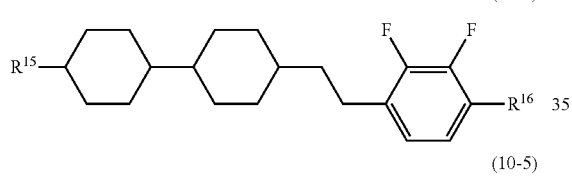
(10-5) 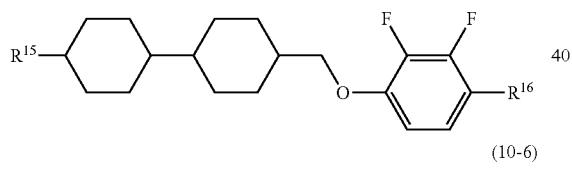
(10-6) 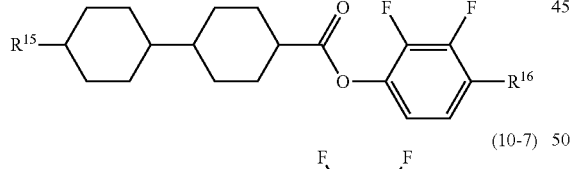
(10-7) 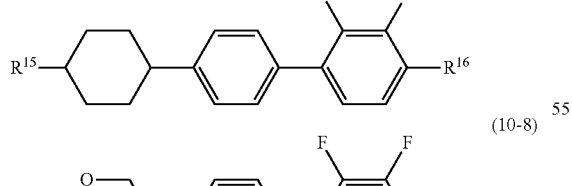
(10-8) 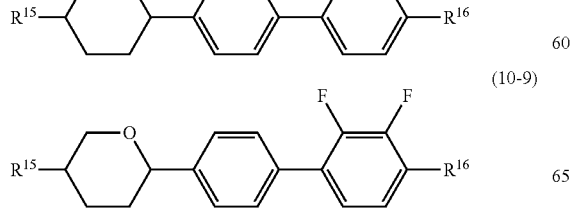
(10-9) 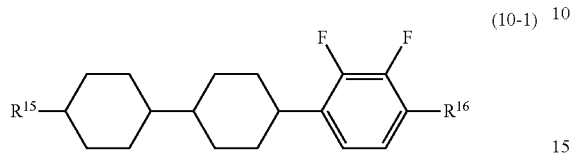
(10-10) 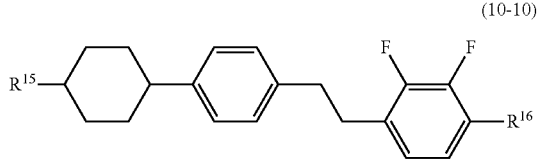
(10-11) 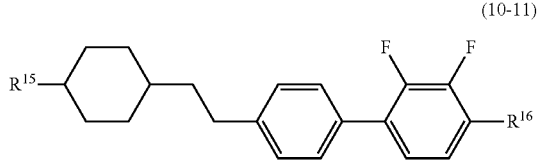
(10-12) 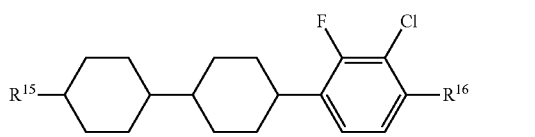
(10-13) 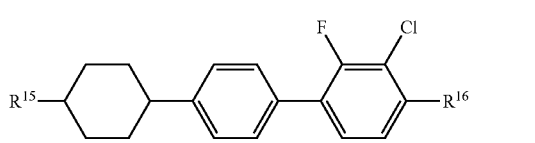
(10-14) 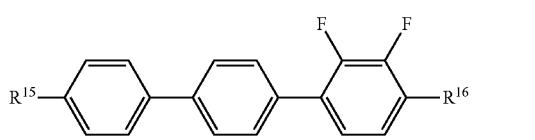
(10-15) 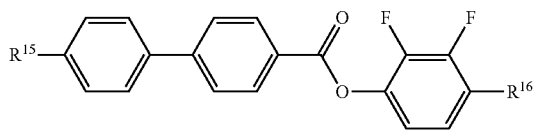
(10-16) 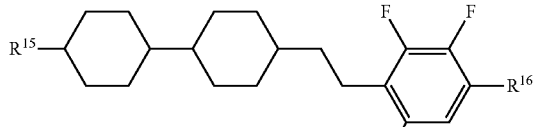
(10-17) 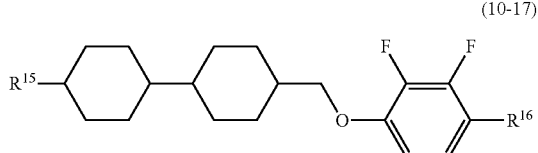
(11-1) 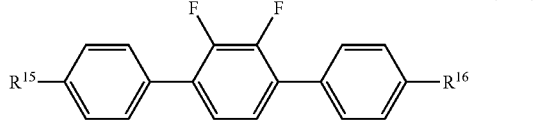

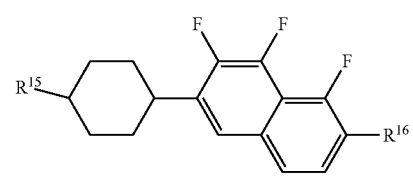
(12-1)
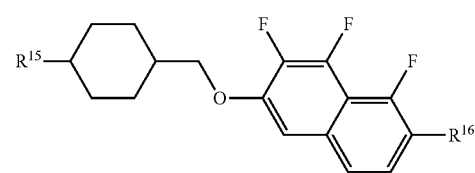
(12-2)
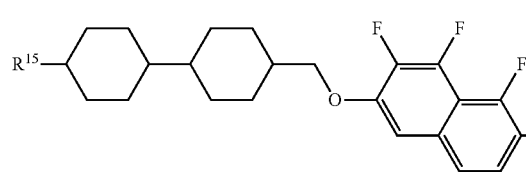
(12-3)
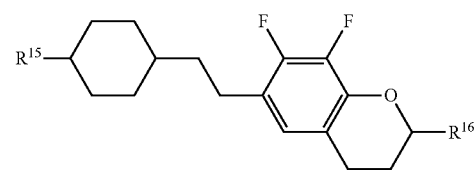
(13-1)
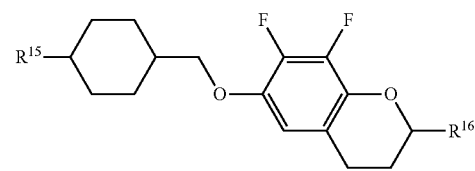
(13-2)
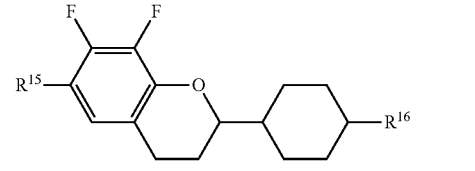
(13-3)
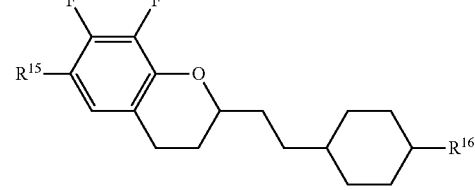
(13-4)
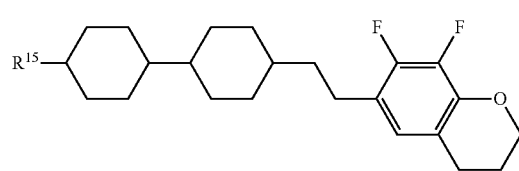
(13-5)
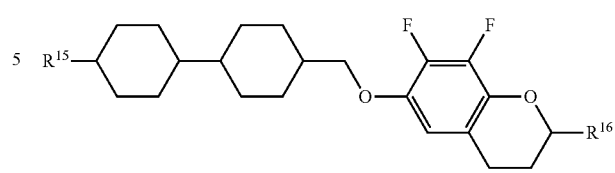
(13-6)
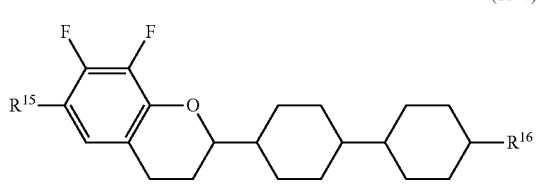
(13-7)
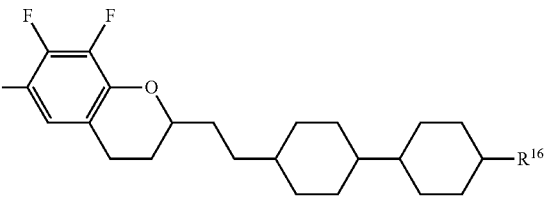
(13-8)
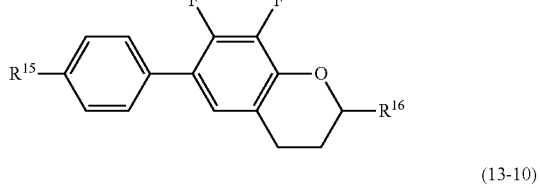
(13-9)
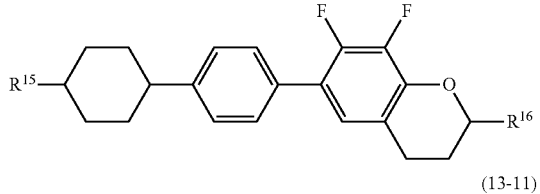
(13-10)
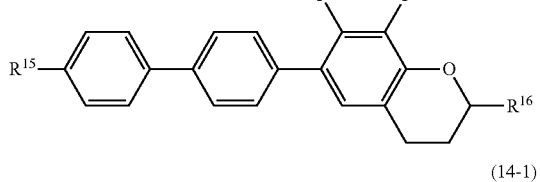
(13-11)
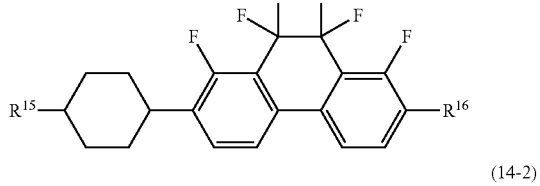
(14-1)
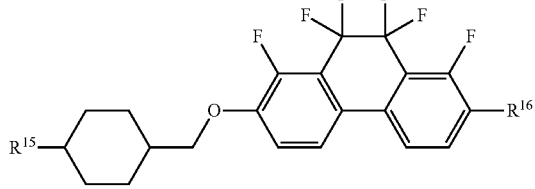
(14-2)

-continued (14-3)
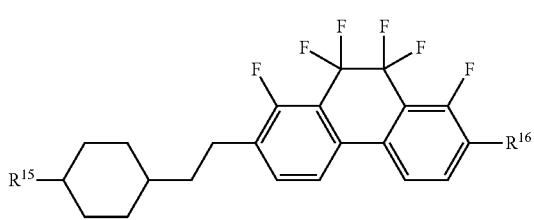

(15-1)
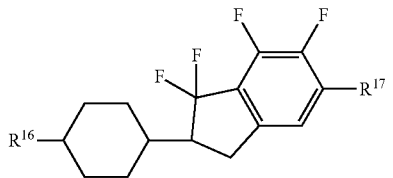

(15-2)
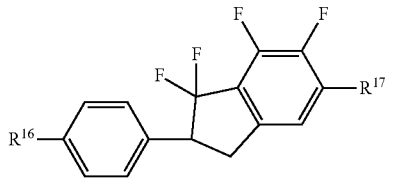

(15-3)
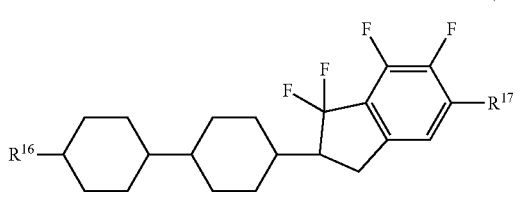

Component E has the negatively large dielectric anisotropy. Component E is used when the composition for the IPS mode, the VA mode, the PSA mode or the like is prepared. As a content of component E is increased, the dielectric anisotropy of the composition is negatively increased, but the viscosity is increased. Thus, as long as a desired value of threshold voltage of the device is met, the content is preferably as small as possible. When the dielectric anisotropy at a degree of −5 is taken into account, the content is preferably 40% by weight or more in order to allow a sufficient voltage driving.

Among components E, compound (9) is a bicyclic compound, and therefore is effective mainly in decreasing the viscosity, adjusting the optical anisotropy or increasing the dielectric anisotropy. Compounds (10) and (11) are a tricyclic compound, and therefore are effective in increasing the maximum temperature, increasing the optical anisotropy or increasing the dielectric anisotropy. Compounds (12) to (15) are effective in increasing the dielectric anisotropy.

When the composition for the IPS mode, the VA mode or the PSA mode is prepared, the content of component E is preferably 40% by weight or more, and further preferably in the range of 50% by weight to 95% by weight, based on the weight of the liquid crystal composition. When component E is added to the composition having the positive dielectric anisotropy, a content of the compounds is preferably 30% by weight or less. Addition of component E allows adjustment of the elastic constant of the composition and adjustment of the voltage-transmittance curve of the device.

The liquid crystal composition satisfying at least one of physical properties such as the high stability to heat and light, the high maximum temperature, the low minimum temperature, the small viscosity, the suitable optical anisotropy, the large dielectric anisotropy, the large specific resistance, the large specific resistance and the suitable elastic constant can be prepared by appropriately combining component B, C, D and E described above. Liquid crystal compounds different from components B, C, D and E may be added when necessary.

3-2. Additive

A liquid crystal composition is prepared according to a known method. For example, the component compounds are mixed and dissolved in each other by heating. According to an application, an additive may be added to the composition. Specific examples of the additive include a polymerizable compound, a polymerization initiator, a polymerization inhibitor, an optically active compound, an antioxidant, an ultraviolet light absorber, a light stabilizer, a heat stabilizer, a dye and an antifoaming agent. Such additives are well known to those skilled in the art, and described in literature.

In the liquid crystal display device having the polymer sustained alignment (PSA) mode, the composition contains a polymer. The polymerizable compound is added for the purpose of forming the polymer in the composition. The polymerizable compound is polymerized by irradiation with ultraviolet light while voltage is applied between electrodes, and thus the polymer is formed in the composition. A suitable pretilt is achieved by the method, and therefore the device in which a response time is shortened and image persistence is improved is prepared.

Specific examples of the preferred polymerizable compound include acrylate, methacrylate, a vinyl compound, a vinyloxy compound, propenyl ether, an epoxy compound (oxirane, oxetane) and vinyl ketone. Further preferred examples include a compound having at least one acryloyloxy, and a compound having at least one methacryloyloxy. Still further preferred examples also include a compound having both acryloyloxy and methacryloyloxy.

Still further preferred examples include compounds (M-1) to (M-17). In the above compounds, $R^{25}$ to $R^{31}$ are independently hydrogen or methyl; s, v and x are independently 0 or 1; and t and u are independently an integer of 1 to 10. $L^{21}$ to $L^{26}$ are independently hydrogen or fluorine; and $L^{27}$ and $L^{28}$ are independently hydrogen, fluorine or methyl.

(M-1)
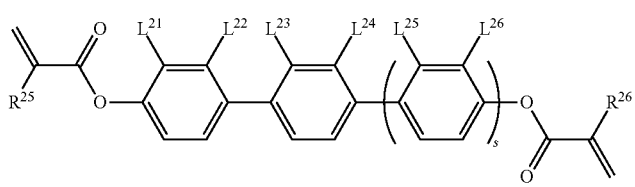

-continued
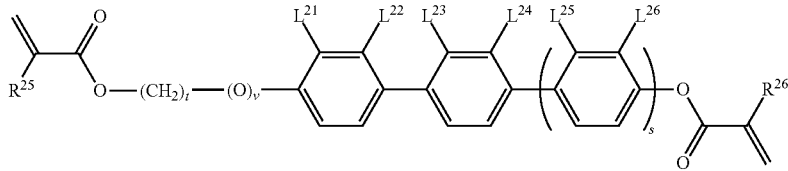
(M-2)
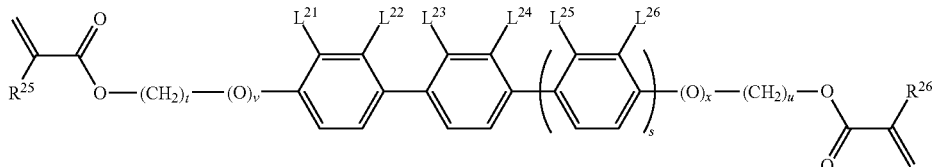
(M-3)
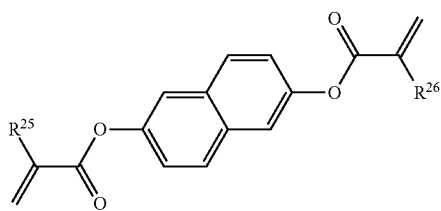
(M-4)
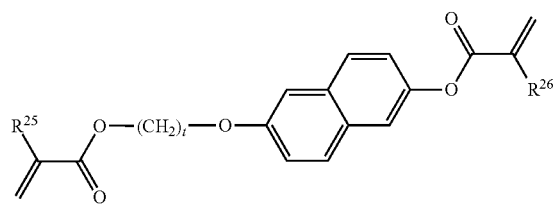
(M-5)
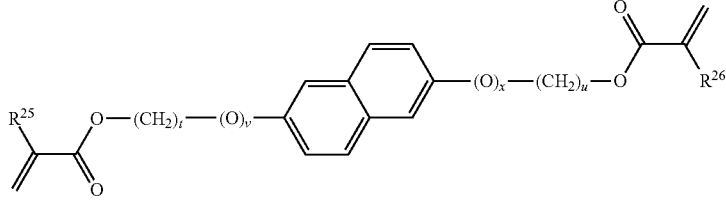
(M-6)
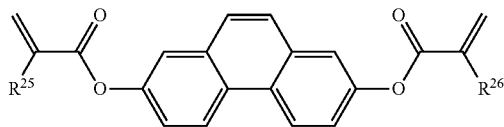
(M-7)
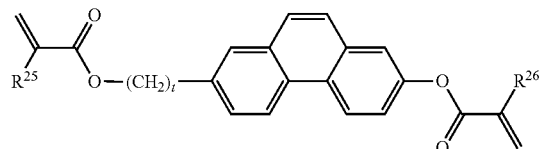
(M-8)
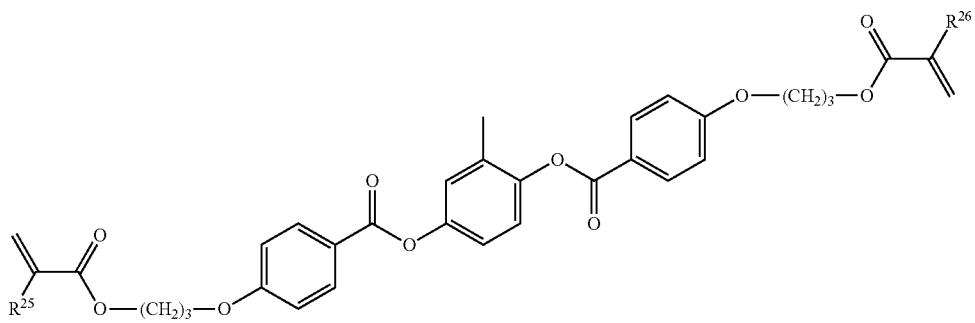
(M-9)
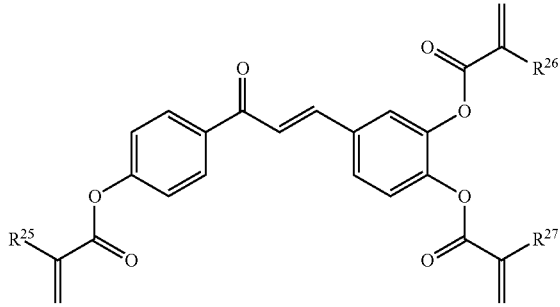
(M-10)

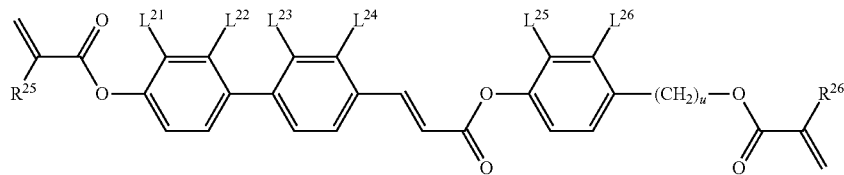
(M-11)
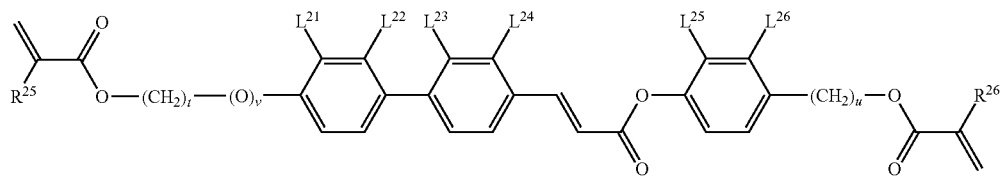
(M-12)
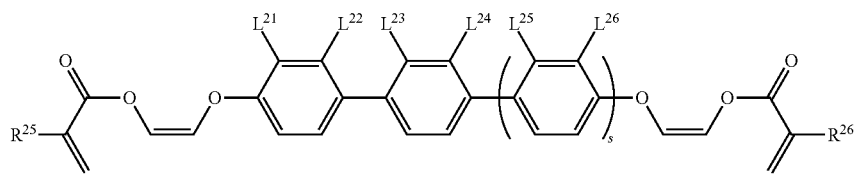
(M-13)
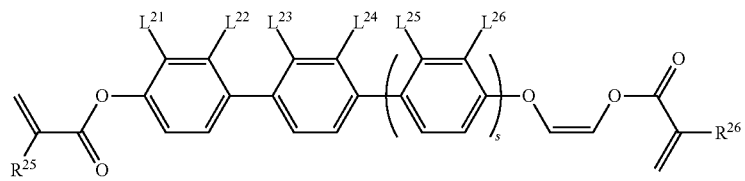
(M-14)
(M-15) (M-16)
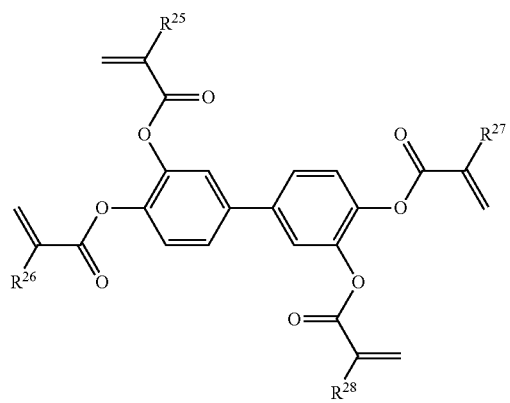
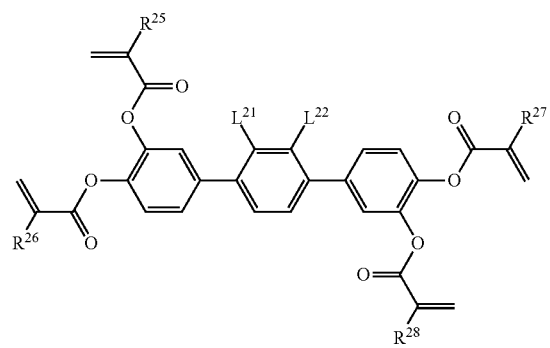
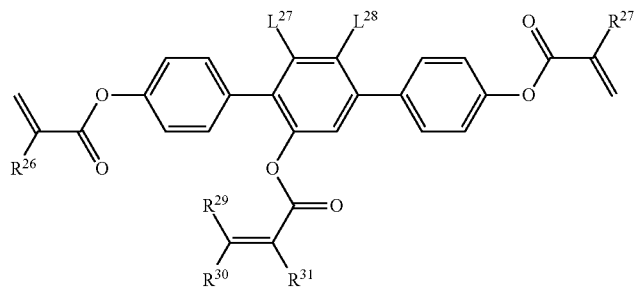
(M-17)

The polymerizable compound can be rapidly polymerized by adding the polymerization initiator. An amount of the remaining polymerizable compound can be decreased by optimizing a reaction temperature. Specific examples of a photoradical polymerization initiator include TPO, 1173 and 4265 from Darocur series of BASF SE, and 184, 369, 500, 651, 784, 819, 907, 1300, 1700, 1800, 1850 and 2959 from Irgacure series.

Additional examples of the photoradical polymerization initiator include 4-methoxyphenyl-2,4-bis(1,3,5-trichloromethyl)triazine, 2-(4-butoxystyryl)-5-trichloromethyl-1,3,4-oxadiazole, 9-phenylacridine, 9,10-benzphenazine, a benzophenone/Michler's ketone mixture, a hexaarylbiimidazole/mercaptobenzimidazole mixture, 1-(4-isopropylphenyl)-2-hydroxy-2-methylpropane-1-one, benzyl dimethyl ketal, 2-methyl-1-[4-(methylthio)phenyl]-2-morpholinopropane-1-one, a 2,4-diethylxanthone/p-dimethylaminobenzoate methyl mixture and a benzophenone/methyltriethanolamine mixture.

After the photoradical polymerization initiator is added to the liquid crystal composition, polymerization can be performed by irradiation with ultraviolet light while an electric field is applied. However, an unreacted polymerization initiator or a decomposition product of the polymerization initiator may cause a poor display such as the image persistence in the device. In order to prevent such an event, photopolymerization may be performed without addition of the polymerization initiator. A preferred wavelength of irradiation light is in the range of 150 nanometers to 500 nanometers. A further preferred wavelength is in the range of 250 nanometers to 450 nanometers, and a most preferred wavelength is in the range of 300 nanometers to 400 nanometers.

Upon storing the polymerizable compound, the polymerization inhibitor may be added thereto for preventing polymerization. The polymerizable compound is ordinarily added to the composition without removing the polymerization inhibitor. Specific examples of the polymerization inhibitor include a hydroquinone derivative such as hydroquinone and methylhydroquinone; 4-t-butylcatechol; 4-methoxyphenol; and phenothiazine.

The optically active compound is effective in inducing a helical structure in liquid crystal molecules to give a required twist angle, and thereby preventing a reverse twist. A helical pitch can be adjusted by adding the optically active compound thereto. Two or more optically active compounds may be added for the purpose of adjusting temperature dependence of the helical pitch. Preferred examples of the optically active compound include compounds (Op-1) to (Op-18) described below. In compound (Op-18), ring J is 1,4-cyclohexylene or 1,4-phenylene, and $R^{28}$ is alkyl having 1 to 10 carbons.

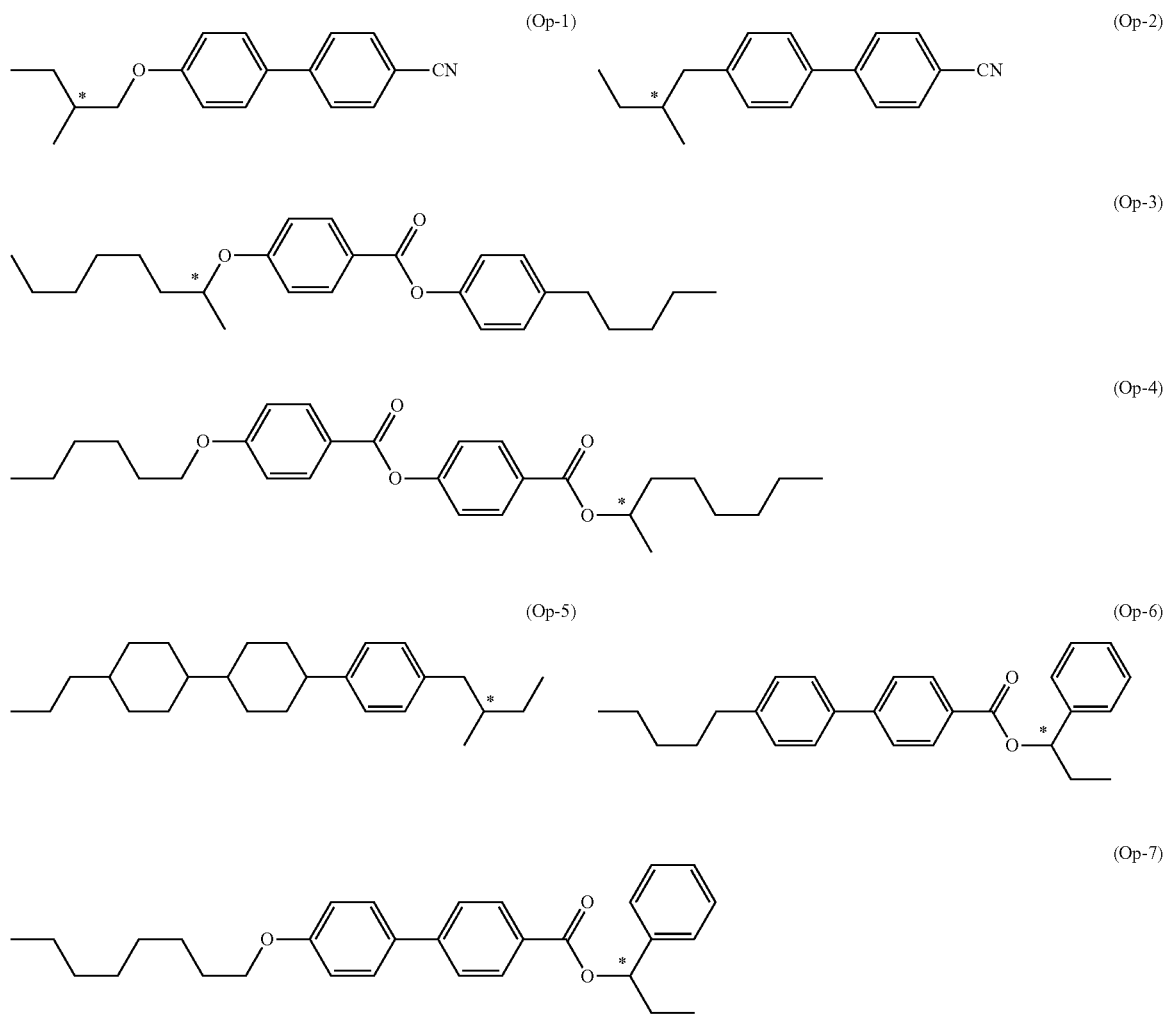

(Op-8)
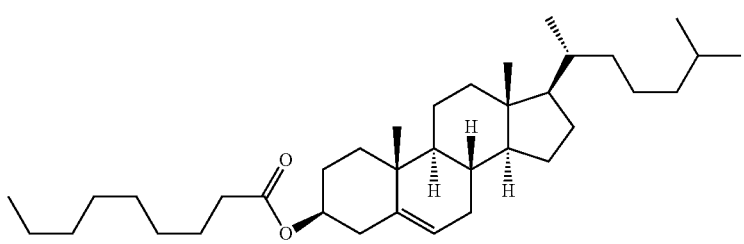
(Op-9)
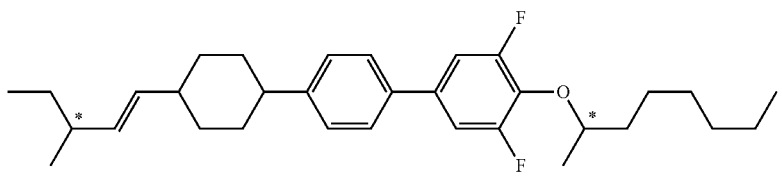
(Op-10)
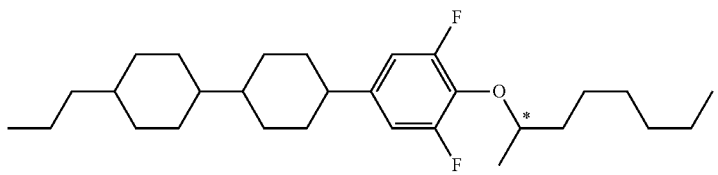
(Op-11)
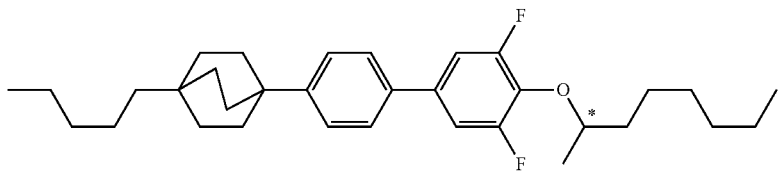
(Op-12)
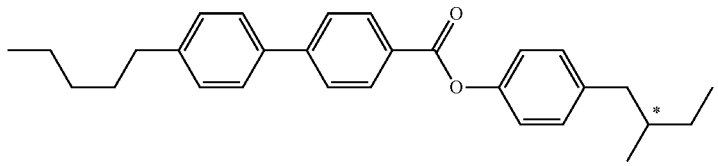
(Op-13)
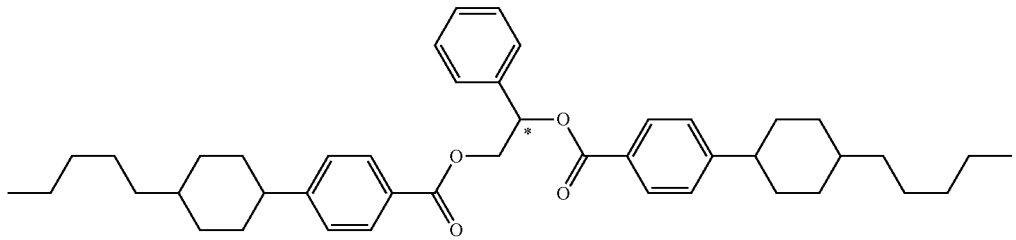
(Op-14)
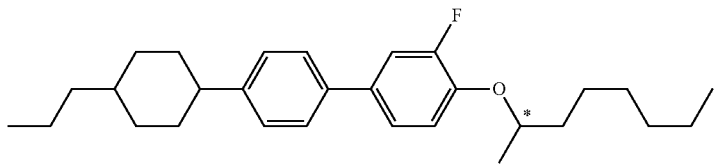
(Op-15)
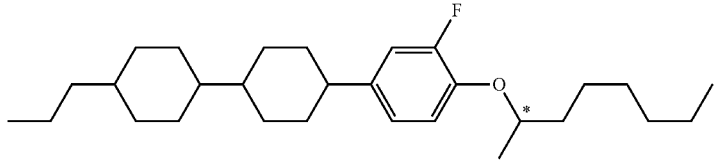

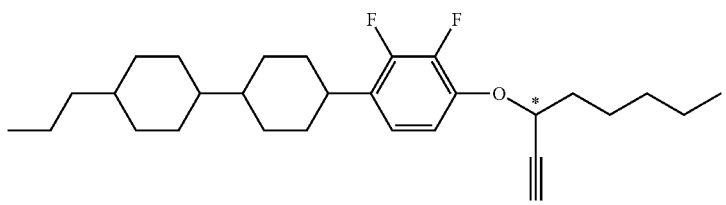

(Op-16)

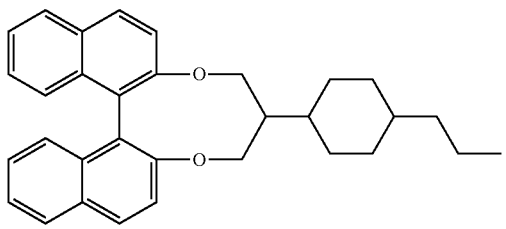

(Op-17)

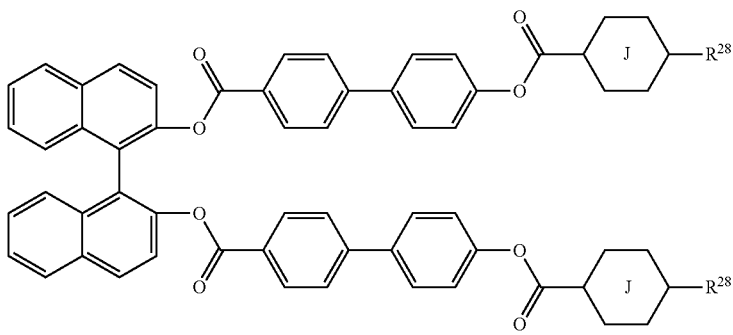

(Op-18)

The antioxidant is effective for maintaining the large voltage holding ratio. Preferred examples of the antioxidant include compounds (AO-1) and (AO-2) described below; IRGANOX 415, IRGANOX 565, IRGANOX 1010, IRGANOX 1035, IRGANOX 3114 and IRGANOX 1098 (trade names: BASF SE). The ultraviolet light absorber is effective for preventing a decrease in the maximum temperature. Preferred examples of the ultraviolet light absorbent include a benzophenone derivative, a benzoate derivative and a triazole derivative, and specific examples includes compound (AO-3) and (AO-4) described below; TINUVIN 329, TINUVIN P, TINUVIN 326, TINUVIN 234, TINUVIN 213, TINUVIN 400, TINUVIN 328, TINUVIN 99-2 (trade names: BASF SE); and 1,4-diazabicyclo[2.2.2]octane (DABCO).

The light stabilizer such as an amine having steric hindrance is preferred for maintaining the large voltage holding ratio. Preferred examples of the light stabilizers include compounds (AO-5) and (AO-6) described below; TINUVIN 144, TINUVIN 765 and TINUVIN 770DF (trade names: BASF SE). The heat stabilizer is also effective for maintaining the large voltage holding ratio, and preferred examples include IRGAFOS 168 (trade names: BASF SE). A dichroic dye such as an azo dye or an anthraquinone dye is added to the composition to be adapted for a device having a guest host (GH) mode. The antifoaming agent is effective for preventing foam formation. Preferred examples of the preferred antifoaming agent include dimethyl silicone oil and methylphenyl silicone oil.

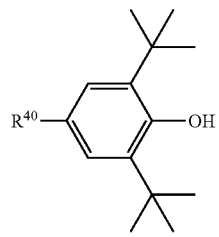

(AO-1)

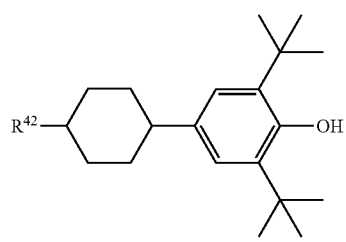

(AO-2)

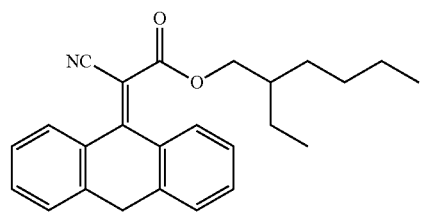

(AO-3)

-continued (AO-4)

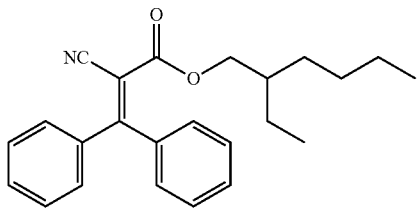

(AO-5)

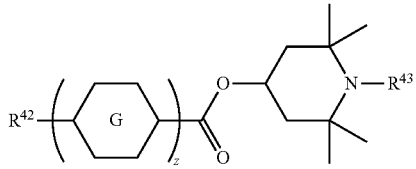

(AO-6)

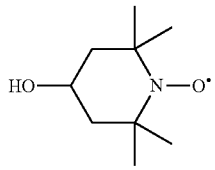

In compound (AO-1), $R^{42}$ is alkyl having 1 to 20 carbons, alkoxy having 1 to 20 carbons, —COOR$^{41}$ or —CH$_2$CH$_2$COOR$^{41}$, where, $R^{41}$ is alkyl having 1 to 20 carbons. In compounds (AO-2) and (AO-5), $R^{42}$ is alkyl having 1 to 20 carbons. In compound (AO-5), $R^{43}$ is hydrogen, methyl or O. (oxygen radical); ring G is 1,4-cyclohexylene or 1,4-phenylene; and z is 1, 2 or 3.

4. Liquid Crystal Display Device

The liquid crystal composition can be used for the liquid crystal device having the operating mode such as the PC mode, the TN mode, the STN mode, the OCB mode and the PSA mode, and driven by an active matrix mode. The composition can also be used for the liquid crystal display device having the operating mode such as the PC mode, the TN mode, the STN mode, the OCB mode, the VA mode and the IPS mode, and driven by a passive matrix mode. The devices can be applied to any of a reflective type, a transmissive type and a transflective type.

The composition is also suitable for a nematic curvilinear aligned phase (NCAP) device, and the composition is microencapsulated herein. The composition can also be used for a polymer dispersed liquid crystal display device (PDLCD) and a polymer network liquid crystal display device (PN-LCD). In the above compositions, a large amount of the liquid crystal compound is added. Meanwhile, when an amount of addition of the polymerizable compound is about 10% by weight or less based on the weight of the liquid crystal composition, the liquid crystal display device having the PSA mode is made. A preferred proportion is in the range of about 0.1% by weight to about 2% by weight. A further preferred proportion is in the range of about 0.2% by weight to about 1.0% by weight based thereon. The device having the PSA mode can be driven by a driving mode such as the active matrix mode and the passive matrix mode. Such devices can be applied to any of the reflective type, the transmissive type and the transflective type.

EXAMPLES

The invention will be described in greater detail by way of Examples (including Synthesis Examples and Use Examples). However, the invention is not limited by the Examples. The invention includes a mixture of a composition in Use Example 1 and a composition in Use Example 2. The invention also contains a composition prepared by mixing at least two of compositions in Use Examples.

1. Example of Compound (1)

Compound (1) was prepared according to procedures described below. The thus prepared compound was identified by methods such as an NMR analysis. Physical properties of the compound and the composition and characteristics of a device were measured by methods described below.

NMR analysis: For measurement, DRX-500 made by Bruker BioSpin Corporation was used. In $^1$H-NMR measurement, a sample was dissolved in a deuterated solvent such as CDCl$_3$, and measurement was carried out under conditions of room temperature, 500 MHz and 16 times of accumulation. Tetramethylsilane was used as an internal standard. In $^{19}$F-NMR measurement, CFCl$_3$ was used as an internal standard, and measurement was carried out under conditions of 24 times of accumulation. In explaining nuclear magnetic resonance spectra, s, d, t, q, quin, sex, m and br stand for a singlet, a doublet, a triplet, a quartet, a quintet, a sextet, a multiplet and a broad, respectively.

Gas chromatographic analysis: For measurement, GC-2010 Gas Chromatograph made by Shimadzu Corporation was used. As a column, a capillary column DB-1 (length 60 m, bore 0.25 mm, film thickness 0.25 µm) made by Agilent Technologies, Inc. was used. As a carrier gas, helium (1 mL/minute) was used. A temperature of a sample vaporizing chamber was set to 300° C., and a temperature of a detector (FID) was set to 300° C. A sample was dissolved in acetone and prepared to be a 1 weight % solution, and then 1 microliter of the solution obtained was injected into the sample vaporizing chamber. As a recorder, GC Solution System made by Shimadzu Corporation or the like was used.

HPLC Analysis: For measurement, Prominence (LC-20AD; SPD-20A) made by Shimadzu Corporation was used. As a column, YMC-Pack ODS-A (length 150 mm, bore 4.6 mm, particle diameter 5 µm) made by YMC Co., Ltd. was used. As an eluate, acetonitrile and water were appropriately mixed and used. As a detector, a UV detector, an RI detector, a CORONA detector or the like was appropriately used. When the UV detector was used, a detection wavelength was set at 254 nanometers. A sample was dissolved in acetonitrile and prepared to be a 0.1 weight % solution, and then 1 microliter of the solution was injected into a sample chamber. As a recorder, C-R$^7$Aplus made by Shimadzu Corporation was used.

Ultraviolet-Visible Spectrophotometry: For measurement, PharmaSpec UV-1700 made by Shimadzu Corporation was used. A detection wavelength was adjusted in the range of 190 nanometers to 700 nanometers. A sample was dissolved in acetonitrile, and prepared to be a solution of 0.01 millimole per liter, and measurement was carried out by putting the solution in a quartz cell (optical path length 1 cm).

Sample for measurement: Upon measuring phase structure and a transition temperature (a clearing point, a melting point, a polymerization starting temperature or the like), a compound itself was used as a sample. Upon measuring physical properties such as a maximum temperature of a nematic phase, viscosity, optical anisotropy and dielectric anisotropy, a mixture of a compound and a base liquid crystal was used as a sample.

When a sample obtained by mixing the compound with the base liquid crystal was used, an extrapolated value was calculated by the following equation, and the value was described. (Extrapolated value)={100×(measured value of a sample)−(% by weight of a base liquid crystal)×(measured value of a base liquid crystal)}/(% by weight of a compound).

Base liquid crystal (A): When the dielectric anisotropy of the compound was zero or positive, base liquid crystal (A) described below was used. A proportion of each component was expressed in terms of % by weight.

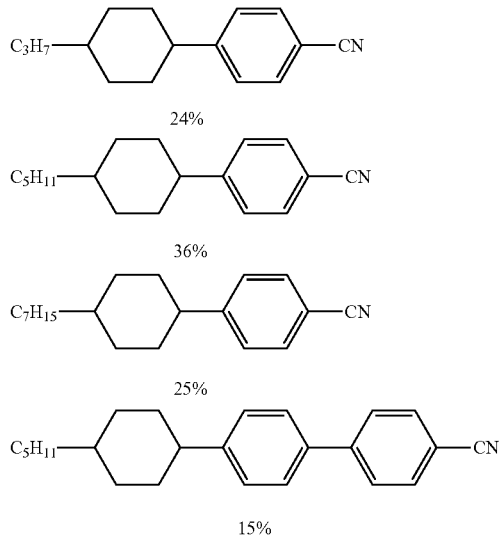

A ratio of the compound to base liquid crystal (A) was set to 15% by weight:85% by weight. When crystals (or a smectic phase) precipitated at the ratio thereof at 25° C., a ratio of the compound to the base liquid crystal was changed step by step in the order of (10% by weight:90% by weight), (5% by weight:95% by weight) and (1% by weight:99% by weight), and a sample was measured at a ratio when no crystals (or no smectic phase) precipitated at 25° C. In addition, unless otherwise noted, the ratio of the compound to base liquid crystal (A) was 15% by weight: 85% by weight.

Base liquid crystal (B): In Comparative Example 2, base liquid crystal (B) containing, as a component, fluorine-based compounds described below was also used. A proportion of each component of base liquid crystal (B) was expressed in terms of % by weight.

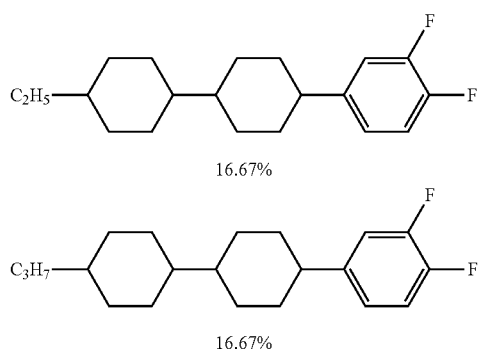

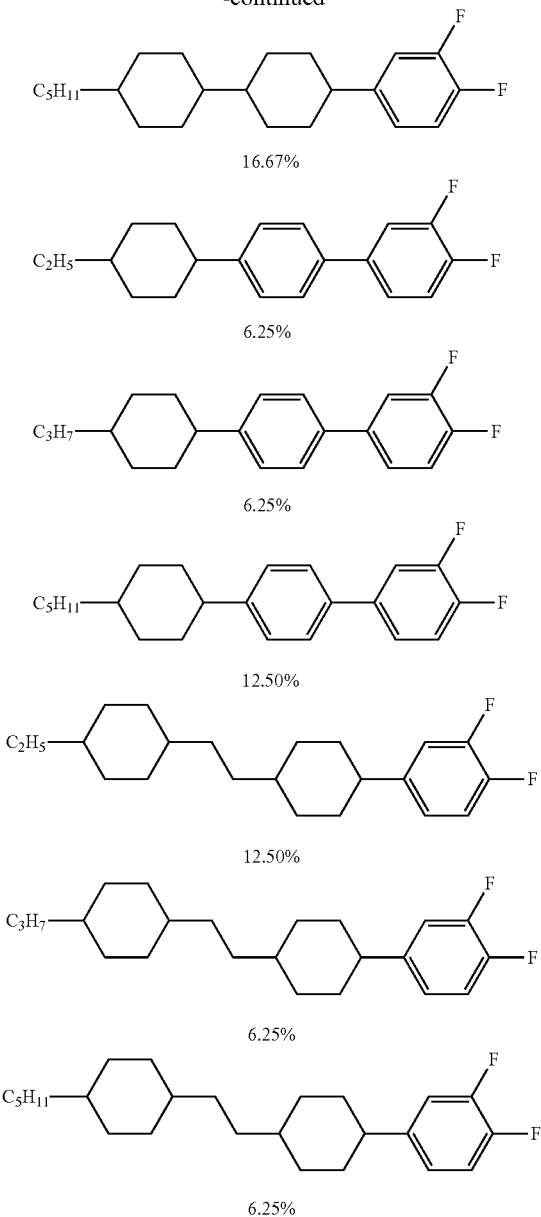

A ratio of the compound to base liquid crystal (B) was set to 20% by weight:80% by weight. When crystals (or a smectic phase) precipitated at the ratio thereof at 25° C., a ratio of the compound to the base liquid crystal was changed step by step in the order of (15% by weight:85% by weight), (10% by weight: 90% by weight) and (5% by weight:95% by weight), and a sample was measured at a ratio when no crystals (or no smectic phase) precipitated at 25° C. In addition, unless otherwise noted, the ratio of the compound to base liquid crystal (B) was 20% by weight:80% by weight.

Measuring method: Measurement of physical properties was carried out by the methods described below. Most of the methods are described in the Standard of Japan Electronics and Information Technology Industries Association (hereinafter, abbreviated as JEITA) discussed and established in JEITA (JEITA ED-2521B). A modification of the methods was also used. No thin film transistor (TFT) was attached to a TN device used for measurement.

(1) Phase Structure

A sample was placed on a hot plate of a melting point apparatus (FP-52 Hot Stage made by Mettler-Toledo International Inc.) equipped with a polarizing microscope. A state of phase and a change thereof were observed with the polarizing microscope while the sample was heated at a rate of 3° C. per minute, and a kind of the phase was specified.

(2) Transition Temperature (° C.)

For measurement, a scanning calorimeter, Diamond DSC System, made by PerkinElmer, Inc., or a high sensitivity differential scanning calorimeter, X-DSC7000, made by SII NanoTechnology Inc. was used. A sample was heated and then cooled at a rate of 3° C. per minute, and a starting point of an endothermic peak or an exothermic peak caused by a phase change of the sample was determined by extrapolation, and thus a transition temperature was determined. A polymerization starting temperature and a melting point of a compound were also measured using the apparatus. Temperature at which a compound undergoes transition from a solid to a liquid crystal phase such as the smectic phase and the nematic phase may be occasionally abbreviated as "minimum temperature of the liquid crystal phase." Temperature at which the compound undergoes transition from the liquid crystal phase to liquid may be occasionally abbreviated as "clearing point."

The crystals were expressed as C. When kinds of the crystals were distinguishable, each of the crystals was expressed as $C_1$ or $C_2$. The smectic phase and the nematic phase were expressed as S and N, respectively. When a smectic A phase, a smectic B phase, a smectic C phase or a smectic F phase was distinguishable among the smectic phases, the phases were expressed as $S_A$, $S_B$, $S_C$ or $S_F$, respectively. A liquid (isotropic) was expressed as I. A transition temperature was expressed as "C, 50.0; N, 100.0; I," for example. The expression indicates that a transition temperature from the crystals to the nematic phase is 50.0° C., and a transition temperature from the nematic phase to the liquid is 100.0° C.

(3) Compatibility at a Low Temperature

Samples in which the base liquid crystal and the compound were mixed for the compound to be 20% by weight, 15% by weight, 10% by weight, 5% by weight, 3% by weight and 1% by weight were prepared, and placed in glass vials. After the glass vials were kept in freezers at −10° C. or −20° C. for a predetermined period of time, whether or not crystals or a smectic phase precipitated was observed.

(4) Maximum Temperature of a Nematic Phase ($T_{NI}$ or NI; ° C.)

A sample was placed on a hot plate of a melting point apparatus equipped with a polarizing microscope, and was heated at a rate of 1° C. per minute. Temperature when part of the sample began to change from a nematic phase to an isotropic liquid was measured. When the sample was a mixture of compound (1) and the base liquid crystal, the maximum temperature was expressed as a symbol $T_{NI}$. When the sample was a mixture of compound (1) and a compound such as component B, compound C and compound D, the maximum temperature was expressed using a symbol NI. A maximum temperature of the nematic phase may be occasionally abbreviated as "maximum temperature."

(5) Minimum Temperature of a Nematic Phase ($T_C$; ° C.)

Samples each having a nematic phase were put in glass vials and kept in freezers at temperatures of 0° C., −10° C., −20° C., −30° C. and −40° C. for 10 days, and then liquid crystal phases were observed. For example, when the sample was maintained in the nematic phase at −20° C. and changed to crystals or a smectic phase at −30° C., $T_C$ of the sample was expressed as Tc<−20° C. A minimum temperature of the nematic phase may be occasionally abbreviated as "minimum temperature."

(6) Viscosity (Bulk Viscosity; η; Measured at 20° C.; mPa·s)

A cone-plate (E type) rotational viscometer made by TOKYO KEIKI INC. was used for measurement.

(7) Viscosity (Rotational Viscosity; γ1; Measured at 25° C.; mPa·s)

Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. A voltage was applied stepwise to the device in the range of 16 V to 19.5 V at an increment of 0.5 V. After a period of 0.2 second with no voltage application, a voltage was repeatedly applied under conditions of only one rectangular wave (rectangular pulse; 0.2 second) and no voltage application (2 seconds). A peak current and a peak time of transient current generated by the applied voltage were measured. A value of rotational viscosity was obtained from the measured values according to calculating equation (8) on page 40 of the paper presented by M. Imai et al. A value of dielectric anisotropy required for the calculation was determined using the device by which the rotational viscosity was measured and by a method described below.

(8) Optical Anisotropy (Refractive Index Anisotropy; Measured at 25° C.; Δn)

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of the optical anisotropy (Δn) was calculated from an equation: Δn=n∥−n⊥.

(9) Dielectric Anisotropy (Δε; Measured at 25° C.)

A sample was put into a TN device in which a distance (cell gap) between two glass substrates was 9 micrometers and a twist angle was 80 degrees. Sine waves (10 V, 1 kHz) were applied to the device, and after 2 seconds, a dielectric constant (∈∥) in a major axis direction of the liquid crystal molecules was measured. Sine waves (0.5 V, 1 kHz) were applied to the device, and after 2 seconds, a dielectric constant (∈⊥) in a minor axis direction of the liquid crystal molecules was measured. A value of dielectric anisotropy was calculated from an equation: Δ∈=∈∥−∈⊥.

(10) Elastic Constant (K; Measured at 25° C.; pN)

For measurement, HP4284A LCR Meter made by Yokogawa-Hewlett-Packard Co. was used. A sample was put in a horizontal alignment device in which a distance (cell gap) between two glass substrates was 20 micrometers. An electric charge of 0 V to 20 V was applied to the device, and electrostatic capacity (C) and an applied voltage (V) were measured. The measured values were fitted to equation (2.98) and equation (2.101) on page 75 of "Liquid Crystal Device Handbook" (Ekisho Debaisu Handobukku, in Japanese; Nikkan Kogyo Shimbun, Ltd.), and values of $K_{11}$ and $K_{33}$ were obtained from equation (2.99). Next, $K_{22}$ was calculated using the previously determined values of $K_{11}$ and $K_{33}$ in equation (3.18) on page 171. Elastic constant K is expressed using a mean value of the thus determined $K_{11}$, $K_{22}$ and $K_{33}$.

(11) Threshold Voltage (Vth; Measured at 25° C.; V)

For measurement, an LCD-5100 luminance meter made by Otsuka Electronics Co., Ltd. was used. A light source was a halogen lamp. A sample was put in a normally white mode TN device in which a distance (cell gap) between two glass substrates was 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage was expressed in terms of a voltage at 90% transmittance.

(12) Voltage Holding Ratio (VHR-1; Measured at 25° C.; %)

A TN device used for measurement had a polyimide alignment film, and a distance (cell gap) between two glass substrates was 5 micrometers. A sample was put in the device, and the device was sealed with an ultraviolet-curable adhesive. The device was charged by applying a pulse voltage (60 microseconds at 5 V) at 25° C. A decaying voltage was measured for 16.7 milliseconds with a high-speed voltmeter, and area A between a voltage curve and a horizontal axis in a unit cycle was determined. Area B was an area without decay. A voltage holding ratio was expressed in terms of a percentage of area A to area B.

(13) Voltage Holding Ratio (VHR-2; Measured at 80° C.; %)

A voltage holding ratio was measured according to the method described above except that a sample was measured at 80° C. in place of 25° C. The thus obtained value was expressed in terms of VHR-2.

(14) Specific Resistance (ρ; Measured at 25° C.; ΩCm)

Into a vessel equipped with electrodes, 1.0 milliliter of a sample was injected. A direct current voltage (10V) was applied to the vessel, and a direct current after 10 seconds was measured. Specific resistance was calculated from the following equation: (specific resistance)={(voltage)×(electric capacity of a vessel)}/{(direct current)×(dielectric constant of vacuum)}.

(15) Response Time (τ; Measured at 25° C.; Ms)

For measurement, an LCD-5100 luminance meter made by Otsuka Electronics Co., Ltd. was used. A light source was a halogen lamp. A light source was a halogen lamp. A low-pass filter was set to 5 kHz. A sample was put in a normally white mode TN device in which a distance (cell gap) between two glass substrates was 5.0 micrometers and a twist angle was 80 degrees. Rectangular waves (60 Hz, 5 V, 0.5 second) were applied to the device. On the occasion, the device was irradiated with light from a direction perpendicular to the device, and an amount of light transmitted through the device was measured. The maximum amount of light corresponds to 100% transmittance and the minimum amount of light corresponds to 0% transmittance. A rise time (τr; ms) was expressed in terms of time required for a change from 90% transmittance to 10% transmittance. A fall time (τf; ms) was expressed in terms of time required for a change from 10% transmittance to 90% transmittance. A response time was represented by a sum of the rise time and the fall time thus obtained.

Raw Material

Solmix A-11 (registered trademark) is a mixture of ethanol (85.5%), methanol (13.4%) and isopropanol (1.1%), and was purchased from Japan Alcohol Trading Co., Ltd. Tetrahydrofuran may be occasionally abbreviated as THF. Tetrabutylammonium bromide may be occasionally abbreviated as TBAB. N,N-dimethylformamide may be occasionally abbreviated as DMF. Then, 2-propanol may be occasionally abbreviated as IPA. Then, 1,2-dimethoxyethane may be occasionally abbreviated as DME. Hexamethyldisilazane potassium may be occasionally abbreviated as KHMDS.

Example 1

Synthesis of Compound (No. 61)

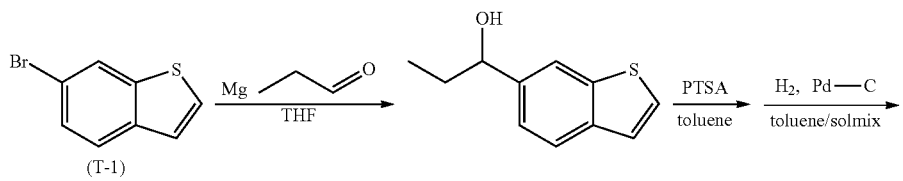

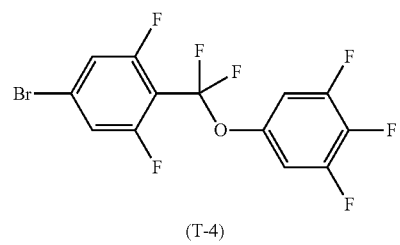

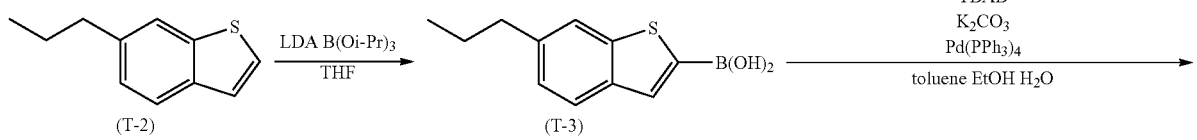

-continued

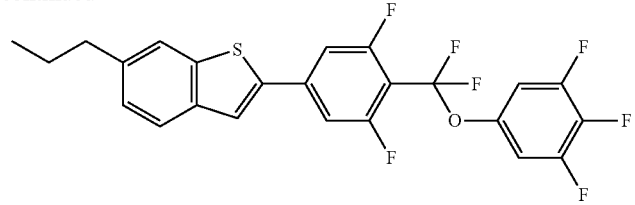

NO. 61

First Step

Under a nitrogen atmosphere, compound (T-1) (3 g) and THF (100 mL) were put in a reaction vessel, and the resulting mixture was cooled to 0° C. Magnesium (0.36 g) was added thereto, and the resulting mixture was stirred for 2 hours. Propanal (0.98 g) was added thereto, the resulting mixture was returned to room temperature, and stirred for 1 hour. The reaction solution was poured into water, and subjected to extraction with toluene. Organic layers combined were washed with water, a saturated aqueous solution of sodium hydrogencarbonate and water, and dried over anhydrous magnesium sulfate. Ten, p-toluenesulfonic acid monohydrate (1 g) was added thereto, and the resulting mixture was refluxed for 1 hour while removing water. The resulting mixture was returned to room temperature, the solution was purified by silica gel column chromatography (toluene), and concentrated into a 100 milliliter solution. Palladium on carbon (1 g) and Solmix (100 mL) were added thereto, and the resulting mixture was stirred under a hydrogen atmosphere overnight. The reaction solution was filtered and concentrated to obtain compound (T-2) (2.8 g).

Second Step

Under a nitrogen atmosphere, compound (T-2) (2.8 g) and THF (100 mL) were put in a reaction vessel, and the resulting mixture was cooled to −60° C. Lithium diisopropylamide (1 M; n-hexane solution; 19.06 mL) was added dropwise thereto, and the resulting mixture was stirred for 2 hours. Then, a THF (10 mL) solution of triisobutyl borate (4.18 g) was added dropwise thereto, and the resulting mixture was stirred for 2 hours while returning to room temperature. The reaction mixture was poured into a hydrochloric acid aqueous solution, and subjected to extraction with ethyl acetate. Organic layers combined were washed with water, a saturated aqueous solution of sodium hydrogencarbonate and water, and dried over anhydrous magnesium sulfate. The resulting solution was concentrated under reduced pressure to obtain compound (T-3) (3.3 g).

Third Step (T-3) (3.3 g) and (T-4) (7 g) commercially available were dissolved in toluene, and water, ethanol, Pd(PPh$_3$)$_4$ (1.7 g), TBAB (0.48 g) and potassium carbonate (6.2 g) were added thereto, and the resulting mixture was heated and refluxed for 6 hours. After completion of the reaction, the reaction solution was subjected to extraction with toluene, and the extract was washed with water and dried over anhydrous magnesium sulfate, and concentrated under reduced pressure to obtain a light-brown solid. The solid was dissolved into a solution, and the solution was subjected to silica gel column chromatography (heptane) and recrystallization (ethanol) to obtain (No. 61) (1.6 g) as a colorless crystal.

$^1$H-NMR (δ ppm; CDCl$_3$): 7.72 (d, 1H), 7.65 (s, 1H), 7.60 (s, 1H), 7.30 (d, 2H), 7.23 (dd, 1H), 6.98 (t, 2H), 2.72 (t, 2H), 1.70 (sex, 2H) and 0.97 (t, 3H).

Physical properties of compound (No. 61) were as described below. Transition temperature: C, 87.3; I. T$_{NI}$=54.4° C.; Δn=0.190; Δ∈=26.1; η=81 mPa·s.

Example 2

Preparation of Compound (No. 71)

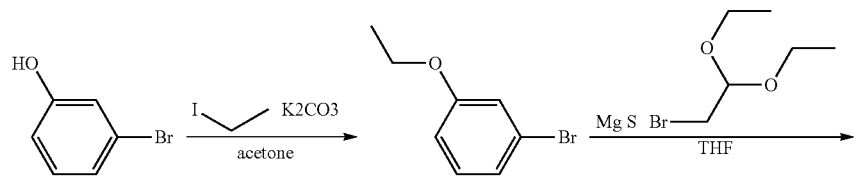

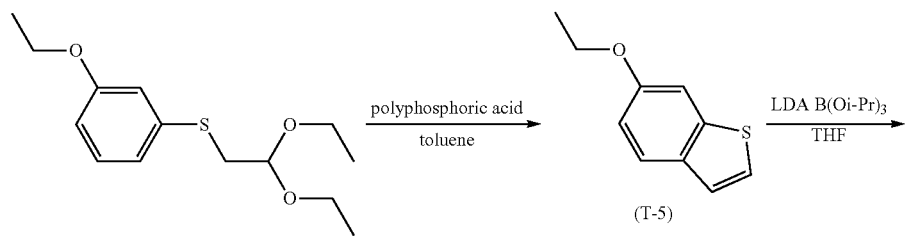

-continued

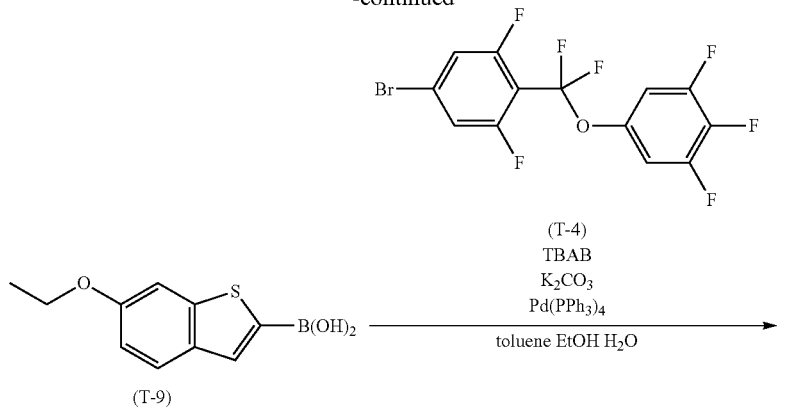

(T-4)
TBAB
K₂CO₃
Pd(PPh₃)₄
toluene EtOH H₂O

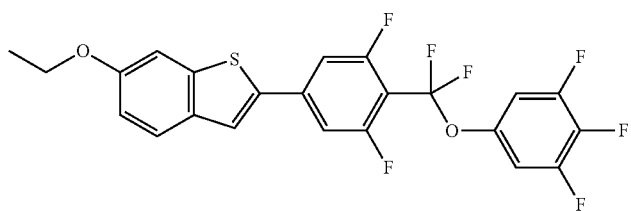

NO.71

Compound (No. 71) was obtained by using compound (T-5) in place of compound (T-2) in Example 1. In addition, (T-5) was prepared by a known method according to the scheme described above.

$^1$H-NMR (δ ppm; CDCl$_3$): 7.68 (d, 1H), 7.55 (s, 1H), 7.29 (d, 1H), 7.26 (d, 2H), 7.01 (dd, 1H), 6.98 (t, 2H), 4.12 (q, 2H) and 1.47 (t, 3H).

Physical properties of compound (No. 71) were as described below. Transition temperature: C, 123; I. $T_{NI}$=85.7° C.; Δn=0.217; Δ∈=27.9; η=76.8 mPa·s.

Example 3

Synthesis of Compound (No. 151)

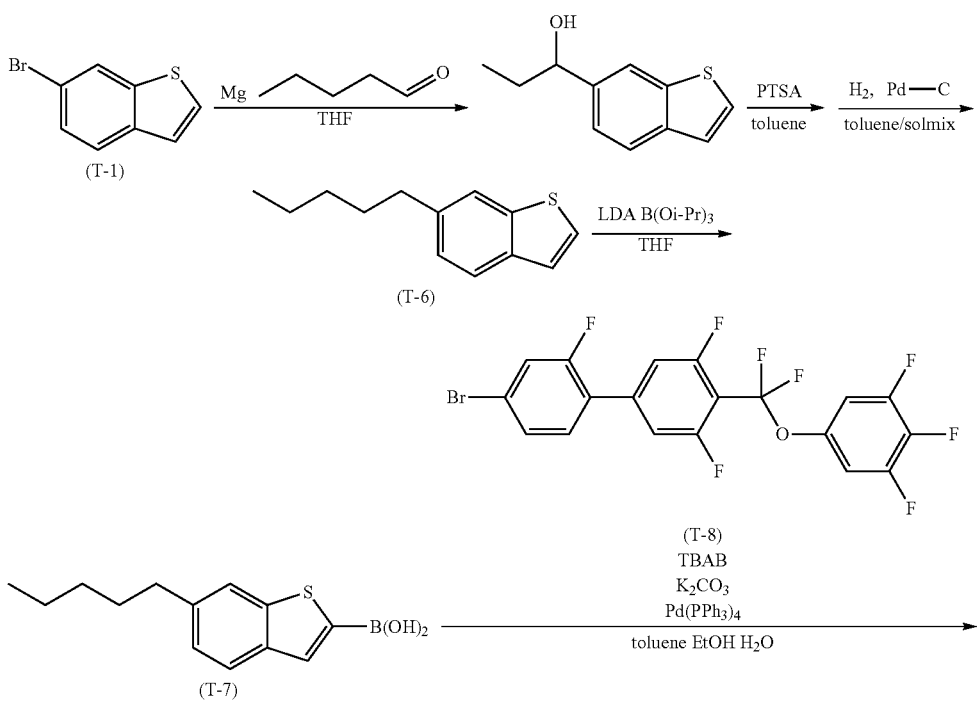

-continued

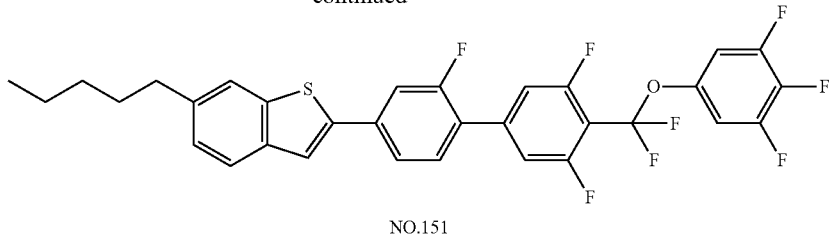

NO.151

Compound (No. 151) was obtained by preparing (T-6) and then (T-7) by using pentanal in place of propanal in the first step in Example 1, and by using (T-8) in place of (T-4) in the third step. In addition, (T-8) can be prepared by the method described in WO 2009-139330 A, or the like.

$^1$H-NMR (δ ppm; CDCl$_3$): 7.71 (d, 1H), 7.65 (s, 1H), 7.60 (s, 1H), 7.59 (dd, 1H), 7.52 (dd, 1H), 7.47 (t, 1H), 7.26 (t, 2H), 7.22 (dd, 1H), 7.00 (t, 2H), 2.73 (t, 2H), 1.67 (quint, 2H), 1.38-1.33 (m, 4H) and 0.91 (t, 3H).

Physical properties of compound (No. 151) were as described below. Transition temperature: C, 92; N, 194; I. $T_{NI}$=137.7° C.; Δn=0.257; Δ∈=29.9; η=108.9 mPa·s.

Comparative Example

Compound (1) was compared with similar compounds from a viewpoint of physical properties. When a sample obtained by mixing the compound with a base liquid crystal was used, a proportion thereof was determined by the method described in the paragraph for base liquid crystal (A) and base liquid crystal (B).

Example 4

Synthesis of compound (No. 74)

Under a nitrogen atmosphere, compound (No. 71) (1.8 g), tetramethylethylenediamine (0.86 g) and diethyl ether (100 mL) were put in a reaction vessel, and the resulting mixture was cooled to −60° C. Then, n-BuLi (1.6 M; n-hexane solution; 4.86 mL) was added dropwise thereto, and the resulting mixture was stirred for 2 hours. N-fluorobenzene sulfonimide (2.68 g) was added thereto, the resulting mixture was returned to room temperature, and stirred for 1 hour. The reaction solution was poured into water, and subjected to extraction with toluene. Organic layers combined were washed with water, and dried over anhydrous magnesium sulfate, and concentrated under reduced pressure to obtain a light-brown solid. The solid was dissolved into a solution, and the solution was subjected to silica gel column chromatography (heptane) and recrystallization (ethanol) to obtain (No. 74) (0.97 g) as a colorless crystal.

$^1$H-NMR (δ ppm; CDCl$_3$): 7.68 (d, 1H), 7.32 (d, 2H), 7.19 (s, 1H), 7.06 (dd, 1H), 6.98 (t, 2H), 4.12 (q, 2H) and 1.48 (t, 3H).

Physical properties of compound (No. 74) were as described below. Transition temperature: C, 125.2; I. $T_{NI}$=91.7° C.; Δn=0.237; Δ∈=38.6; η=66.8 mPa·s.

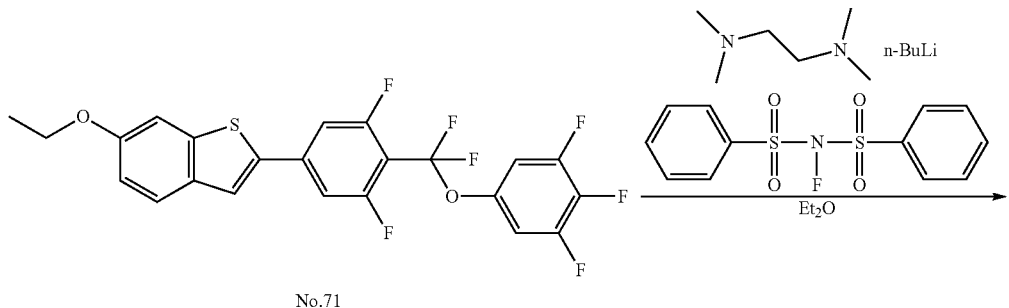

No.71

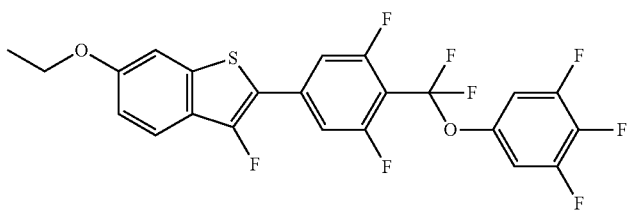

No.74

Example 5
Synthesis of Compound (No. 211)
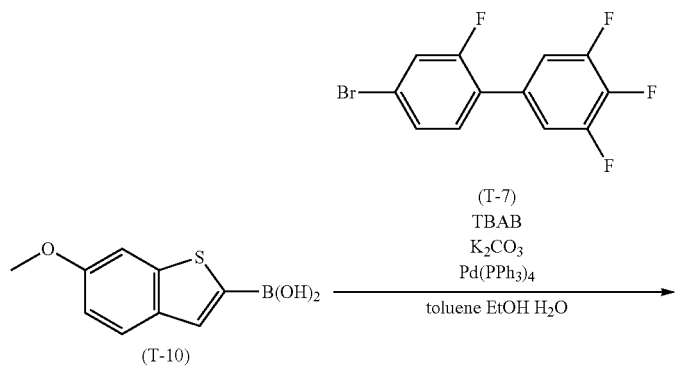
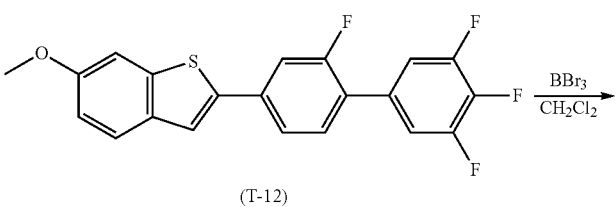
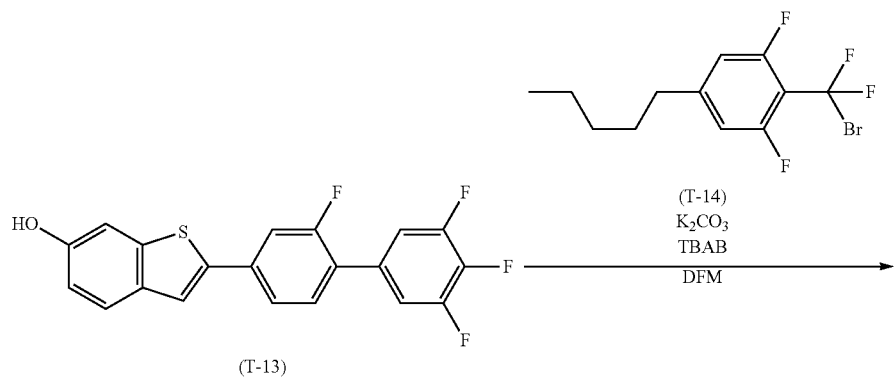
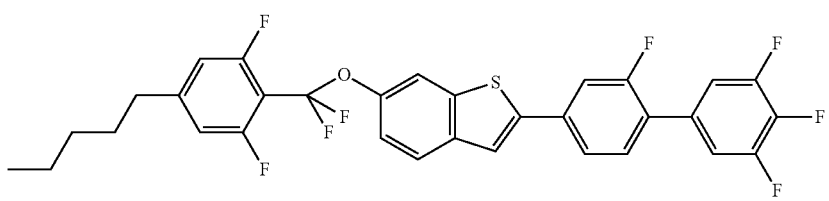
No. 211

First Step (T-10) (2.7 g) and (T-7) (4 g) were dissolved in toluene, and water, ethanol, Pd(PPh$_3$)$_4$ (1.5 g), TBAB (0.42 g) and potassium carbonate (5.4 g) were added thereto, and the resulting mixture was heated and refluxed for 6 hours. After completion of the reaction, the reaction solution was subjected to extraction with toluene, and the extract was washed with water, and dried over anhydrous magnesium sulfate, and concentrated under reduced pressure to obtain a light-brown solid. The solid was dissolved into a solution, and the solution was subjected to silica gel column chromatography (heptane) and recrystallization (ethanol) to obtain (T-12) (5 g) as a colorless crystal.

Second Step

Under a nitrogen atmosphere, compound (T-12) (5 g) and dichloromethane (100 mL) were put in a reaction vessel, and the resulting mixture was cooled to about 5° C. Boron tribromide (4.84 g) was added thereto, and the resulting mixture was stirred for 2 hours. The reaction mixture was slowly poured into ice water, and subjected to extraction with ethyl acetate. Organic layers combined were washed with water, and dried over anhydrous magnesium sulfate. The solution was concentrated under reduced pressure to obtain compound (T-13) (4.82 g).

Third Step

Under a nitrogen atmosphere, compound (T-13) (2 g), (T-14) (2.5 g), calcium carbonate (2.2 g), TBAB (0.42 g) and DMF (100 mL) were put in a reaction vessel, and the resulting mixture was stirred at 70° C. for 2 hours. The reaction solution was poured into water, and subjected to extraction with toluene. Organic layers combined were washed with water, and dried over anhydrous magnesium sulfate, and concentrated under reduced pressure to obtain a light-brown solid. The solid was dissolved into a solution, and the solution was subjected to silica gel column chromatography (heptane) and recrystallization (ethanol) to obtain (No. 211) (2.2 g) as a colorless crystal.

$^1$H-NMR (δ ppm; CDCl$_3$): 7.76 (s, 1H), 7.75 (d, 1H), 7.57 (s, 1H), 7.54 (dd, 1H), 7.48 (dd, 1H), 7.43 (t, 1H), 7.31 (dd, 1H), 7.22 (t, 2H), 6.80 (d, 2H), 2.61 (t, 2H), 1.61 (quint, 2H), 1.36-1.28 (m, 4H) and 0.90 (t, 3H).

Physical properties of compound (No. 211) were as described below. Transition temperature: C, 111; N, 175; I. T$_{NI}$=110.7° C.; Δn=0.237; Δ∈=27.9; η=119 mPa·s.

Comparative Example 1

Compound (S-1) described below similar to compound (No. 61) was selected. (S-1) was a known compound.

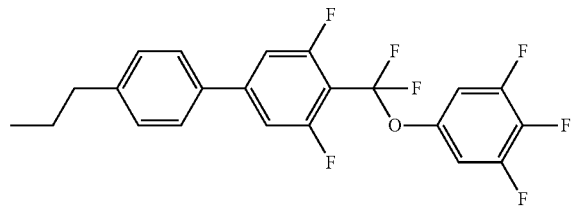

(S-1)

Physical properties of compound (S-1) were as described below. Transition temperature: C, 45.9; I. T$_{NI}$=−4.3° C.; Δn=0.12; Δ∈=27.7; η=37.2 mPa·s.

Compound (No. 61) according to the invention exhibited a higher maximum temperature (T$_{NI}$=54.4) and larger optical anisotropy (Δn=0.190) in comparison with compound (S-1).

According to the synthesis method of compound (1) described above and the synthesis procedures described in Examples 1 and 2, compounds (No. 1) to (No. 210) described below can be prepared.

| No. | |
|---|---|
| 1 | 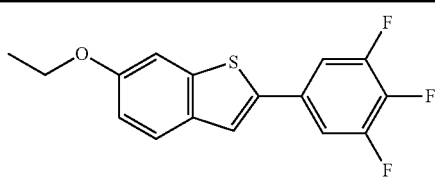 |
| 2 | 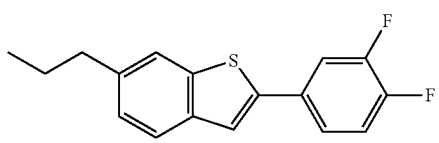 [SMILES: CCCc1ccc2cc(-c3ccc(F)c(F)c3)sc2c1] |
| 3 | 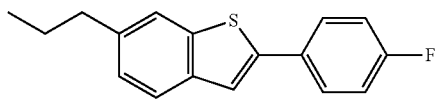 [SMILES: CCCc1ccc2cc(-c3ccc(F)cc3)sc2c1] |
| 4 | 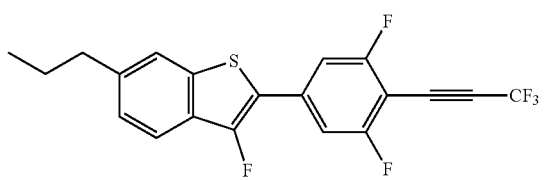 [SMILES: CCCc1ccc2c(F)c(-c3cc(F)c(C#CC(F)(F)F)c(F)c3)sc2c1] |

| No. | |
|---|---|
| 5 | 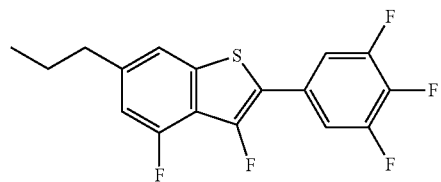 [SMILES: CCCc1cc(F)c2c(F)c(-c3cc(F)c(F)c(F)c3)sc2c1] |
| 6 | 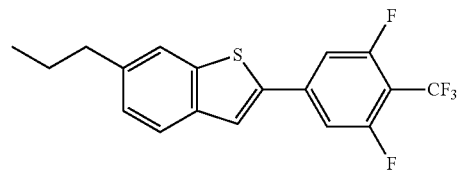 [SMILES: CCCc1ccc2cc(-c3cc(F)c(C(F)(F)F)c(F)c3)sc2c1] |
| 7 | 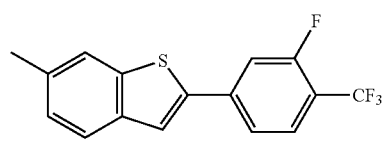 [SMILES: Cc1ccc2cc(-c3ccc(C(F)(F)F)c(F)c3)sc2c1] |
| 8 | 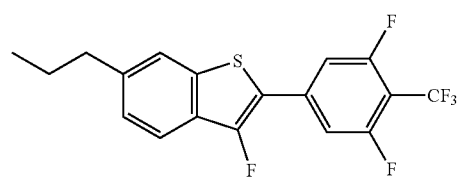 [SMILES: CCCc1ccc2c(F)c(-c3cc(F)c(C(F)(F)F)c(F)c3)sc2c1] |
| 9 | 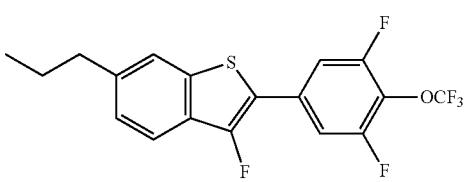 [SMILES: CCCc1ccc2c(F)c(-c3cc(F)c(OC(F)(F)F)c(F)c3)sc2c1] |
| 10 | 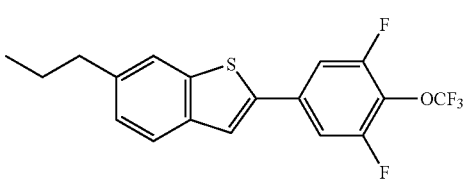 [SMILES: CCCc1ccc2cc(-c3cc(F)c(OC(F)(F)F)c(F)c3)sc2c1] |
| 11 | 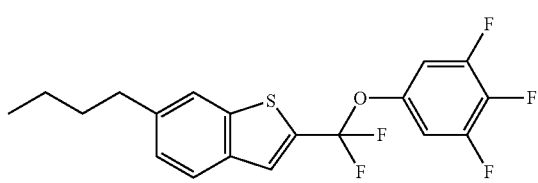 [SMILES: CCCCc1ccc2cc(C(F)(F)Oc3cc(F)c(F)c(F)c3)sc2c1] |
| 12 | 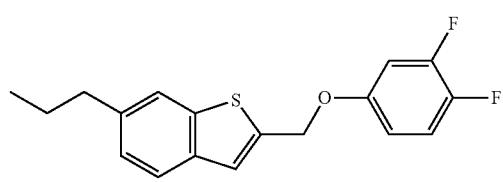 [SMILES: CCCc1ccc2cc(COc3ccc(F)c(F)c3)sc2c1] |
| 13 | 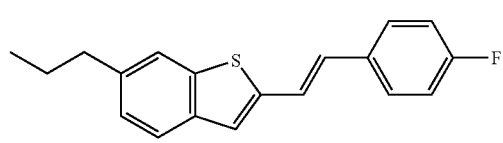 [SMILES: CCCc1ccc2cc(/C=C/c3ccc(F)cc3)sc2c1] |

-continued
| No. | |
|---|---|
| 14 | 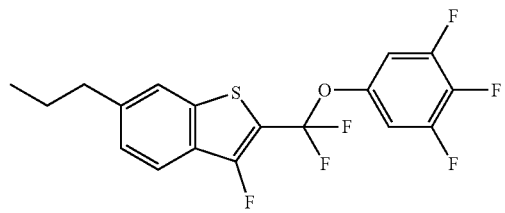 [SMILES: CCCc1ccc2c(F)c(C(F)(F)Oc3cc(F)c(F)c(F)c3)sc2c1] |
| 15 | 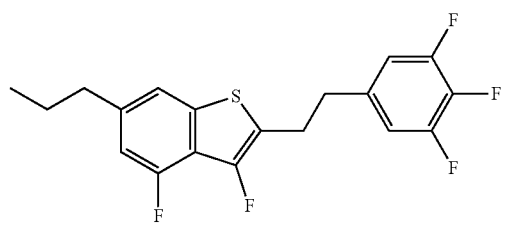 [SMILES: CCCc1cc(F)c2c(F)c(CCc3cc(F)c(F)c(F)c3)sc2c1] |
| 16 | 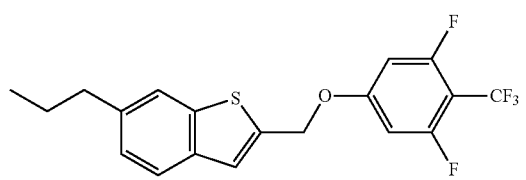 [SMILES: CCCc1ccc2cc(COc3cc(F)c(C(F)(F)F)c(F)c3)sc2c1] |
| 17 | 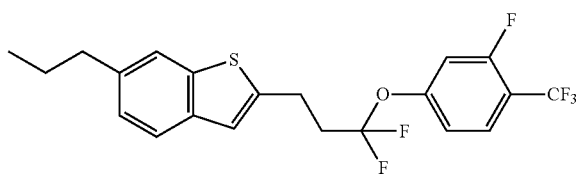 [SMILES: CCCc1ccc2cc(CCC(F)(F)Oc3ccc(C(F)(F)F)c(F)c3)sc2c1] |
| 18 | 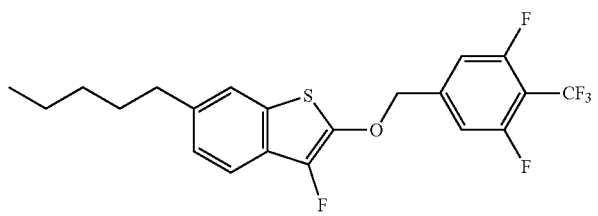 [SMILES: CCCCCc1ccc2c(F)c(OCc3cc(F)c(C(F)(F)F)c(F)c3)sc2c1] |
| 19 | 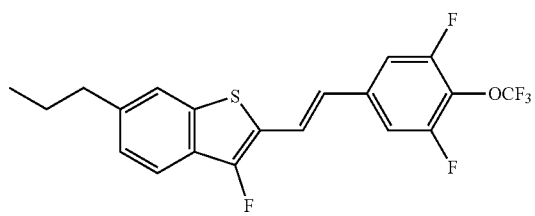 [SMILES: CCCc1ccc2c(F)c(/C=C/c3cc(F)c(OC(F)(F)F)c(F)c3)sc2c1] |
| 20 | 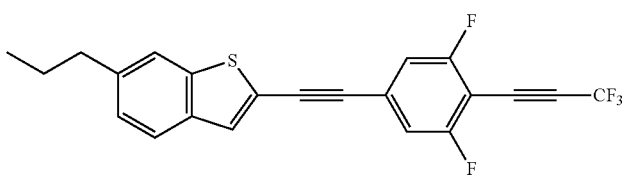 [SMILES: CCCc1ccc2cc(C#Cc3cc(F)c(C#CC(F)(F)F)c(F)c3)sc2c1] |

| No. | |
|---|---|
| 21 | 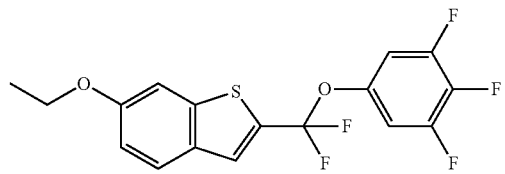 [SMILES: CCOc1ccc2cc(C(F)(F)Oc3cc(F)c(F)c(F)c3)sc2c1] |
| 22 | 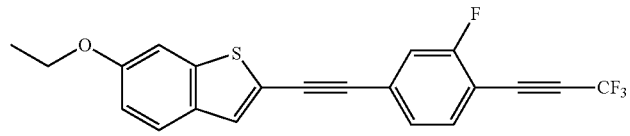 [SMILES: CCOc1ccc2cc(C#Cc3ccc(C#CC(F)(F)F)c(F)c3)sc2c1] |
| 23 | 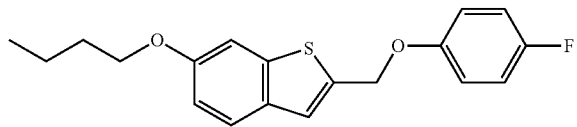 [SMILES: CCCCOc1ccc2cc(COc3ccc(F)cc3)sc2c1] |
| 24 | 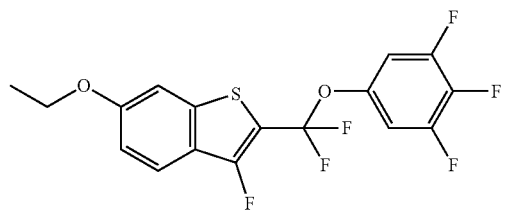 [SMILES: CCOc1ccc2c(F)c(C(F)(F)Oc3cc(F)c(F)c(F)c3)sc2c1] |
| 25 | 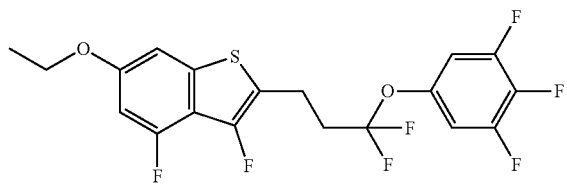 [SMILES: CCOc1cc(F)c2c(F)c(CCC(F)(F)Oc3cc(F)c(F)c(F)c3)sc2c1] |
| 26 | 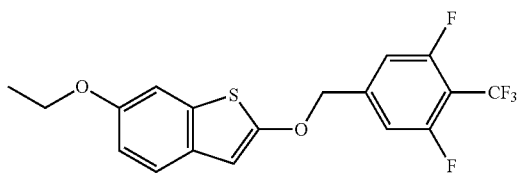 [SMILES: CCOc1ccc2cc(OCc3cc(F)c(C(F)(F)F)c(F)c3)sc2c1] |
| 27 | 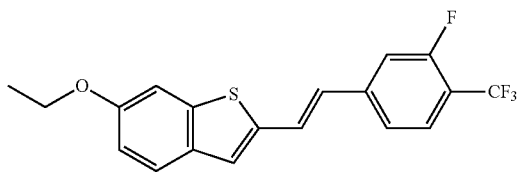 [SMILES: CCOc1ccc2cc(/C=C/c3ccc(C(F)(F)F)c(F)c3)sc2c1] |
| 28 | 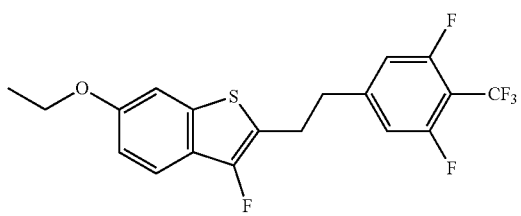 [SMILES: CCOc1ccc2c(F)c(CCc3cc(F)c(C(F)(F)F)c(F)c3)sc2c1] |

-continued
| No. | |
|---|---|
| 29 | 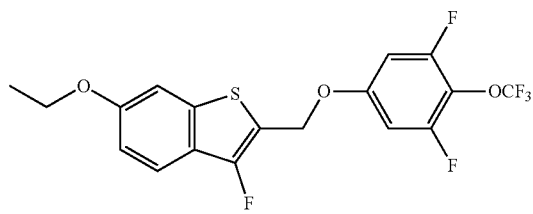 [SMILES: CCOc1ccc2c(F)c(COc3cc(F)c(OC(F)(F)F)c(F)c3)sc2c1] |
| 30 | 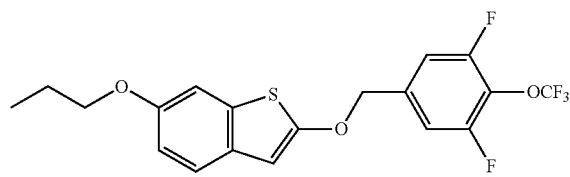 [SMILES: CCCOc1ccc2cc(OCc3cc(F)c(OC(F)(F)F)c(F)c3)sc2c1] |
| 31 | 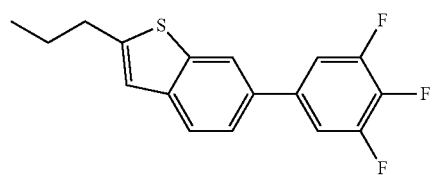 [SMILES: CCCc1cc2ccc(-c3cc(F)c(F)c(F)c3)cc2s1] |
| 32 | 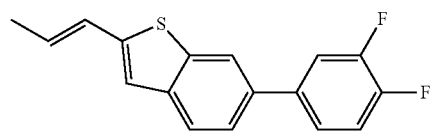 [SMILES: C/C=C/c1cc2ccc(-c3ccc(F)c(F)c3)cc2s1] |
| 33 | 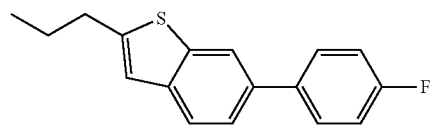 [SMILES: CCCc1cc2ccc(-c3ccc(F)cc3)cc2s1] |
| 34 | 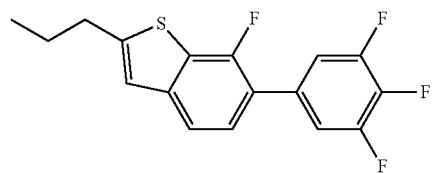 [SMILES: CCCc1cc2ccc(-c3cc(F)c(F)c(F)c3)c(F)c2s1] |
| 35 | 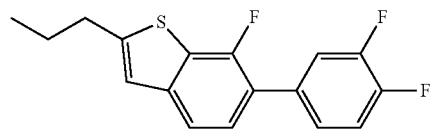 [SMILES: CCCc1cc2ccc(-c3ccc(F)c(F)c3)c(F)c2s1] |
| 36 | 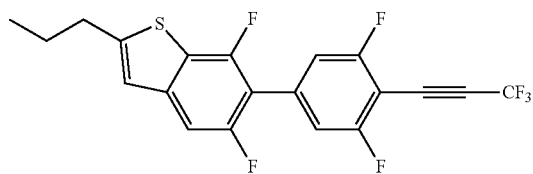 [SMILES: CCCc1cc2cc(F)c(-c3cc(F)c(C#CC(F)(F)F)c(F)c3)c(F)c2s1] |
| 37 | 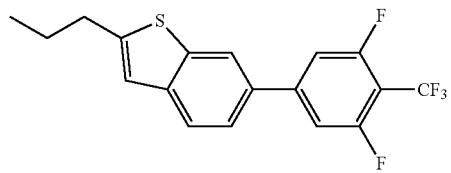 [SMILES: CCCc1cc2ccc(-c3cc(F)c(C(F)(F)F)c(F)c3)cc2s1] |

-continued
| No. | |
|---|---|
| 38 | 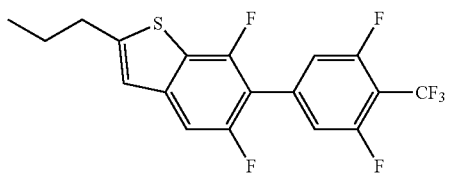 [SMILES: CCCc1cc2cc(F)c(-c3cc(F)c(C(F)(F)F)c(F)c3)c(F)c2s1] |
| 39 | 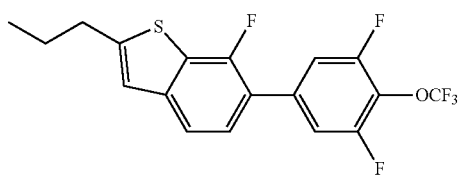 [SMILES: CCCc1cc2ccc(-c3cc(F)c(OC(F)(F)F)c(F)c3)c(F)c2s1] |
| 40 | 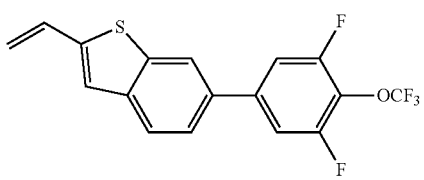 [SMILES: C=Cc1cc2ccc(-c3cc(F)c(OC(F)(F)F)c(F)c3)cc2s1] |
| 41 | 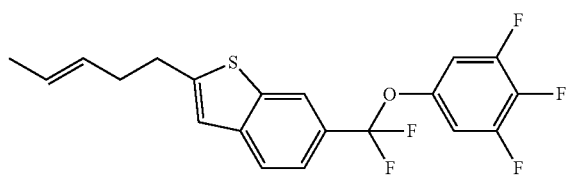 [SMILES: C/C=C/CCc1cc2ccc(C(F)(F)Oc3cc(F)c(F)c(F)c3)cc2s1] |
| 42 | 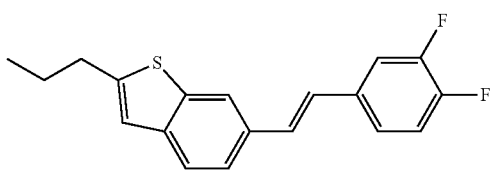 [SMILES: CCCc1cc2ccc(/C=C/c3ccc(F)c(F)c3)cc2s1] |
| 43 | 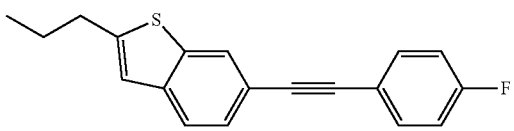 [SMILES: CCCc1cc2ccc(C#Cc3ccc(F)cc3)cc2s1] |
| 44 | 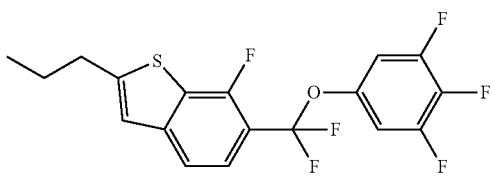 [SMILES: CCCc1cc2ccc(C(F)(F)Oc3cc(F)c(F)c(F)c3)c(F)c2s1] |
| 45 | 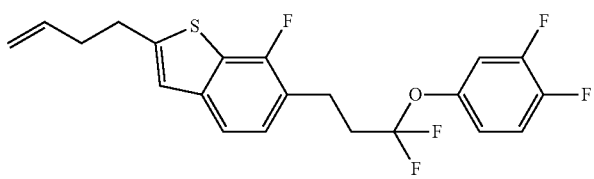 [SMILES: C=CCCc1cc2ccc(CCC(F)(F)Oc3ccc(F)c(F)c3)c(F)c2s1] |

-continued
| No. |
|---|
| 46 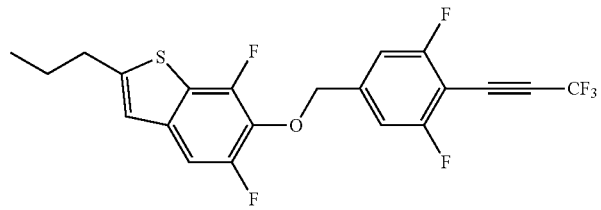 [SMILES: CCCc1cc2cc(F)c(OCc3cc(F)c(C#CC(F)(F)F)c(F)c3)c(F)c2s1] |
| 47 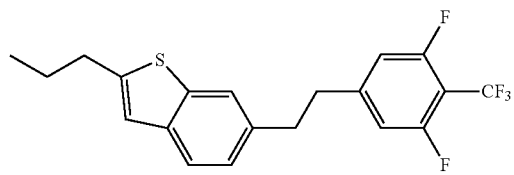 [SMILES: CCCc1cc2ccc(CCc3cc(F)c(C(F)(F)F)c(F)c3)cc2s1] |
| 48 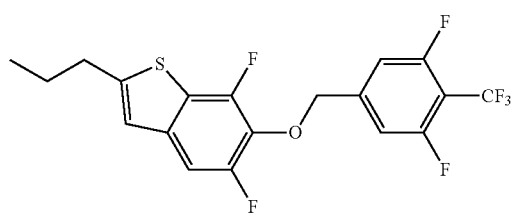 [SMILES: CCCc1cc2cc(F)c(OCc3cc(F)c(C(F)(F)F)c(F)c3)c(F)c2s1] |
| 49 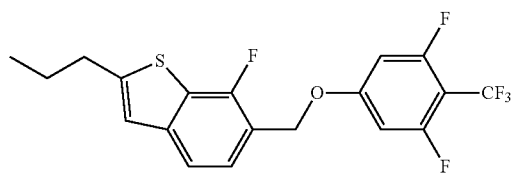 [SMILES: CCCc1cc2ccc(COc3cc(F)c(C(F)(F)F)c(F)c3)c(F)c2s1] |
| 50 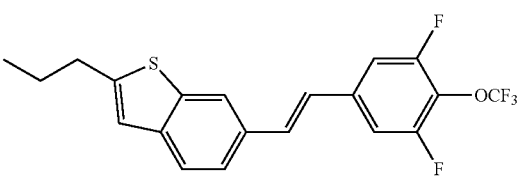 [SMILES: CCCc1cc2ccc(/C=C/c3cc(F)c(OC(F)(F)F)c(F)c3)cc2s1] |
| 51 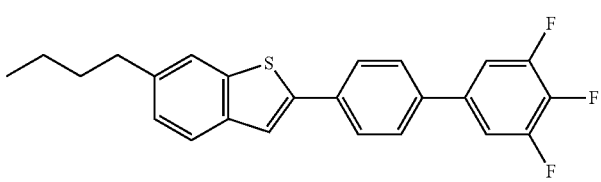 [SMILES: CCCCc1ccc2cc(-c3ccc(-c4cc(F)c(F)c(F)c4)cc3)sc2c1] |
| 52 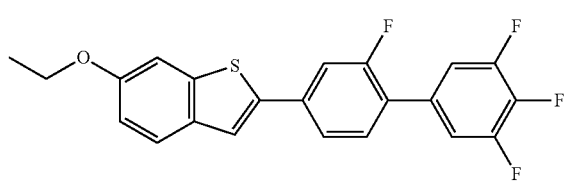 [SMILES: CCOc1ccc2cc(-c3ccc(-c4cc(F)c(F)c(F)c4)c(F)c3)sc2c1] |
| 53 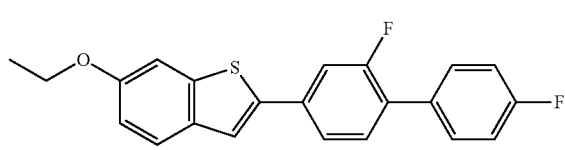 [SMILES: CCOc1ccc2cc(-c3ccc(-c4ccc(F)cc4)c(F)c3)sc2c1] |

-continued
| No. | |
|---|---|
| 54 | 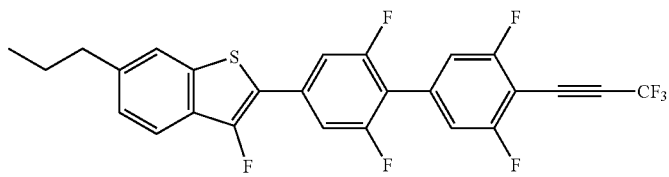 [SMILES: CCCc1ccc2c(F)c(-c3cc(F)c(-c4cc(F)c(C#CC(F)(F)F)c(F)c4)c(F)c3)sc2c1] |
| 55 | 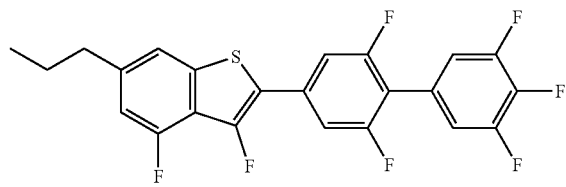 [SMILES: CCCc1cc(F)c2c(F)c(-c3cc(F)c(-c4cc(F)c(F)c(F)c4)c(F)c3)sc2c1] |
| 56 | 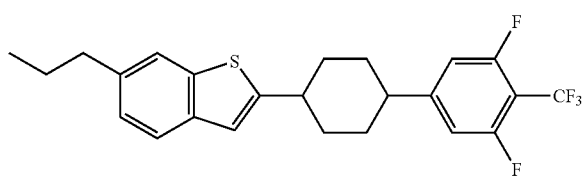 [SMILES: CCCc1ccc2cc(C3CCC(c4cc(F)c(C(F)(F)F)c(F)c4)CC3)sc2c1] |
| 57 | 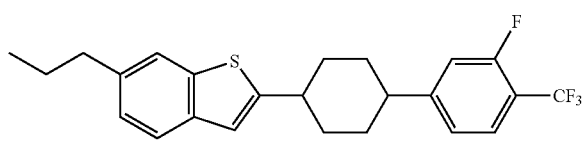 [SMILES: CCCc1ccc2cc(C3CCC(c4ccc(C(F)(F)F)c(F)c4)CC3)sc2c1] |
| 58 | 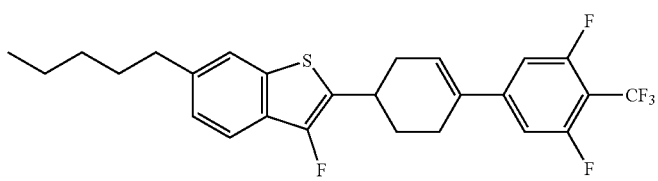 [SMILES: CCCCCc1ccc2c(F)c(C3CC=C(c4cc(F)c(C(F)(F)F)c(F)c4)CC3)sc2c1] |
| 59 | 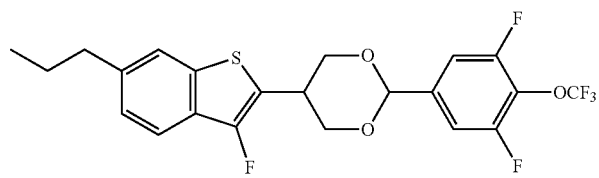 [SMILES: CCCc1ccc2c(F)c(C3COC(c4cc(F)c(OC(F)(F)F)c(F)c4)OC3)sc2c1] |
| 60 | 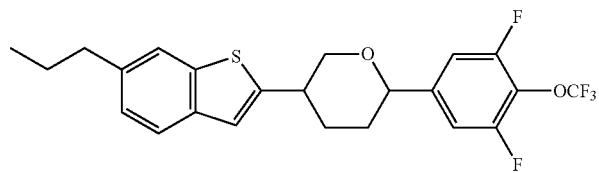 [SMILES: CCCc1ccc2cc(C3CCC(c4cc(F)c(OC(F)(F)F)c(F)c4)OC3)sc2c1] |
| 61 | 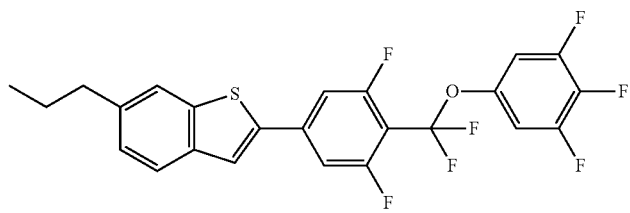 |

| No. | |
|---|---|
| 62 | 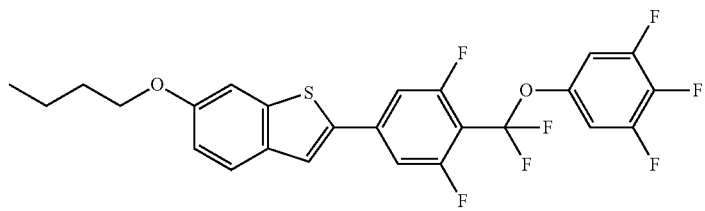 [SMILES: CCCCOc1ccc2cc(-c3cc(F)c(C(F)(F)Oc4cc(F)c(F)c(F)c4)c(F)c3)sc2c1] |
| 63 | 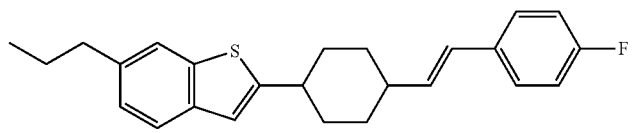 |
| 64 | 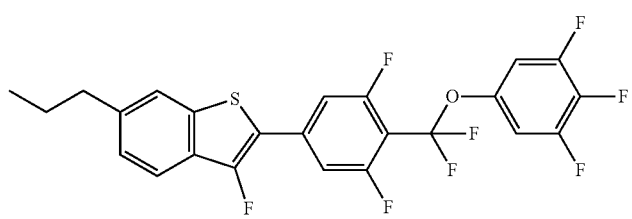 [SMILES: CCCc1ccc2c(F)c(-c3cc(F)c(C(F)(F)Oc4cc(F)c(F)c(F)c4)c(F)c3)sc2c1] |
| 65 | 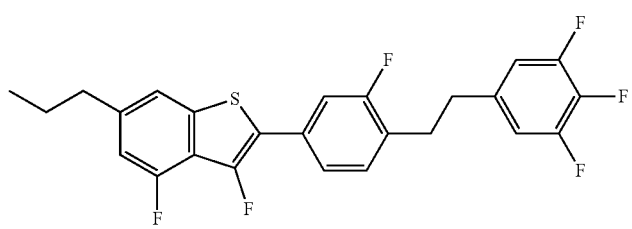 [SMILES: CCCc1cc(F)c2c(F)c(-c3ccc(CCc4cc(F)c(F)c(F)c4)c(F)c3)sc2c1] |
| 66 | 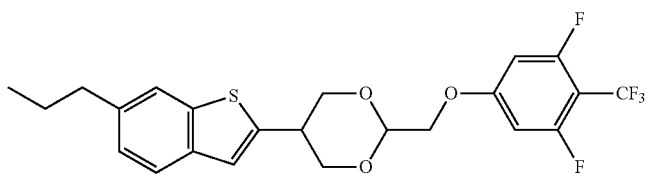 [SMILES: CCCc1ccc2cc(C3COC(COc4cc(F)c(C(F)(F)F)c(F)c4)OC3)sc2c1] |
| 67 | 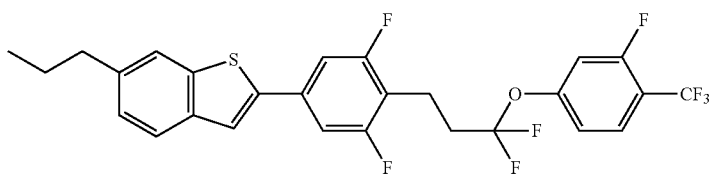 [SMILES: CCCc1ccc2cc(-c3cc(F)c(CCC(F)(F)Oc4ccc(C(F)(F)F)c(F)c4)c(F)c3)sc2c1] |
| 68 | 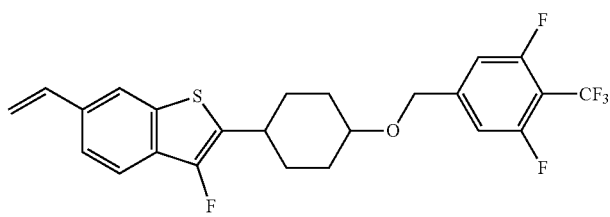 [SMILES: C=Cc1ccc2c(F)c(C3CCC(OCc4cc(F)c(C(F)(F)F)c(F)c4)CC3)sc2c1] |
| 69 | 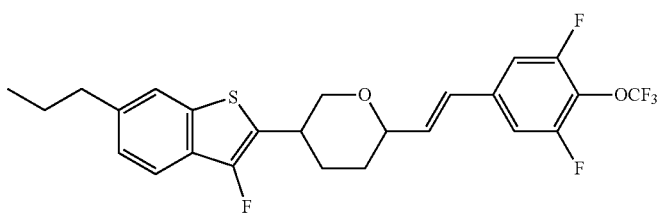 [SMILES: CCCc1ccc2c(F)c(C3CCC(/C=C/c4cc(F)c(OC(F)(F)F)c(F)c4)OC3)sc2c1] |

| No. | |
|---|---|
| 70 | 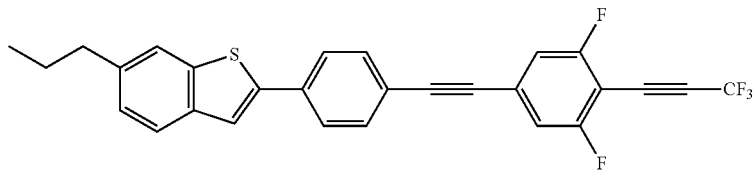 [SMILES: CCCc1ccc2cc(-c3ccc(C#Cc4cc(F)c(C#CC(F)(F)F)c(F)c4)cc3)sc2c1] |
| 71 | 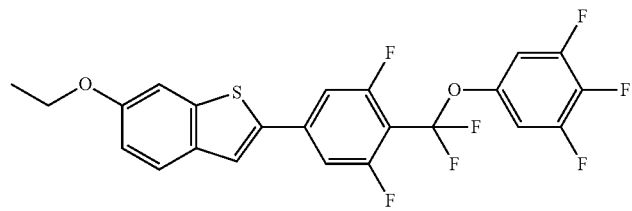 [SMILES: CCOc1ccc2cc(-c3cc(F)c(C(F)(F)Oc4cc(F)c(F)c(F)c4)c(F)c3)sc2c1] |
| 72 | 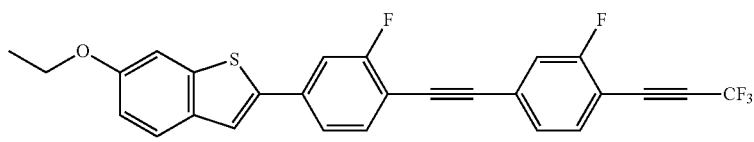 [SMILES: CCOc1ccc2cc(-c3ccc(C#Cc4ccc(C#CC(F)(F)F)c(F)c4)c(F)c3)sc2c1] |
| 73 | 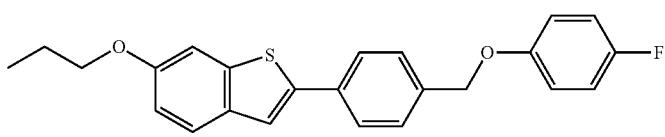 [SMILES: CCCOc1ccc2cc(-c3ccc(COc4ccc(F)cc4)cc3)sc2c1] |
| 74 | 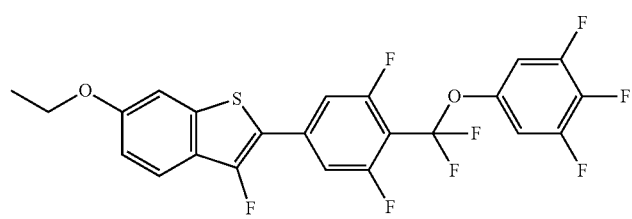 [SMILES: CCOc1ccc2c(F)c(-c3cc(F)c(C(F)(F)Oc4cc(F)c(F)c(F)c4)c(F)c3)sc2c1] |
| 75 | 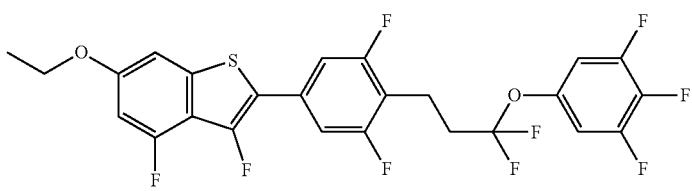 [SMILES: CCOc1cc(F)c2c(F)c(-c3cc(F)c(CCC(F)(F)Oc4cc(F)c(F)c(F)c4)c(F)c3)sc2c1] |
| 76 | 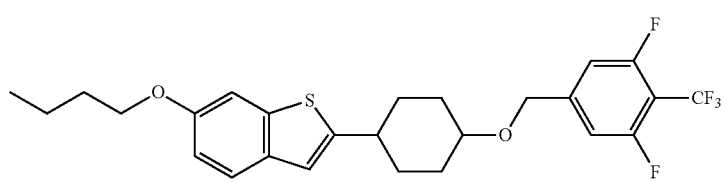 [SMILES: CCCCOc1ccc2cc(C3CCC(OCc4cc(F)c(C(F)(F)F)c(F)c4)CC3)sc2c1] |
| 77 | 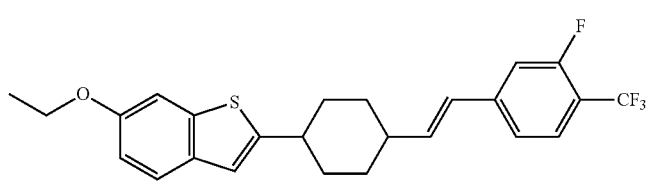 [SMILES: CCOc1ccc2cc(C3CCC(/C=C/c4ccc(C(F)(F)F)c(F)c4)CC3)sc2c1] |

-continued
| No. | |
|---|---|
| 78 | 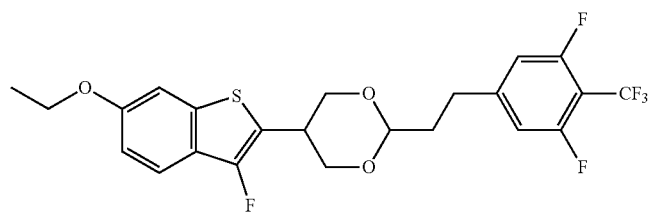 [SMILES: CCOc1ccc2c(F)c(C3COC(CCc4cc(F)c(C(F)(F)F)c(F)c4)OC3)sc2c1] |
| 79 | 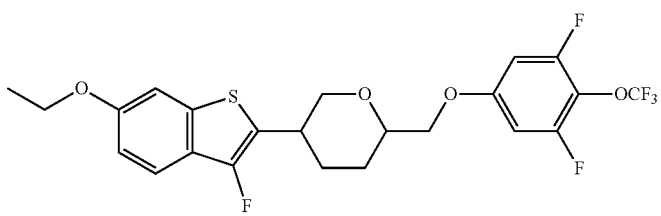 [SMILES: CCOc1ccc2c(F)c(C3CCC(COc4cc(F)c(OC(F)(F)F)c(F)c4)OC3)sc2c1] |
| 80 | 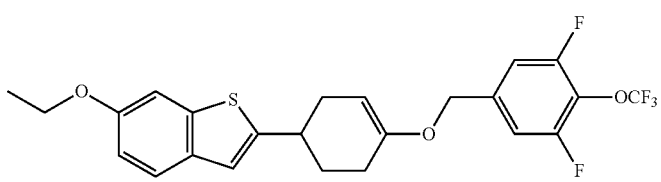 [SMILES: CCOc1ccc2cc(C3CC=C(OCc4cc(F)c(OC(F)(F)F)c(F)c4)CC3)sc2c1] |
| 81 | 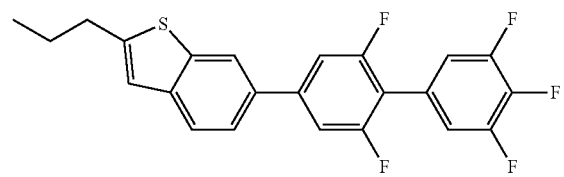 [SMILES: CCCc1cc2ccc(-c3cc(F)c(-c4cc(F)c(F)c(F)c4)c(F)c3)cc2s1] |
| 82 | 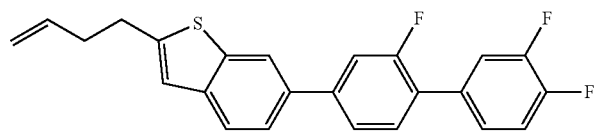 [SMILES: C=CCCc1cc2ccc(-c3ccc(-c4ccc(F)c(F)c4)c(F)c3)cc2s1] |
| 83 | 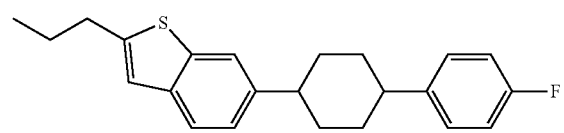 [SMILES: CCCc1cc2ccc(C3CCC(c4ccc(F)cc4)CC3)cc2s1] |
| 84 | 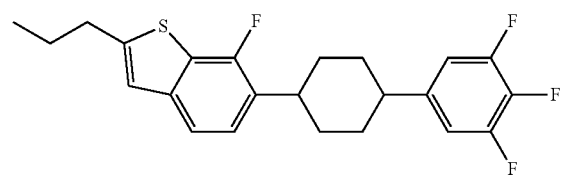 [SMILES: CCCc1cc2ccc(C3CCC(c4cc(F)c(F)c(F)c4)CC3)c(F)c2s1] |
| 85 | 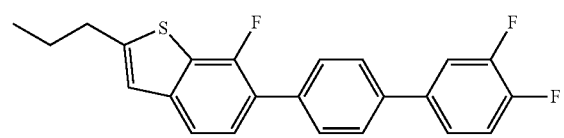 [SMILES: CCCc1cc2ccc(-c3ccc(-c4ccc(F)c(F)c4)cc3)c(F)c2s1] |
| 86 | 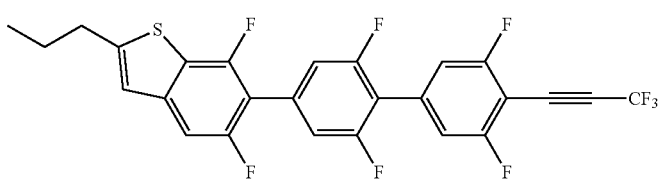 |

| No. | |
|---|---|
| 87 | 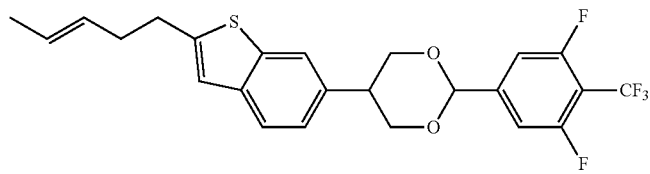 [SMILES: C/C=C/CCc1cc2ccc(C3COC(c4cc(F)c(C(F)(F)F)c(F)c4)OC3)cc2s1] |
| 88 | 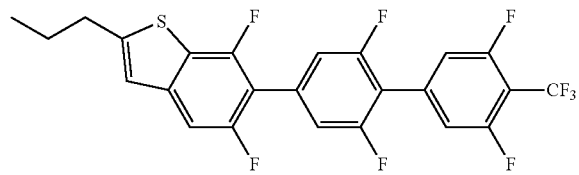 [SMILES: CCCc1cc2cc(F)c(-c3cc(F)c(-c4cc(F)c(C(F)(F)F)c(F)c4)c(F)c3)c(F)c2s1] |
| 89 | 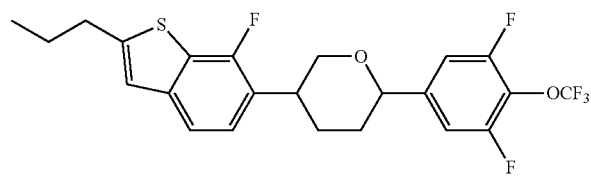 |
| 90 | 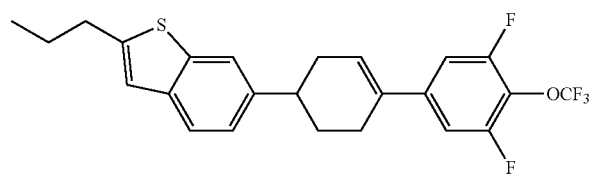 [SMILES: CCCc1cc2ccc(C3CC=C(c4cc(F)c(OC(F)(F)F)c(F)c4)CC3)cc2s1] |
| 91 | 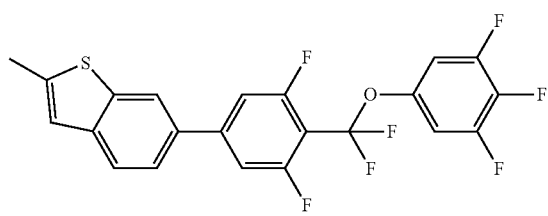 [SMILES: Cc1cc2ccc(-c3cc(F)c(C(F)(F)Oc4cc(F)c(F)c(F)c4)c(F)c3)cc2s1] |
| 92 | 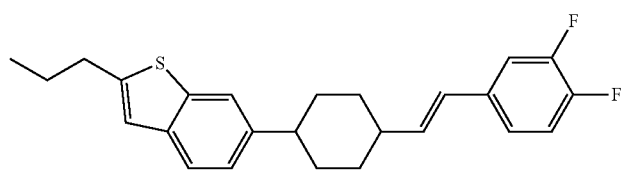 [SMILES: CCCc1cc2ccc(C3CCC(/C=C/c4ccc(F)c(F)c4)CC3)cc2s1] |
| 93 | 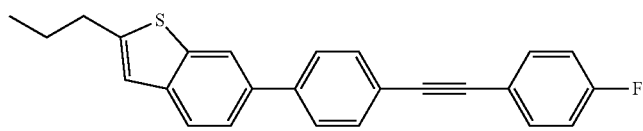 [SMILES: CCCc1cc2ccc(-c3ccc(C#Cc4ccc(F)cc4)cc3)cc2s1] |
| 94 | 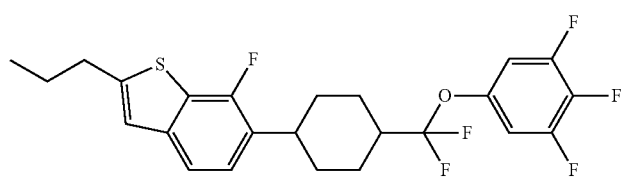 [SMILES: CCCc1cc2ccc(C3CCC(C(F)(F)Oc4cc(F)c(F)c(F)c4)CC3)c(F)c2s1] |

-continued
| No. |  |
|---|---|
| 95 | 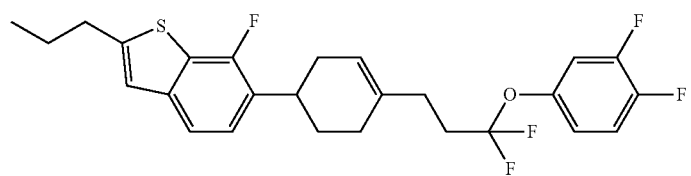 [SMILES: CCCc1cc2ccc(C3CC=C(CCC(F)(F)Oc4ccc(F)c(F)c4)CC3)c(F)c2s1] |
| 96 | 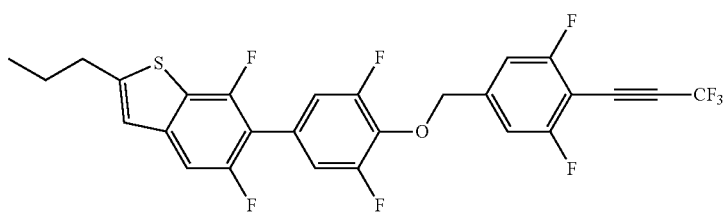 [SMILES: CCCc1cc2cc(F)c(-c3cc(F)c(OCc4cc(F)c(C#CC(F)(F)F)c(F)c4)c(F)c3)c(F)c2s1] |
| 97 | 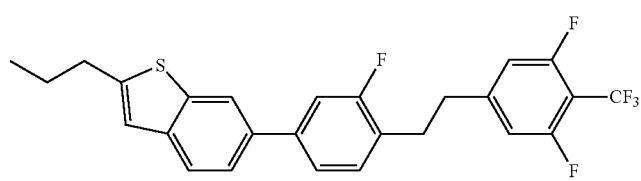 [SMILES: CCCc1cc2ccc(-c3ccc(CCc4cc(F)c(C(F)(F)F)c(F)c4)c(F)c3)cc2s1] |
| 98 | 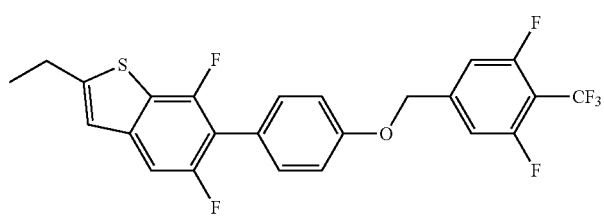 [SMILES: CCc1cc2cc(F)c(-c3ccc(OCc4cc(F)c(C(F)(F)F)c(F)c4)cc3)c(F)c2s1] |
| 99 | 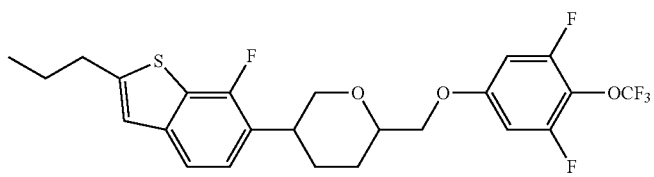 [SMILES: CCCc1cc2ccc(C3CCC(COc4cc(F)c(OC(F)(F)F)c(F)c4)OC3)c(F)c2s1] |
| 100 | 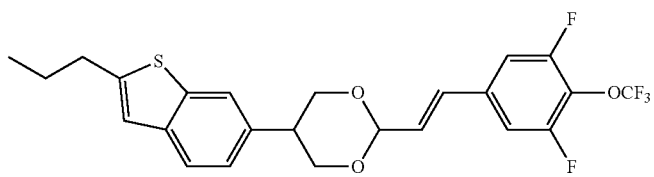 [SMILES: CCCc1cc2ccc(C3COC(/C=C/c4cc(F)c(OC(F)(F)F)c(F)c4)OC3)cc2s1] |
| 101 | 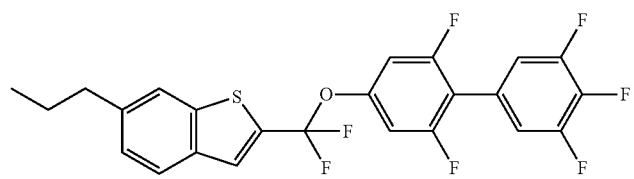 |
| 102 | 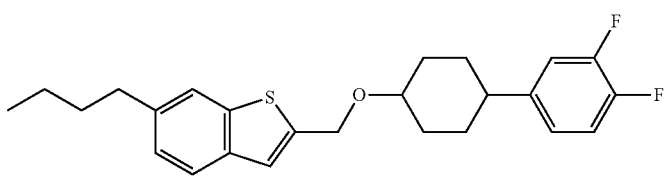 [SMILES: CCCCc1ccc2cc(COC3CCC(c4ccc(F)c(F)c4)CC3)sc2c1] |

| No. | |
|---|---|
| 103 | 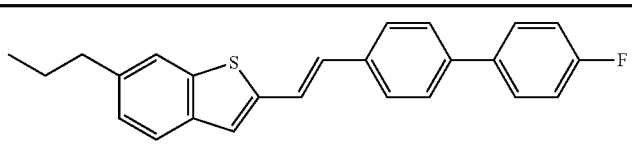 |
| 104 | 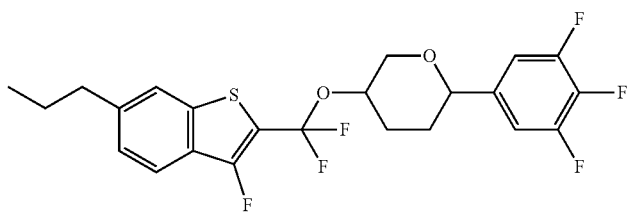 [SMILES: CCCc1ccc2c(F)c(C(F)(F)OC3CCC(c4cc(F)c(F)c(F)c4)OC3)sc2c1] |
| 105 | 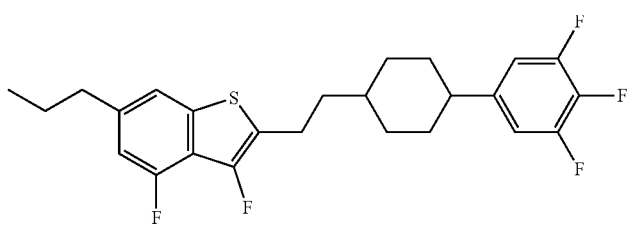 [SMILES: CCCc1cc(F)c2c(F)c(CCC3CCC(c4cc(F)c(F)c(F)c4)CC3)sc2c1] |
| 106 | 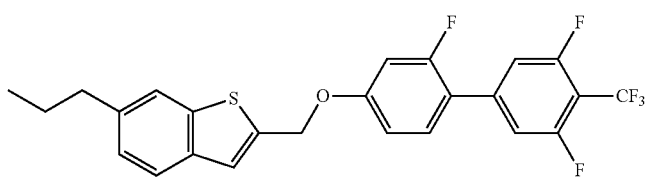 [SMILES: CCCc1ccc2cc(COc3ccc(-c4cc(F)c(C(F)(F)F)c(F)c4)c(F)c3)sc2c1] |
| 107 | 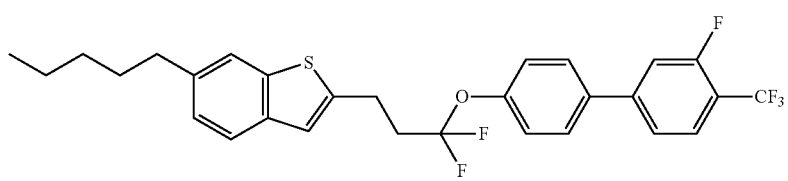 [SMILES: CCCCCc1ccc2cc(CCC(F)(F)Oc3ccc(-c4ccc(C(F)(F)F)c(F)c4)cc3)sc2c1] |
| 108 | 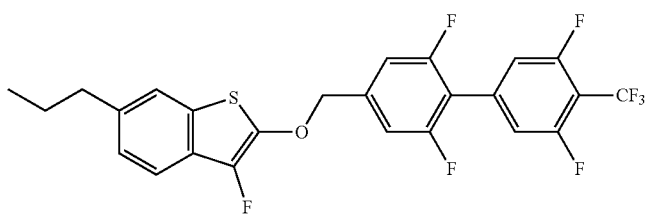 |
| 109 | 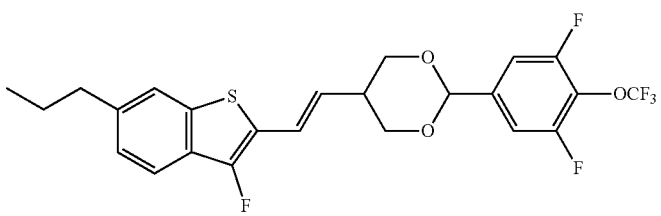 [SMILES: CCCc1ccc2c(F)c(/C=C/C3COC(c4cc(F)c(OC(F)(F)F)c(F)c4)OC3)sc2c1] |
| 110 | 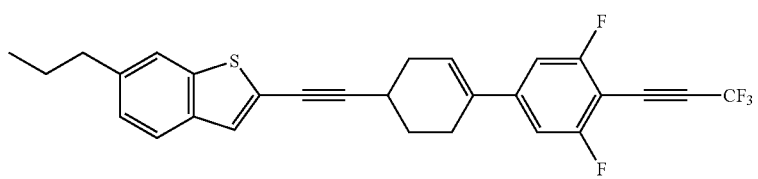 [SMILES: CCCc1ccc2cc(C#CC3CC=C(c4cc(F)c(C#CC(F)(F)F)c(F)c4)CC3)sc2c1] |

| No. |
|---|
| 111 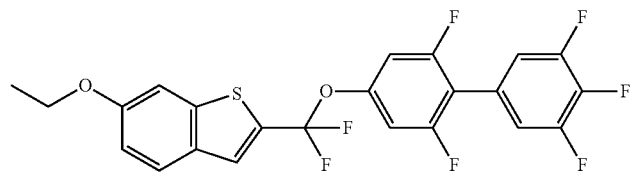 [SMILES: CCOc1ccc2cc(C(F)(F)Oc3cc(F)c(-c4cc(F)c(F)c(F)c4)c(F)c3)sc2c1] |
| 112 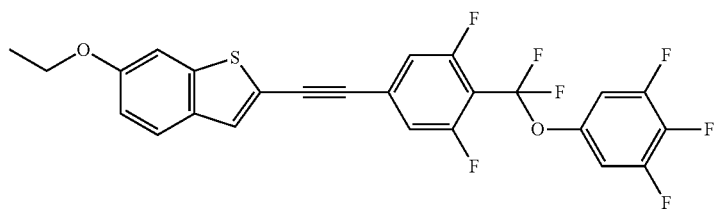 [SMILES: CCOc1ccc2cc(C#Cc3cc(F)c(C(F)(F)Oc4cc(F)c(F)c(F)c4)c(F)c3)sc2c1] |
| 113 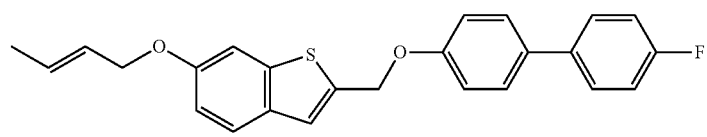 [SMILES: C/C=C/COc1ccc2cc(COc3ccc(-c4ccc(F)cc4)cc3)sc2c1] |
| 114 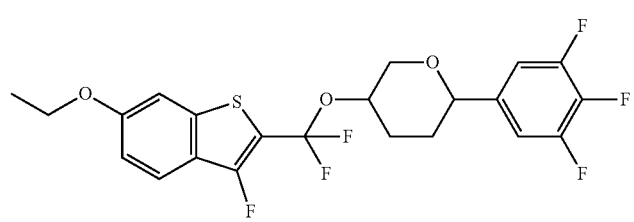 [SMILES: CCOc1ccc2c(F)c(C(F)(F)OC3CCC(c4cc(F)c(F)c(F)c4)OC3)sc2c1] |
| 115 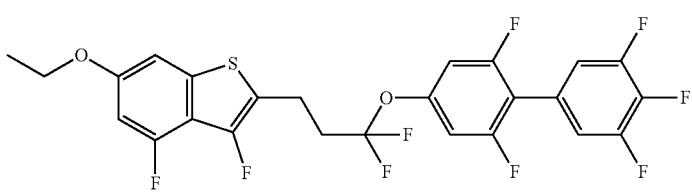 [SMILES: CCOc1cc(F)c2c(F)c(CCC(F)(F)Oc3cc(F)c(-c4cc(F)c(F)c(F)c4)c(F)c3)sc2c1] |
| 116 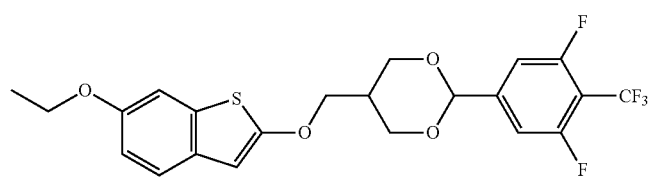 [SMILES: CCOc1ccc2cc(OCC3COC(c4cc(F)c(C(F)(F)F)c(F)c4)OC3)sc2c1] |
| 117 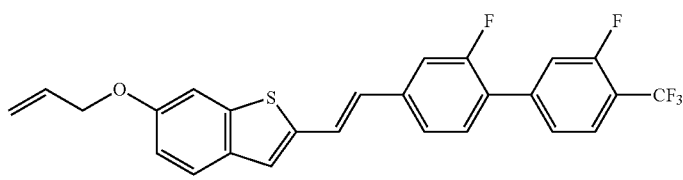 [SMILES: C=CCOc1ccc2cc(/C=C/c3ccc(-c4ccc(C(F)(F)F)c(F)c4)c(F)c3)sc2c1] |
| 118 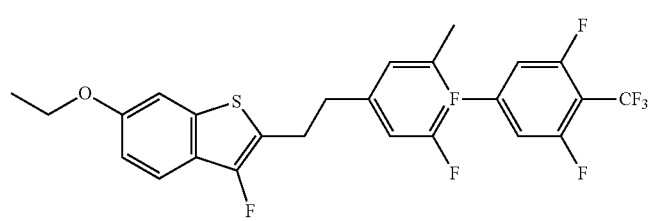 |

-continued
| No. | |
|---|---|
| 119 | 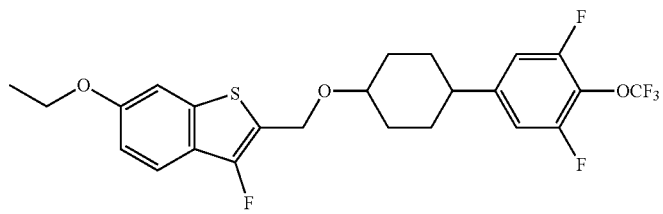 [SMILES: CCOc1ccc2c(F)c(COC3CCC(c4cc(F)c(OC(F)(F)F)c(F)c4)CC3)sc2c1] |
| 120 | 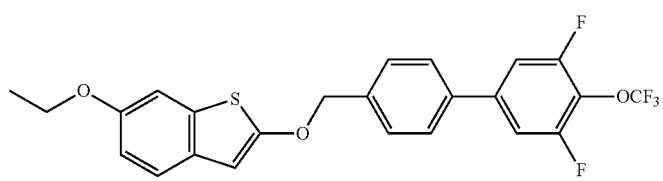 [SMILES: CCOc1ccc2cc(OCc3ccc(-c4cc(F)c(OC(F)(F)F)c(F)c4)cc3)sc2c1] |
| 121 | 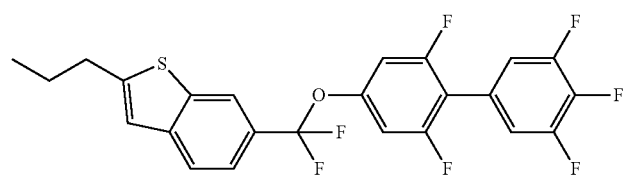 [SMILES: CCCc1cc2ccc(C(F)(F)Oc3cc(F)c(-c4cc(F)c(F)c(F)c4)c(F)c3)cc2s1] |
| 122 | 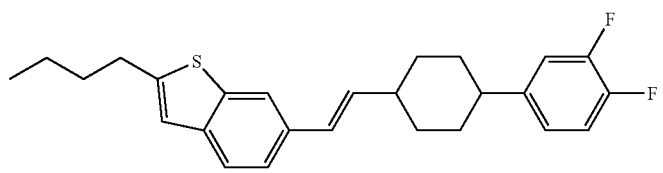 [SMILES: CCCCc1cc2ccc(/C=C/C3CCC(c4ccc(F)c(F)c4)CC3)cc2s1] |
| 123 | 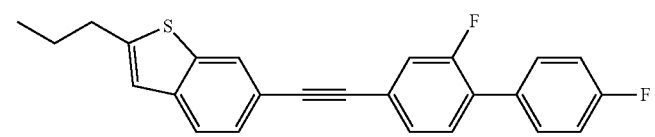 [SMILES: CCCc1cc2ccc(C#Cc3ccc(-c4ccc(F)cc4)c(F)c3)cc2s1] |
| 124 | 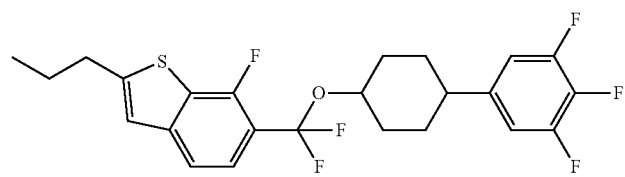 [SMILES: CCCc1cc2ccc(C(F)(F)OC3CCC(c4cc(F)c(F)c(F)c4)CC3)c(F)c2s1] |
| 125 | 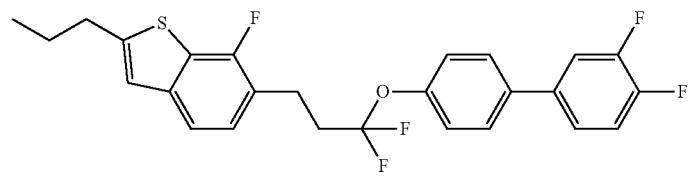 [SMILES: CCCc1cc2ccc(CCC(F)(F)Oc3ccc(-c4ccc(F)c(F)c4)cc3)c(F)c2s1] |
| 126 | 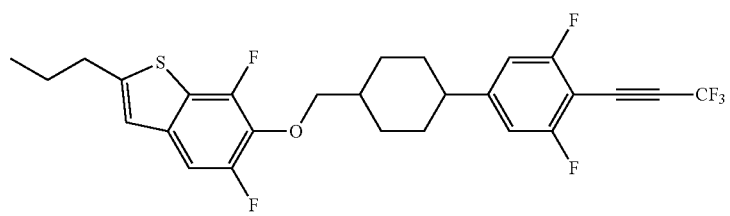 [SMILES: CCCc1cc2cc(F)c(OCC3CCC(c4cc(F)c(C#CC(F)(F)F)c(F)c4)CC3)c(F)c2s1] |

-continued
| No. | |
|---|---|
| 127 | 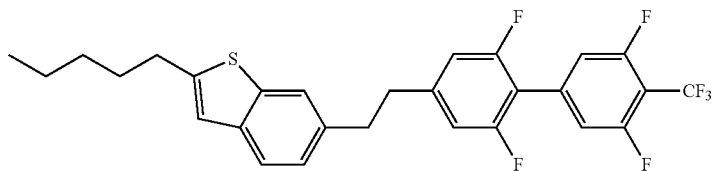 [SMILES: CCCCCc1cc2ccc(CCc3cc(F)c(-c4cc(F)c(C(F)(F)F)c(F)c4)c(F)c3)cc2s1] |
| 128 | 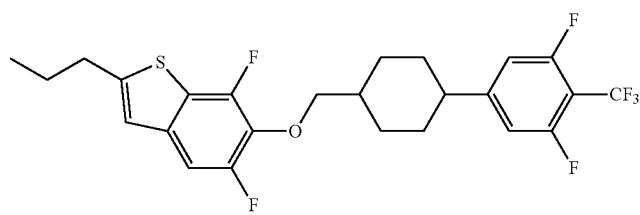 [SMILES: CCCc1cc2cc(F)c(OCC3CCC(c4cc(F)c(C(F)(F)F)c(F)c4)CC3)c(F)c2s1] |
| 129 | 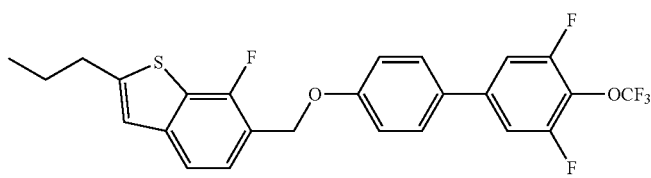 [SMILES: CCCc1cc2ccc(COc3ccc(-c4cc(F)c(OC(F)(F)F)c(F)c4)cc3)c(F)c2s1] |
| 130 | 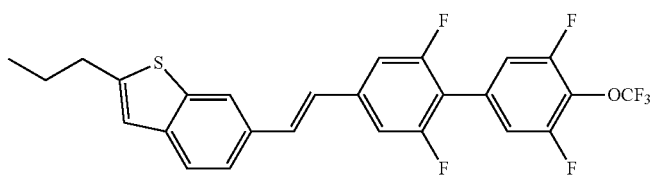 [SMILES: CCCc1cc2ccc(/C=C/c3cc(F)c(-c4cc(F)c(OC(F)(F)F)c(F)c4)c(F)c3)cc2s1] |
| 131 | 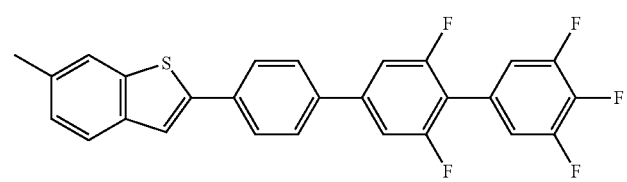 [SMILES: Cc1ccc2cc(-c3ccc(-c4cc(F)c(-c5cc(F)c(F)c(F)c5)c(F)c4)cc3)sc2c1] |
| 132 | 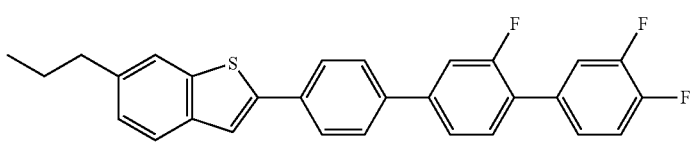 [SMILES: CCCc1ccc2cc(-c3ccc(-c4ccc(-c5ccc(F)c(F)c5)c(F)c4)cc3)sc2c1] |
| 133 | 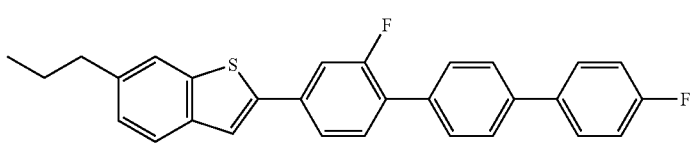 [SMILES: CCCc1ccc2cc(-c3ccc(-c4ccc(-c5ccc(F)cc5)cc4)c(F)c3)sc2c1] |
| 134 | 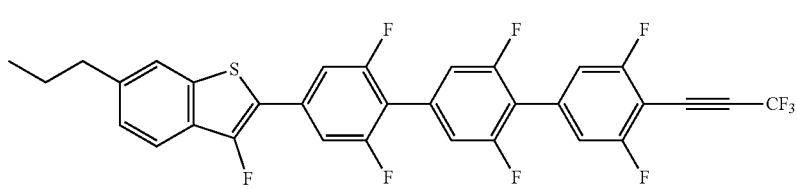 [SMILES: CCCc1ccc2c(F)c(-c3cc(F)c(-c4cc(F)c(-c5cc(F)c(C#CC(F)(F)F)c(F)c5)c(F)c4)c(F)c3)sc2c1] |

-continued
| No. | |
|---|---|
| 135 | 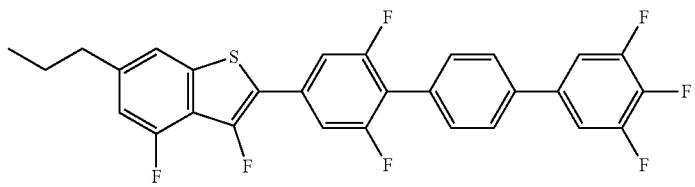 [SMILES: CCCc1cc(F)c2c(F)c(-c3cc(F)c(-c4ccc(-c5cc(F)c(F)c(F)c5)cc4)c(F)c3)sc2c1] |
| 136 | 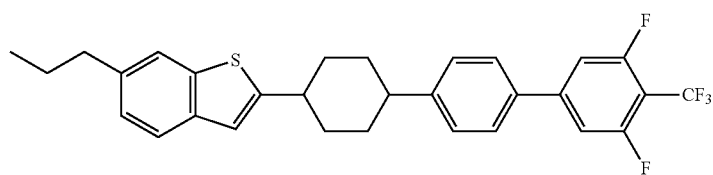 [SMILES: CCCc1ccc2cc(C3CCC(c4ccc(-c5cc(F)c(C(F)(F)F)c(F)c5)cc4)CC3)sc2c1] |
| 137 | 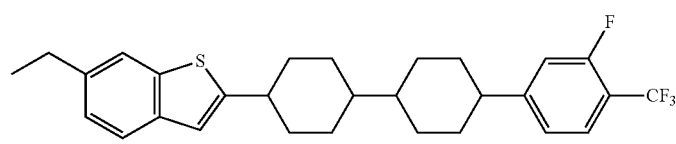 [SMILES: CCc1ccc2cc(C3CCC(C4CCC(c5ccc(C(F)(F)F)c(F)c5)CC4)CC3)sc2c1] |
| 138 | 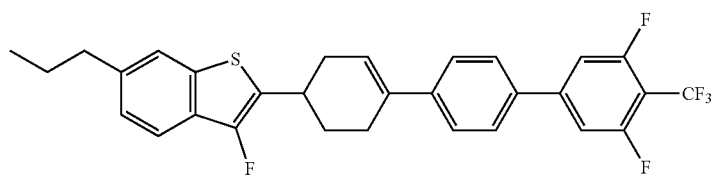 [SMILES: CCCc1ccc2c(F)c(C3CC=C(c4ccc(-c5cc(F)c(C(F)(F)F)c(F)c5)cc4)CC3)sc2c1] |
| 139 | 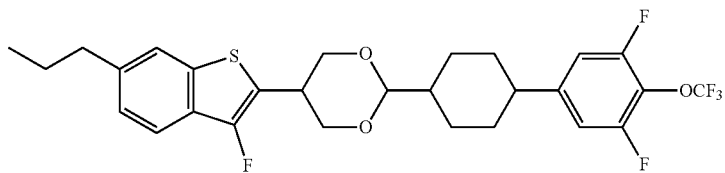 [SMILES: CCCc1ccc2c(F)c(C3COC(C4CCC(c5cc(F)c(OC(F)(F)F)c(F)c5)CC4)OC3)sc2c1] |
| 140 | 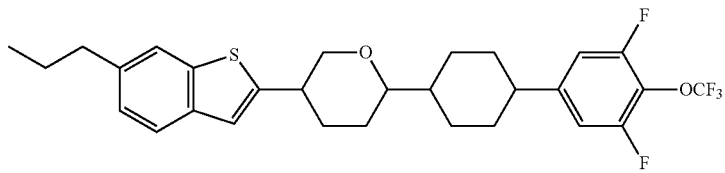 [SMILES: CCCc1ccc2cc(C3CCC(C4CCC(c5cc(F)c(OC(F)(F)F)c(F)c5)CC4)OC3)sc2c1] |
| 141 | 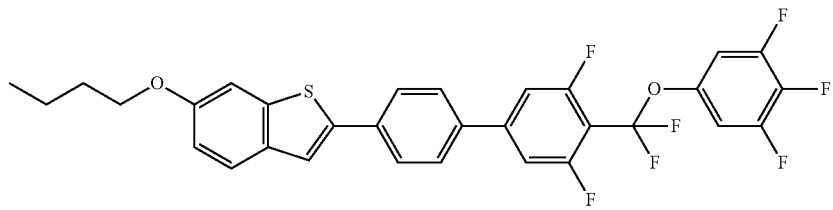 [SMILES: CCCCOc1ccc2cc(-c3ccc(-c4cc(F)c(C(F)(F)Oc5cc(F)c(F)c(F)c5)c(F)c4)cc3)sc2c1] |
| 142 | 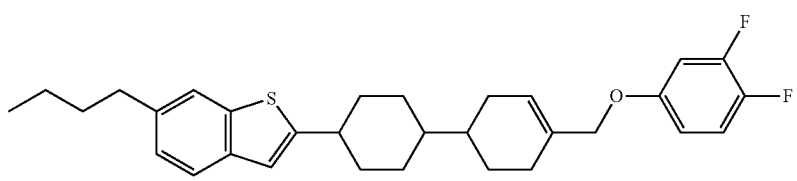 [SMILES: CCCCc1ccc2cc(C3CCC(C4CC=C(COc5ccc(F)c(F)c5)CC4)CC3)sc2c1] |
| 143 | 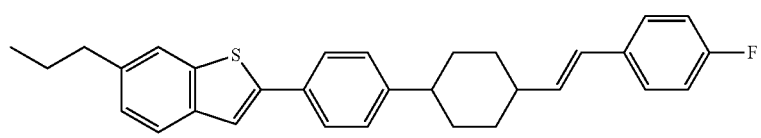 [SMILES: CCCc1ccc2cc(-c3ccc(C4CCC(/C=C/c5ccc(F)cc5)CC4)cc3)sc2c1] |

| No. | |
|---|---|
| 144 | 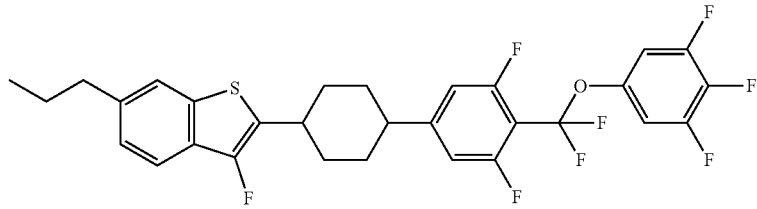 [SMILES: CCCc1ccc2c(F)c(C3CCC(c4cc(F)c(C(F)(F)Oc5cc(F)c(F)c(F)c5)c(F)c4)CC3)sc2c1] |
| 145 | 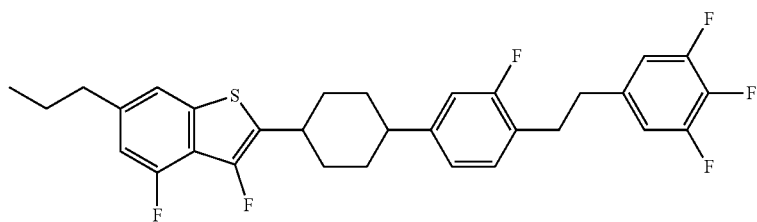 [SMILES: CCCc1cc(F)c2c(F)c(C3CCC(c4ccc(CCc5cc(F)c(F)c(F)c5)c(F)c4)CC3)sc2c1] |
| 146 | 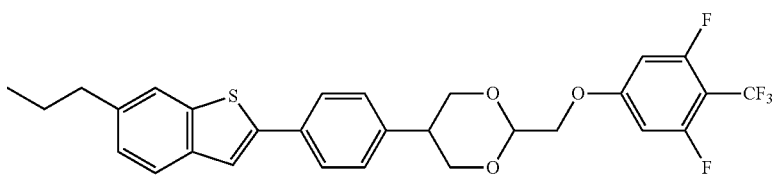 [SMILES: CCCc1ccc2cc(-c3ccc(C4COC(COc5cc(F)c(C(F)(F)F)c(F)c5)OC4)cc3)sc2c1] |
| 147 | 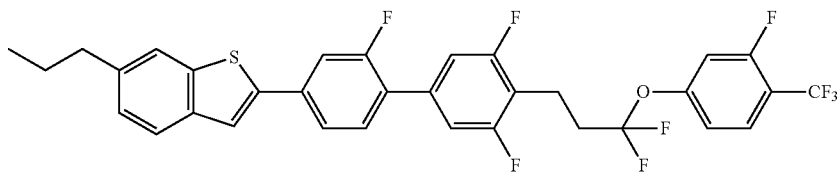 [SMILES: CCCc1ccc2cc(-c3ccc(-c4cc(F)c(CCC(F)(F)Oc5ccc(C(F)(F)F)c(F)c5)c(F)c4)c(F)c3)sc2c1] |
| 148 | 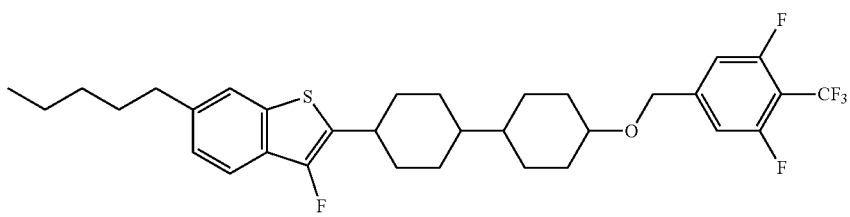 [SMILES: CCCCCc1ccc2c(F)c(C3CCC(C4CCC(OCc5cc(F)c(C(F)(F)F)c(F)c5)CC4)CC3)sc2c1] |
| 149 | 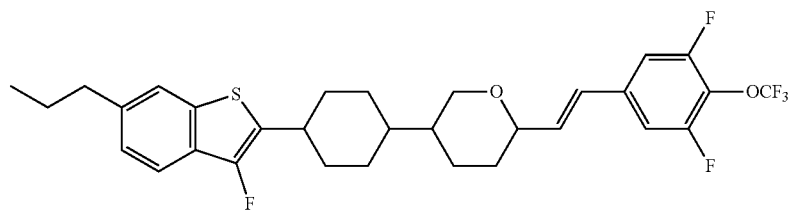 [SMILES: CCCc1ccc2c(F)c(C3CCC(C4CCC(/C=C/c5cc(F)c(OC(F)(F)F)c(F)c5)OC4)CC3)sc2c1] |
| 150 | 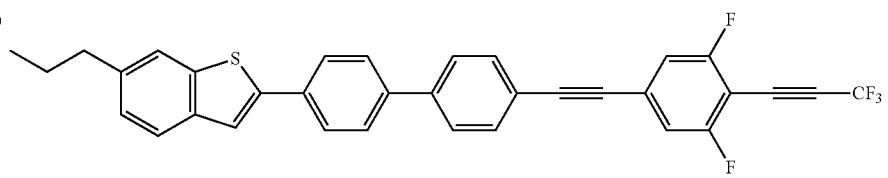 |

| No. |
|---|
| 151 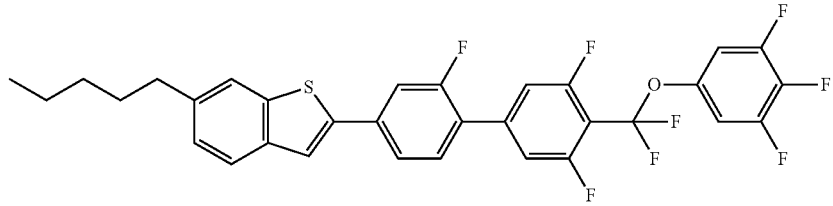 [SMILES: CCCCCc1ccc2cc(-c3ccc(-c4cc(F)c(C(F)(F)Oc5cc(F)c(F)c(F)c5)c(F)c4)c(F)c3)sc2c1] |
| 152 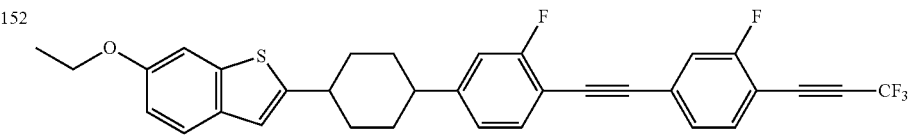 |
| 153 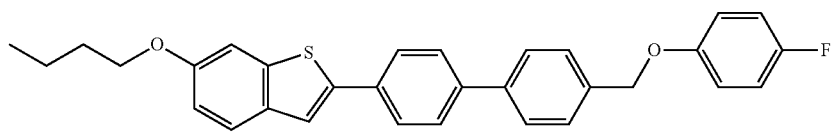 [SMILES: CCCCOc1ccc2cc(-c3ccc(-c4ccc(COc5ccc(F)cc5)cc4)cc3)sc2c1] |
| 154 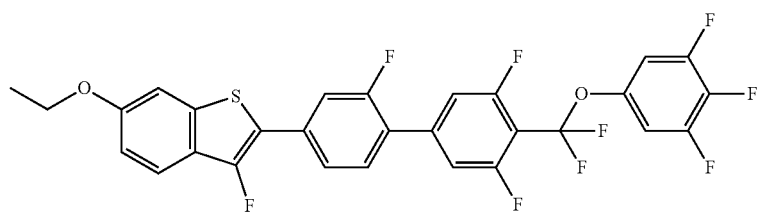 [SMILES: CCOc1ccc2c(F)c(-c3ccc(-c4cc(F)c(C(F)(F)Oc5cc(F)c(F)c(F)c5)c(F)c4)c(F)c3)sc2c1] |
| 155 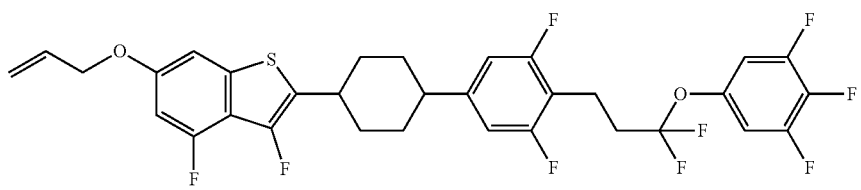 [SMILES: C=CCOc1cc(F)c2c(F)c(C3CCC(c4cc(F)c(CCC(F)(F)Oc5cc(F)c(F)c(F)c5)c(F)c4)CC3)sc2c1] |
| 156 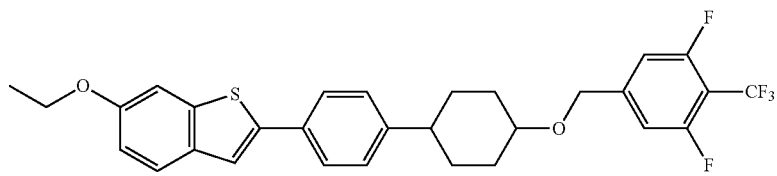 [SMILES: CCOc1ccc2cc(-c3ccc(C4CCC(OCc5cc(F)c(C(F)(F)F)c(F)c5)CC4)cc3)sc2c1] |
| 156 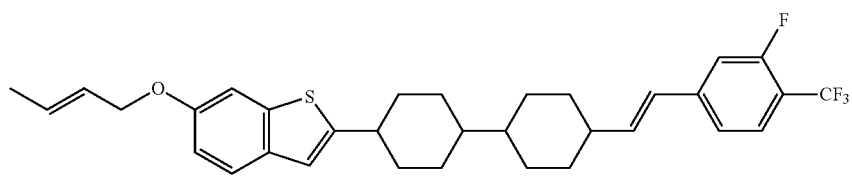 [SMILES: C/C=C/COc1ccc2cc(C3CCC(C4CCC(/C=C/c5ccc(C(F)(F)F)c(F)c5)CC4)CC3)sc2c1] |
| 158 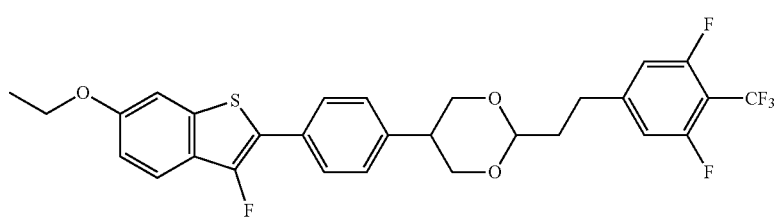 [SMILES: CCOc1ccc2c(F)c(-c3ccc(C4COC(CCc5cc(F)c(C(F)(F)F)c(F)c5)OC4)cc3)sc2c1] |

-continued
| No. | |
|---|---|
| 159 | 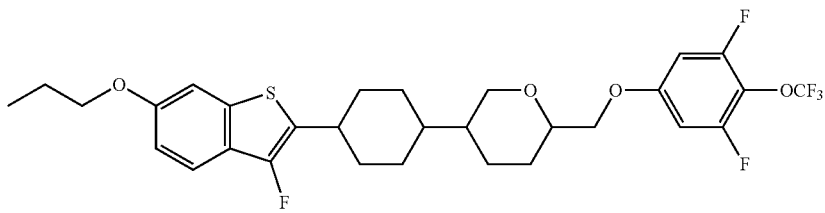 [SMILES: CCCOc1ccc2c(F)c(C3CCC(C4CCC(COc5cc(F)c(OC(F)(F)F)c(F)c5)OC4)CC3)sc2c1] |
| 160 | 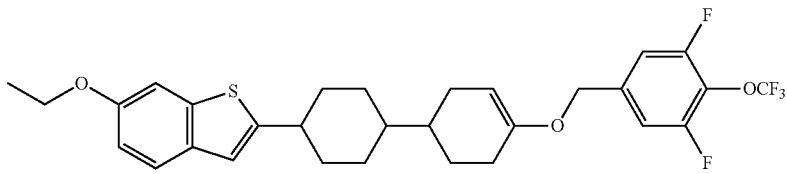 [SMILES: CCOc1ccc2cc(C3CCC(C4CC=C(OCc5cc(F)c(OC(F)(F)F)c(F)c5)CC4)CC3)sc2c1] |
| 161 | 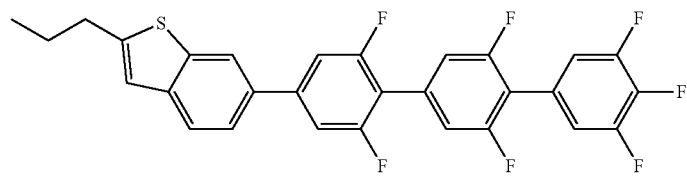 [SMILES: CCCc1cc2ccc(-c3cc(F)c(-c4cc(F)c(-c5cc(F)c(F)c(F)c5)c(F)c4)c(F)c3)cc2s1] |
| 162 | 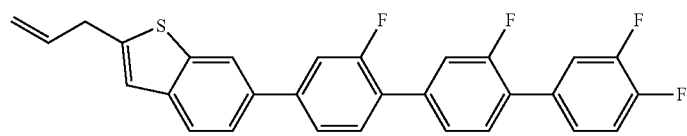 |
| 163 | 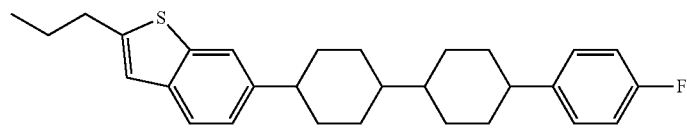 |
| 164 | 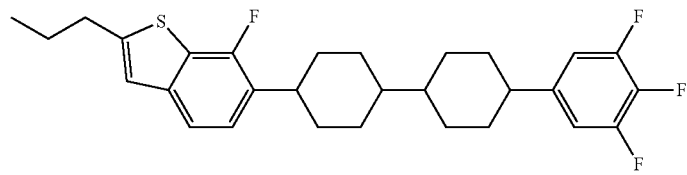 [SMILES: CCCc1cc2ccc(C3CCC(C4CCC(c5cc(F)c(F)c(F)c5)CC4)CC3)c(F)c2s1] |
| 165 | 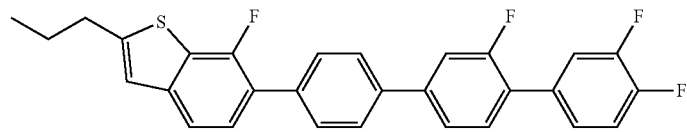 |
| 166 | 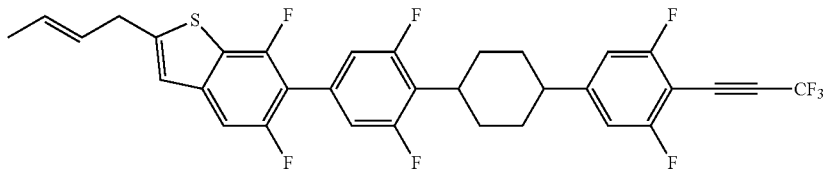 [SMILES: C/C=C/Cc1cc2cc(F)c(-c3cc(F)c(C4CCC(c5cc(F)c(C#CC(F)(F)F)c(F)c5)CC4)c(F)c3)c(F)c2s1] |
| 167 | 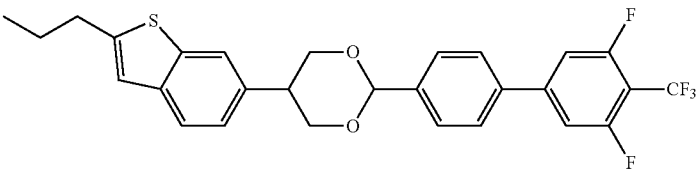 [SMILES: CCCc1cc2ccc(C3COC(c4ccc(-c5cc(F)c(C(F)(F)F)c(F)c5)cc4)OC3)cc2s1] |

-continued
| No. | |
|---|---|
| 168 | 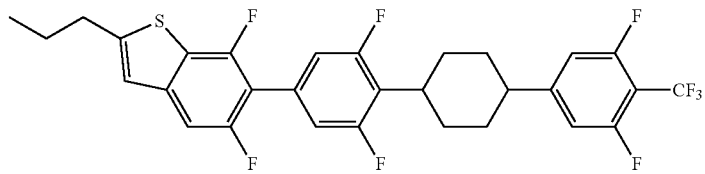 [SMILES: CCCc1cc2cc(F)c(-c3cc(F)c(C4CCC(c5cc(F)c(C(F)(F)F)c(F)c5)CC4)c(F)c3)c(F)c2s1] |
| 169 | 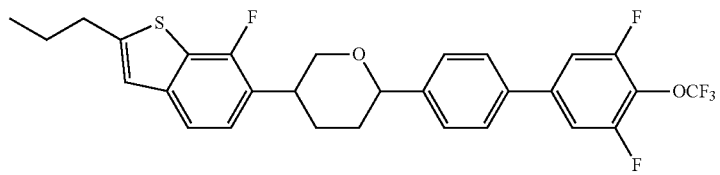 [SMILES: CCCc1cc2ccc(C3CCC(c4ccc(-c5cc(F)c(OC(F)(F)F)c(F)c5)cc4)OC3)c(F)c2s1] |
| 170 | 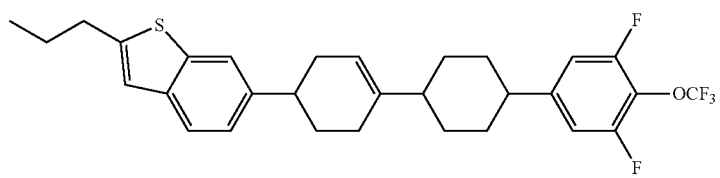 [SMILES: CCCc1cc2ccc(C3CC=C(C4CCC(c5cc(F)c(OC(F)(F)F)c(F)c5)CC4)CC3)cc2s1] |
| 171 | 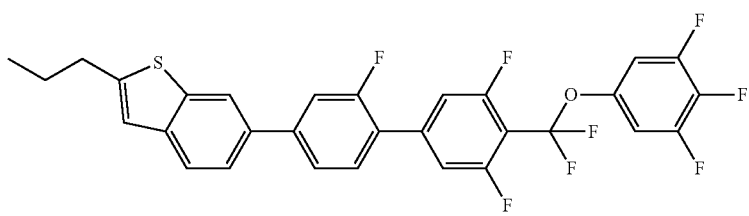 [SMILES: CCCc1cc2ccc(-c3ccc(-c4cc(F)c(C(F)(F)Oc5cc(F)c(F)c(F)c5)c(F)c4)c(F)c3)cc2s1] |
| 172 | 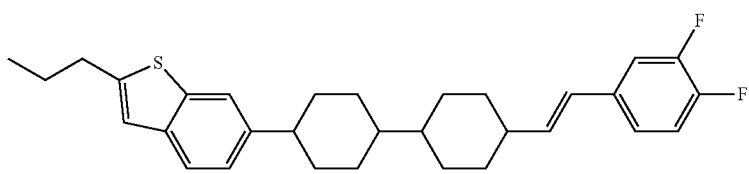 [SMILES: CCCc1cc2ccc(C3CCC(C4CCC(/C=C/c5ccc(F)c(F)c5)CC4)CC3)cc2s1] |
| 173 | 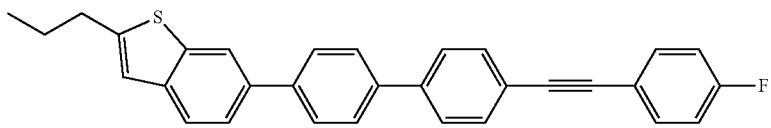 [SMILES: CCCc1cc2ccc(-c3ccc(-c4ccc(C#Cc5ccc(F)cc5)cc4)cc3)cc2s1] |
| 174 | 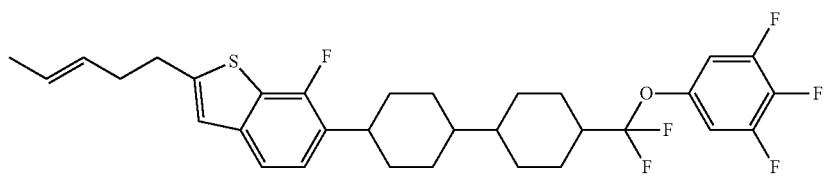 [SMILES: C/C=C/CCc1cc2ccc(C3CCC(C4CCC(C(F)(F)Oc5cc(F)c(F)c(F)c5)CC4)CC3)c(F)c2s1] |
| 175 | 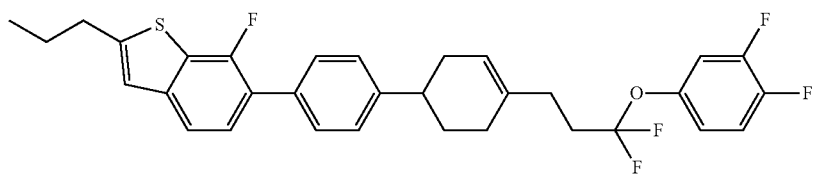 |

| No. | |
|---|---|
| 176 | 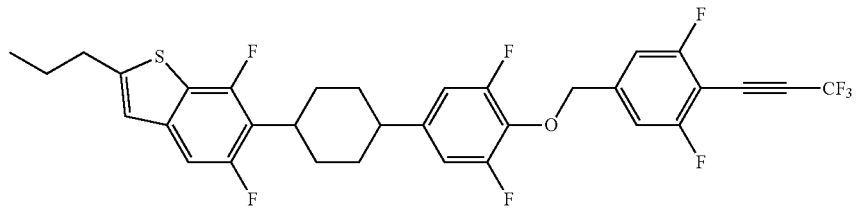 [SMILES: CCCc1cc2cc(F)c(C3CCC(c4cc(F)c(OCc5cc(F)c(C#CC(F)(F)F)c(F)c5)c(F)c4)CC3)c(F)c2s1] |
| 177 | 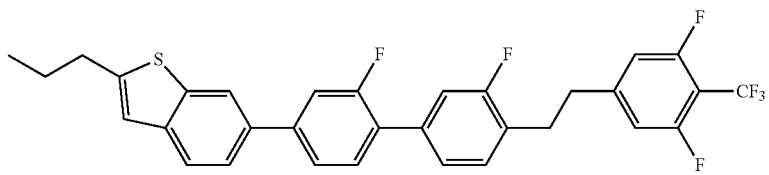 [SMILES: CCCc1cc2ccc(-c3ccc(-c4ccc(CCc5cc(F)c(C(F)(F)F)c(F)c5)c(F)c4)c(F)c3)cc2s1] |
| 178 | 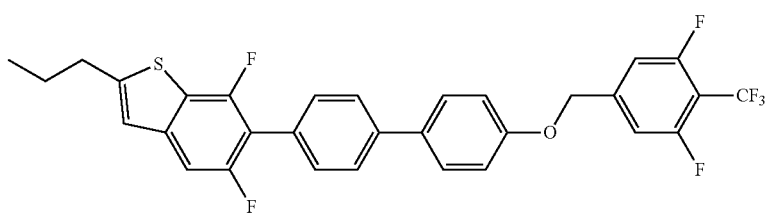 [SMILES: CCCc1cc2cc(F)c(-c3ccc(-c4ccc(OCc5cc(F)c(C(F)(F)F)c(F)c5)cc4)cc3)c(F)c2s1] |
| 179 | 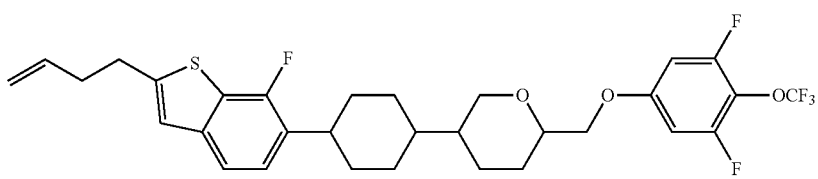 [SMILES: C=CCCc1cc2ccc(C3CCC(C4CCC(COc5cc(F)c(OC(F)(F)F)c(F)c5)OC4)CC3)c(F)c2s1] |
| 180 | 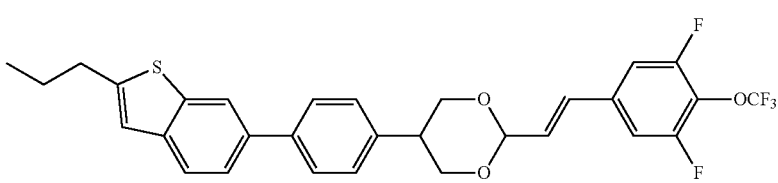 [SMILES: CCCc1cc2ccc(-c3ccc(C4COC(/C=C/c5cc(F)c(OC(F)(F)F)c(F)c5)OC4)cc3)cc2s1] |
| 181 | 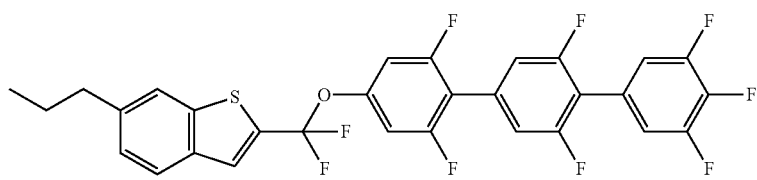 [SMILES: CCCc1ccc2cc(C(F)(F)Oc3cc(F)c(-c4cc(F)c(-c5cc(F)c(F)c(F)c5)c(F)c4)c(F)c3)sc2c1] |
| 182 | 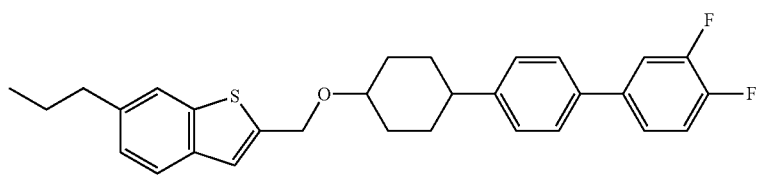 [SMILES: CCCc1ccc2cc(COC3CCC(c4ccc(-c5ccc(F)c(F)c5)cc4)CC3)sc2c1] |
| 183 | 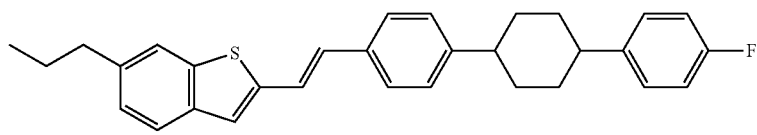 |

-continued
| No. | |
|---|---|
| 184 | 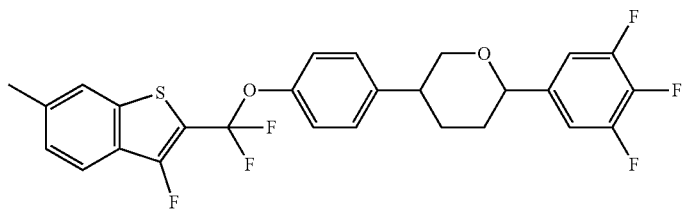 [SMILES: Cc1ccc2c(F)c(C(F)(F)Oc3ccc(C4CCC(c5cc(F)c(F)c(F)c5)OC4)cc3)sc2c1] |
| 185 | 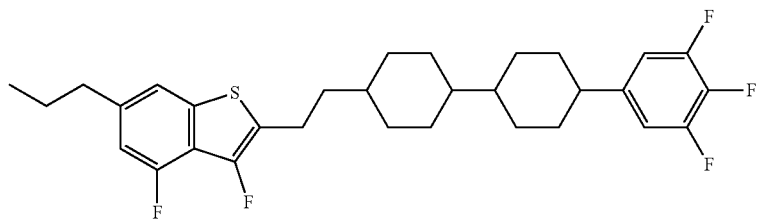 [SMILES: CCCc1cc(F)c2c(F)c(CCC3CCC(C4CCC(c5cc(F)c(F)c(F)c5)CC4)CC3)sc2c1] |
| 186 | 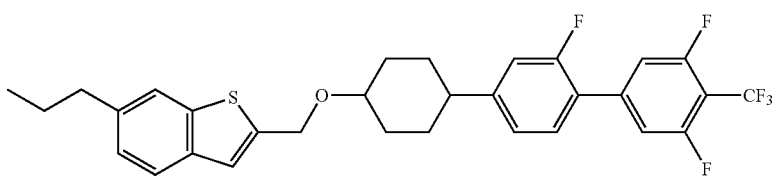 [SMILES: CCCc1ccc2cc(COC3CCC(c4ccc(-c5cc(F)c(C(F)(F)F)c(F)c5)c(F)c4)CC3)sc2c1] |
| 187 | 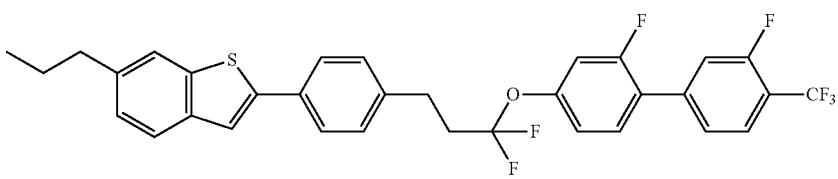 [SMILES: CCCc1ccc2cc(-c3ccc(CCC(F)(F)Oc4ccc(-c5ccc(C(F)(F)F)c(F)c5)c(F)c4)cc3)sc2c1] |
| 188 | 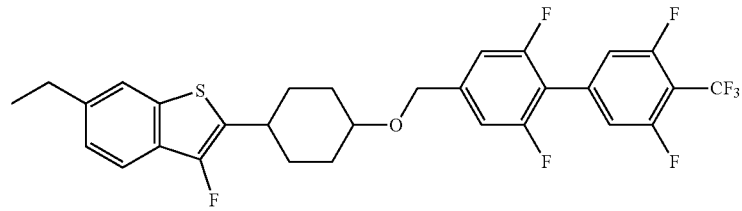 [SMILES: CCc1ccc2c(F)c(C3CCC(OCc4cc(F)c(-c5cc(F)c(C(F)(F)F)c(F)c5)c(F)c4)CC3)sc2c1] |
| 189 | 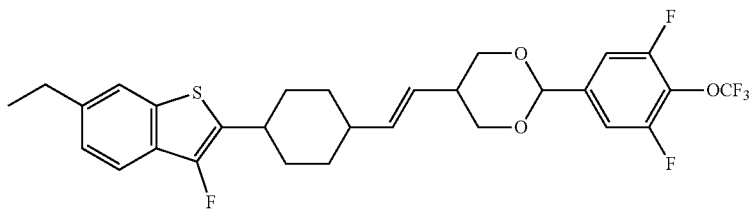 [SMILES: CCc1ccc2c(F)c(C3CCC(/C=C/C4COC(c5cc(F)c(OC(F)(F)F)c(F)c5)OC4)CC3)sc2c1] |
| 190 | 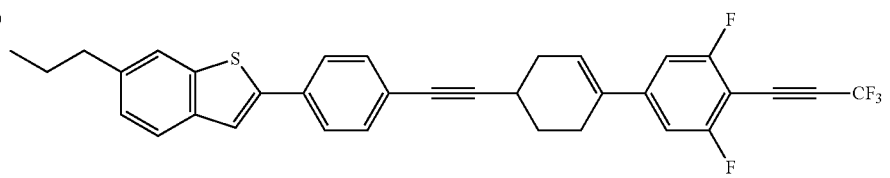 |
| 191 | 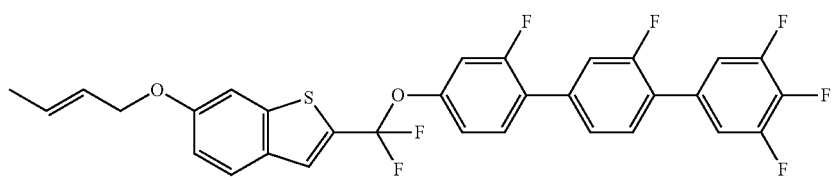 [SMILES: C/C=C/COc1ccc2cc(C(F)(F)Oc3ccc(-c4ccc(-c5cc(F)c(F)c(F)c5)c(F)c4)c(F)c3)sc2c1] |

-continued
| No. |
|---|
| 192 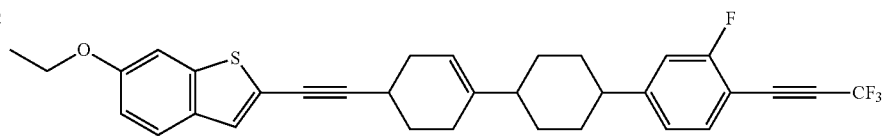 |
| 193 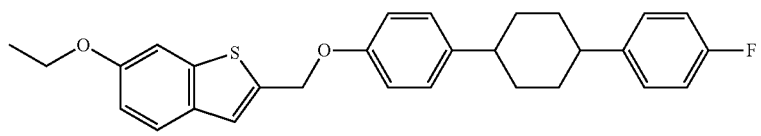 [SMILES: CCOc1ccc2cc(COc3ccc(C4CCC(c5ccc(F)cc5)CC4)cc3)sc2c1] |
| 194 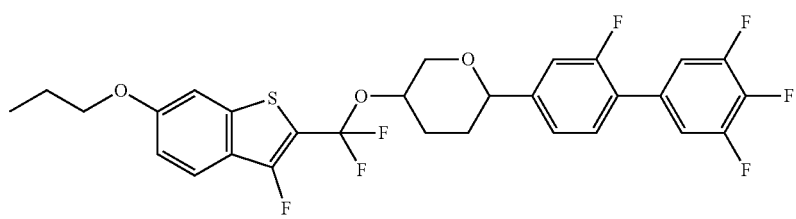 [SMILES: CCCOc1ccc2c(F)c(C(F)(F)OC3CCC(c4ccc(-c5cc(F)c(F)c(F)c5)c(F)c4)OC3)sc2c1] |
| 195 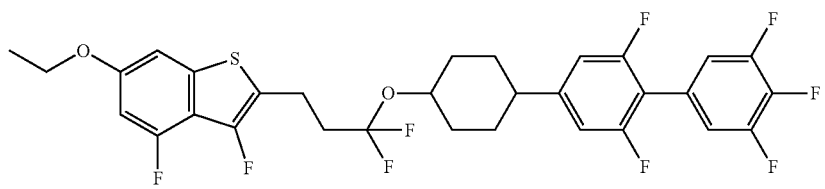 [SMILES: CCOc1cc(F)c2c(F)c(CCC(F)(F)OC3CCC(c4cc(F)c(-c5cc(F)c(F)c(F)c5)c(F)c4)CC3)sc2c1] |
| 196 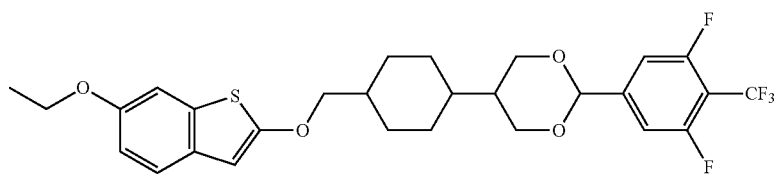 [SMILES: CCOc1ccc2cc(OCC3CCC(C4COC(c5cc(F)c(C(F)(F)F)c(F)c5)OC4)CC3)sc2c1] |
| 197 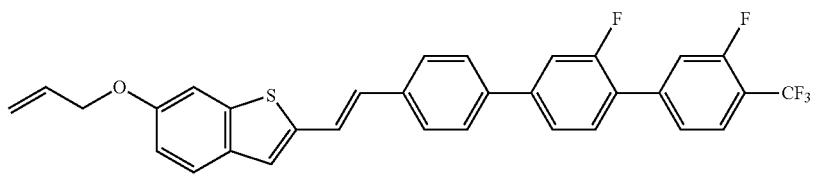 [SMILES: C=CCOc1ccc2cc(/C=C/c3ccc(-c4ccc(-c5ccc(C(F)(F)F)c(F)c5)c(F)c4)cc3)sc2c1] |
| 198 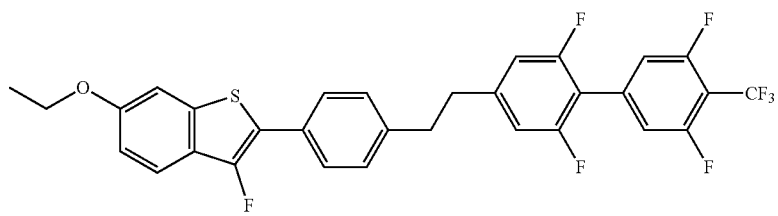 [SMILES: CCOc1ccc2c(F)c(-c3ccc(CCc4cc(F)c(-c5cc(F)c(C(F)(F)F)c(F)c5)c(F)c4)cc3)sc2c1] |
| 199 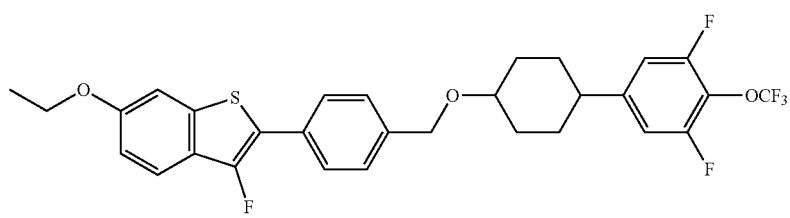 [SMILES: CCOc1ccc2c(F)c(-c3ccc(COC4CCC(c5cc(F)c(OC(F)(F)F)c(F)c5)CC4)cc3)sc2c1] |

-continued
| No. |
|---|
| 200 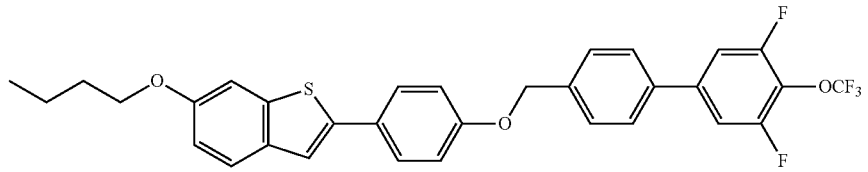 [SMILES: CCCCOc1ccc2cc(-c3ccc(OCc4ccc(-c5cc(F)c(OC(F)(F)F)c(F)c5)cc4)cc3)sc2c1] |
| 201 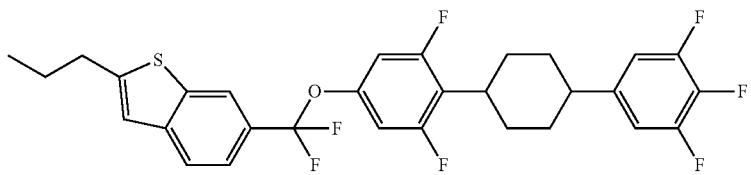 [SMILES: CCCc1cc2ccc(C(F)(F)Oc3cc(F)c(C4CCC(c5cc(F)c(F)c(F)c5)CC4)c(F)c3)cc2s1] |
| 202 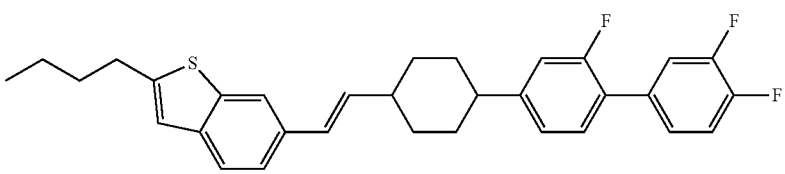 [SMILES: CCCCc1cc2ccc(/C=C/C3CCC(c4ccc(-c5ccc(F)c(F)c5)c(F)c4)CC3)cc2s1] |
| 203 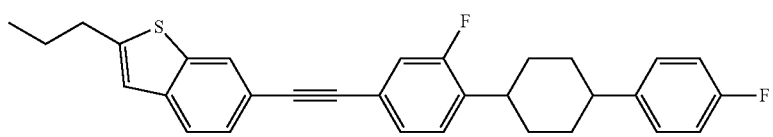 |
| 204 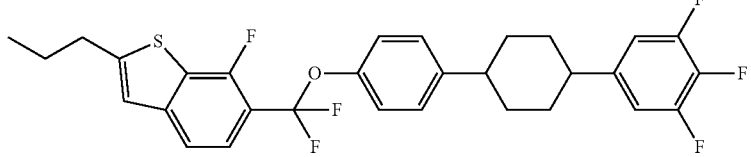 |
| 205 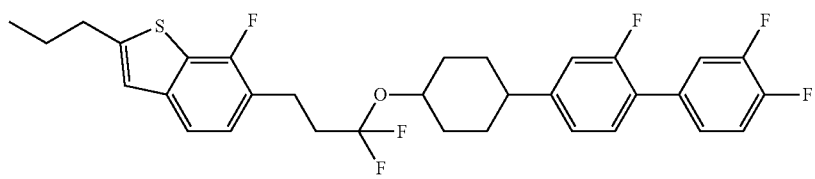 [SMILES: CCCc1cc2ccc(CCC(F)(F)OC3CCC(c4ccc(-c5ccc(F)c(F)c5)c(F)c4)CC3)c(F)c2s1] |
| 206 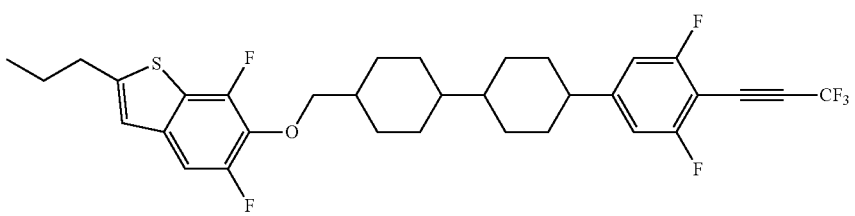 [SMILES: CCCc1cc2cc(F)c(OCC3CCC(C4CCC(c5cc(F)c(C#CC(F)(F)F)c(F)c5)CC4)CC3)c(F)c2s1] |
| 207 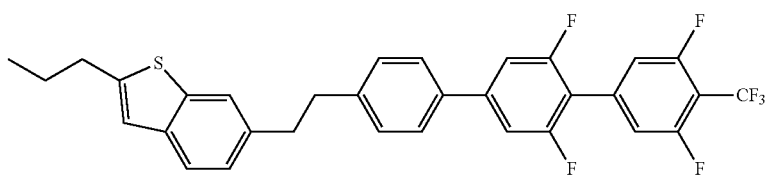 [SMILES: CCCc1cc2ccc(CCc3ccc(-c4cc(F)c(-c5cc(F)c(C(F)(F)F)c(F)c5)c(F)c4)cc3)cc2s1] |

-continued

| No. | |
|---|---|
| 208 | 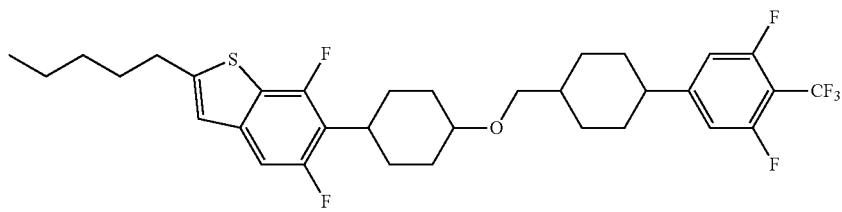 [SMILES: CCCCCc1cc2cc(F)c(C3CCC(OCC4CCC(c5cc(F)c(C(F)(F)F)c(F)c5)CC4)CC3)c(F)c2s1] |
| 209 | 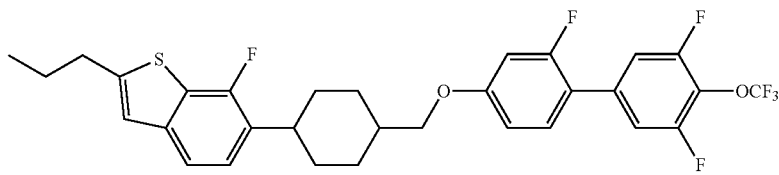 [SMILES: CCCc1cc2ccc(C3CCC(COc4ccc(-c5cc(F)c(OC(F)(F)F)c(F)c5)c(F)c4)CC3)c(F)c2s1] |
| 210 | 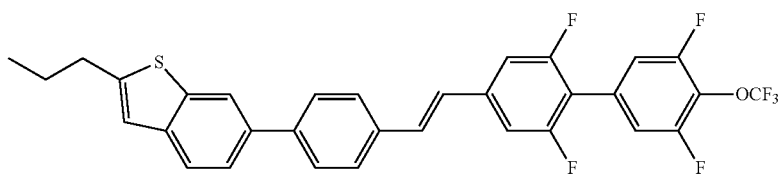 [SMILES: CCCc1cc2ccc(-c3ccc(/C=C/c4cc(F)c(-c5cc(F)c(OC(F)(F)F)c(F)c5)c(F)c4)cc3)cc2s1] |
| 211 | 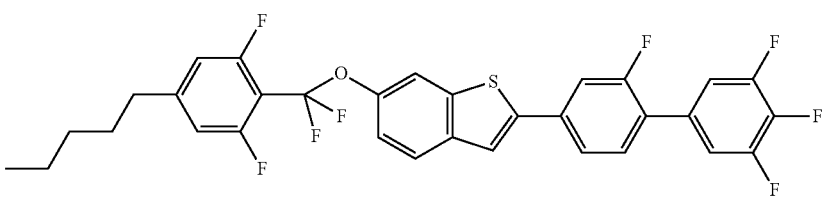 [SMILES: CCCCCc1cc(F)c(C(F)(F)Oc2ccc3cc(-c4ccc(-c5cc(F)c(F)c(F)c5)c(F)c4)sc3c2)c(F)c1] |
| 212 | 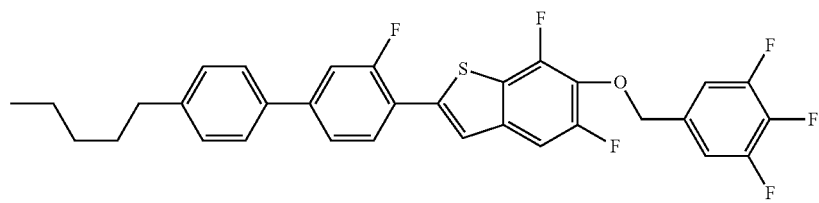 [SMILES: CCCCCc1ccc(-c2ccc(-c3cc4cc(F)c(OCc5cc(F)c(F)c(F)c5)c(F)c4s3)c(F)c2)cc1] |

2. Example of a Composition

The composition according to the invention will be described in detail by way of Examples. The invention includes a mixture of a composition in Use Example 1 and a composition in Use Example 2. The invention also includes a mixture of at least two of compositions in Use Examples. Compounds in Use Examples were expressed using symbols according to definitions described in Table 1 below. In Table 1, a configuration of 1,4-cyclohexylene is trans. Parenthesized numbers described after the symbols in Use Examples represent formulas to which the compounds belong. A symbol (-) means other liquid crystal compounds. A ratio (percentage) of the liquid crystal compound is expressed in terms of weight percent (% by weight) based on the weight of the liquid crystal composition. Values of physical properties of the composition were summarized in a last part. The physical properties were measured in accordance with the methods described above, and measured values were directly described (without extrapolation).

TABLE 1

Method for Description of Compounds using Symbols $$R—(A_1)—Z_1— \ldots —Z_n—(A_n)—R'$$

| | Symbol |
|---|---|
| 1) Left-terminal Group R— | |
| $C_nH_{2n+1}$— | n- |
| $C_nH_{2n+1}O$— | nO- |
| $C_mH_{2m+1}OC_nH_{2n}$— | mOn- |
| $CH_2$=CH— | V- |
| $C_nH_{2n+1}$—CH=CH— | nV- |
| $CH_2$=CH—$C_nH_{2n}$— | Vn- |
| $C_mH_{2m+1}$—CH=CH—$C_nH_{2n}$— | mVn- |
| $CF_2$=CH— | VFF- |
| $CF_2$=CH—$C_nH_{2n}$— | VFFn- |
| 2) Right-terminal Group —R' | |
| —$C_nH_{2n+1}$ | -n |
| —$OC_nH_{2n+1}$ | -On |
| —CH=$CH_2$ | -V |
| —CH=CH—$C_nH_{2n+1}$ | -Vn |
| —$C_nH_{2n}$—CH=$CH_2$ | -nV |
| —$C_mH_{2m}$—CH=CH—$C_nH_{2n+1}$ | -mVn |

TABLE 1-continued

Method for Description of Compounds using Symbols

R—(A₁)—Z₁—...—Zₙ—(Aₙ)—R'

| | Symbol |
|---|---|
| —CH=CF₂ | -VFF |
| —F | -F |
| —Cl | -CL |
| —OCF₃ | -OCF3 |
| —OCF₂H | -OCF2H |
| —CF₃ | -CF3 |
| —C≡N | -C |

3) Bonding Group —Zₙ—

| | |
|---|---|
| —CₙH₂ₙ— | n |
| —COO— | E |
| —CH=CH— | V |
| —CH₂O— | 1O |
| —OCH₂— | O1 |
| —CF₂O— | X |
| —C≡C— | T |

4) Ring Structure —Aₙ—

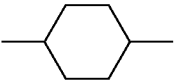 H

 B

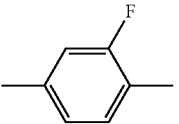 B(F)

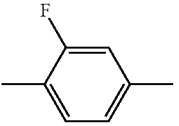 B(2F)

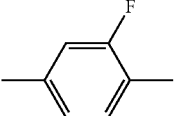 B(F,F)

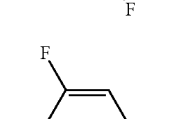 B(2F,5F)

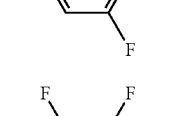 B(2F,3F)

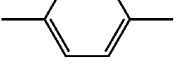 Py

 G

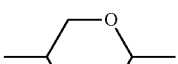 dh

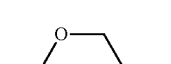 Dh

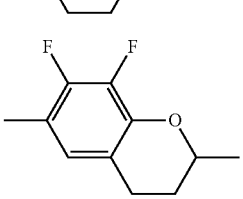 Cro

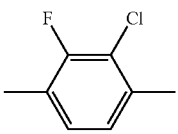 B(2F,3CL)

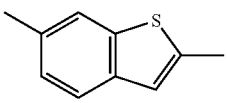 bt

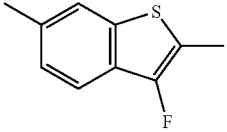 bt(3F)

5) Examples of Description

Example 1.    2O-btB(F,F)XB(F,F)-F

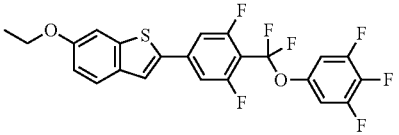

Example 2.    3-HB-O2

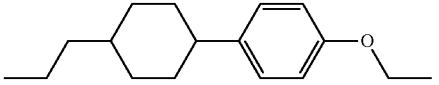

Use Example 1

| | | |
|---|---|---|
| 3-btB(F,F)XB(F,F)-F | (No. 61) | 5% |
| 3-HB-CL | (5-2) | 10% |
| 3-HH-4 | (2-1) | 12% |
| 3-HB-O2 | (2-5) | 7% |
| 3-HHB(F,F)-F | (6-3) | 3% |

-continued

| | | |
|---|---|---|
| 3-HBB(F,F)-F | (6-24) | 29% |
| 5-HBB(F,F)-F | (6-24) | 24% |
| 5-HBB(F)B-2 | (4-5) | 5% |
| 5-HBB(F)B-3 | (4-5) | 5% |

NI=72.8° C.; η=23.2 mPa·s; Δn=0.121; Δ∈=6.4.

Use Example 2

| | | |
|---|---|---|
| 2O-btB(F,F)XB(F,F)-F | (No. 71) | 5% |
| 2-HB-C | (8-1) | 5% |
| 3-HB-C | (8-1) | 12% |
| 3-HB-O2 | (2-5) | 12% |
| 2-BTB-1 | (2-10) | 3% |
| 3-HHB-F | (6-1) | 4% |
| 3-HHB-1 | (3-1) | 7% |
| 3-HHB-O1 | (3-1) | 5% |
| 3-HHB-3 | (3-1) | 14% |
| 3-HHEB-F | (6-10) | 4% |
| 5-HHEB-F | (6-10) | 3% |
| 2-HHB(F)-F | (6-2) | 7% |
| 3-HHB(F)-F | (6-2) | 7% |
| 5-HHB(F)-F | (6-2) | 7% |
| 3-HHB(F,F)-F | (6-3) | 5% |

NI=101.1° C.; η=20.8 mPa·s; Δn=0.106; Δ∈=5.9.

Use Example 3

| | | |
|---|---|---|
| 4O-btB(F,F)XB(F,F)-F | (No. 62) | 5% |
| 7-HB(F,F)-F | (5-4) | 3% |
| 3-HB-O2 | (2-5) | 6% |
| 2-HHB(F)-F | (6-2) | 10% |
| 3-HHB(F)-F | (6-2) | 10% |
| 5-HHB(F)-F | (6-2) | 9% |
| 2-HBB(F)-F | (6-23) | 8% |
| 3-HBB(F)-F | (6-23) | 9% |
| 5-HBB(F)-F | (6-23) | 15% |
| 2-HBB-F | (6-22) | 3% |
| 3-HBB-F | (6-22) | 4% |
| 5-HBB-F | (6-22) | 3% |
| 3-HBB(F,F)-F | (6-24) | 5% |
| 5-HBB(F,F)-F | (6-24) | 10% |

Use Example 4

| | | |
|---|---|---|
| 2O-btB(F)B(F,F)-F | (No. 52) | 4% |
| 5-HB-CL | (5-2) | 15% |
| 3-HH-4 | (2-1) | 12% |
| 3-HH-5 | (2-1) | 4% |
| 3-HHB-F | (6-1) | 3% |
| 3-HHB-CL | (6-1) | 3% |
| 4-HHB-CL | (6-1) | 4% |
| 3-HHB(F)-F | (6-2) | 9% |
| 4-HHB(F)-F | (6-2) | 8% |
| 5-HHB(F)-F | (6-2) | 10% |
| 7-HHB(F)-F | (6-2) | 8% |
| 5-HBB(F)-F | (6-23) | 3% |
| 1O1-HBBH-5 | (4-1) | 3% |
| 3-HHBB(F,F)-F | (7-6) | 2% |
| 4-HHBB(F,F)-F | (7-6) | 3% |
| 5-HHBB(F,F)-F | (7-6) | 3% |
| 3-HH2BB(F,F)-F | (7-15) | 3% |
| 4-HH2BB(F,F)-F | (7-15) | 3% |

Use Example 5

| | | |
|---|---|---|
| 4O-btBB(F,F)XB(F,F)-F | (No. 141) | 5% |
| 3-HHB(F,F)-F | (6-3) | 9% |
| 3-H2HB(F,F)-F | (6-15) | 7% |
| 4-H2HB(F,F)-F | (6-15) | 8% |
| 5-H2HB(F,F)-F | (6-15) | 7% |
| 3-HBB(F,F)-F | (6-24) | 21% |
| 5-HBB(F,F)-F | (6-24) | 18% |
| 3-H2BB(F,F)-F | (6-27) | 10% |
| 5-HHBB(F,F)-F | (7-6) | 3% |
| 5-HHEBB-F | (7-17) | 2% |
| 3-HH2BB(F,F)-F | (7-15) | 3% |
| 1O1-HBBH-4 | (4-1) | 4% |
| 1O1-HBBH-5 | (4-1) | 3% |

Use Example 6

| | | |
|---|---|---|
| 2O-btB(F,F)-F | (No. 1) | 5% |
| 5-HB-F | (5-2) | 10% |
| 6-HB-F | (5-2) | 9% |
| 7-HB-F | (5-2) | 6% |
| 2-HHB-OCF3 | (6-1) | 7% |
| 3-HHB-OCF3 | (6-1) | 7% |
| 4-HHB-OCF3 | (6-1) | 6% |
| 5-HHB-OCF3 | (6-1) | 5% |
| 3-HH2B-OCF3 | (6-4) | 4% |
| 5-HH2B-OCF3 | (6-4) | 4% |
| 3-HHB(F,F)-OCF2H | (6-3) | 3% |
| 3-HHB(F,F)-OCF3 | (6-3) | 5% |
| 3-HH2B(F)-F | (6-5) | 3% |
| 3-HBB(F)-F | (6-23) | 10% |
| 5-HBB(F)-F | (6-23) | 10% |
| 5-HBBH-3 | (4-1) | 3% |
| 3-HB(F)BH-3 | (4-2) | 3% |

Use Example 7

| | | |
|---|---|---|
| 2O-bt(3F)B(F,F)XB(F,F)-F | (No. 74) | 3% |
| 5-HB-CL | (5-2) | 11% |
| 3-HB-O2 | (2-5) | 8% |
| 3-HHB-1 | (3-1) | 5% |
| 3-HHB(F,F)-F | (6-3) | 8% |
| 3-HBB(F,F)-F | (6-24) | 18% |
| 5-HBB(F,F)-F | (6-24) | 15% |
| 3-HHEB(F,F)-F | (6-12) | 9% |
| 4-HHEB(F,F)-F | (6-12) | 3% |
| 5-HHEB(F,F)-F | (6-12) | 3% |
| 2-HBEB(F,F)-F | (6-39) | 3% |
| 3-HBEB(F,F)-F | (6-39) | 5% |
| 5-HBEB(F,F)-F | (6-39) | 3% |
| 3-HHBB(F,F)-F | (7-6) | 6% |

NI=81.0° C.; η=23.2 mPa·s; Δn=0.107; Δ∈=9.5.

Use Example 8

| | | |
|---|---|---|
| 2O-btTB(F,F)XB(F,F)-F | (No. 112) | 5% |
| 3-HB-CL | (5-2) | 5% |
| 5-HB-CL | (5-2) | 4% |
| 3-HHB-OCF3 | (6-1) | 5% |
| 3-H2HB-OCF3 | (6-13) | 4% |
| 5-H4HB-OCF3 | (6-19) | 15% |
| V-HHB(F)-F | (6-2) | 4% |
| 3-HHB(F)-F | (6-2) | 5% |
| 5-HHB(F)-F | (6-2) | 5% |

Use Example 9

| | | |
|---|---|---|
| 2O-btB(F,F)XB(F,F)-F | (No. 71) | 4% |
| 5-HB-CL | (5-2) | 15% |
| 7-HB(F,F)-F | (5-4) | 3% |
| 3-HH-4 | (2-1) | 10% |
| 3-HH-5 | (2-1) | 5% |
| 3-HB-O2 | (2-5) | 14% |
| 3-HHB-1 | (3-1) | 8% |
| 3-HHB-O1 | (3-1) | 5% |
| 2-HHB(F)-F | (6-2) | 7% |
| 3-HHB(F)-F | (6-2) | 6% |
| 5-HHB(F)-F | (6-2) | 7% |
| 3-HHB(F,F)-F | (6-3) | 6% |
| 3-H2HB(F,F)-F | (6-15) | 5% |
| 4-H2HB(F,F)-F | (6-15) | 5% |

NI=73.2° C.; η=16.5 mPa·s; Δn=0.080; Δ∈=3.7.

Use Example 10

| | | |
|---|---|---|
| 3-btB(F,F)XB(F,F)-F | (No. 61) | 5% |
| 5-HB-CL | (5-2) | 3% |
| 7-HB(F)-F | (5-3) | 7% |
| 3-HH-4 | (2-1) | 10% |
| 3-HH-5 | (2-1) | 9% |
| 3-HB-O2 | (2-5) | 11% |
| 3-HHEB-F | (6-10) | 8% |
| 5-HHEB-F | (6-10) | 8% |
| 3-HHEB(F,F)-F | (6-12) | 10% |
| 4-HHEB(F,F)-F | (6-12) | 5% |
| 3-GHB(F,F)-F | (6-109) | 5% |
| 4-GHB(F,F)-F | (6-109) | 5% |
| 5-GHB(F,F)-F | (6-109) | 6% |
| 2-HHB(F)-F | (6-3) | 3% |
| 3-HHB(F)-F | (6-3) | 5% |

NI=71.9° C.; η=21.3 mPa·s; Δn=0.073; Δ∈=6.6.

Use Example 11

| | | |
|---|---|---|
| 4O-btB(F,F)XB(F,F)-F | (No. 62) | 5% |
| 3-HB-O1 | (2-5) | 15% |
| 3-HH-4 | (2-1) | 5% |
| 3-HB(2F,3F)-O2 | (9-1) | 11% |
| 5-HB(2F,3F)-O2 | (9-1) | 10% |
| 2-HHB(2F,3F)-1 | (10-1) | 12% |
| 3-HHB(2F,3F)-1 | (10-1) | 11% |
| 3-HHB(2F,3F)-O2 | (10-1) | 13% |
| 5-HHB(2F,3F)-O2 | (10-1) | 12% |
| 3-HHB-1 | (3-1) | 6% |

Use Example 12

| | | |
|---|---|---|
| 2O-btB(F)B(F,F)-F | (No. 52) | 3% |
| 2-HH-5 | (2-1) | 3% |
| 3-HH-4 | (2-1) | 14% |
| 3-HH-5 | (2-1) | 4% |
| 3-HB-O2 | (2-5) | 12% |
| 3-H2B(2F,3F)-O2 | (9-4) | 14% |
| 5-H2B(2F,3F)-O2 | (9-4) | 15% |
| 3-HHB(2F,3CL)-O2 | (10-12) | 5% |
| 2-HBB(2F,3F)-O2 | (10-7) | 3% |
| 3-HBB(2F,3F)-O2 | (10-7) | 8% |
| 5-HBB(2F,3F)-O2 | (10-7) | 9% |
| 3-HHB-1 | (3-1) | 3% |
| 3-HHB-3 | (3-1) | 4% |
| 3-HHB-O1 | (3-1) | 3% |

Use Example 13

| | | |
|---|---|---|
| 4O-btBB(F,F)XB(F,F)-F | (No. 141) | 5% |
| 2-HH-3 | (2-1) | 10% |
| 2-HH-5 | (2-1) | 10% |
| 3-HH-4 | (2-1) | 9% |
| 1-BB-3 | (2-8) | 8% |
| 3-HB-O2 | (2-5) | 2% |
| 3-BB(2F,3F)-O2 | (9-3) | 8% |
| 5-BB(2F,3F)-O2 | (9-3) | 6% |
| 2-HH1OB(2F,3F)-O2 | (10-5) | 13% |
| 3-HH1OB(2F,3F)-O2 | (10-5) | 20% |
| 3-HHB-1 | (3-1) | 4% |
| 3-HHB-O1 | (3-1) | 3% |
| 5-B(F)BB-2 | (3-8) | 2% |

Use Example 14

| | | |
|---|---|---|
| 2O-btB(F,F)-F | (No. 1) | 5% |
| 2-HH-3 | (2-1) | 16% |
| 7-HB-1 | (2-5) | 9% |
| 5-HB-O2 | (2-5) | 8% |
| 3-HB(2F,3F)-O2 | (9-1) | 16% |
| 5-HB(2F,3F)-O2 | (9-1) | 14% |
| 3-HHB(2F,3CL)-O2 | (10-12) | 3% |
| 4-HHB(2F,3CL)-O2 | (10-12) | 3% |
| 5-HHB(2F,3CL)-O2 | (10-12) | 2% |
| 3-HH1OCro-5 | (13-6) | 5% |
| 5-HBB(F)B-2 | (4-5) | 9% |
| 5-HBB(F)B-3 | (4-5) | 10% |

Use Example 15

| | | |
|---|---|---|
| 2O-bt(3F)B(F,F)XB(F,F)-F | (No. 74) | 2% |
| 1-BB-3 | (2-8) | 8% |
| 3-HH-V | (2-1) | 27% |
| 3-BB(2F,3F)-O2 | (9-3) | 12% |
| 5-BB(2F,3F)-O2 | (9-3) | 3% |
| 2-HH1OB(2F,3F)-O2 | (10-5) | 20% |
| 3-HH1OB(2F,3F)-O2 | (10-5) | 14% |
| 3-HHB-1 | (3-1) | 8% |
| 5-B(F)BB-2 | (3-8) | 6% |

NI=76.1° C.; η=17.2 mPa·s; Δn=0.110; Δ∈=−3.1.

-continued

| | | |
|---|---|---|
| 3-H4HB(F,F)-CF3 | (6-21) | 8% |
| 5-H4HB(F,F)-CF3 | (6-21) | 10% |
| 5-H2HB(F,F)-F | (6-15) | 4% |
| 5-H4HB(F,F)-F | (6-21) | 7% |
| 2-H2BB(F)-F | (6-26) | 4% |
| 3-H2BB(F)-F | (6-26) | 10% |
| 3-HBEB(F,F)-F | (6-39) | 5% |

Use Example 16

| | | |
|---|---|---|
| 2O-btTB(F,F)XB(F,F)-F | (No. 112) | 4% |
| 2-HH-3 | (2-1) | 6% |
| 3-HH-V1 | (2-1) | 10% |
| 1V2-HH-1 | (2-1) | 8% |
| 1V2-HH-3 | (2-1) | 7% |
| 3-BB(2F,3F)-O2 | (9-3) | 8% |
| 3-H1OB(2F,3F)-O2 | (9-5) | 7% |
| 2-HH1OB(2F,3F)-O2 | (10-5) | 8% |
| 3-HH1OB(2F,3F)-O2 | (10-5) | 19% |
| 3-HDhB(2F,3F)-O2 | (10-3) | 7% |
| 3-HHB-1 | (3-1) | 3% |
| 3-HHB-3 | (3-1) | 2% |
| 2-BB(2F,3F)B-3 | (11-1) | 11% |

Use Example 17

| | | |
|---|---|---|
| 2O-btB(F,F)XB(F,F)-F | (No. 71) | 5% |
| 1V2-BEB(F,F)-C | (8-15) | 5% |
| 3-HB-C | (8-1) | 15% |
| 2-BTB-1 | (2-10) | 10% |
| 5-HH-VFF | (2-1) | 29% |
| 3-HHB-1 | (3-1) | 4% |
| VFF-HHB-1 | (3-1) | 8% |
| VFF2-HHB-1 | (3-1) | 11% |
| 3-H2BTB-2 | (3-17) | 5% |
| 3-H2BTB-3 | (3-17) | 4% |
| 3-H2BTB-4 | (3-17) | 4% |

NI=83.8° C.; η=14.5 mPa·s; Δn=0.135; Δ∈=6.8.

Use Example 18

| | | |
|---|---|---|
| 3-btB(F,F)XB(F,F)-F | (No. 61) | 5% |
| 5-HB(F)B(F,F)XB(F,F)-F | (7-41) | 5% |
| 3-BB(F)B(F,F)XB(F,F)-F | (7-47) | 3% |
| 4-BB(F)B(F,F)XB(F,F)-F | (7-47) | 7% |
| 5-BB(F)B(F,F)XB(F,F)-F | (7-47) | 3% |
| 3-HH-V | (2-1) | 38% |
| 3-HH-V1 | (2-1) | 6% |
| 3-HHEH-5 | (3-13) | 3% |
| 3-HHB-1 | (3-1) | 4% |
| V-HHB-1 | (3-1) | 4% |
| V2-BB(F)B-1 | (3-6) | 5% |
| 1V2-BB-F | (5-1) | 3% |
| 3-BB(F,F)XB(F,F)-F | (6-97) | 11% |
| 3-HHBB(F,F)-F | (7-6) | 3% |

NI=80.8° C.; η=16.8 mPa·s; Δn=0.112; Δ∈=7.6.

Use Example 19

| | | |
|---|---|---|
| 4O-btB(F,F)XB(F,F)-F | (No. 62) | 4% |
| 3-GB(F)B(F,F)XB(F,F)-F | (7-75) | 5% |
| 3-BB(F)B(F,F)XB(F,F)-F | (7-47) | 3% |
| 4-BB(F)B(F,F)XB(F,F)-F | (7-47) | 3% |
| 5-BB(F)B(F,F)XB(F,F)-F | (7-47) | 3% |
| 3-HH-V | (2-1) | 41% |
| 3-HH-V1 | (2-1) | 5% |
| 3-HHEH-5 | (3-13) | 3% |
| 3-HHB-1 | (3-1) | 4% |
| V-HHB-1 | (3-1) | 5% |
| V2-BB(F)B-1 | (3-6) | 5% |
| 1V2-BB-F | (5-1) | 5% |
| 3-BB(F,F)XB(F,F)-F | (6-97) | 6% |
| 3-GB(F,F)XB(F,F)-F | (6-113) | 5% |
| 3-HHBB(F,F)-F | (7-6) | 3% |

Use Example 20

| | | |
|---|---|---|
| 5-btB(F)B(F,F)XB(F,F)-F | (No. 151) | 5% |
| 5-HB-F | (5-2) | 12% |
| 6-HB-F | (5-2) | 9% |
| 7-HB-F | (5-2) | 7% |
| 2-HHB-OCF3 | (6-1) | 5% |
| 3-HHB-OCF3 | (6-1) | 5% |
| 4-HHB-OCF3 | (6-1) | 7% |
| 5-HHB-OCF3 | (6-1) | 5% |
| 3-HH2B-OCF3 | (6-4) | 4% |
| 5-HH2B-OCF3 | (6-4) | 4% |
| 3-HHB(F,F)-OCF2H | (6-3) | 3% |
| 3-HHB(F,F)-OCF3 | (6-3) | 5% |
| 3-HH2B(F)-F | (6-5) | 3% |
| 3-HBB(F)-F | (6-23) | 10% |
| 5-HBB(F)-F | (6-23) | 10% |
| 5-HBBH-3 | (4-1) | 3% |
| 3-HB(F)BH-3 | (4-2) | 3% |

NI=87.1° C.; η=19.1 mPa·s; Δn=0.100; Δ∈=5.6.

Use Example 21

| | | |
|---|---|---|
| 5-B(F,F)XbtB(F)B(F,F)-F | (No. 211) | 5% |
| 5-HB-CL | (5-2) | 4% |
| 7-HB(F)-F | (5-3) | 7% |
| 3-HH-4 | (2-1) | 10% |
| 3-HH-5 | (2-1) | 9% |
| 3-HB-O2 | (2-5) | 11% |
| 3-HHEB-F | (6-10) | 8% |
| 5-HHEB-F | (6-10) | 8% |
| 3-HHEB(F,F)-F | (6-12) | 8% |
| 4-HHEB(F,F)-F | (6-12) | 4% |
| 3-GHB(F,F)-F | (6-109) | 5% |
| 4-GHB(F,F)-F | (6-109) | 6% |
| 5-GHB(F,F)-F | (6-109) | 6% |
| 2-HHB(F,F)-F | (6-3) | 4% |
| 3-HHB(F,F)-F | (6-3) | 5% |

NI=72.6° C.; η=22.8 mPa·s; Δn=0.075; Δ∈=6.8.

INDUSTRIAL APPLICABILITY

A liquid crystal compound according to the invention satisfies at least one of physical properties such as high stability to heat and light, a high clearing point (or a high maximum temperature), a low minimum temperature of a liquid crystal phase, small viscosity, suitable optical anisotropy, large dielectric anisotropy, a suitable elastic constant and excellent compatibility with other liquid crystal compounds. In particular, the compound has the excellent compatibility with other liquid crystal compounds. A liquid crystal composition according to the invention contains the compound, and satisfies at least one of physical properties such as a high maximum temperature, a low minimum temperature, small viscosity, suitable optical anisotropy, large dielectric anisotropy and a suitable elastic constant. The composition has a suitable balance regarding at least two of the physical properties. A liquid crystal display device according to the invention includes the composition, and has a wide temperature range in which the device can be used, a short response time, a large voltage holding ratio, a low threshold voltage, a large contrast ratio and a long service life. Therefore, the device can be widely applied to a liquid crystal display to be used for a personal computer, a television and so forth.

What is claimed is:

1. A liquid crystal compound, represented by formula (1):

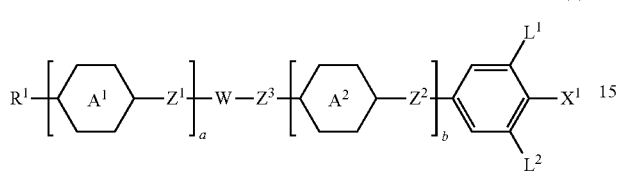

wherein, in formula (1),
- $R^1$ is hydrogen, fluorine or alkyl having 1 to 20 carbons, and in the alkyl, at least one —$CH_2$— may be replaced by —O— or —S—, and at least one —$CH_2CH_2$— may be replaced by —CH=CH—, and in the groups, at least one hydrogen may be replaced by fluorine;
- ring $A^1$ and ring $A^2$ are independently 1,4-cyclohexylene, 1,4-cyclohexenylene, 1,4-phenylene, tetrahydropyran-2,5-diyl, 1,3-dioxane-2,5-diyl, pyrimidine-2,5-diyl, 2,6,7-trioxabicyclo[2.2.2]octane-1,4-diyl, naphthalene-2,6-diyl or pyridine-2,5-diyl, and at least one hydrogen on the rings may be replaced by halogen;
- $Z^1$, $Z^2$ and $Z^3$ are independently a single bond or alkylene having 1 to 4 carbons, and in the alkylene, at least one —$CH_2$— may be replaced by —O— or —COO—, and at least one —$(CH_2)_2$— may be replaced by —CH=CH— or —C≡C—, and in the groups, at least one hydrogen may be replaced by halogen;
- $X^1$ is fluorine, chlorine, —$SF_5$, —C≡N, —N=C=S, —C≡C—$CF_3$, —C≡C—CN, polyfluoroalkyl having 1 to 7 carbons, perfluoroalkyl having 1 to 7 carbons, polyfluoroalkenyl having 1 to 7 carbons, perfluoroalkoxy having 1 to 7 carbons, polyfluoroalkoxy having 1 to 7 carbons or perfluoroalkoxy having 1 to 7 carbons;
- $L^1$ and $L^2$ are independently hydrogen, fluorine or chlorine;
- a and b are independently 0, 1, 2 or 3, and a sum of a and b is 3 or less, and when a or b is two or more, two of rings $A^1$ and $A^2$ and two of $Z^1$ and $Z^2$ may be identical or different; and
- W is a group represented by formula (1a) or formula (1b);

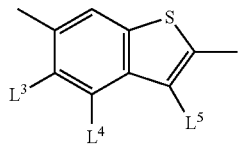

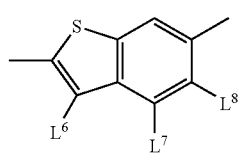

wherein, in formula (1a) and formula (1b),
$L^3$, $L^4$, $L^5$, $L^6$, $L^7$ and $L^8$ are independently hydrogen, fluorine, or chlorine.

2. The compound according to claim 1, wherein,
in formula (1),
$R^1$ is hydrogen, fluorine or alkyl having 1 to 20 carbons, and in the alkyl, at least one —$CH_2$— may be replaced by —O—, and at least one —$CH_2CH_2$— may be replaced by —CH=CH—, and in the groups, at least one hydrogen may be replaced by fluorine;
ring $A^1$ and ring $A^2$ are independently 1,4-cyclohexylene, 1,4-cyclohexenylene, 1,4-phenylene in which one at least hydrogen may be replaced by halogen, 1,3-dioxane-2,5-diyl or tetrahydropyran-2,5-diyl;
$Z^1$, $Z^2$ and $Z^3$ are independently a single bond, —$(CH_2)_2$—, —CH=CH—, —CF=CF—, —C≡C—, —COO—, —OCO—, —$CF_2O$—, —$OCF_2$—, —$CH_2O$—, —$OCH_2$—, —$(CH_2)_4$—, —$(CH_2)_2CF_2O$—, —$(CH_2)_2OCF_2$—, —$CF_2O(CH_2)_2$—, —$OCF_2(CH_2)_2$—, —CH=CH—$(CH_2)_2$— or —$(CH_2)_2$—CH=CH—;
$X^1$ is fluorine, chlorine, —$SF_5$, —C≡N, —N=C=S, —C≡C—$CF_3$, —C≡C—C≡N, polyfluoroalkyl having 1 to 3 carbons, perfluoroalkyl having 1 to 3 carbons, polyfluoroalkenyl having 1 to 3 carbons, perfluoroalkenyl having 1 to 3 carbons, polyfluoroalkoxy having 1 to 3 carbons or perfluoroalkoxy having 1 to 3 carbons; and
$L^1$ and $L^2$ are independently hydrogen or fluorine.

3. The compound according to claim 1, wherein, in formula (1), a sum of a and b is 0, 1 or 2.

4. The compound according to claim 1, represented by any one of formulas (1-1) to (1-12):

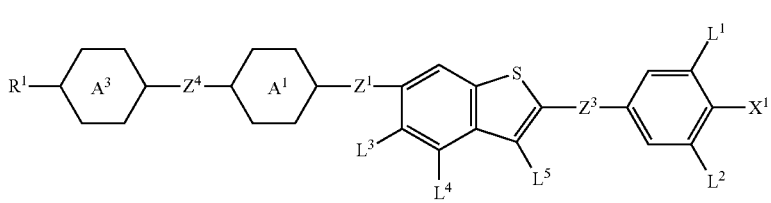

(1-2)
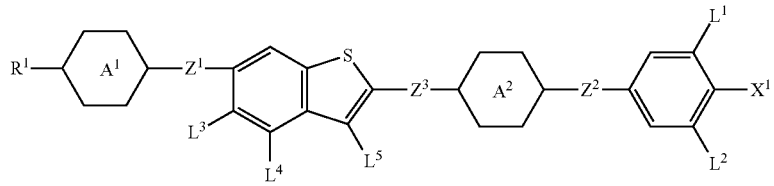
(1-3)
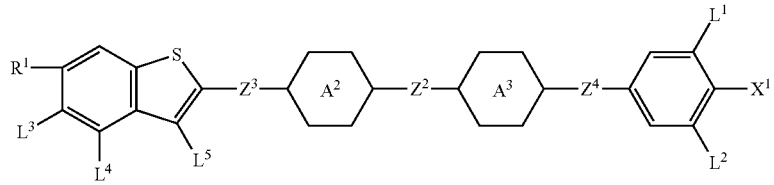
(1-4)
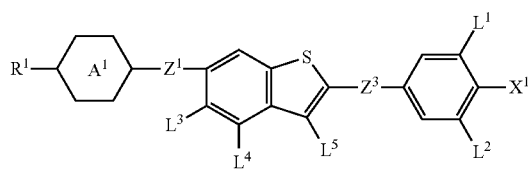
(1-5)
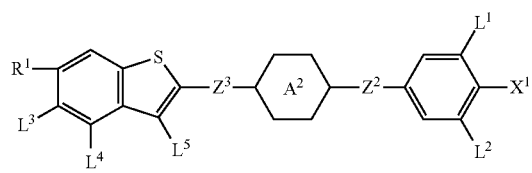
(1-6)
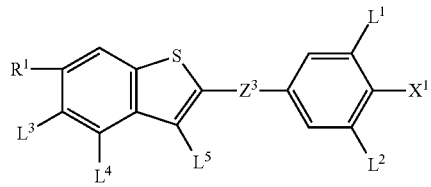
(1-7)
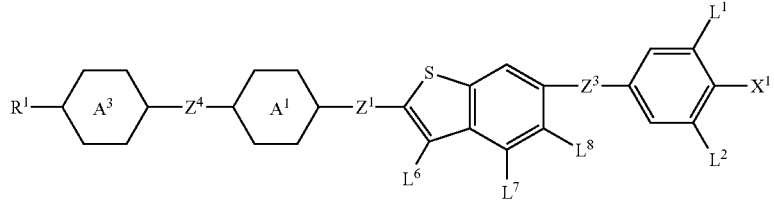
(1-8)
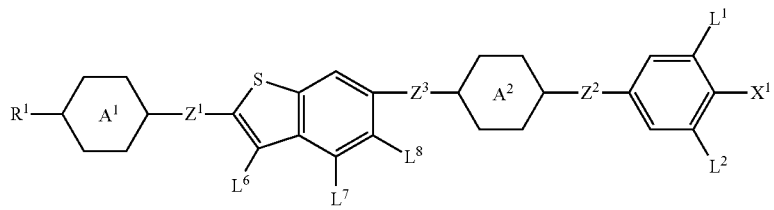
(1-9)
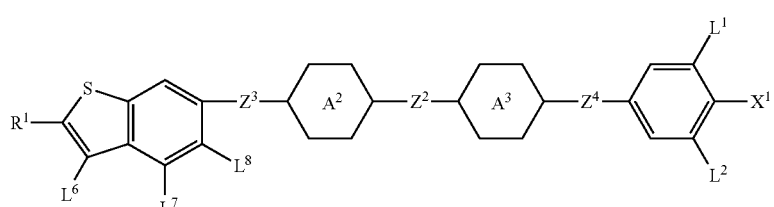
(1-10)
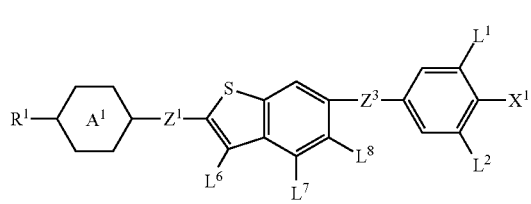
(1-11)
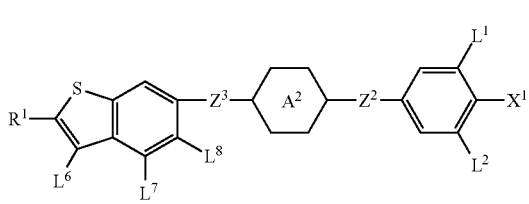

(1-12)

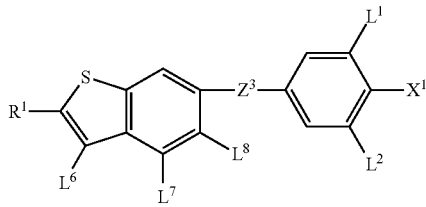

wherein, in formulas (1-1) to (1-12), $R^1$ is hydrogen, fluorine or alkyl having 1 to 10 carbons, and in the alkyl, at least one —$CH_2$— may be replaced by —O—, and at least one —$CH_2CH_2$— may be replaced by —CH=CH—, and in the groups, at least one hydrogen may be replaced by fluorine;

ring $A^1$, ring $A^2$ and ring $A^3$ are independently 1,4-cyclohexylene, 1,4-cyclohexenylene, 1,4-phenylene in which at least one hydrogen may be replaced by halogen, 1,3-dioxane-2,5-diyl or tetrahydropyran-2,5-diyl;

$Z^1$, $Z^2$, $Z^3$ and $Z^4$ are independently a single bond, —$(CH_2)_2$—, —CH=CH—, —CF=CF—, —C≡C—, —COO—, —OCO—, —$CF_2O$—, —$OCF_2$—, —$CH_2O$—, —$OCH_2$—, —$(CH_2)_4$—, —$(CH_2)_2CF_2O$—, —$(CH_2)_2OCF_2$—, —$CF_2O(CH_2)_2$—, —$OCF_2(CH_2)_2$—, —CH=CH—$(CH_2)_2$— or —$(CH_2)_2$—CH=CH—;

$X^1$ is fluorine, —$CF_3$ or —$OCF_3$;

$L^1$ and $L^2$ are independently hydrogen or fluorine; and $L^3$, $L^4$, $L^5$, $L^6$, $L^7$ and $L^8$ are independently hydrogen or fluorine.

5. The compound according to claim 4, wherein, in formulas (1-1) to (1-12), $R^1$ is alkyl having 1 to 10 carbons, and in the alkyl, at least one —$CH_2$— may be replaced by —O—, and at least one —$CH_2CH_2$— may be replaced by —CH=CH—, and in the groups, at least one hydrogen may be replaced by fluorine; and $Z^1$, $Z^2$, $Z^3$ and $Z^4$ are independently a single bond, —$(CH_2)_2$—, —CH=CH—, —$CF_2O$—, —$OCF_2$—, —$CH_2O$—, —C≡C—, —$(CH_2)_2OCF_2$— or —$OCH_2$—.

6. The compound according to claim 5, represented by any one of formulas (1-3), (1-5), (1-6), (1-9), (1-11) and (1-12):

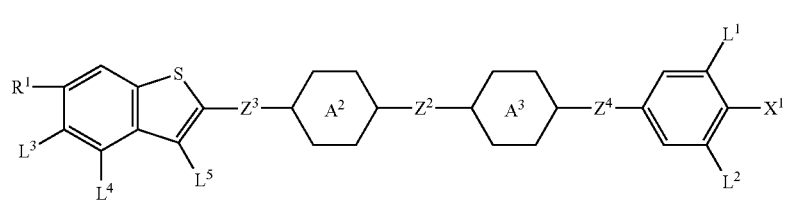

(1-3)

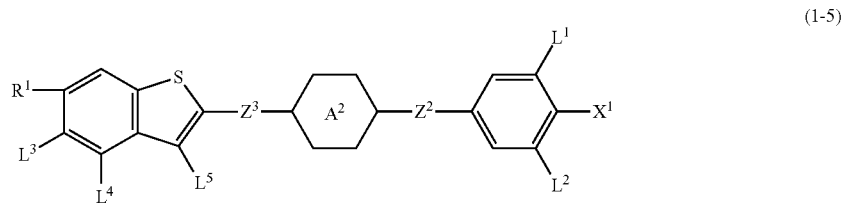

(1-5)

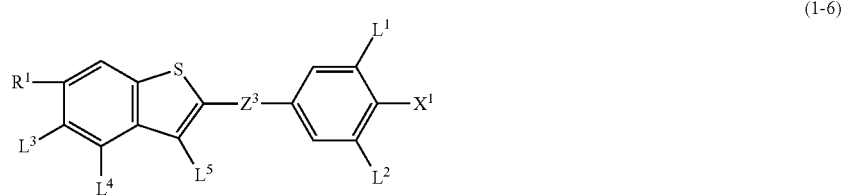

(1-6)

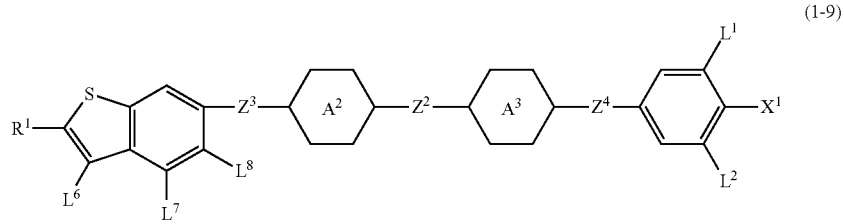

(1-9)

-continued (1-11)

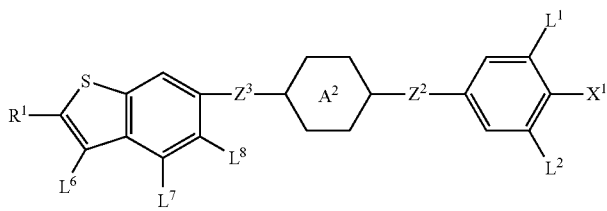

(1-12)

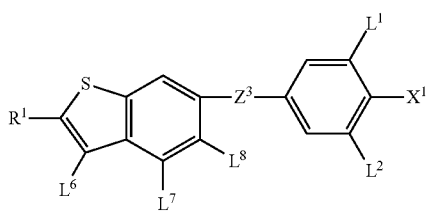

wherein R¹ is alkyl having 1 to 10 carbons, and in the alkyl, at least one —CH₂— may be replaced by —O—, and at least one —CH₂CH₂— may be replaced by —CH=CH—, and in the groups, at least one hydrogen may be replaced by fluorine;

ring A² and ring A³ are independently 1,4-cyclohexylene, 1,4-cyclohexenylene, 1,4-phenylene in which at least one hydrogen may be replaced by halogen, 1,3-dioxane-2,5-diyl or tetrahydropyran-2,5-diyl;

Z², Z³ and Z⁴ are independently a single bond, —(CH₂)₂—, —CH=CH—, —CF₂O—, —OCF₂—, —CH₂O—, —C≡C—, —(CH₂)₂OCF₂— or —OCH₂—;

X¹ is fluorine, —CF₃ or —OCF₃;

L¹ and L² are independently hydrogen or fluorine; and L³, L⁴, L⁵, L⁶, L⁷ and L⁸ are independently hydrogen or fluorine.

7. The compound according to claim 5, represented by any one of formulas (1-3), (1-5) and (1-6), and R¹ being alkoxy having 1 to 6 carbons:

wherein R¹ is alkyl having 1 to 10 carbons, and in the alkyl, at least one —CH₂— may be replaced by —O—, and at least one —CH₂CH₂— may be replaced by —CH=CH—, and in the groups, at least one hydrogen may be replaced by fluorine;

ring A² and ring A³ are independently 1,4-cyclohexylene, 1,4-cyclohexenylene, 1,4-phenylene in which at least one hydrogen may be replaced by halogen, 1,3-dioxane-2,5-diyl or tetrahydropyran-2,5-diyl;

Z², Z³ and Z⁴ are independently a single bond, —(CH₂)₂—, —CH=CH—, —CF₂O—, —OCF₂—, —CH₂O—, —C≡C—, —(CH₂)₂OCF₂— or —OCH₂—;

X¹ is fluorine, —CF₃ or —OCF₃;

L¹ and L² are independently hydrogen, fluorine or chlorine; and

L³, L⁴ and L⁵ are independently hydrogen or fluorine.

8. A liquid crystal composition, containing the compound according to claim 1.

(1-3)

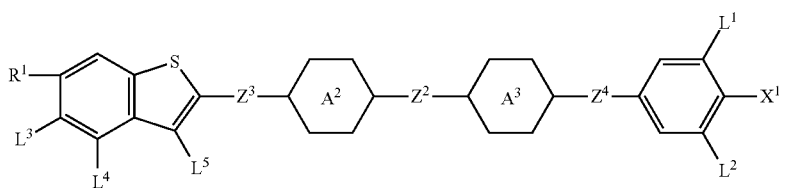

(1-5)

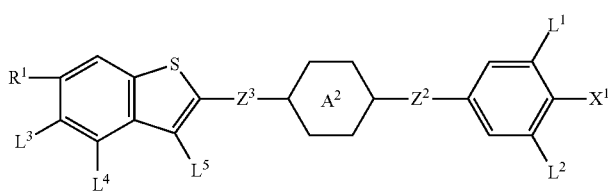

(1-6)

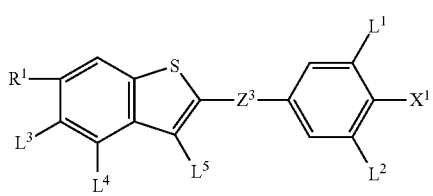

9. The liquid crystal composition according to claim 8, further containing at least one compound selected from the group of compounds represented by formulas (2) to (4):

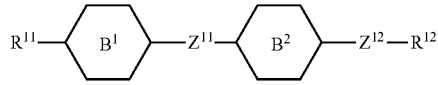
(2)

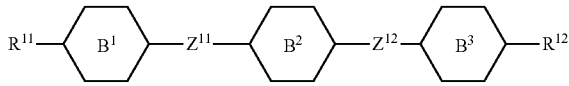
(3)

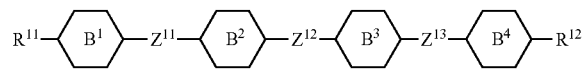
(4)

wherein, in formulas (2) to (4),
- $R^{11}$ and $R^{12}$ are independently alkyl having 1 to 10 carbons or alkenyl having 2 to 10 carbons, in the alkyl or the alkenyl, at least one —$CH_2$— may be replaced by —O—, and at least one hydrogen may be replaced by fluorine;
- ring $B^1$, ring $B^2$, ring $B^3$ and ring $B^4$ are independently 1,4-cyclohexylene, 1,4-phenylene, 2-fluoro-1,4-phenylene, 2,5-difluoro-1,4-phenylene or pyrimidine-2,5-diyl; and
- $Z^{11}$, $Z^{12}$ and $Z^{13}$ are independently a single bond, —$CH_2CH_2$—, —CH=CH—, —C≡C— or —COO—.

10. The liquid crystal composition according to claim 8, further containing at least one compound selected from the group of compounds represented by formulas (5) to (7):

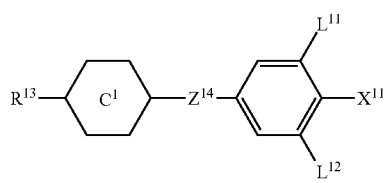
(5)

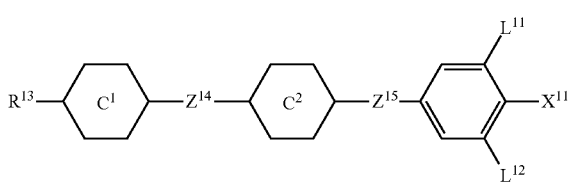
(6)

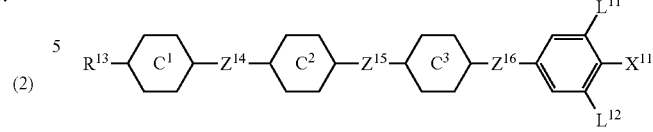
(7)

wherein, in formulas (5) to (7),
- $R^{13}$ is alkyl having 1 to 10 carbons or alkenyl having 2 to 10 carbons, and in the alkyl and the alkenyl, at least one —$CH_2$— may be replaced by —O—, and at least one hydrogen may be replaced by fluorine;
- $X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;
- ring $C^1$, ring $C^2$ and ring $C^3$ are independently 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
- $Z^{14}$, $Z^{15}$ and $Z^{16}$ are independently a single bond, —$CH_2CH_2$—, —CH=CH—, —C≡C—, —COO—, —$CF_2O$—, —$OCF_2$—, —$CH_2O$— or —$(CH_2)_4$—; and
- $L^{11}$ and $L^{12}$ are independently hydrogen or fluorine.

11. The liquid crystal composition according to claim 8, further containing at least one compound selected from the group of compounds represented by formula (8):

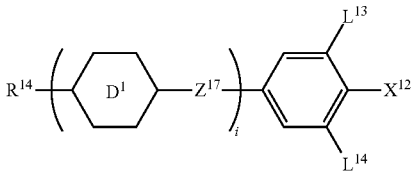
(8)

wherein, in formula (8),
- $R^{14}$ is alkyl having 1 to 10 carbons or alkenyl having 2 to 10 carbons, and in the alkyl and the alkenyl, at least one —$CH_2$— may be replaced by —O—, and at least one hydrogen may be replaced by fluorine;
- $X^{12}$ is —C≡N or —C≡C—C≡N;
- ring $D^1$ is 1,4-cyclohexylene, 1,4-phenylene in which at least one hydrogen may be replaced by fluorine, tetrahydropyran-2,5-diyl, 1,3-dioxane-2,5-diyl or pyrimidine-2,5-diyl;
- $Z^{17}$ is a single bond, —$CH_2CH_2$—, —C≡C—, —COO—, —$CF_2O$—, —$OCF_2$— or —$CH_2O$—;
- $L^{13}$ and $L^{14}$ are independently hydrogen or fluorine; and
- i is 1, 2, 3 or 4.

12. The liquid crystal composition according to claim 8, further containing at least one compound selected from the group of compounds represented by formulas (9) to (15):

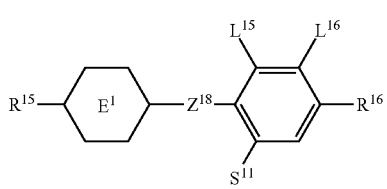
(9)

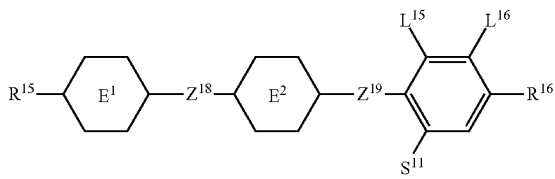

(10)

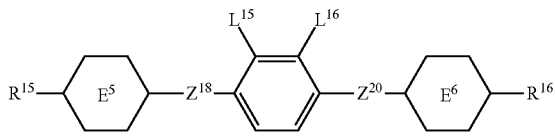

(11)

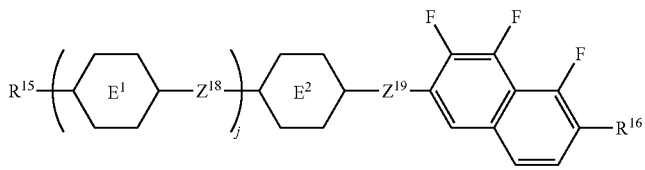

(12)

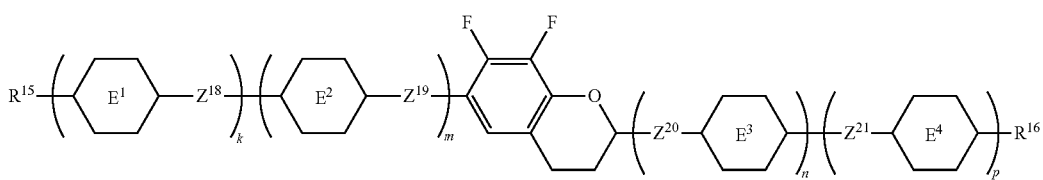

(13)

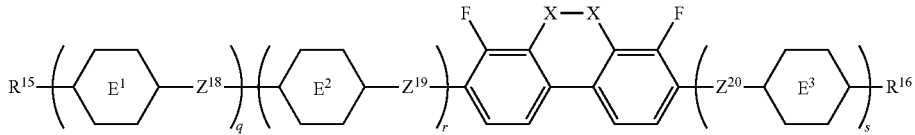

(14)

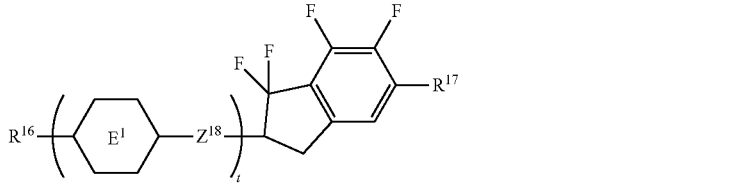

(15)

wherein, in formulas (9) to (15), $R^{15}$ and $R^{16}$ are independently alkyl having 1 to 10 carbons or alkenyl having 2 to 10 carbons, and in the alkyl and the alkenyl, at least one —$CH_2$— may be replaced by —O—, and at least one hydrogen may be replaced by fluorine;

$R^{17}$ is hydrogen, fluorine, alkyl having 1 to 10 carbons or alkenyl having 2 to 10 carbons, and in the alkyl and the alkenyl, at least one —$CH_2$— may be replaced by —O—, and at least one hydrogen may be replaced by fluorine;

ring $E^1$, ring $E^2$, ring $E^3$ and ring $E^4$ are independently 1,4-cyclohexylene, 1,4-cyclohexenylene, 1,4-phenylene in which at least one hydrogen may be replaced by fluorine, tetrahydropyran-2,5-diyl or decahydronaphthalene-2,6-diyl;

ring $E^5$ and ring $E^6$ are independently 1,4-cyclohexylene, 1,4-cyclohexenylene, 1,4-phenylene, tetrahydropyran-2,5-diyl or decahydronaphthalene-2,6-diyl;

$Z^{18}$, $Z^{19}$, $Z^{20}$ and $Z^{21}$ are independently a single bond, —$CH_2CH_2$—, —COO—, —$CH_2O$—, —$OCF_2$— or —$OCF_2CH_2CH_2$—;

$L^{15}$ and $L^{16}$ are independently fluorine or chlorine;

$S^{11}$ is hydrogen or methyl;

X is —CHF— or —$CF_2$—; and j, k, m, n, p, q, r and s are independently 0 or 1, a sum of k, m, n and p is 1 or 2, a sum of q, r and s is 0, 1, 2 or 3, and t is 1, 2 or 3.

13. The liquid crystal composition according to claim 8, further containing at least one of a polymerizable compound, a polymerization initiator, a polymerization inhibitor, an optically active compound, an antioxidant, an ultraviolet light absorber, a light stabilizer, a heat stabilizer, a dye and an antifoaming agent.

14. A liquid crystal device, including the liquid crystal composition according to claim 8.

* * * * *